(12) United States Patent
Adams et al.

(10) Patent No.: US 7,566,706 B2
(45) Date of Patent: Jul. 28, 2009

(54) ANALOGS OF BENZOQUINONE-CONTAINING ANSAMYCINS AND METHODS OF USE THEREOF

(75) Inventors: Julian Adams, Boston, MA (US); Yun Gao, Southborough, MA (US); Asimina T. Georges Evangelinos, Chestnut Hill, MA (US); Louis Grenier, Brookline, MA (US); Roger H. Pak, Boxborough, MA (US); James R. Porter, Brighton, MA (US); James L. Wright, Lexington, MA (US)

(73) Assignee: Infinity Pharmaceuticals, Inc., Cambridge, MA (US)

(*) Notice: Subject to any disclaimer, the term of this patent is extended or adjusted under 35 U.S.C. 154(b) by 60 days.

(21) Appl. No.: 11/105,203

(22) Filed: Apr. 13, 2005

(65) Prior Publication Data

US 2006/0019939 A1    Jan. 26, 2006

Related U.S. Application Data

(63) Continuation of application No. 11/022,057, filed on Dec. 23, 2004.

(60) Provisional application No. 60/540,142, filed on Jan. 29, 2004, provisional application No. 60/547,381, filed on Feb. 23, 2004, provisional application No. 60/561,718, filed on Apr. 12, 2004, provisional application No. 60/567,565, filed on May 3, 2004, provisional application No. 60/606,283, filed on Sep. 1, 2004, provisional application No. 60/626,286, filed on Nov. 9, 2004, provisional application No. 60/632,858, filed on Dec. 3, 2004, provisional application No. 60/532,080, filed on Dec. 23, 2003.

(51) Int. Cl.
*A61P 35/00* (2006.01)

(52) U.S. Cl. ............ 514/183; 514/229.8; 514/375

(58) Field of Classification Search ............ 514/183, 514/229.8, 375
See application file for complete search history.

(56) References Cited

U.S. PATENT DOCUMENTS

| | | | |
|---|---|---|---|
| 4,261,989 A | 4/1981 | Sasaki et al. | |
| 4,762,857 A | 8/1988 | Bollin, Jr. et al. | |
| 5,387,584 A | 2/1995 | Schnur | |
| 5,932,566 A | 8/1999 | Schnur et al. | |
| 6,872,715 B2 | 3/2005 | Santi et al. | |
| 7,465,718 B2 | 12/2008 | Zhang et al. | |
| 2006/0205705 A1 | 9/2006 | Ross et al. | |

FOREIGN PATENT DOCUMENTS

| | | |
|---|---|---|
| GB | 2106111 A | 4/1983 |
| WO | WO 93/14215 | 7/1993 |
| WO | WO 95/01342 | 1/1995 |
| WO | WO 03/013430 A2 | 2/2003 |
| WO | WO 03/026571 A2 | 4/2003 |
| WO | WO 03/066005 A2 | 8/2003 |
| WO | WO-2005/095347 | 10/2005 |
| WO | WO-2006/098761 | 9/2006 |
| WO | WO 2007/001049 | 1/2007 |
| WO | WO-2007/002093 | 1/2007 |
| WO | WO-2007/009007 | 1/2007 |
| WO | WO-2008/128063 | 10/2008 |

OTHER PUBLICATIONS

International Search Report dated Apr. 25, 2005.
Clevenger, R. C. et al., "Design, Synthesis, and Evaluation of a Radicicol and Geldamycin Chimera, Radamide", *Organic Letters*, 6(24):4459-4462 (2004).
Guo, W. et al., "Formation of 17-Allylamino-Demethoxygeldanamycin (17-AAG) Hydroquinone by NAD(P)H:Quinone Oxireductase 1: Role of 17-AAG Hydroquinone in Heat Shock Protein 90 Inhibition", *Cancer Res.*, 65(21):10006-10015 (Nov. 21, 2005).
Mitsiades, C. S. et al., "Antimyeloma activity of heat shock protein-90 inhibition", *Blood*, 107(3):1092-1100 (Feb. 1, 2006).
Hu, Z. et al., "Isolation and Characterization of Novel Geldanamycin Analogues", *Journ. Antibiot*, 57(7):421-428 (Jul. 2004).
Kelland, L. R. et al., "DT-Diaphorase Expression and Tumor Cell Sensitivity to 127-Allylamino, 17-demethoxygeldanamycin, an Inhibitor of Heat Shock Protein 90", *Journ. of the Nat. Cancer Inst.*, 91(22):1940-1949 (Nov. 17, 1999).
Schnur, R. C. et al., "Inhibition of the Oncogene Product p 185erbB-2 in Vitro and in Vivo by Geldanamycin and Dihydrogeldanamycin Derivatives", *J. Med. Chem.*, 38:3806-3812 (1995).
Fritz et al., "Comparison of the cellular and biochemical properties of ansamycin and non-ansamycin based Hsp90 inhibitors," Infinity Pharmaceuticals, Inc., Presented by Christian Fritz on Oct. 22, 2008 at the 20th EORTC-NCI-AACR Symposium on "Molecular Targets and Cancer Therapeutics," (Geneva, Switzerland, Oct. 21-24, 2008).
Ge et al., "Design, Synthesis, and Biological Evaluation of Hydroquinone Derivatives of 17 Amino-17-demethoxygeldanamycin as Potent, Water-Soluble Inhibitors of Hsp90," J. Med. Chem., 49:4606-4615 (2006).
Maroney et al., "Dihydroquinone Ansamycins: Toward Resolving the Conflict between Low in Vitro Affinity and High Cellular Potency of Geldanamycin Derivatives," Biochemistry, 45:5678-5685 (2006).

(Continued)

*Primary Examiner*—Bruck Kifle
(74) *Attorney, Agent, or Firm*—Foley Hoag LLP

(57) ABSTRACT

The present invention provides analogs of benzoquinone-containing ansamycins and uses thereof for treating and modulating disorders associated with hyperproliferation, such as cancer. The present invention provides analogs of benzoquinone-containing ansamycins where the benzoquinone is reduced to a hydroquinone and trapped by reaction with a suitable acid, preferably ones that increase the solubility and air stability of the resulting 17-ammonium hydroquinone ansamycin analog.

27 Claims, 87 Drawing Sheets

OTHER PUBLICATIONS

O'Brien, P.J, "Molecular Mechanisms of Quinone Cytotoxicity," Chem. -Biol. Interactions, 80:1041 (1991).

Oh et al., "A single arm Phase 2 trial of IPI-504 in patients with castration resistant prostate cancer (CRPC)," Abstract submitted Oct. 24, 2008, for the 2009 ASCO Genitourinary Cancers Symposium, Orlando, FL, Feb. 26-28, 2009.

Onoha et al., "Mechanistic Studies on Hsp90 Inhibition by Ansamycin Derivatives," J. Mol. Biol., 372:287-297 (2007).

Syndor et al., "Development of 17-allylamino-17-demethoxygeldanamycin hydroquinone hydrochloride (IPI-504), an anti-cancer agent directed against Hsp90," PNAS, 103(46);17408-17413 (2006).

Porter, James R, "Synthesis and Biological Evaluation of IPI-504, and Aqueous Soluble Analog of 17-AAG and Potent Inhibitor of Hsp90," Presentation by James Porter at ACS Meeting: MEDI-210, Mar. 29, 2006.

"Infinity Provides Update On Phase 2 Signal-Finding Clinical Study of IPI-504 in Advanced Prostate Cancer," Infinity Pharmaceuticals, Inc. Press Release, Jul. 14, 2008.

Hostein et al., "Inhibition of Signal Transduction by the Hsp90 Inhibitor 17-Allylamino-17-demethoxygeldanamycin Results in Cytostasis and Apoptosis," Cancer Research, 61:4003-4009 (2001).

Office action mailed Feb. 19, 2009, in U.S. Appl. No. 11/180,314.

Request for Continued Examination filed Oct. 31, 2008, in U.S. Appl. No. 11/180,314.

Office action dated Jul. 31, 2008, in U.S. Appl. No. 11/180,314.

Response under C.F.R. Section 1.111 dated Mar. 25, 2008, in U.S. Appl. No. 11/180,314.

Office action dated Oct. 26, 2007, in U.S. Appl. No. 11/180,314.

Guo, et al., "A Potential Role for DAD(P)H:quinine oxideductase1 (NQO1) in the Mechanism of Action of the Hsp90 Inhibitors Geldanamycin and 17AAG" AACR Annual Meeting, Apr. 2005, vol. 46, 4936.

Miller, et al., "Depletion of the erbB-2 Gene Product p 185 by Benzoquinoid Ansamycins," Cancer Research 1994, 54, 2724-2730.

Mitsiades, et al., "IPI-504: A Novel Hsp90 Inhibitor with In vitro and In vivo Antitumor Activity" Blood (2004) 104:660A.

Oku, et al., "Combined NMR and Quantum Chemical Studies on the Interaction between Trehalose and Dienes Relevant to the Antioxidant Function of Trehalose," J.Phys. Chem. (2005) 109:3032-3040.

Oku, et al., "NMR and Quantum Chemical Study on the OH . . . pi and CH . . . O Interactions between Trehalose and Unsaturated Fatty Acids: Implication for the Mechanism of Antioxidant Function of Trehalose" J. Am. Chem. Soc. (2003) 125:12739-12748.

Palombella, et al., "Antitumor Activity of IPI-504, a novel Hsp90 Inhibitor in Multiple Myeloma" Blood (2004) 104:312B-313B.

Reigner, et al., "Simultaneous Assay of Pentachlorophenol and Its Metabolite Tetrachlorohydroquinone, by Gas Chromatography Without Derivitation" J. Chromatography (1990) 533:111-124.

Schnur, et al., "erbB-2 Oncogene Inhibition by Geldanamycin Derivatives: Synthesis, Mechanism of Action, and Structure-Activity Relationships" J. Med. Chem (1995) 38; 3813-3820.

European Search Report for EP 06773618.1.

International Search Report for PCT/US2006/023987.

International Search Report for PCT/US2006/027113.

International Search Report for PCT/US2008/060063.

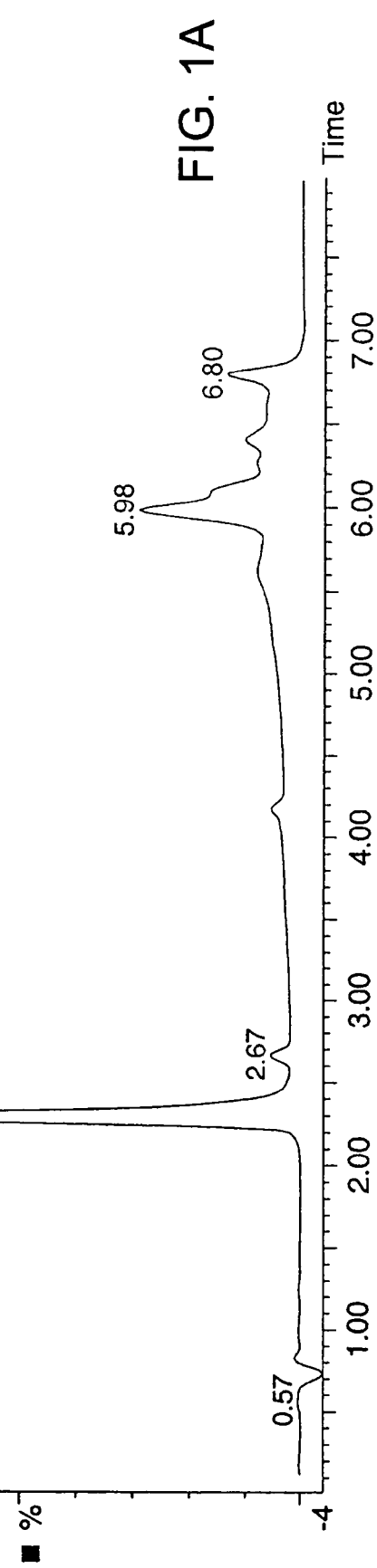

| FIG. 5A |
| FIG. 5B |
| FIG. 5C |

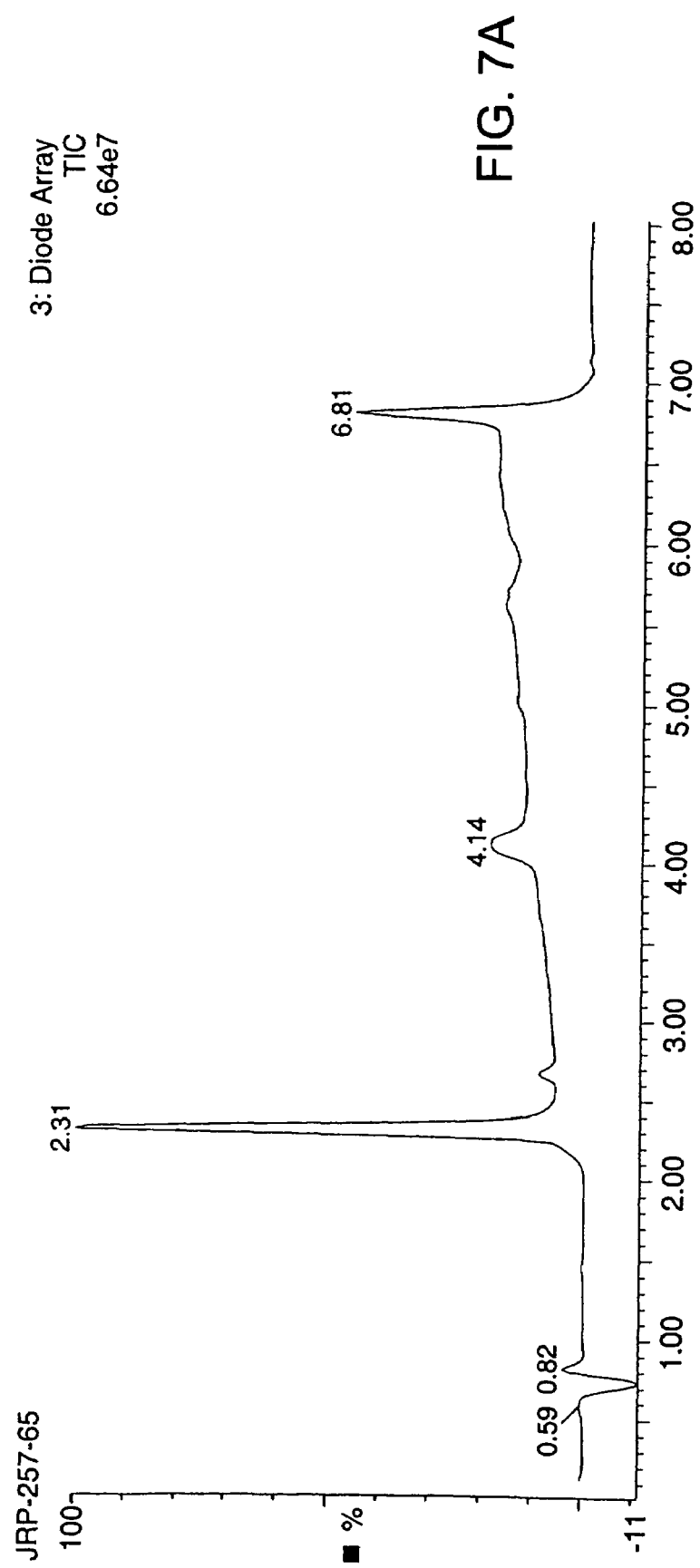

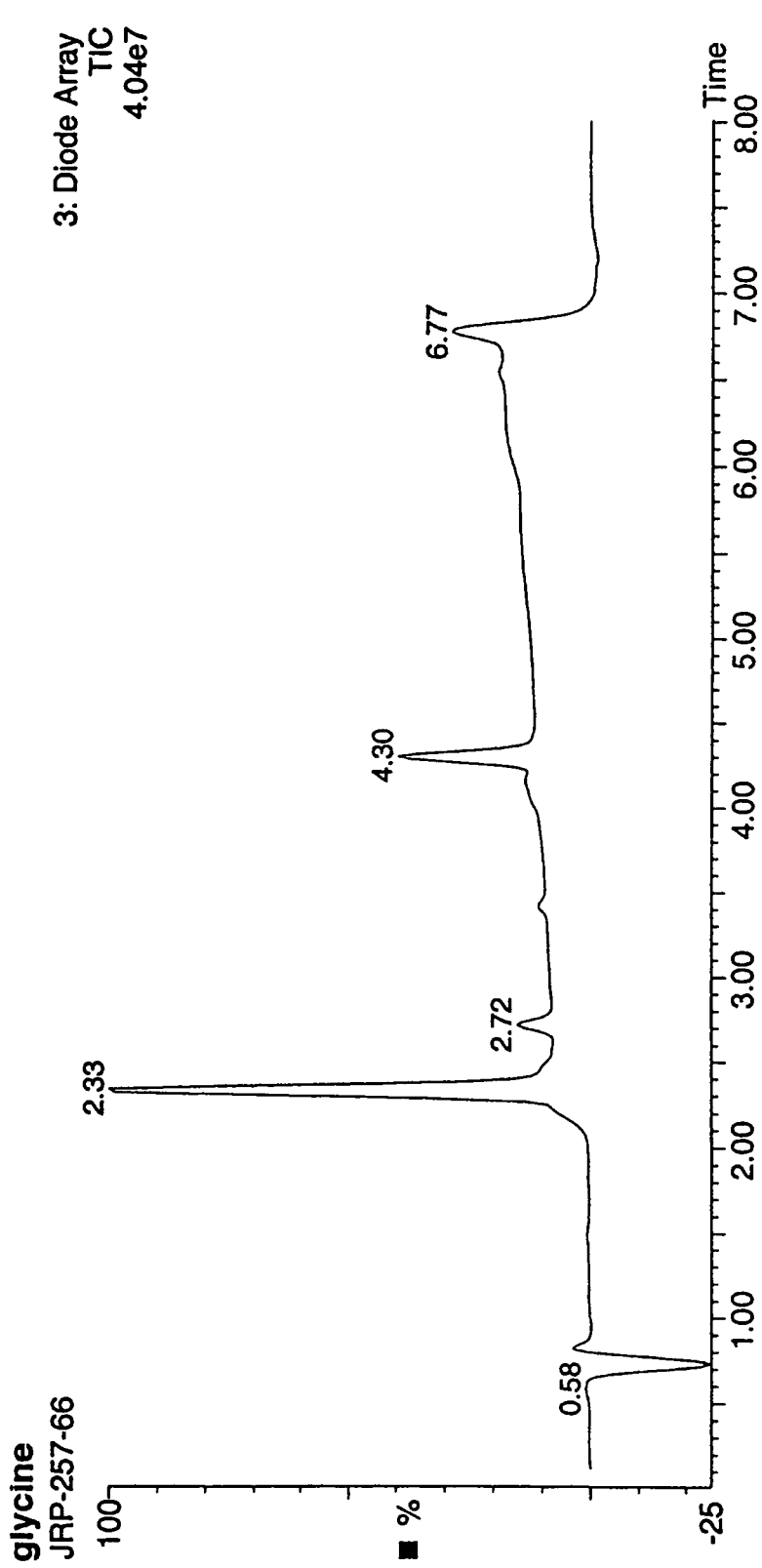

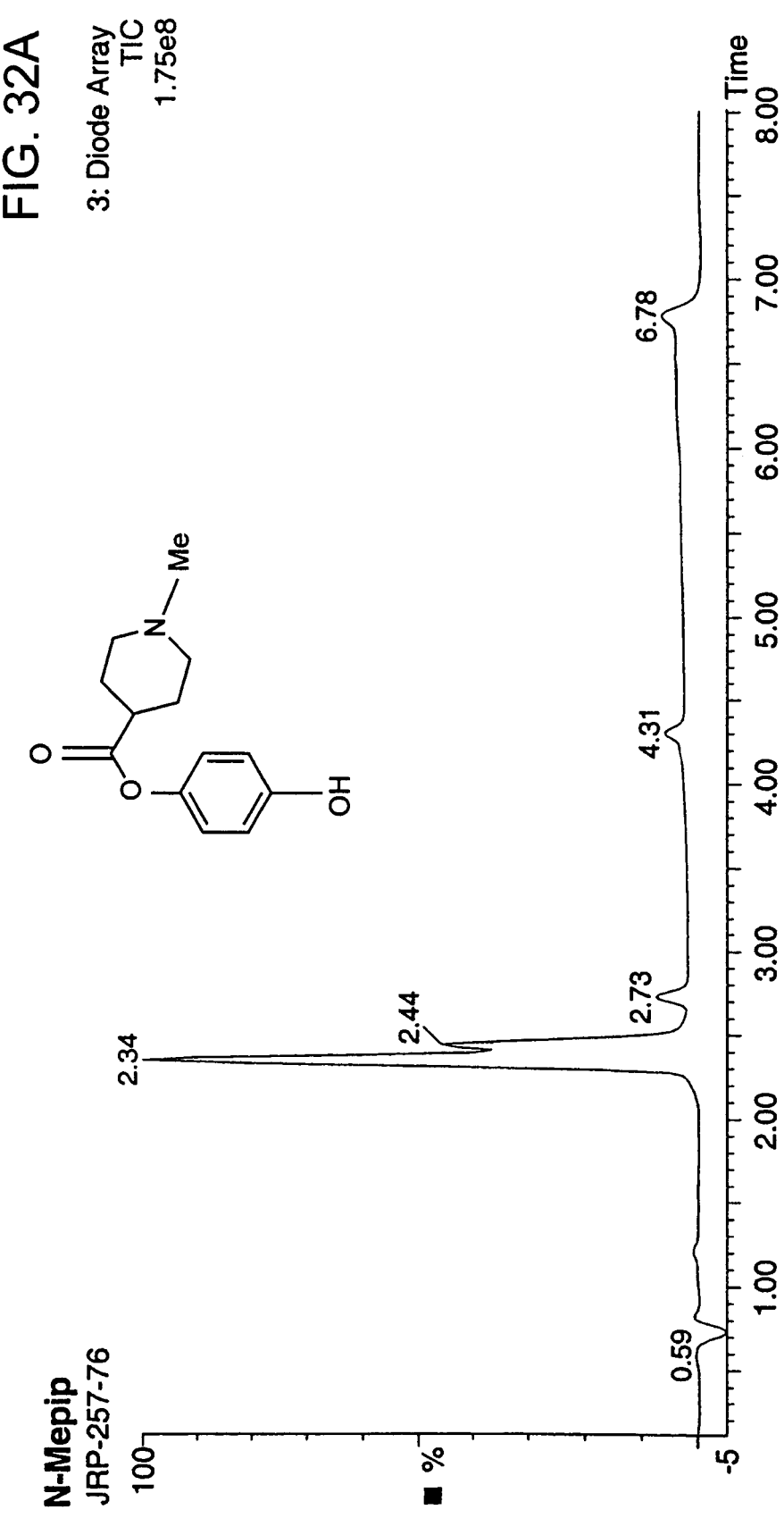

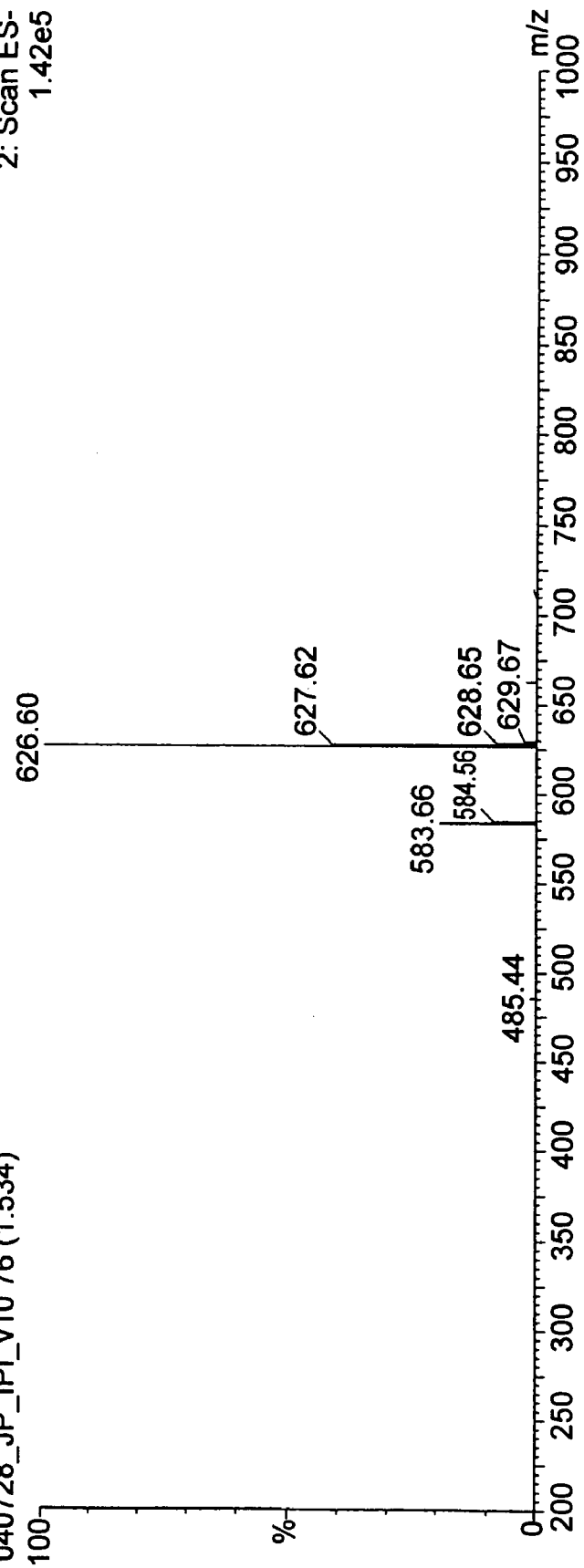

FIG. 65B

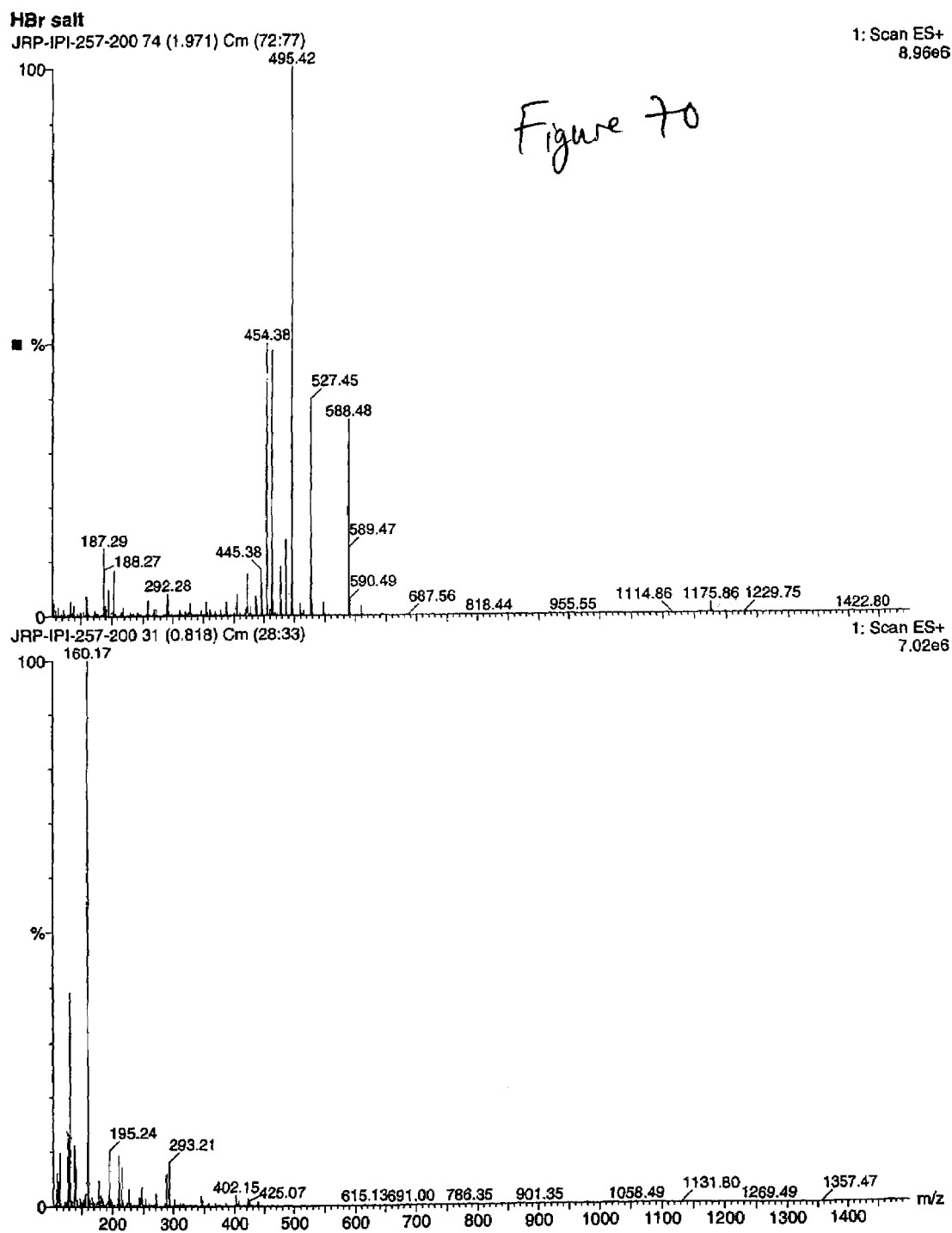

US 7,566,706 B2

ANALOGS OF BENZOQUINONE-CONTAINING ANSAMYCINS AND METHODS OF USE THEREOF

RELATED APPLICATIONS

This application is a continuation of U.S. patent application Ser. No. 11/022,057, filed Dec. 23, 2004 which claims the benefit of priority to U.S. Provisional Patent Application Ser. No. 60/532,080, filed Dec. 23, 2003; U.S. Provisional Patent Application Ser. No. 60/540,142, filed Jan. 29, 2004; U.S. Provisional Patent Application Ser. No. 60/547,381, filed Feb. 23, 2004; U.S. Provisional Patent Application Ser. No. 60/561,718, filed Apr. 12, 2004; U.S. Provisional Patent Application Ser. No. 60/567,565, filed May 3, 2004; U.S. Provisional Patent Application Ser. No. 60/606,283, filed Sep. 1, 2004; U.S. Provisional Patent Application Ser. No. 60/626,286, filed Nov. 9, 2004; U.S. Provisional Patent Application Ser. No. 60/632,858, filed Dec. 3, 2004; the specifications of all of them are hereby incorporated in their entirety.

BACKGROUND OF THE INVENTION

Geldanamycin is a macrocyclic lactam that is a member of the benzoquinone-containing ansamycins family of natural products. The isolation, preparation and various uses of geldanamycin are described in U.S. Pat. No. 3,595,955. Like most naturally-occurring members of this class of molecules, geldanamycin is typically produced as a fermentation product of *Streptomyces hygroscopicus* var. *geldanus* var. *nova* strain (Journal of Antibiotics Vol. 23, Page 442 (1970)). Other analogs and derivatives of geldanamycin have been identified or synthesized, and their use as antitumor agents is described in U.S. Pat. Nos. 4,261,989 and 5,387,584, and published PCT applications WO 00/03737 and WO 03/072794. One member of this family that has been examined in some detail is 17-allylamino-17-demethoxygeldanamycin ("17-AAG"). Geldanamycin and its derivative have been shown to bind to HSP90 and antagonize the protein's activity.

HSP90 is a highly abundant protein which is essential for cell viability and it exhibits dual chaperone functions (*J. Cell Biol.* (2001) 154:267-273, *Trends Biochem. Sci.* (1999) 24:136-141). It plays a key role in the cellular stress response by interacting with many proteins after their native conformation has been altered by various environmental stresses, such as heat shock, ensuring adequate protein folding and preventing non-specific aggregation (*Pharmacological Rev.* (1998) 50:493-513). In addition, recent results suggest that HSP90 may also play a role in buffering against the effects of mutation, presumably by correcting the inappropriate folding of mutant proteins (*Nature* (1998) 396:336-342). However, HSP90 also has an important regulatory role under normal physiological conditions and is responsible for the conformational stability and maturation of a number of specific client proteins, of which about 40 are known (see. *Expert. Opin. Biol Ther.* (2002) 2(1): 3-24). These can be subdivided into three groups: steroid hormone receptors, serine/threonine or tyrosine kinases and a collection of apparently unrelated proteins, including mutant p53 and the catalytic subunit of telomerase hTERT. All of these proteins play regulatory roles in physiological and biochemical processes in the cell.

HSP90 antagonists are currently being explored in a large number of biological contexts where a therapeutic effect can be obtained for a condition or disorder by inhibiting one or more aspects of HSP90 activity. Although the primary focus has been on proliferative disorders, such as cancers, other conditions are showing levels of treatment using HSP90 antagonist. For example, U.S. Published Patent Application 2003/0216369, discloses the use of HSP90 inhibitors for treatment of viral disorders. HSP90 inhibitors have also been implicated in a wide variety of other utilities, including use as anti-inflammation agents, agents for treating autoimmunity, agents for treating stroke, ischemia, cardiac disorders and agents useful in promoting nerve regeneration (See, e. g., WO 02/09696(PCT/US01/23640); WO 99/51223(PCT/US99/07242); U.S. Pat. No. 6,210,974 B1; and U.S. Pat. No. 6,174,875). There are reports in the literature that fibrogenetic disorders including but not limited to scleroderma, polymyositis, systemic lupus, rheumatoid arthritis, liver cirrhosis, keloid formation, interstitial nephritis, and pulmonary fibrosis may be treatable using HSP90 inhibitors. (Strehlow, WO 02/02123; PCT/US01/20578).

Geldanamycin's nanomolar potency and apparent selectivity for killing tumor cells, as well as the discovery that its primary target in mammalian cells is HSP90, has stimulated interest in its development as an anti-cancer drug. However, the extremely low solubility of these molecules and the association of hepatotoxicity with the administration of geldanamycin has led to difficulties in developing an approvable agent for therapeutic applications. In particular, geldanamycin has poor water solubility, making it difficult to deliver in therapeutically effective doses.

More recently, attention has focused on 17-amino derivatives of geldanamycin, in particular 17-AAG, that show reduced hepatotoxicity while maintaining HSP90 binding. See U.S. Pat. Nos. 4,261,989; 5,387,584; and 5,932,566. Like geldanamycin, 17-AAG has very limited aqueous solubility. This property requires the use of a solubilizing carrier, e.g., egg phospholipid with DMSO, or Cremophore® (BASF Aktiengesellschaft), a polyethoxylated castor oil; the presence of either of these carriers results in serious side reactions in some patients.

Consequently, there remains a need to discover more soluble analogs of benzoquinone-containing ansamycins and specific and general methods for creating them, particularly geldanamycin and its analogs, such as 17-AAG.

SUMMARY OF THE INVENTION

The present invention provides reduced forms of benzoquinone-containing ansamycins, and salts thereof in isolated form and in pharmaceutical preparations, and uses of them for treating and modulating disorders associated with hyperproliferation, such as cancer. Generally, the present invention provides soluble, stable drug forms of benzoquinone-containing ansamycins. The present invention provides reduced analogs of benzoquinone-containing ansamycins, such as 17-amino analogs of geldanamycin in isolated form and in pharmaceutical preparations, wherein the benzoquinone is reduced to a hydroquinone and trapped in an air-stable and isolated form, such as an HCl or $H_2SO_4$ salt. Alternatively, the hydroquinones may be trapped as co-salts with an amino acid such as glycine. Such analogs are remarkably water soluble (1-3 orders of magnitude more soluble than the non-reduced form, e.g., 35 µg/mL for 17-AAG vs. 1-3 mg/mL for the hydroquinone of 17-AAG, and >200 mg/mL for salts of hydroquinone derivatives of 17-AAG) and stable; and they can be isolated and formulated for human administration without the problems associated with the formulation, storage and instability of the non-reduced parent forms and other formulations of ansamycins.

In one embodiment, the present invention provides a pure and isolated compound of formula 1:

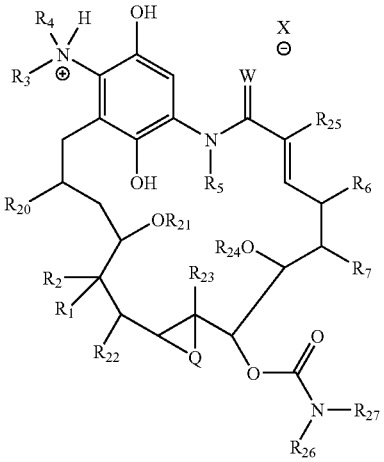

or the free base thereof;
wherein independently for each occurrence;
W is oxygen or sulfur;
Q is oxygen, NR, N(acyl) or a bond;
$X^-$ is a conjugate base of a pharmaceutically acceptable acid;
R for each occurrence is independently selected from the group consisting of hydrogen, alkyl, cycloalkyl, heterocycloalkyl, aralkyl, heteroaryl, and heteroaralkyl;
$R_1$ is hydroxyl, alkoxyl, —OC(O)$R_8$, —OC(O)O$R_9$, —OC(O)N$R_{10}R_{11}$, —OSO$_2R_{12}$, —OC(O)NHSO$_2$N$R_{13}R_{14}$, —N$R_{13}R_{14}$, or halide; and $R_2$ is hydrogen, alkyl, or aralkyl; or $R_1$ and $R_2$ taken together, along with the carbon to which they are bonded, represent —(C=O)—, —(C=N—OR)—, —(C=N—NHR)—, or —(C=N—R)—;
$R_3$ and $R_4$ are each independently selected from the group consisting of hydrogen, alkyl, alkenyl, alkynyl, aryl, cycloalkyl, heterocycloalkyl, aralkyl, heteroaryl, heteroaralkyl, and —[(CR$_2)_p$]—R$_{16}$; or $R_3$ taken together with $R_4$ represent a 4-8 membered optionally substituted heterocyclic ring;
$R_5$ is selected from the group consisting of H, alkyl, aralkyl, and a group having the formula 1a:

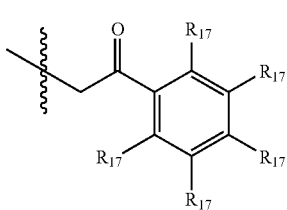

wherein $R_{17}$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —COR$_{18}$, —CO$_2$R$_{18}$, —N(R$_{18}$)CO$_2$R$_{19}$, —OC(O)N(R$_{18}$)(R$_{19}$), —N(R$_{18}$)SO$_2$R$_{19}$, —N(R$_{18}$)C(O)N(R$_{18}$)(R$_{19}$), and —CH$_2$O-heterocyclyl;
$R_6$ and $R_7$ are both hydrogen; or $R_6$ and $R_7$ taken together form a bond;

$R_8$ is hydrogen, alkyl, alkenyl, alkynyl, aryl, cycloalkyl, heterocycloalkyl, aralkyl, heteroaryl, heteroaralkyl, or —[(CR$_2)_p$]—R$_{16}$;
$R_9$ is alkyl, alkenyl, alkynyl, aryl, cycloalkyl, heterocycloalkyl, aralkyl, heteroaryl, heteroaralkyl, or —[(CR$_2)_p$]—R$_{16}$;
$R_{10}$ and $R_{11}$ are each independently selected from the group consisting of hydrogen, alkyl, alkenyl, alkynyl, aryl, cycloalkyl, heterocycloalkyl, aralkyl, heteroaryl, heteroaralkyl, and —[(CR$_2)_p$]—R$_{16}$; or $R_{10}$ and $R_{11}$ taken together with the nitrogen to which they are bonded represent a 4-8 membered optionally substituted heterocyclic ring;
$R_{12}$ is alkyl, alkenyl, alkynyl, aryl, cycloalkyl, heterocycloalkyl, aralkyl, heteroaryl, heteroaralkyl, or —[(CR$_2)_p$]—R$_{16}$;
$R_{13}$ and $R_{14}$ are each independently selected from the group consisting of hydrogen, alkyl, alkenyl, alkynyl, aryl, cycloalkyl, heterocycloalkyl, aralkyl, heteroaryl, heteroaralkyl, and —[(CR$_2)_p$]—R$_{16}$; or $R_{13}$ and $R_{14}$ taken together with the nitrogen to which they are bonded represent a 4-8 membered optionally substituted heterocyclic ring;
$R_{16}$ for each occurrence is independently selected from the group consisting of hydrogen, hydroxyl, acylamino, —N(R$_{18}$)COR$_{19}$, —N(R$_{18}$)C(O)OR$_{19}$, —N(R$_{18}$)SO$_2$(R$_{19}$), —CON(R$_{18}$)(R$_{19}$), —OC(O)N(R$_{18}$)(R$_{19}$), —SO$_2$N(R$_{18}$)(R$_{19}$), —N(R$_{18}$)(R$_{19}$), —OC(O)OR$_{18}$, —COOR$_{18}$, —C(O)N(OH)(R$_{18}$), —OS(O)$_2$OR$_{18}$, —S(O)$_2$OR$_{18}$, —OP(O)(OR$_{18}$)(OR$_{19}$), —N(R$_{18}$)P(O)(OR$_{18}$)(OR$_{19}$), and —P(O)(OR$_{18}$)(OR$_{19}$);
p is 1,2,3, 4, 5, or 6;
$R_{18}$ for each occurrence is independently selected from the group consisting of hydrogen, alkyl, aryl, cycloalkyl, heterocycloalkyl, aralkyl, heteroaryl, and heteroaralkyl;
$R_{19}$ for each occurrence is independently selected from the group consisting of hydrogen, alkyl, aryl, cycloalkyl, heterocycloalkyl, aralkyl, heteroaryl, and heteroaralkyl; or $R_{18}$ taken together with $R_{19}$ represent a 4-8 membered optionally substituted ring;
$R_{20}$, $R_{21}$, $R_{22}$, $R_{24}$, and $R_{25}$, for each occurrence are independently alkyl;
$R_{23}$ is alkyl, —CH$_2$OH, —CHO, —COOR$_{18}$, or —CH(OR$_{18}$)$_2$;
$R_{26}$ and $R_{27}$ for each occurrence are independently selected from the group consisting of hydrogen, alkyl, aryl, cycloalkyl, heterocycloalkyl, aralkyl, heteroaryl, and heteroaralkyl;
provided that when $R_1$ is hydroxyl, $R_2$ is hydrogen, $R_6$ and $R_7$ taken together form a double bond, $R_{20}$ is methyl, $R_{21}$ is methyl, $R_{22}$ is methyl, $R_{23}$ is methyl, $R_{24}$ is methyl, $R_{25}$ is methyl, $R_{26}$ is hydrogen, $R_{27}$ is hydrogen, Q is a bond, and W is oxygen; $R_3$ and $R_4$ are not both hydrogen nor when taken together represent an unsubstituted azetidine; and
the absolute stereochemistry at a stereogenic center of formula 1 may be R or S or a mixture thereof and the stereochemistry of a double bond may be E or Z or a mixture thereof.

In another embodiment the present invention provides a pure and isolated compound with absolute sterochemistry as shown in formula 2:

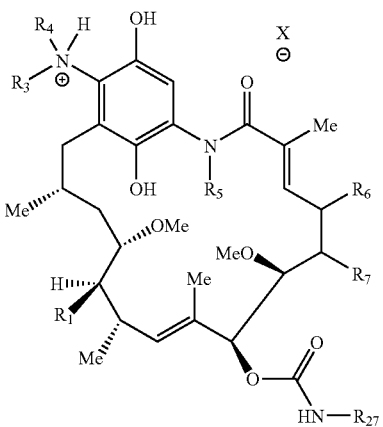

or the free base thereof;
wherein independently for each occurrence;

X⁻ is selected from the group consisting of chloride, bromide, iodide, $H_2PO_4^-$, $HSO_4^-$, methylsulfonate, benzenesulfonate, p-toluenesulfonate, trifluoromethylsulfonate, 10-camphorsulfonate, naphthalene-1-sulfonic acid-5-sulfonate, ethan-1-sulfonic acid-2-sulfonate, cyclamic acid salt, thiocyanic acid salt, naphthalene-2-sulfonate, and oxalate.

$R_1$ is hydroxyl or —$OC(O)R_8$;

$R_3$ and $R_4$ are hydrogen, alkyl, alkenyl, alkynyl, cycloalkyl, aralkyl, heteroaralkyl, or —$[(CR_2)_p]$—$R_{16}$; or $R_3$ taken together with $R_4$ represent a 4-8 membered optionally substituted heterocyclic ring;

$R_5$ is hydrogen or has a formula 1a:

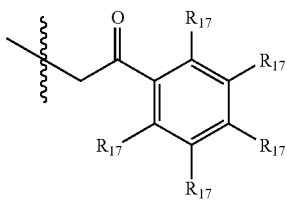

wherein $R_{17}$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —$COR_{18}$, —$CO_2R_{18}$, —$N(R_{18})CO_2R_{19}$, —$OC(O)N(R_{18})(R_{19})$, —$N(R_{18})SO_2R_{19}$, —$N(R_{18})C(O)N(R_{18})(R_{19})$, and —$CH_2O$-heterocyclyl;

$R_6$ and $R_7$ are both hydrogen; or $R_6$ and $R_7$ taken together form a bond;

$R_8$ is hydrogen, alkyl, alkenyl, alkynyl, aryl, cycloalkyl, heterocycloalkyl, aralkyl, heteroaryl, heteroaralkyl, or —$[(CR_2)_p]$—$R_{16}$;

$R_{16}$ for each occurrence is independently selected from the group consisting of hydrogen, hydroxyl, acylamino, —$N(R_{18})COR_{19}$, —$N(R_{18})C(O)OR_{19}$, —$N(R_{18})SO_2(R_{19})$, —$CON(R_{18})(R_{19})$, —$OC(O)N(R_{18})(R_{19})$, —$SO_2N(R_{18})(R_{19})$, —$N(R_{18})(R_{19})$, —$OC(O)OR_{18}$, —$COOR_{18}$, —$C(O)N(OH)(R_{18})$, —$OS(O)_2OR_{18}$, —$S(O)_2OR_{18}$, —$OP(O)(OR_{18})(OR_{19})$, —$N(R_{18})P(O)(OR_{18})(OR_{19})$, and —$P(O)(OR_{18})(OR_{19})$;

p is 1,2,3,4,5, or 6;

$R_{18}$ for each occurrence is independently selected from the group consisting of hydrogen, alkyl, aryl, cycloalkyl, heterocycloalkyl, aralkyl, heteroaryl, and heteroaralkyl;

$R_{19}$ for each occurrence is independently selected from the group consisting of hydrogen, alkyl, aryl, cycloalkyl, heterocycloalkyl, aralkyl, heteroaryl, and heteroaralkyl; or $R_{18}$ taken together with $R_{19}$ represent a 4-8 membered optionally substituted ring;

$R_{27}$ is hydrogen, alkyl, aryl, cycloalkyl, heterocycloalkyl, aralkyl, heteroaryl, or heteroaralkyl;

provided that when $R_1$ is hydroxyl, $R_2$ is hydrogen, $R_6$ and $R_7$ taken together form a double bond, $R_{27}$ is hydrogen; $R_3$ and $R_4$ are not both hydrogen nor when taken together represent an unsubstituted azetidine; and the stereochemistry of a double bond may be E or Z or a mixture thereof.

In another embodiment the present invention provides a pure and isolated compound with absolute sterochemistry as shown in formula 3:

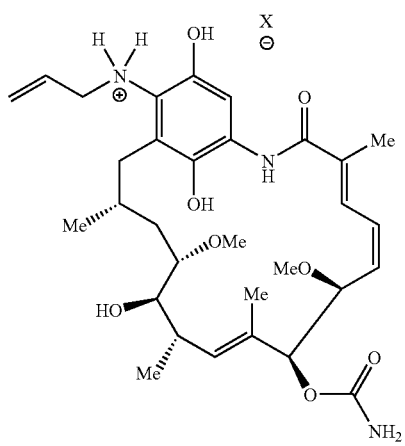

wherein X⁻ is selected from the group consisting of chloride, bromide, iodide, $H_2PO_4^-$, $HSO_4^-$, methylsulfonate, benzenesulfonate, p-toluenesulfonate, trifluoromethylsulfonate, and 10-camphorsulfonate, naphthalene-1-sulfonic acid-5-sulfonate, ethan-1-sulfonic acid-2-sulfonate, cyclamic acid salt, thiocyanic acid salt, naphthalene-2-sulfonate, and oxalate.

In one embodiment the present invention provides a compound of formula 4:

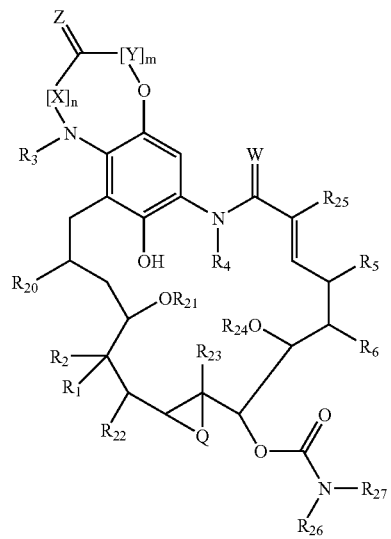

or a pharmaceutically acceptable salt thereof;
wherein, independently for each occurrence, W is oxygen or sulfur;

Z is oxygen or sulfur;

Q is oxygen, NR, N(acyl) or a bond;

n is equal to 0, 1, or 2;

m is equal to 0, 1, or 2;

X and Y are independently $C(R_{30})_2$; wherein $R_{30}$ for each occurrence is independently selected from the group consisting of hydrogen, alkyl, cycloalkyl, heterocycloalkyl, aralkyl, heteroaryl, and heteroaralkyl; or $—[(CR_2)_p]—R_{16}$;

R for each occurrence is independently selected from the group consisting of hydrogen, alkyl, cycloalkyl, heterocycloalkyl, aralkyl, heteroaryl, and heteroaralkyl;

$R_1$ is hydroxyl, alkoxyl, $—OC(O)R_8$, $—OC(O)OR_9$, $—OC(O)NR_{10}R_{11}$, $—OSO_2R_{12}$, $—OC(O)NHSO_2NR_{13}R_{14}$, $NR_{13}R_{14}$, or halide; and $R_2$ is hydrogen, alkyl, or aralkyl; or $R_1$ and $R_2$ taken together, along with the carbon to which they are bonded, represent $—(C=O)—$, $—(C=N—OR)—$, $—(C=N—NHR)—$, or $—(C=N—R)—$;

$R_3$ are each independently selected from the group consisting of hydrogen, alkyl alkenyl, alkynyl, aryl, cycloalkyl, heterocycloalkyl, aralkyl, hetero)yl, heteroaralkyl, and $—[(CR_2)_p]—R_{16}$;

$R_4$ is selected from the group consisting of H, alkyl, aralkyl, and a group having the Formula 4a:

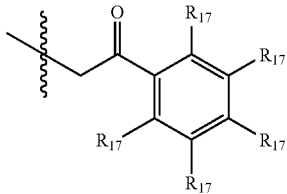

4a wherein $R_{17}$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, $—COR_{18}$, $—CO_2R_{18}$, $—N(R_{18})CO_2R_{19}$, $—OC(O)N(R_{18})(R_{19})$, $—N(R_{18})SO_2R_{19}$, $—N(R_{18})C(O)N(R_{18})(R_{19})$, and $—CH_2O$-heterocyclyl;

$R_5$ and $R_6$ are both hydrogen; or $R_5$ and $R_6$ taken together form a bond;

$R_8$ is hydrogen, alkyl, alkenyl, alkynyl, aryl, cycloalkyl, heterocycloalkyl, aralkyl, heteroaryl, heteroaralkyl, or $—[(CR_2)_p]—R_{16}$;

$R_9$ is alkyl, alkenyl, alkynyl, aryl, cycloalkyl, heterocycloalkyl, aralkyl, heteroaryl, heteroaralkyl, or $—[(CR_2)_p]—R_{16}$;

$R_{10}$ and $R_{11}$ are each independently selected from the group consisting of hydrogen, alkyl, alkenyl, alkynyl, aryl, cycloalkyl, heterocycloalkyl, aralkyl, heteroaryl, heteroaralkyl, and $—[(CR_2)_p]—R_{16}$; or $R_{10}$ and $R_{11}$ taken together with the nitrogen to which they are bonded represent a 4-8 membered optionally substituted heterocyclic ring;

$R_{12}$ is alkyl, alkenyl, alkynyl, aryl, cycloalkyl, heterocycloalkyl, aralkyl, heteroaryl, heteroaralkyl, or $—[(CR_2)_p]—R_{16}$;

$R_{13}$ and $R_{14}$ are each independently selected from the group consisting of hydrogen, alkyl, alkenyl, alkynyl, aryl, cycloalkyl, heterocycloalkyl, aralkyl, heteroaryl, heteroaralkyl, and $—[(CR_2)_p]—R_{16}$; or $R_{13}$ and $R_{14}$ taken together with the nitrogen to which they are bonded represent a 4-8 membered optionally substituted heterocyclic ring;

$R_{16}$ for each occurrence is independently selected from the group consisting of hydrogen, hydroxyl, acylarino, $—N(R_{18})COR_{19}$, $—N(R_{18})C(O)OR_{19}$, $—N(R_{18})SO_2(R_{19})$, $—CON(R_{18})(R_{19})$, $—OC(O)N(R_{18})(R_{19})$, $—SO_2N(R_{18})(R_{19})$, $—N(R_{18})(R_{19})$, $—OC(O)OR_{18}$, $—COOR_{18}$, $—C(O)N(OH)(R_8)$, $—OS(O)_2OR_{18}$, $—S(O)_2OR_{18}$, $—OP(O)(OR_{18})(OR_{19})$, $—N(R_{18})P(O)(OR_{18})(OR_{19})$, and $—P(O)(OR_{18})(OR_{19})$;

p is 1,2,3,4,5,or 6;

$R_{18}$ for each occurrence is independently selected from the group consisting of hydrogen, alkyl, aryl, cycloalkyl, heterocycloalkyl, aralkyl, heteroaryl, and heteroaralkyl;

$R_{19}$ for each occurrence is independently selected from the group consisting of hydrogen, alkyl, aryl, cycloalkyl, heterocycloalkyl, aralkyl, heteroaryl, and heteroaralkyl; or $R_{18}$ taken together with $R_{19}$ represent a 4-8 membered optionally substituted ring;

$R_{20}$, $R_{21}$, $R_{22}$, $R_{24}$, and $R_{25}$, for each occurrence are independently alkyl;

$R_{23}$ is alkyl, $—CH_2OH$, $—CHO$, $—COOR_{18}$, or $—CH(OR_{18})_2$;

$R_{26}$ and $R_{27}$ for each occurrence are independently selected from the group consisting of hydrogen, alkyl, aryl, cycloalkyl, heterocycloalkyl, aralkyl, heteroaryl, and heteroaralkyl; and the absolute stereochemistry at a stereogenic center of formula 4 may be R or S or a mixture thereof and the stereochemistry of a double bond may be E or Z-or a mixture thereof.

In another embodiment the present invention provides a compound with absolute sterochemistry as shown in formula 5:

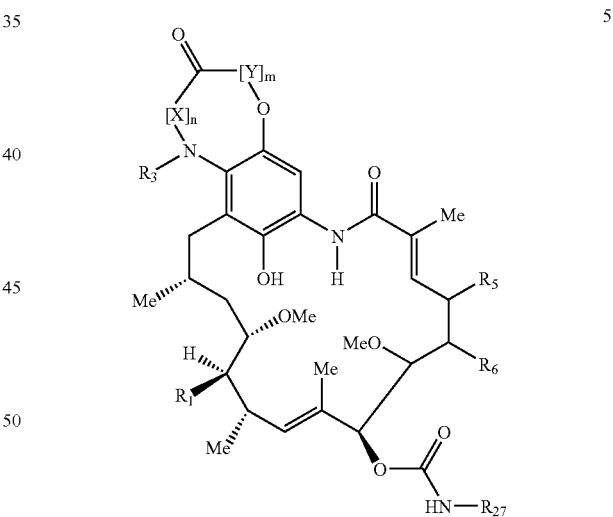

5 wherein independently for each occurrence:

n is equal to 0, 1, or 2;

m is equal to 0, 1,or 2;

X and Y are independently $C(R_{30})_2$; wherein $R_{30}$ for each occurrence is independently selected from the group consisting of hydrogen, alkyl, cycloalkyl, heterocycloalkyl, aralkyl, heteroaryl, and heteroaralkyl; or $—[(CR_2)_p]—R_{16}$;

$R_1$ is hydroxyl or $—OC(O)R_8$;

$R_3$ is hydrogen, alkyl, alkenyl, alkynyl, cycloalkyl, aralkyl, heteroaralkyl, or $—[(CR_2)_p]—R_{16}$;

$R_5$ and $R_6$ are both hydrogen; or $R_5$ and $R_6$ taken together form a bond;

$R_8$ is hydrogen, alkyl, alkenyl, alkynyl, aryl, cycloalkyl, heterocycloalkyl, aralkyl, heteroaryl, heteroaralkyl, or —[(CR$_2$)$_p$]—R$_{16}$;

$R_{16}$ for each occurrence is independently selected from the group consisting of hydrogen, hydroxyl, acylamino, —N(R$_{18}$)COR$_{19}$, —N(R$_{18}$)C(O)OR$_{19}$, —N(R$_{18}$)SO$_2$(R$_{19}$), —CON(R$_{18}$)(R$_{19}$), —OC(O)N(R$_{18}$)(R$_{19}$), —SO$_2$N(R$_{18}$)(R$_{19}$), —N(R$_{18}$)(R$_{19}$), —OC(O)OR$_{18}$, —COOR$_{18}$, —C(O)N(OH)(R$_{18}$), —OS(O)$_2$OR$_{18}$, —S(O)$_2$OR$_{18}$, —OP(O)(OR$_{18}$)(OR$_{19}$), —N(R$_{18}$)P(O)(OR$_{18}$)(OR$_{19}$), and —P(O)(OR$_{18}$)(OR$_{19}$);

p is 1,2,3,4,5,or 6;

$R_{18}$ for each occurrence is independently selected from the group consisting of hydrogen, alkyl, aryl, cycloalkyl, heterocycloalkyl, aralkyl, heteroaryl, and heteroaralkyl;

$R_{19}$ for each occurrence is independently selected from the group consisting of hydrogen, alkyl, aryl, cycloalkyl, heterocycloalkyl, aralkyl, heteroaryl, and heteroaralkyl; or $R_{18}$ taken together with $R_{19}$ represent a 4-8 membered optionally substituted ring;

$R_{27}$ is hydrogen, alkyl, aryl, cycloalkyl, heterocycloalkyl, aralkyl, heteroaryl, or heteroaralkyl; and the stereochemistry of a double bond may be E or Z or a mixture thereof.

In another embodiment the present invention provides a compound selected from the group consisting of:

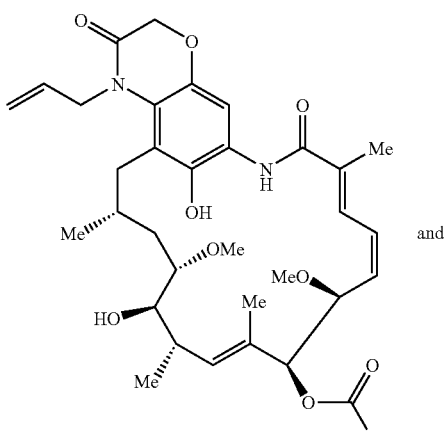

and

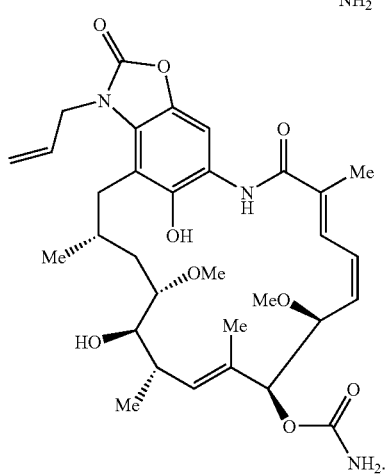

In another embodiment, the present invention provides a pharmaceutical composition comprising: at least one pharmaceutically acceptable excipient; and a compound of formula 6:

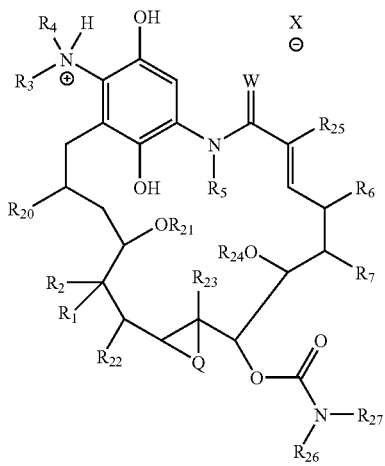

or the free base thereof;
wherein independently for each occurrence:
W is oxygen or sulfur;
Q is oxygen, NR, N(acyl) or a bond;
$X^-$ is a conjugate base of a pharmaceutically acceptable acid;
R for each occurrence is independently selected from the group consisting of hydrogen, alkyl, cycloalkyl, heterocycloalkyl, aralkyl, heteroaryl, and heteroaralkyl;
$R_1$ is hydroxyl, alkoxyl, —OC(O)R$_8$, —OC(O)OR$_9$, —OC(O)NR$_{10}$R$_{11}$, —OSO$_2$R$_{12}$, —OC(O)NHSO$_2$NR$_{13}$R$_{14}$, —NR$_{13}$R$_{14}$, or halide; and R$_2$ is hydrogen, alkyl, or aralkyl; or $R_1$ and $R_2$ taken together, along with the carbon to which they are bonded, represent —(C═O)—, —(C═N—OR)—, —(C═N—NHR)—, or —(C═N—R)—;
$R_3$ and $R_4$ are each independently selected from the group consisting of hydrogen, alkyl, alkenyl, alkynyl, aryl, cycloalkyl, heterocycloalkyl, aralkyl, heteroaryl, heteroaralkyl, and —[(CR$_2$)$_p$]—R$_{16}$; or $R_3$ taken together with $R_4$ represent a 4-8 membered optionally substituted heterocyclic ring;
$R_5$ is selected from the group consisting of H, alkyl, aralkyl, and a group having the formula 6a:

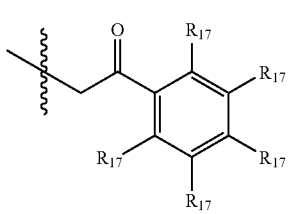

wherein $R_{17}$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —COR$_{18}$, —CO$_2$R$_{18}$, —N(R$_{18}$)CO$_2$R$_{19}$, —OC(O)N(R$_{18}$)(R$_{19}$), —N(R$_{18}$)SO$_2$R$_{19}$, —N(R$_{18}$)C(O)N(R$_{18}$)(R$_{19}$), and —CH$_2$O-heterocyclyl;

$R_6$ and $R_7$ are both hydrogen; or $R_6$ and $R_7$ taken together form a bond;

$R_8$ is hydrogen, alkyl, alkenyl, alkynyl, aryl, cycloalkyl, heterocycloalkyl, aralkyl, heteroaryl, heteroaralkyl, or —$[(CR_2)_p]$—$R_{16}$;

$R_9$ is alkyl, alkenyl, alkynyl, aryl, cycloalkyl, heterocycloalkyl, aralkyl, heteroaryl, heteroaralkyl, or —$[(CR_2)_p]$—$R_{16}$;

$R_{10}$ and $R_{11}$ are each independently selected from the group consisting of hydrogen, alkyl, alkenyl, alkynyl, aryl, cycloalkyl, heterocycloalkyl, aralkyl, heteroaryl, heteroaralkyl, and —$[(CR_2)_p]$—$R_{16}$; or $R_{10}$ and $R_{11}$ taken together with the nitrogen to which they are bonded represent a 4-8 membered optionally substituted heterocyclic ring;

$R_{12}$ is alkyl, alkenyl, alkynyl, aryl, cycloalkyl, heterocycloalkyl, aralkyl, heteroaryl, heteroaralkyl, or —$[(CR_2)_p]$—$R_{16}$;

$R_{13}$ and $R_{14}$ are each independently selected from the group consisting of hydrogen, alkyl, alkenyl, alkynyl, aryl, cycloalkyl, heterocycloalkyl, aralkyl, heteroaryl, heteroaralkyl, and —$[(CR_2)_p]$—$R_{16}$; or $R_{13}$ and $R_{14}$ taken together with the nitrogen to which they are bonded represent a 4-8 membered optionally substituted heterocyclic ring;

$R_{16}$ for each occurrence is independently selected from the group consisting of hydrogen, hydroxyl, acylamino, —$N(R_{18})COR_{19}$, —$N(R_{18})C(O)OR_{19}$, —$N(R_{18})SO_2(R_{19})$, —$CON(R_{18})(R_{19})$, —$OC(O)N(R_{18})(R_{19})$, —$SO_2N(R_{18})(R_{19})$, —$N(R_{18})(R_{19})$, —$OC(O)OR_{18}$, —$COOR_{18}$, —$C(O)N(OH)(R_{18})$, —$OS(O)_2OR_{18}$, —$S(O)_2OR_{18}$, —$OP(O)(OR_{18})(OR_{19})$, —$N(R_{18})P(O)(OR_{18})(OR_{19})$, and —$P(O)(OR_{18})(OR_{19})$;

p is 1,2,3,4,5, or 6;

$R_{18}$ for each occurrence is independently selected from the group consisting of hydrogen, alkyl, aryl, cycloalkyl, heterocycloalkyl, aralkyl, heteroaryl, and heteroaralkyl;

$R_{19}$ for each occurrence is independently selected from the group consisting of hydrogen, alkyl, aryl, cycloalkyl, heterocycloalkyl, aralkyl, heteroaryl, and heteroaralkyl; or $R_{18}$ taken together with $R_{19}$ represent a 4-8 membered optionally substituted ring;

$R_{20}$, $R_{21}$, $R_{22}$, $R_{24}$, and $R_{25}$, for each occurrence are independently alkyl;

$R_{23}$ is alkyl, —$CH_2OH$, —$CHO$, —$COOR_{18}$, or —$CH(OR_{18})_2$;

$R_{26}$ and $R_{27}$ for each occurrence are independently selected from the group consisting of hydrogen, alkyl, aryl, cycloalkyl, heterocycloalkyl, aralkyl, heteroaryl, and heteroaralkyl;

provided that when $R_1$ is hydroxyl, $R_2$ is hydrogen, $R_6$ and $R_7$ taken together form a double bond, $R_{20}$ is methyl, $R_{21}$ is methyl, $R_{22}$ is methyl, $R_{23}$ is methyl, $R_{24}$ is methyl, $R_{25}$ is methyl, $R_{26}$ is hydrogen, $R_{27}$ is hydrogen, Q is a bond, and W is oxygen; $R_3$ and $R_4$ are not both hydrogen nor when taken together represent an unsubstituted azetidine; and the absolute stereochemistry at a stereogenic center of formula 6 may be R or S or a mixture thereof and the stereochemistry of a double bond may be E or Z or a mixture thereof.

In another embodiment, the present invention provides a pharmaceutical composition comprising: at least one pharmaceutically acceptable excipient; a compound of formula 6:

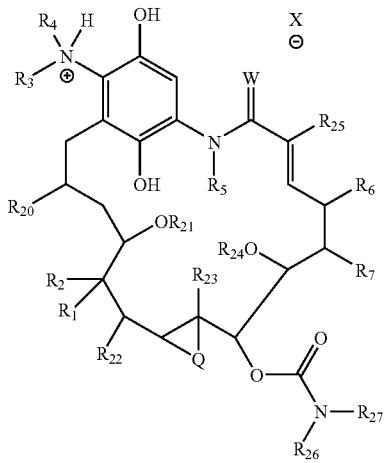

or the free base thereof; and a compound of formula 10, wherein said compound of formula 10 is present in the range of about 0.00001% to about 5% (m/v):

10 or pharmaceutically acceptable salt thereof;
wherein independently for each occurrence;
W is oxygen or sulfur;
Q is oxygen, NR, N(acyl) or a bond;
$X^-$ is a conjugate base of a pharmaceutically acceptable acid;
R for each occurrence is independently selected from the group consisting of hydrogen, alkyl, cycloalkyl, heterocycloalkyl, aralkyl, heteroaryl, and heteroaralkyl;

$R_1$ is hydroxyl, alkoxyl, —$OC(O)R_8$, —$OC(O)OR_9$, —$OC(O)NR_{10}R_{11}$, —$OSO_2R_{12}$, —$OC(O)NHSO_2NR_{13}R_{14}$, —$NR_{13}R_{14}$, or halide, and $R_2$ is hydrogen, alkyl, or aralkyl; or $R_1$ and $R_2$ taken together, along with the carbon to which they are bonded, represent —(C=O)—, —(C=N—OR)—, —(C=N—NHR)—, or —(C=N—R)—;

$R_3$ and $R_4$ are each independently selected from the group consisting of hydrogen, alkyl, alkenyl, alkynyl, aryl, cycloalkyl, heterocycloalkyl, aralkyl, heteroaryl, heteroaralkyl, and —$[(CR_2)_p]$—$R_{16}$; or $R_3$ taken together with $R_4$ represent a 4-8 membered optionally substituted heterocyclic ring;

R$_5$ is selected from the group consisting of H, alkyl, aralkyl, and a group having the formula 6a:

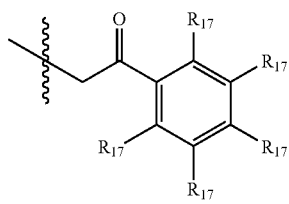

wherein R$_{17}$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —COR$_{18}$, —CO$_2$R$_{18}$, —N(R$_{18}$)CO$_2$R$_{19}$, —OC(O)N(R$_{18}$)(R$_{19}$), —N(R$_{18}$)SO$_2$R$_{19}$, —N(R$_{18}$)C(O)N(R$_{18}$)(R$_{19}$), and —CH$_2$O-heterocyclyl;

R$_6$ and R$_7$ are both hydrogen; or R$_6$ and R$_7$ taken together form a bond;

R$_8$ is hydrogen, alkyl, alkenyl, alkynyl, aryl, cycloalkyl, heterocycloalkyl, aralkyl, heteroaryl, heteroaralkyl, or —[(CR$_2$)$_p$]—R$_{16}$;

R$_9$ is alkyl, alkenyl, alkynyl, aryl, cycloalkyl, heterocycloalkyl, aralkyl, heteroaryl, heteroaralkyl, or —[(CR$_2$)$_p$]—R$_{16}$;

R$_{10}$ and R$_{11}$ are each independently selected from the group consisting of hydrogen, alkyl, alkenyl, alkynyl, aryl, cycloalkyl, heterocycloalkyl, aralkyl, heteroaryl, heteroaralkyl, and —[(CR$_2$)$_p$]—R$_{16}$; or R$_{10}$ and R$_{11}$ taken together with the nitrogen to which they are bonded represent a 4-8 membered optionally substituted heterocyclic ring;

R$_{12}$ is alkyl, alkenyl, alkynyl, aryl, cycloalkyl, heterocycloalkyl, aralkyl, heteroaryl, heteroaralkyl, or —[(CR$_2$)$_p$]—R$_{16}$;

R$_{13}$ and R$_{14}$ are each independently selected from the group consisting of hydrogen, alkyl, alkenyl, alkynyl, aryl, cycloalkyl, heterocycloalkyl, aralkyl, heteroaryl, heteroaralkyl, and —[(CR$_2$)$_p$]—R$_{16}$; or R$_{13}$ and R$_{14}$ taken together with the nitrogen to which they are bonded represent a 4-8 membered optionally substituted heterocyclic ring;

R$_{16}$ for each occurrence is independently selected from the group consisting of hydrogen, hydroxyl, acylamino, —N(R$_{18}$)COR$_{19}$, —N(R$_{18}$)C(O)OR$_{19}$, —N(R$_{18}$)SO$_2$(R$_{19}$), —CON(R$_{18}$)(R$_{19}$), —OC(O)N(R$_{18}$)(R$_{19}$), —SO$_2$N(R$_{18}$)(R$_{19}$), —N(R$_{18}$)(R$_{19}$), —OC(O)OR$_{18}$, —COOR$_{18}$, —C(O)N(OH)(R$_{18}$), —OS(O)$_2$OR$_{18}$, —S(O)$_2$OR$_{18}$, —OP(O)(OR$_{18}$)(OR$_{19}$), —N(R$_{18}$)P(O)(OR$_{18}$)(OR$_{19}$), and —P(O)(OR$_{18}$)(OR$_{19}$);

p is 1,2,3,4,5, or 6;

R$_{18}$ for each occurrence is independently selected from the group consisting of hydrogen, alkyl, aryl, cycloalkyl, heterocycloalkyl, aralkyl, heteroaryl, and heteroaralkyl;

R$_{19}$ for each occurrence is independently selected from the group consisting of hydrogen, alkyl, aryl, cycloalkyl, heterocycloalkyl, aralkyl, heteroaryl, and heteroaralkyl; or R$_{18}$ taken together with R$_{19}$ represent a 4-8 membered optionally substituted ring;

R$_{20}$, R$_{21}$, R$_{22}$, R$_{24}$, and R$_{25}$, for each occurrence are independently alkyl;

R$_{23}$ is alkyl, —CH$_2$OH, —CHO, —COOR$_{18}$, or —CH(OR$_{18}$)$_2$;

R$_{26}$ and R$_{27}$ for each occurrence are independently selected from the group consisting of hydrogen, alkyl, aryl, cycloalkyl, heterocycloalkyl, aralkyl, heteroaryl, and heteroaralkyl;

provided that when R$_1$ is hydroxyl, R$_2$ is hydrogen, R$_6$ and R$_7$ taken together form a double bond, R$_{20}$ is methyl, R$_{21}$ is methyl, R$_{22}$ is methyl, R$_{23}$ is methyl, R$_{24}$ is methyl, R$_{25}$ is methyl, R$_{26}$ is hydrogen, R$_{27}$ is hydrogen, Q is a bond, and W is oxygen; R$_3$ and R$_4$ are not both hydrogen nor when taken together represent an unsubstituted azetidine; and the absolute stereochemistry at a stereogenic center of formula 6 or 10 may be R or S or a mixture thereof and the stereochemistry of a double bond may be E or Z or a mixture thereof.

In other embodiments, the present invention relates to a method of treating cancer, comprising administering to a mammal in need thereof a therapeutically effective amount of a compound of the present invention; or a therapeutically effective amount of a pharmaceutical composition of the present invention.

Another aspect of the invention relates to a method of preparing a compound, comprising: combining a compound of formula 7 with a reducing agent in a reaction solvent to give a compound of formula 8; and

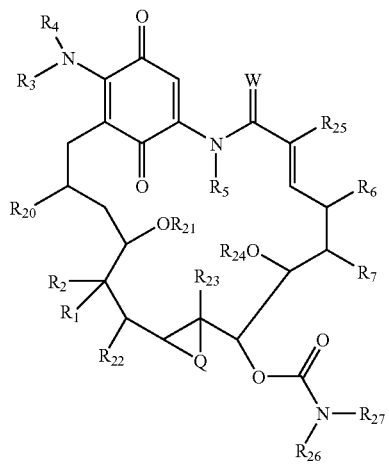

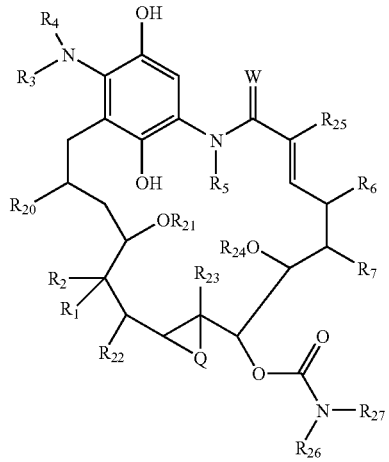

combining said compound of formula 8 with a pharmaceutically acceptable acid to give said compound of formula 1;

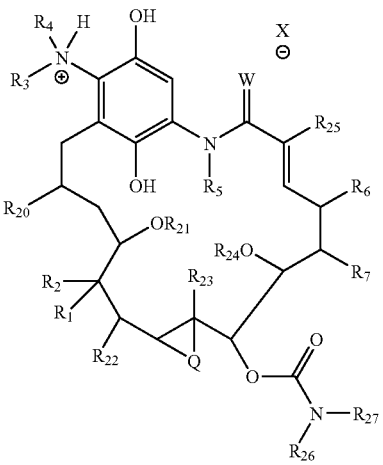

1 wherein independently for each occurrence:

W is oxygen or sulfur;

Q is oxygen, NR, N(acyl) or a bond;

$X^-$ is a conjugate base of a pharmaceutically acceptable acid;

R for each occurrence is independently selected from the group consisting of hydrogen, alkyl, cycloalkyl, heterocycloalkyl, aralkyl, heteroaryl, and heteroaralkyl;

$R_1$ is hydroxyl, alkoxyl, —OC(O)$R_8$, —OC(O)O$R_9$, —OC(O)N$R_{10}R_{11}$, —OSO$_2R_{12}$, —OC(O)NHSO$_2$N$R_{13}R_{14}$, —N$R_{13}R_{14}$, or halide; and $R_2$ is hydrogen, alkyl, or aralkyl; or $R_1$ and $R_2$ taken together, along with the carbon to which they are bonded, represent —(C=O)—, —(C=N—OR)—, —(C=N—NHR)—, or —(C=N—R)—;

$R_3$ and $R_4$ are each independently selected from the group consisting of hydrogen, alkyl, alkenyl, alkynyl, aryl, cycloalkyl, heterocycloalkyl, aralkyl, heteroaryl, heteroaralkyl, and —[(CR$_2$)$_p$]—R$_{16}$; or $R_3$ taken together with $R_4$ represent a 4-8 membered optionally substituted heterocyclic ring;

$R_5$ is selected from the group consisting of H, alkyl, aralkyl, and a group having the formula 1a:

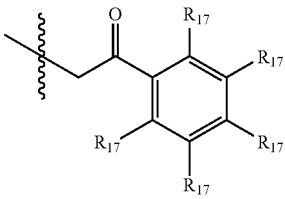

1a wherein $R_{17}$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —COR$_{18}$, —CO$_2$R$_{18}$, —N(R$_{18}$)CO$_2$R$_{19}$, —OC(O)N(R$_{18}$)(R$_{19}$), —N(R$_{18}$)SO$_2$R$_{19}$, —N(R$_{18}$)C(O)N(R$_{18}$)(R$_{19}$), and —CH$_2$O-heterocyclyl;

$R_6$ and $R_7$ are both hydrogen; or $R_6$ and $R_7$ taken together form a bond;

$R_8$ is hydrogen, alkyl, alkenyl, alkynyl, aryl, cycloalkyl, heterocycloalkyl, aralkyl, heteroaryl, heteroaralkyl, or —[(CR$_2$)$_p$]—R$_{16}$;

$R_9$ is alkyl, alkenyl, alkynyl, aryl, cycloalkyl, heterocycloalkyl, aralkyl, heteroaryl, heteroaralkyl, or —[(CR$_2$)$_p$]—R$_{16}$;

$R_{10}$ and $R_{11}$ are each independently selected from the group consisting of hydrogen, alkyl, alkenyl, alkynyl, aryl, cycloalkyl, heterocycloalkyl, aralkyl, heteroaryl, heteroaralkyl, and —[(CR$_2$)$_p$]—R$_{16}$; or $R_{10}$ and $R_{11}$ taken together with the nitrogen to which they are bonded represent a 4-8 membered optionally substituted heterocyclic ring;

$R_{12}$ is alkyl, alkenyl, alkynyl, aryl, cycloalkyl, heterocycloalkyl, aralkyl, heteroaryl, heteroaralkyl, or —[(CR$_2$)$_p$]—R$_{16}$;

$R_{13}$ and $R_{14}$ are each independently selected from the group consisting of hydrogen, alkyl, alkenyl, alkynyl, aryl, cycloalkyl, heterocycloalkyl, aralkyl, heteroaryl, heteroaralkyl, and —[(CR$_2$)$_p$]—R$_{16}$; or $R_{13}$ and $R_{14}$ taken together with the nitrogen to which they are bonded represent a 4-8 membered optionally substituted heterocyclic ring;

$R_{16}$ for each occurrence is independently selected from the group consisting of hydrogen, hydroxyl, acylamino, —N(R$_{18}$)COR$_{19}$, —N(R$_{18}$)C(O)OR$_{19}$, —N(R$_{18}$)SO$_2$(R$_{19}$), —CON(R$_{18}$)(R$_{19}$), —OC(O)N(R$_{18}$)(R$_{19}$), —SO$_2$N(R$_{18}$)(R$_{19}$), —N(R$_{18}$)(R$_{19}$), —OC(O)OR$_{18}$, —COOR$_{18}$, —C(O)N(OH)(R$_{18}$), —OS(O)$_2$OR$_{18}$, —S(O)$_2$OR$_{18}$, —OP(O)(OR$_{18}$)(OR$_{19}$), —N(R$_{18}$)P(O)(OR$_{18}$)(OR$_{19}$), and —P(O)(OR$_{18}$)(OR$_{19}$);

p is 1,2,3,4,5, or 6;

$R_{18}$ for each occurrence is independently selected from the group consisting of hydrogen, alkyl, aryl, cycloalkyl, heterocycloalkyl, aralkyl, heteroaryl, and heteroaralkyl;

$R_{19}$ for each occurrence is independently selected from the group consisting of hydrogen, alkyl, aryl, cycloalkyl, heterocycloalkyl, aralkyl, heteroaryl, and heteroaralkyl; or $R_{18}$ taken together with $R_1$ represent a 4-8 membered optionally substituted ring;

$R_{20}$, $R_{21}$, $R_{22}$, $R_{24}$, and $R_{25}$, for each occurrence are independently alkyl;

$R_{23}$ is alkyl, —CH$_2$OH, —CHO, —COOR$_{18}$, or —CH(OR$_{18}$)$_2$;

$R_{26}$ and $R_{27}$ for each occurrence are independently selected from the group consisting of hydrogen, alkyl, aryl, cycloalkyl, heterocycloalkyl, aralkyl, heteroaryl, and heteroaralkyl;

provided that when $R_1$ is hydroxyl, $R_2$ is hydrogen, $R_6$ and $R_7$ taken together form a double bond, $R_{20}$ is methyl, $R_{21}$ is methyl, $R_{22}$ is methyl, $R_{23}$ is methyl, $R_{24}$ is methyl, $R_{25}$ is methyl, $R_{26}$ is hydrogen, $R_{27}$ is hydrogen, Q is a bond, and W is oxygen; $R_3$ and $R_4$ are not both hydrogen nor when taken together represent an unsubstituted azetidine; and the absolute stereochemistry at a stereogenic center of formula 1 may be R or S or a mixture thereof and the stereochemistry of a double bond may be E or Z or a mixture thereof.

BRIEF DESCRIPTION OF THE FIGURES

FIG. 70 depicts a mass spectrum from a LCMS analysis of the HBr Salt of the Hydroquinone of 17-AAG prepared according to the procedure described in Example 31.

DETAILED DESCRIPTION OF THE INVENTION

Overview

Figure 1B:
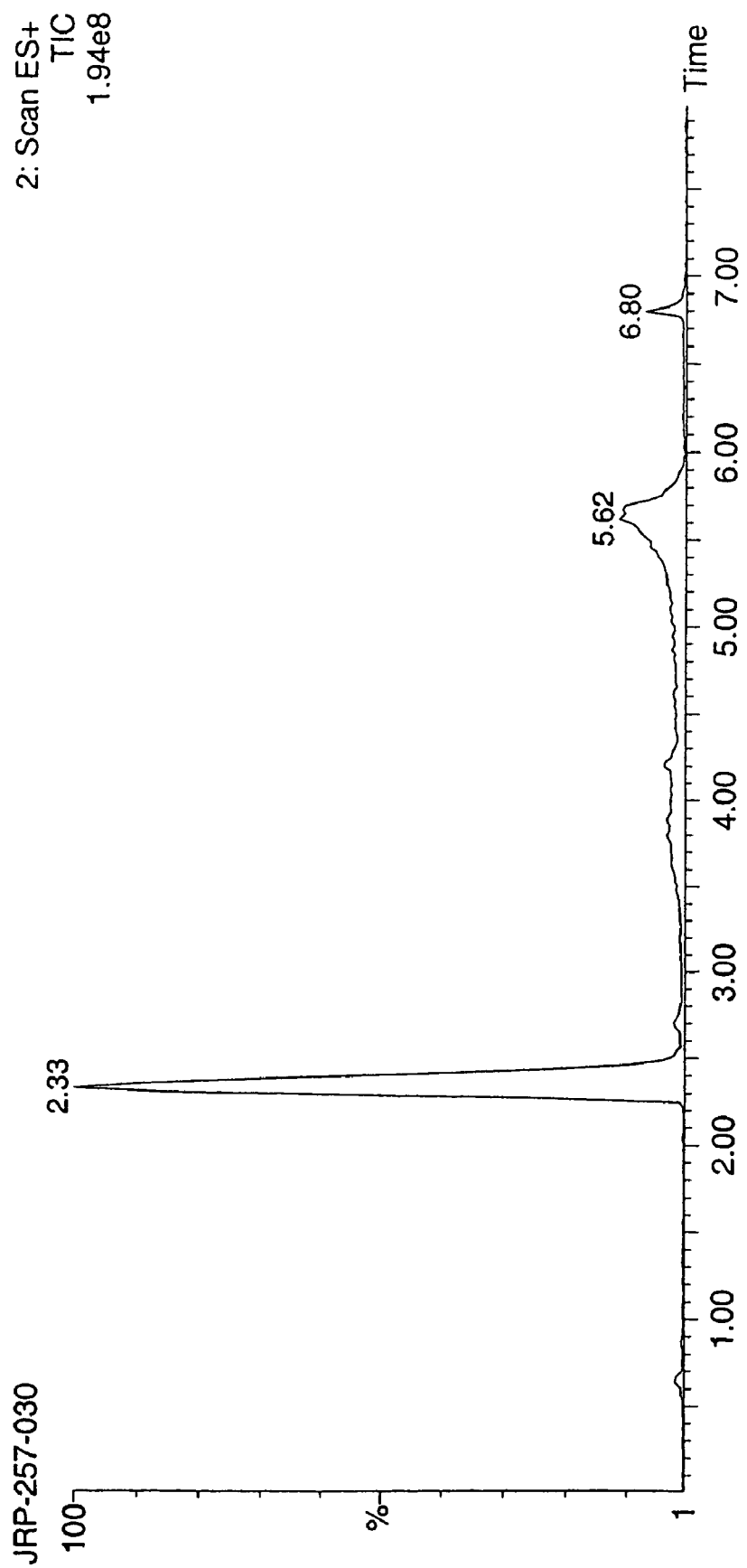
FIG. 1 depicts chromatograms from a LCMS analysis of the Dimethylamino Acetate Co-Salt of the Hydroquinone of 17-AAG prepared according to the procedure described in Example 3.
Figure 1C:
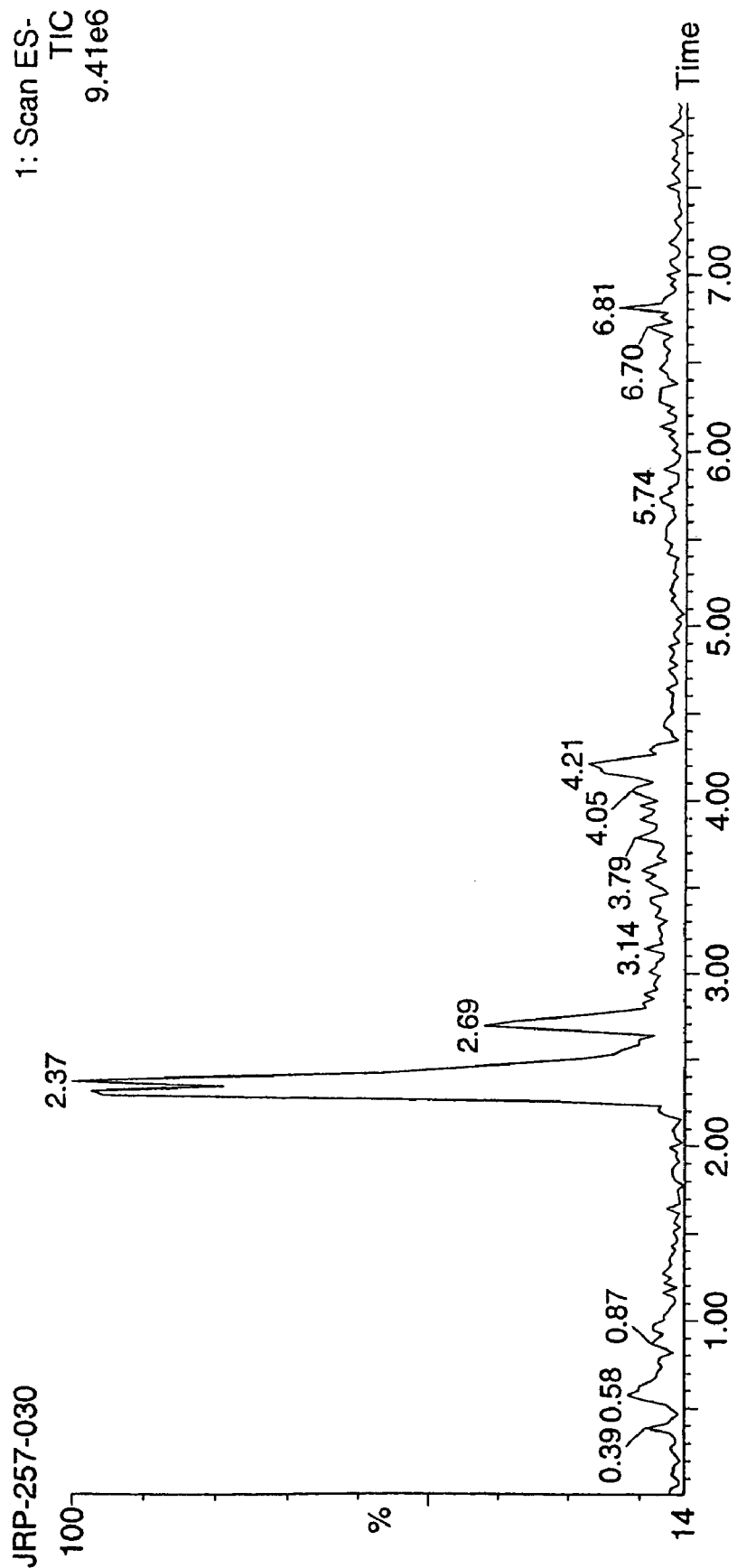
Figure 2A:
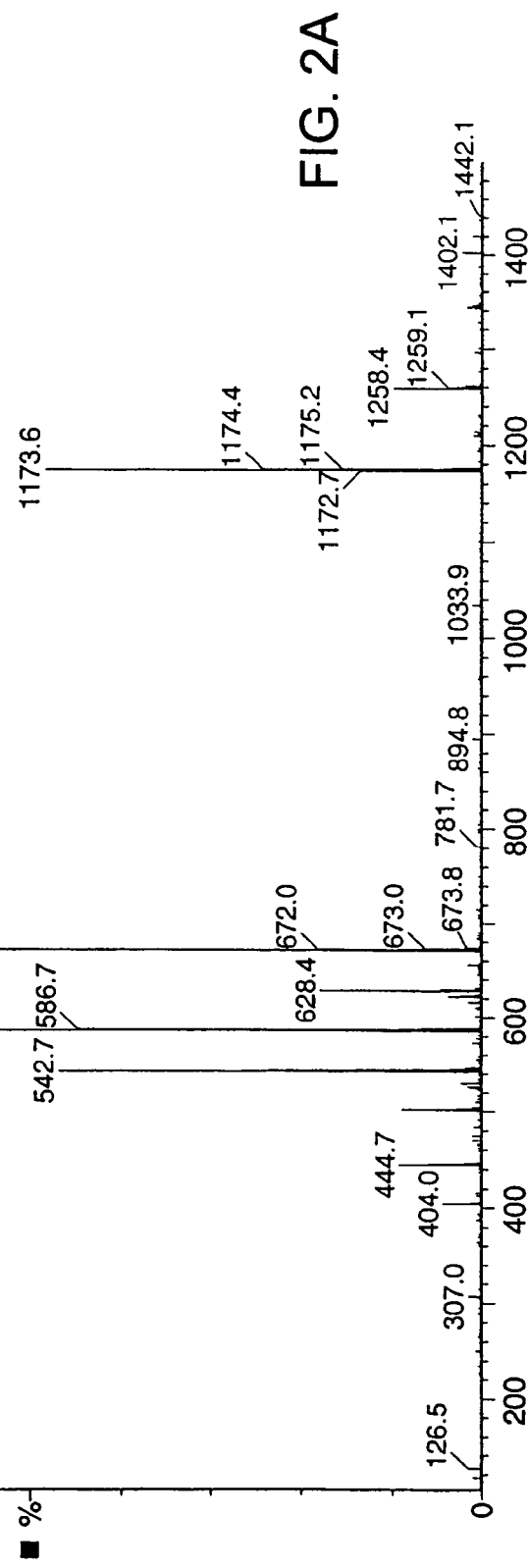
FIG. 2 depicts mass spectra from a LCMS analysis of the Dimethylamino Acetate Co-Salt of the Hydroquinone of 17-AAG prepared according to the procedure described in Example 3.
Figure 2B:
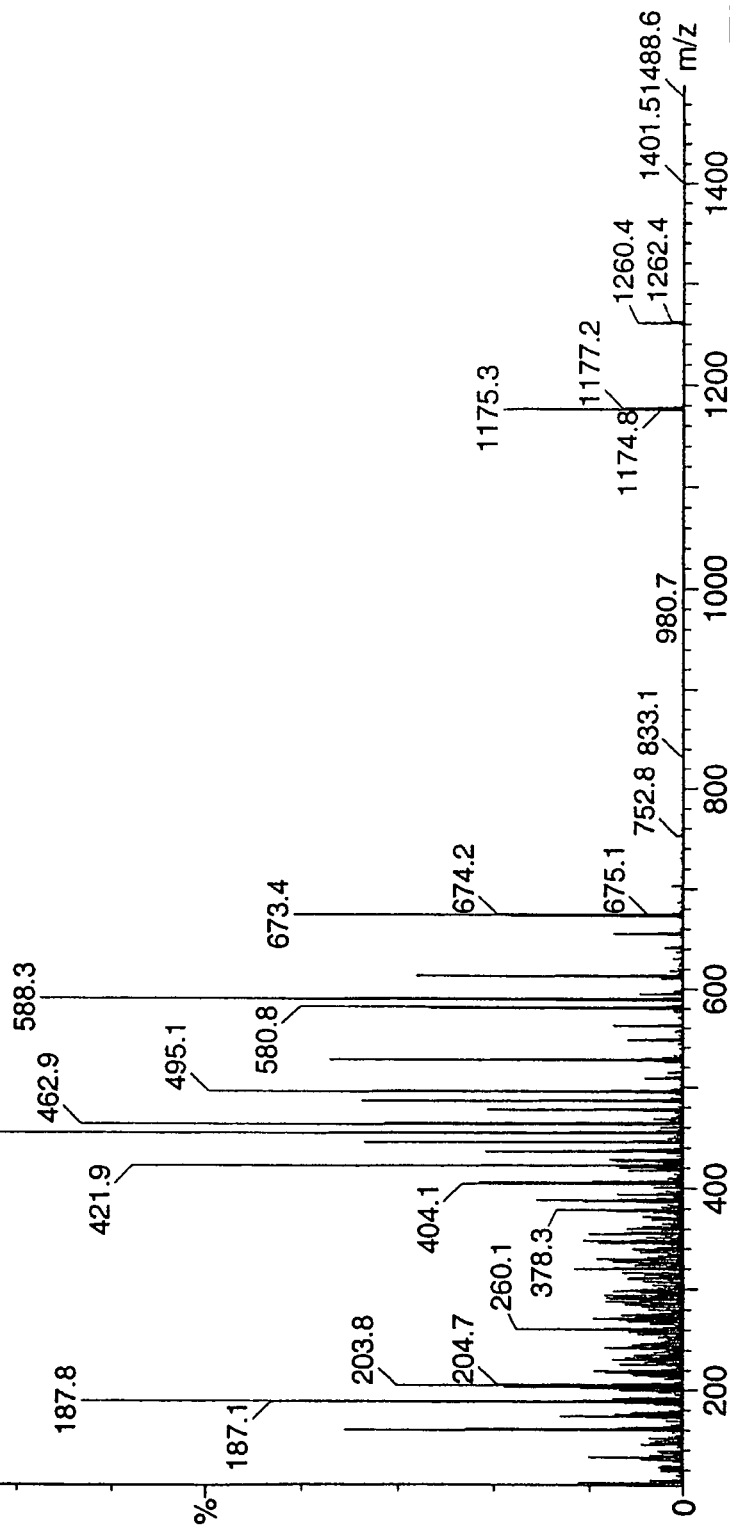
Figure 3:
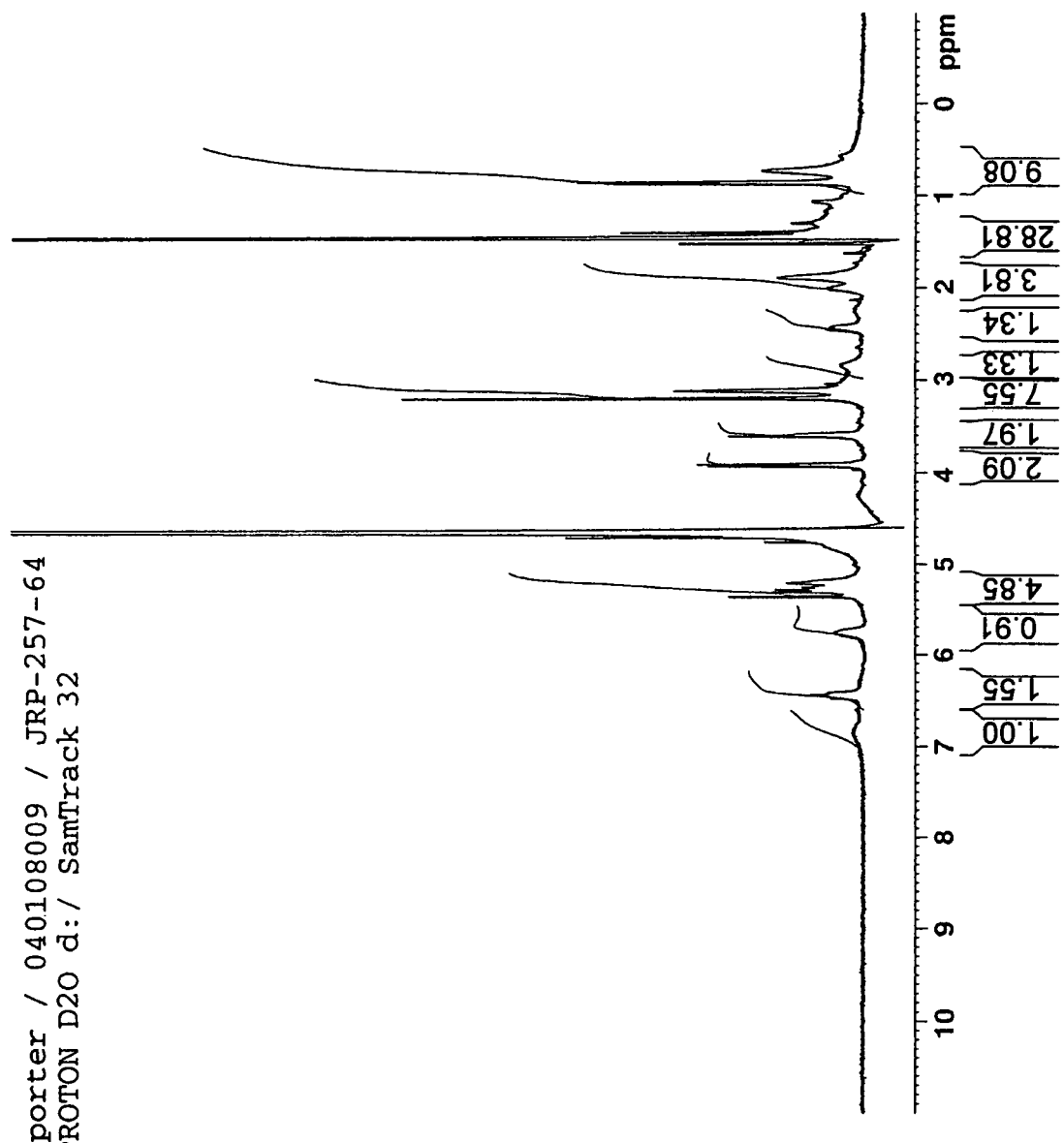
FIG. 3 depicts a $^1$H NMR spectrum of the α-Aminoisobutyrate Co-Salt of the Hydroquinone of 17-AAG prepared according to the procedure described in Example 4.
Figure 4:
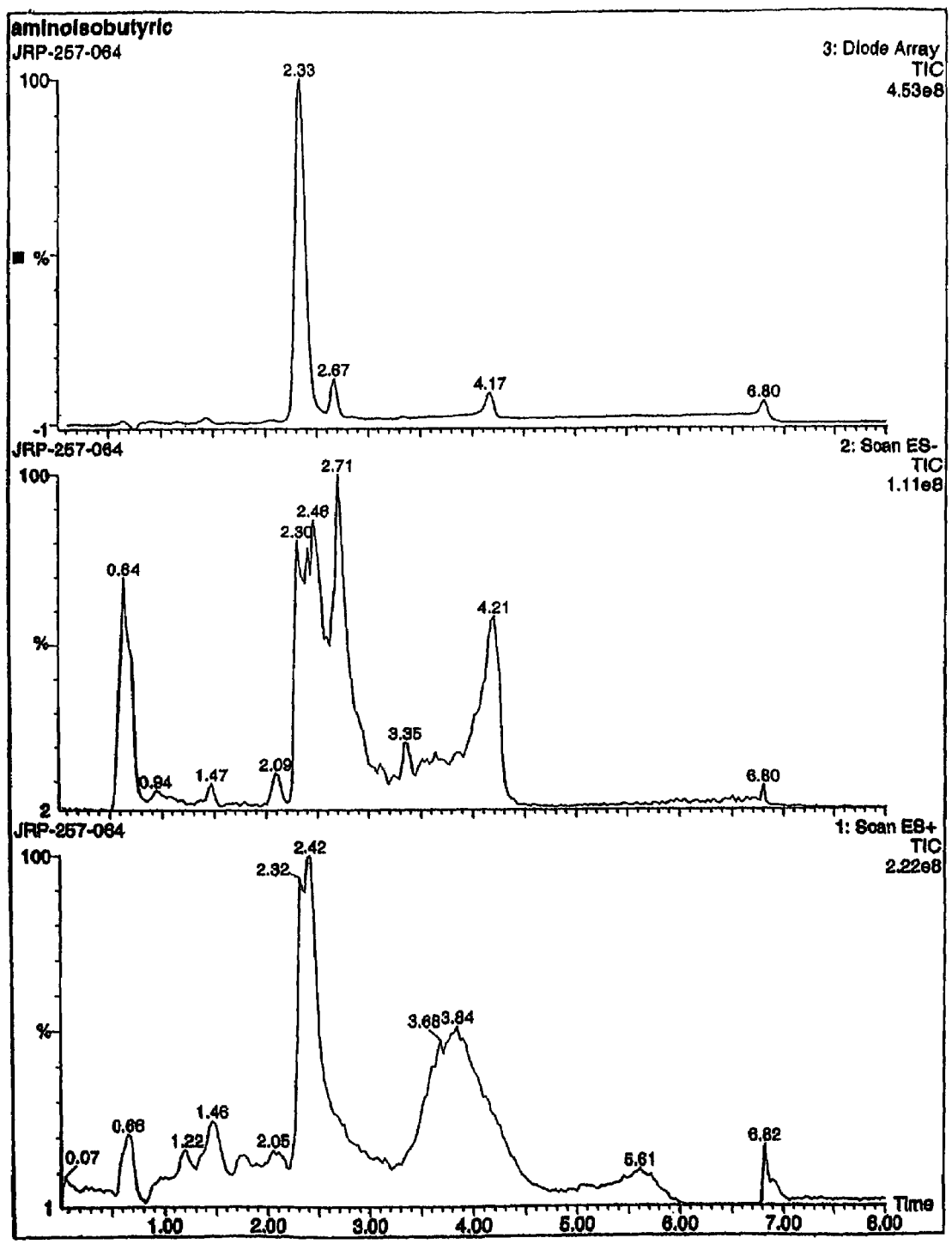
FIG. 4 depicts chromatograms from a LCMS analysis of the α-Aminoisobutyrate Co-Salt of the Hydroquinone of 17-AAG prepared according to the procedure described in Example 4.
Figures 5, 5A:
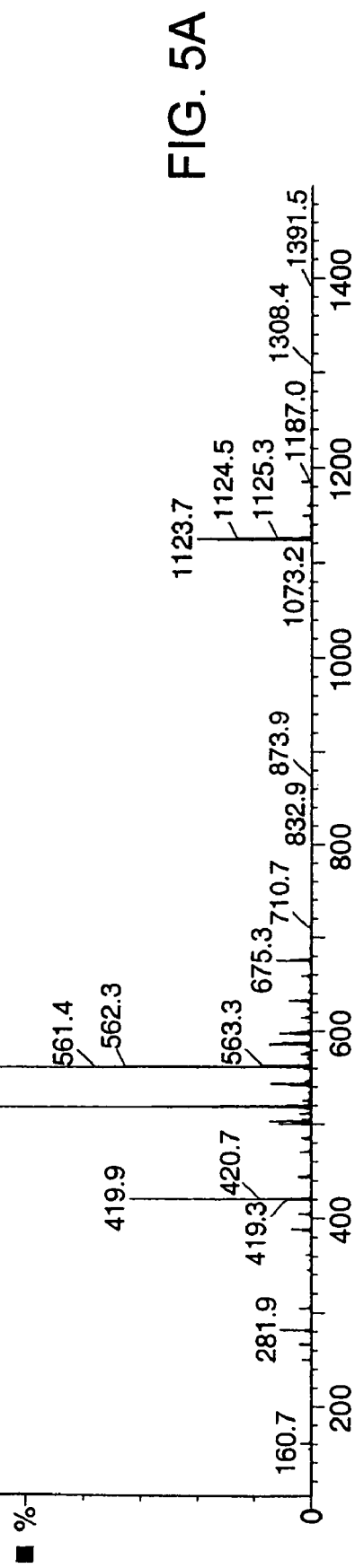
FIG. 5 depicts a mass spectrum from a LCMS analysis of the α-Aminoisobutyrate Co-Salt of the Hydroquinone of 17-AAG prepared according to the procedure described in Example 4.
Figure 5B:
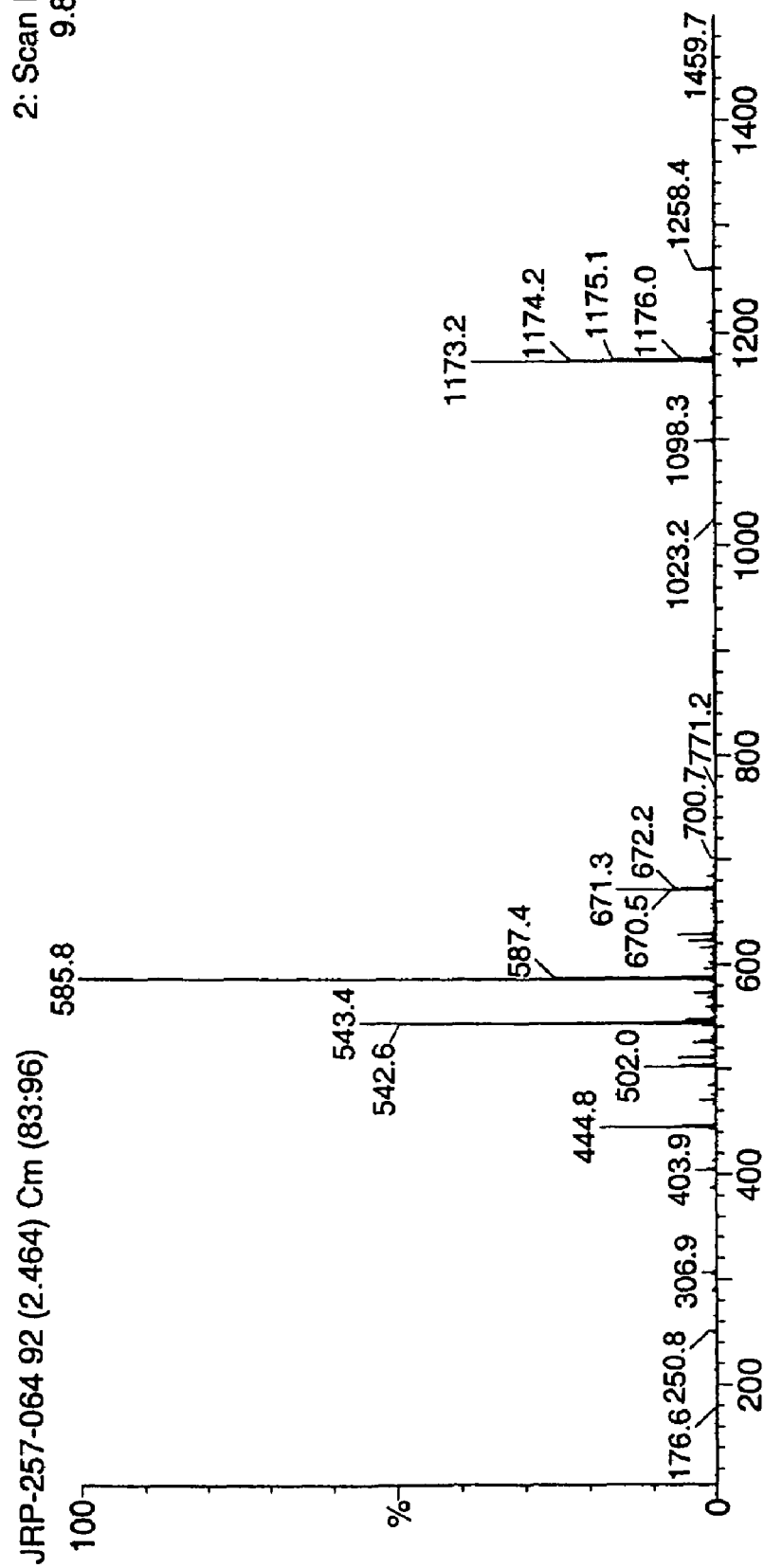
Figure 5C:
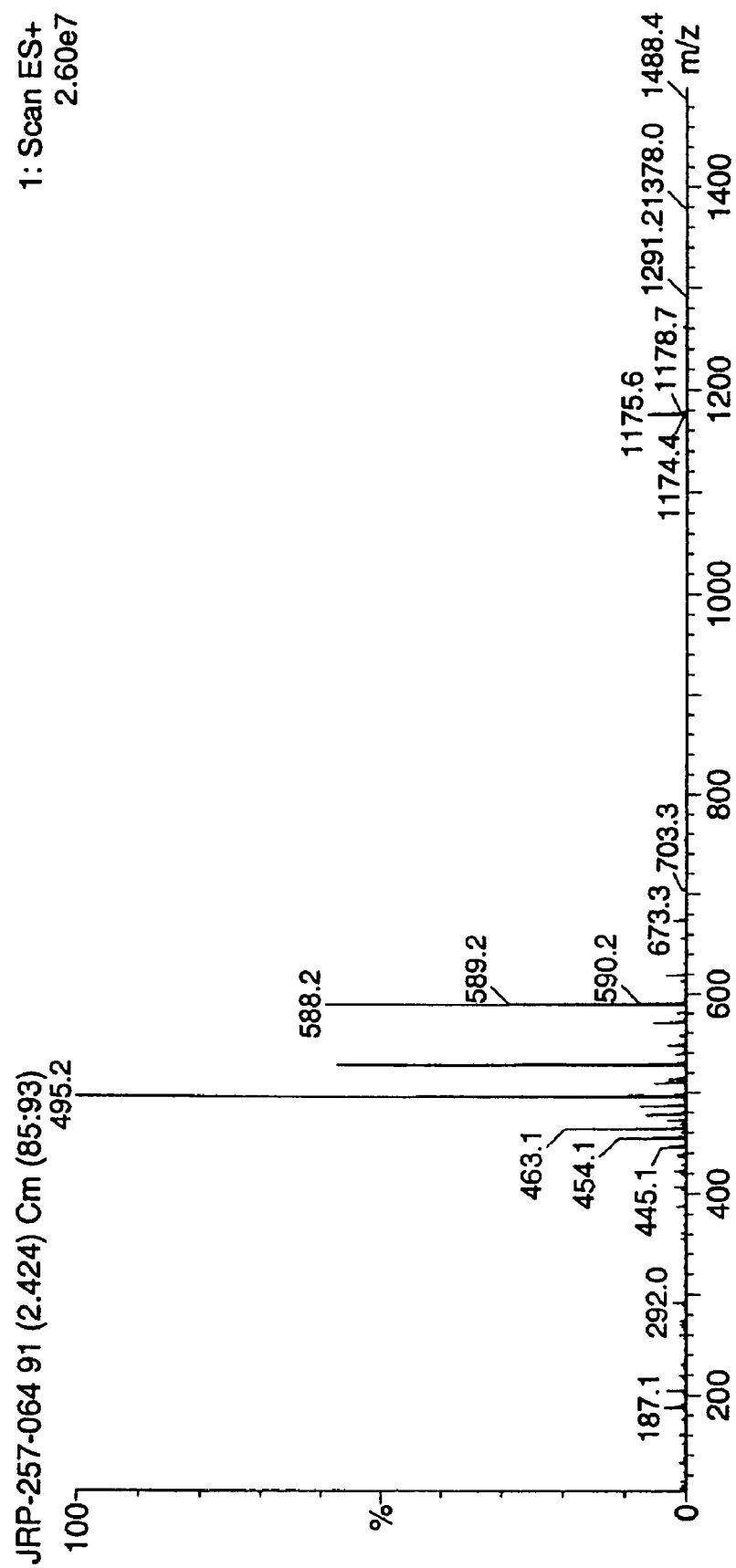
Figure 6:
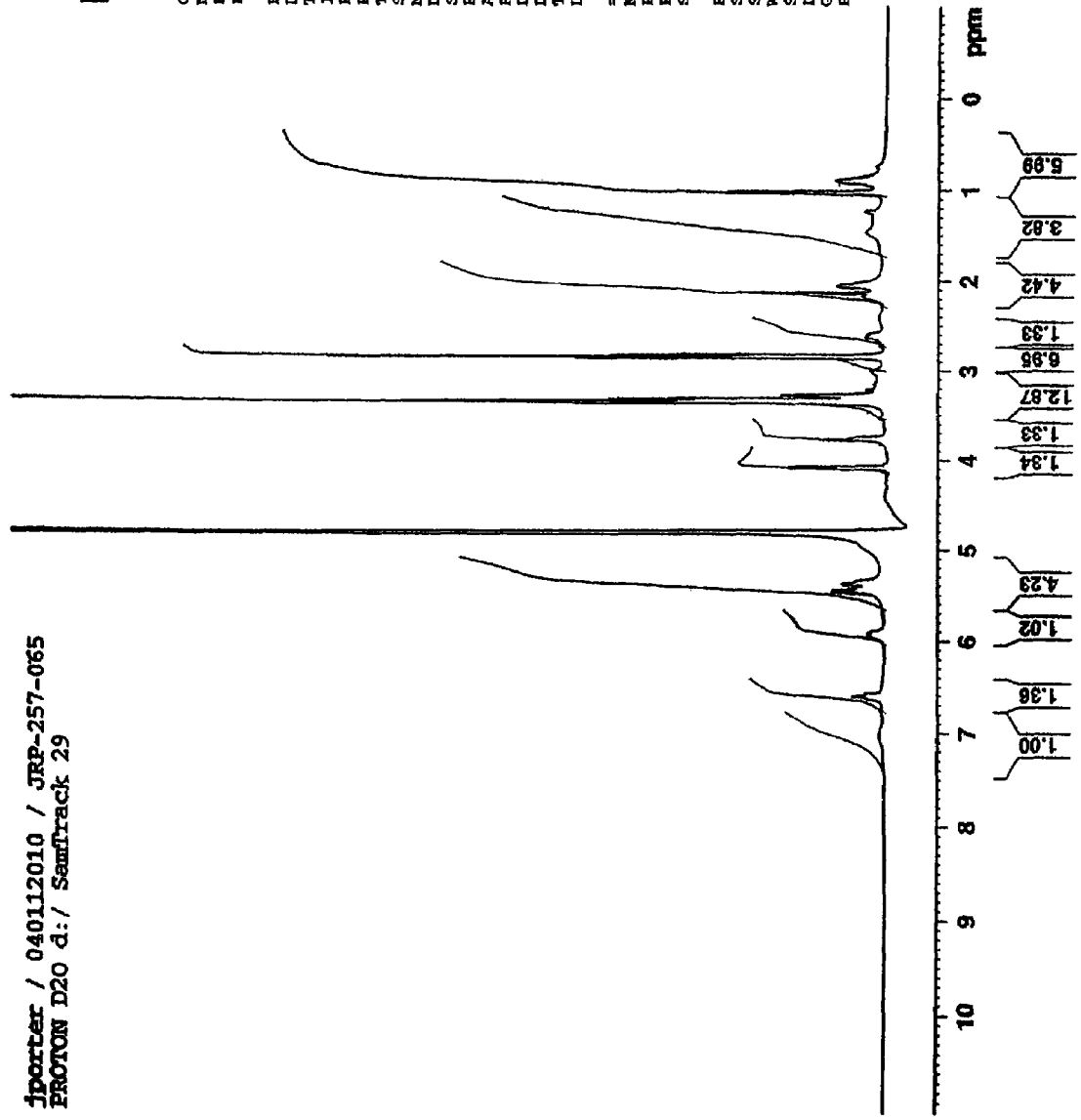
FIG. 6 depicts a $^1$H NMR spectrum of the β-Alanine Co-Salt of the Hydroquinone of 17-AAG prepared according to the procedure described in Example 5.
Figure 7B:
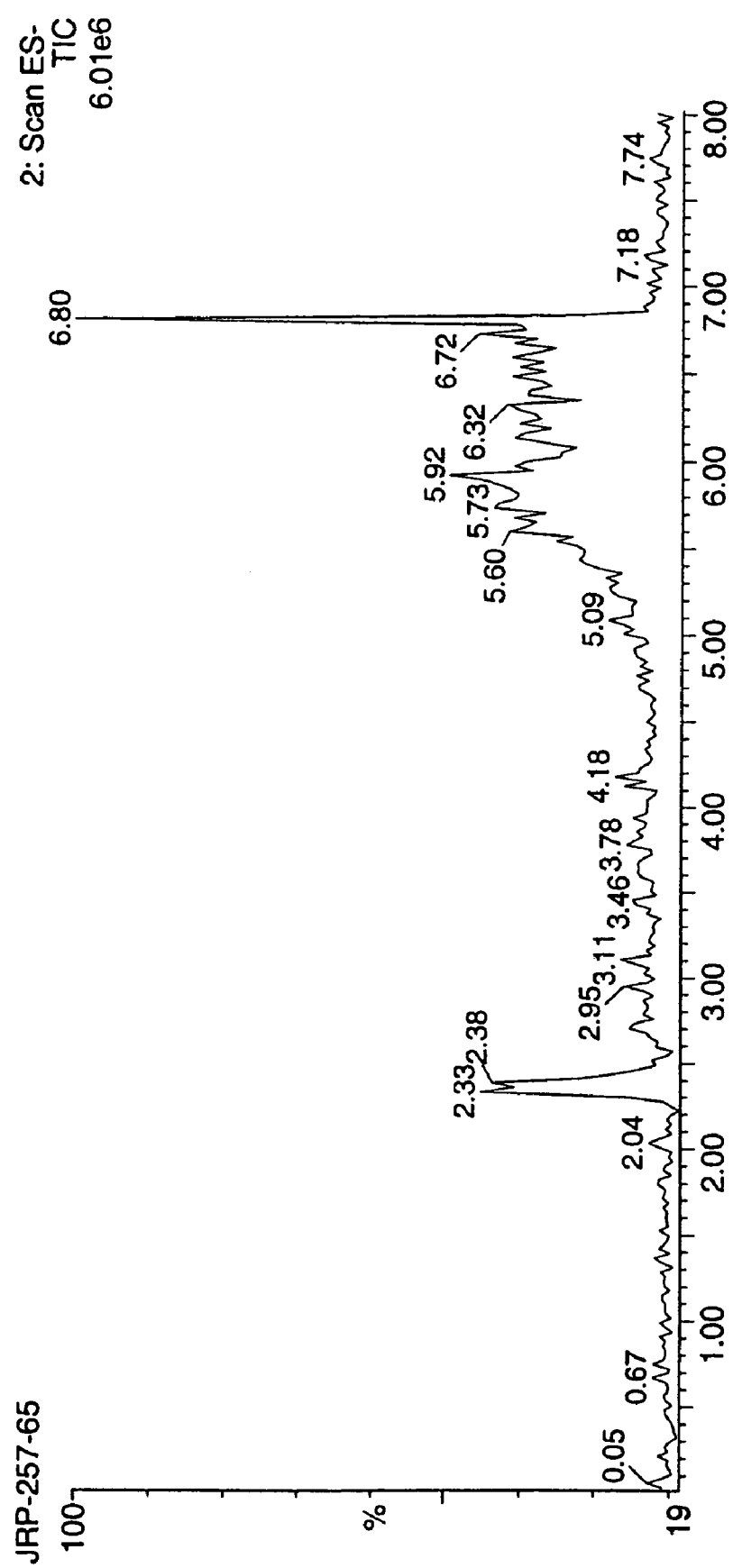
FIG. 7 depicts chromatograms from a LCMS analysis of the β-Alanine Co-Salt of the Hydroquinone of 17-AAG prepared according to the procedure described in Example 5.
Figure 7C:
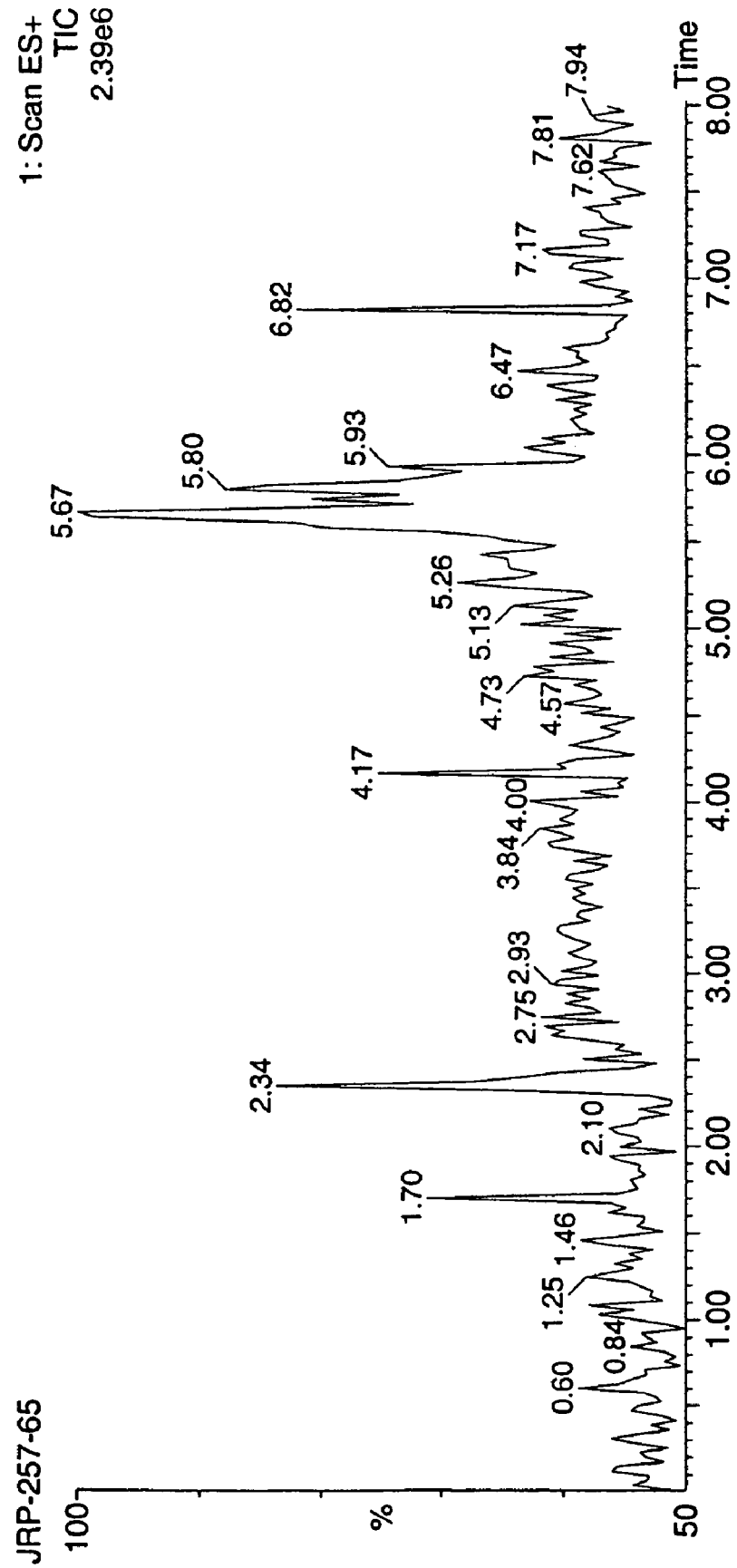
Figure 8:
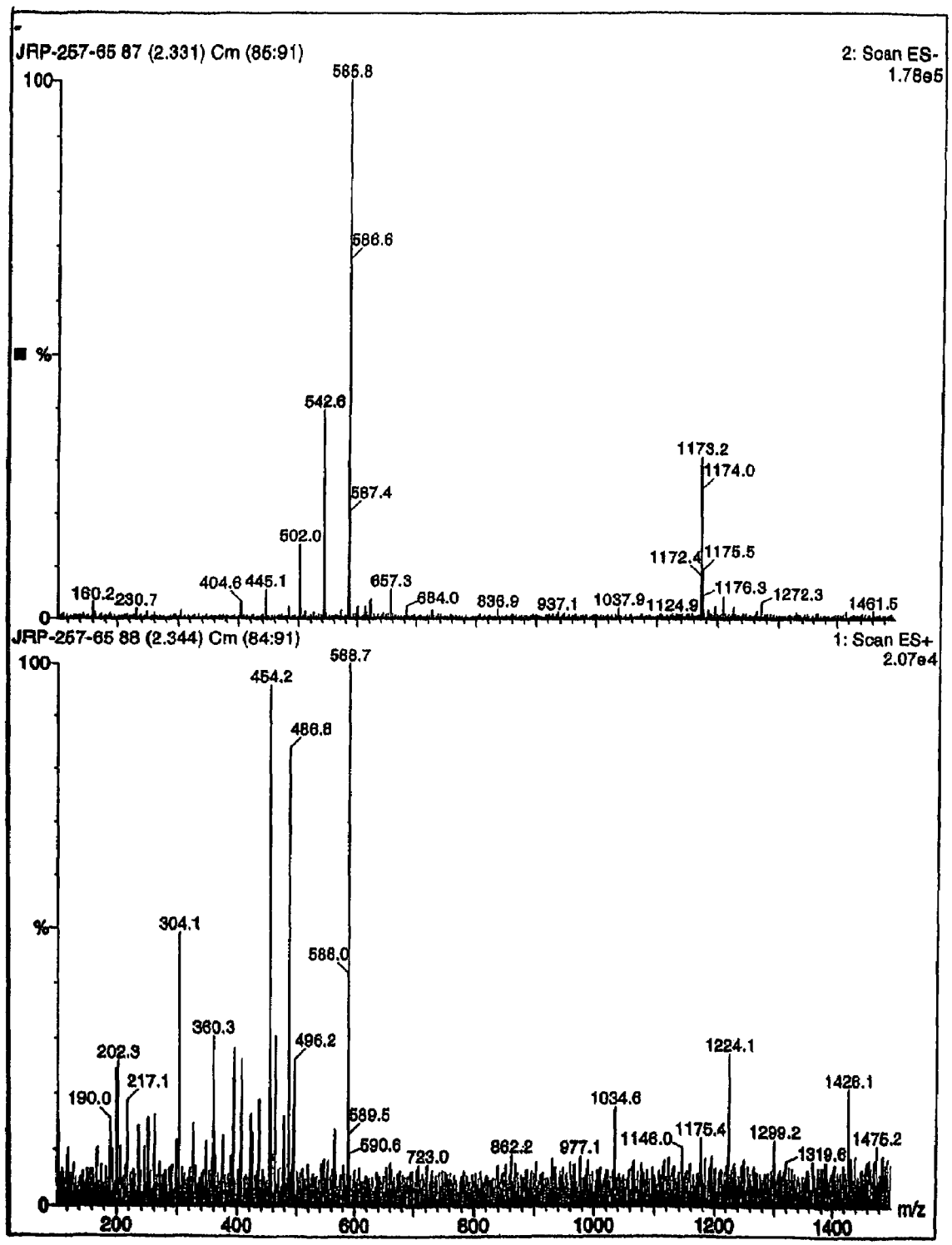
FIG. 8 depicts mass spectra from a LCMS analysis of the β-Alanine Co-Salt of the Hydroquinone of 17-AAG prepared according to the procedure described in Example 5.
Figure 9:
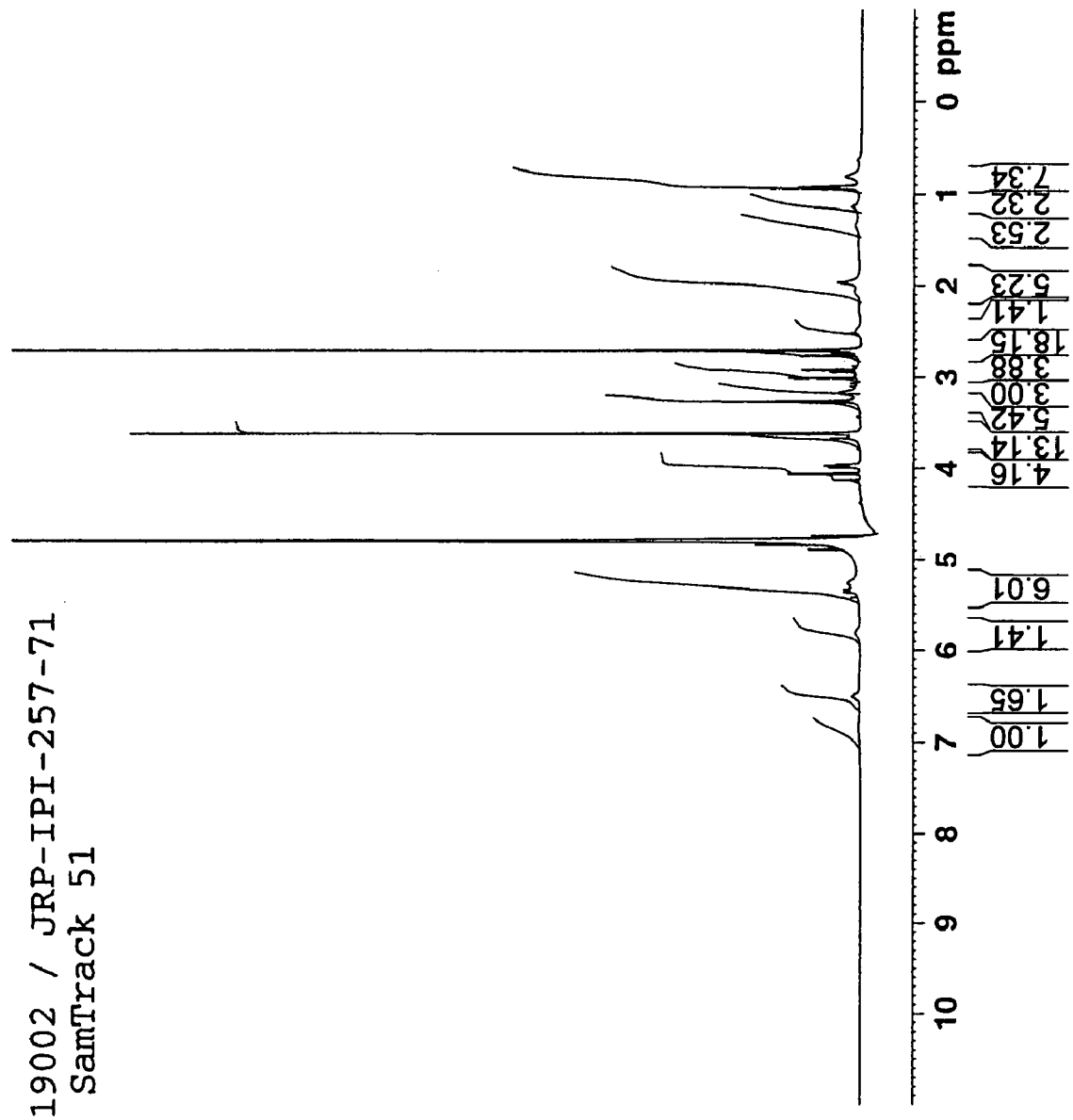
FIG. 9 depicts a $^1$H NMR spectrum of the N-Methyl Glycine Co-Salt of the Hydroquinone of 17-AAG prepared according to the procedure described in Example 6.
Figure 10:
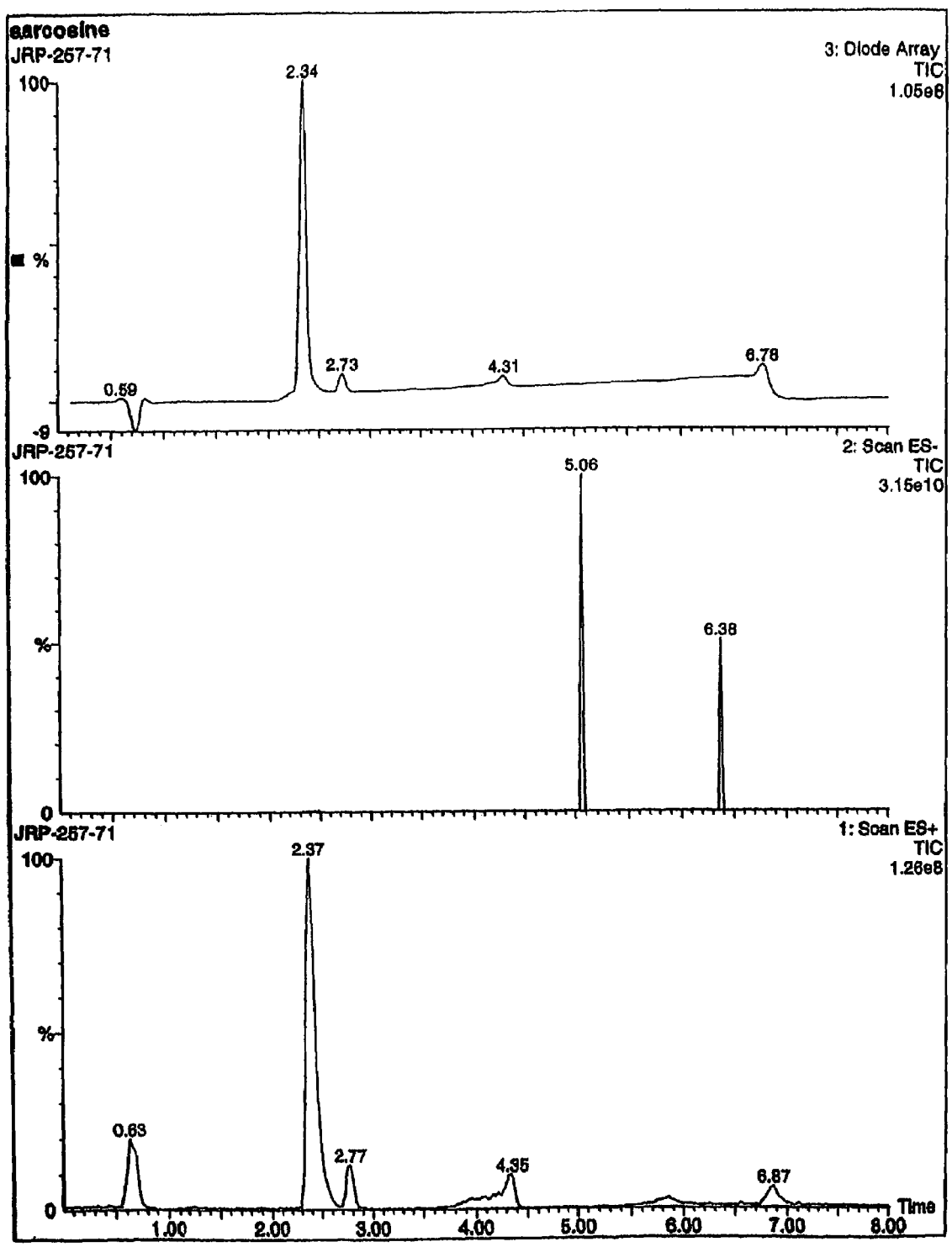
FIG. 10 depicts chromatograms from a LCMS analysis of the N-Methyl Glycine Co-Salt of the Hydroquinone of 17-AAG prepared according to the procedure described in Example 6.
Figure 11:
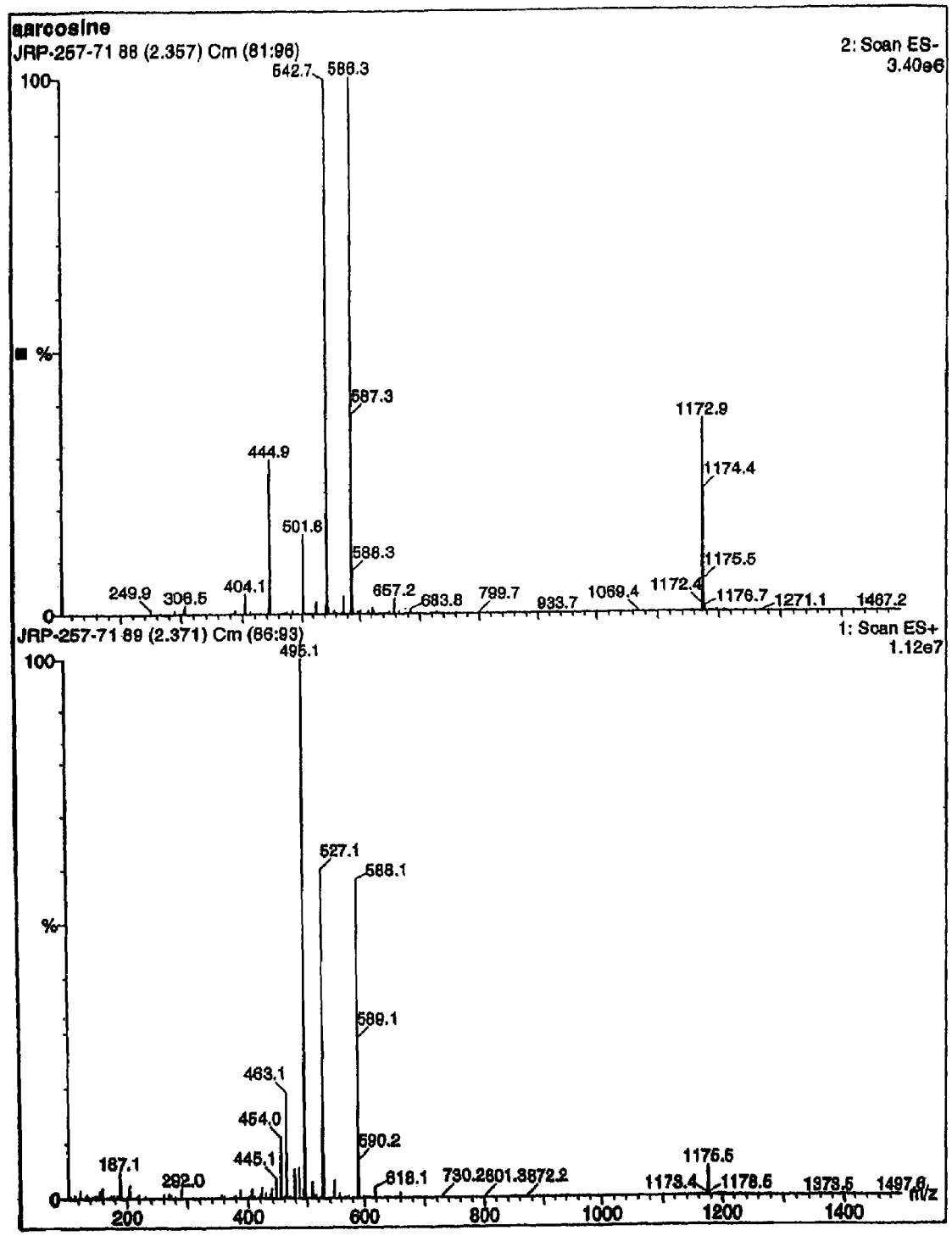
FIG. 11 depicts mass spectra from a LCMS analysis of the N-Methyl Glycine Co-Salt of the Hydroquinone of 17-AAG prepared according to the procedure described in Example 6.
Figure 12:
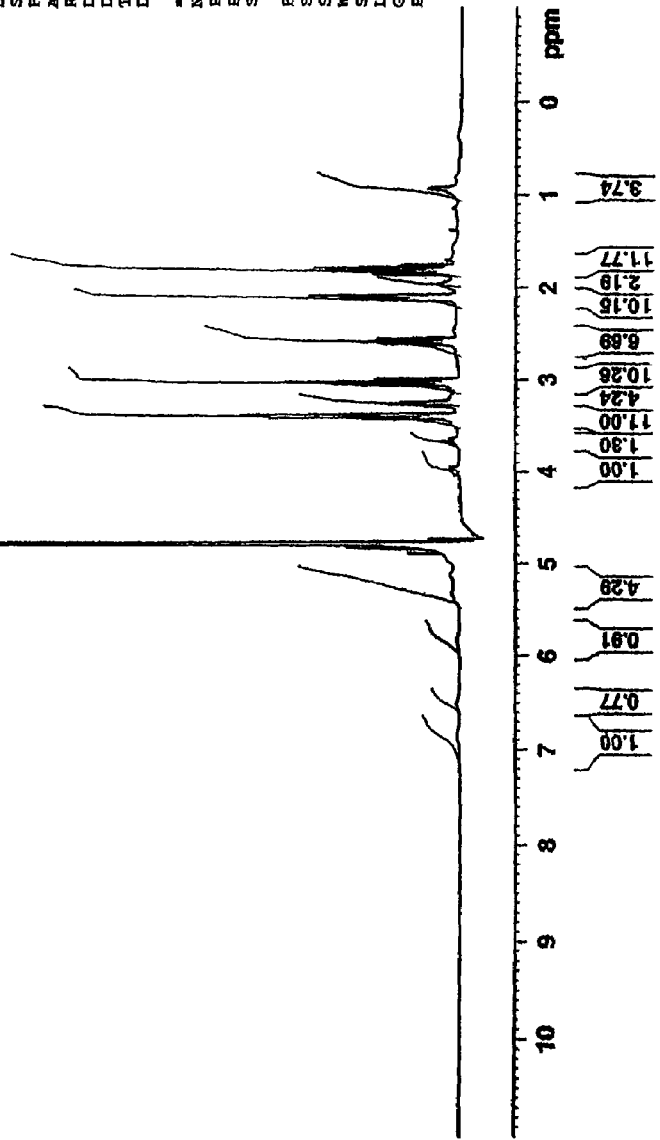
FIG. 12 depicts a $^1$H NMR spectrum of the Piperidine Carboxylate Co-Salt of the Hydroquinone of 17-AAG prepared according to the procedure described in Example 7.
Figure 13:
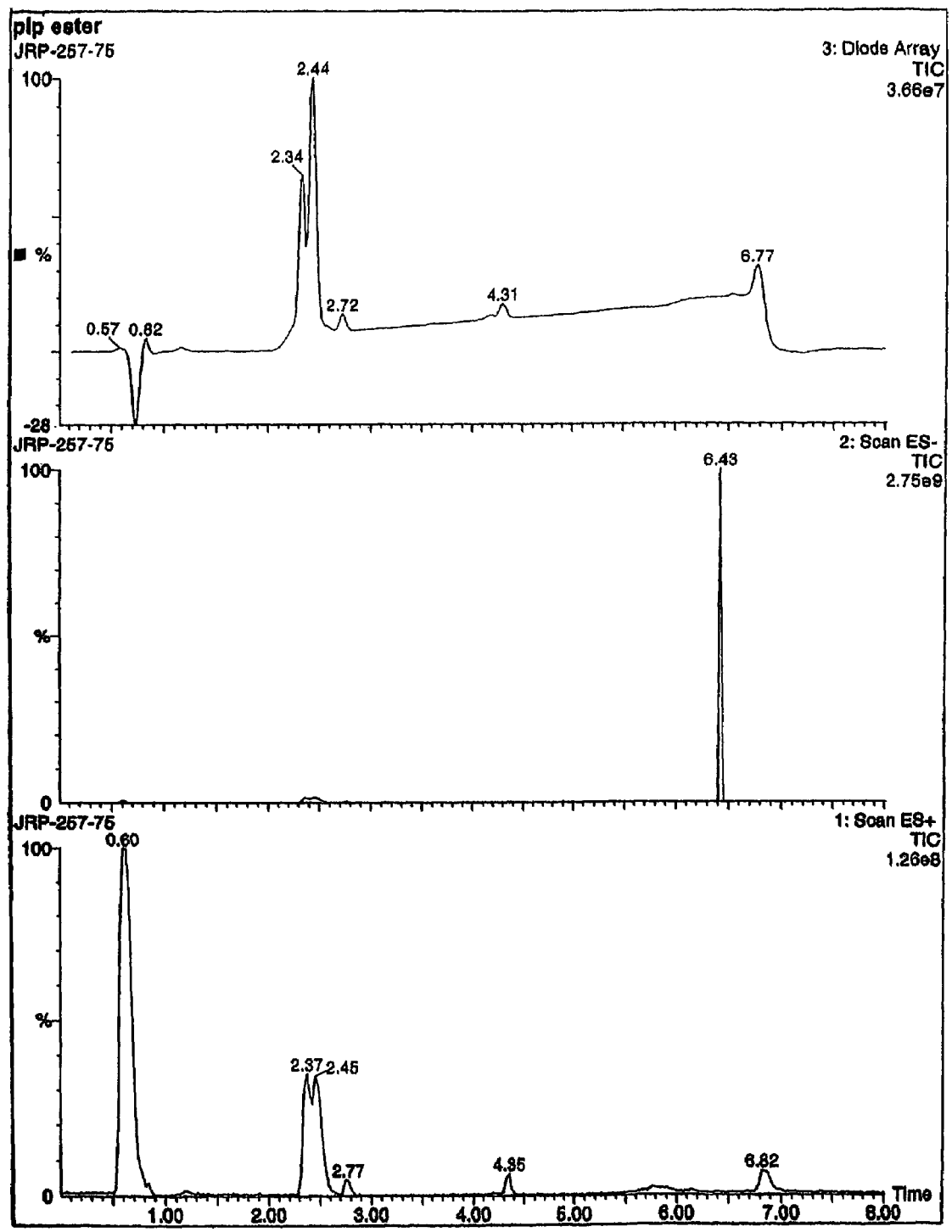
FIG. 13 depicts chromatograms from a LCMS analysis of the Piperidine Carboxylate Co-Salt of the Hydroquinone of 17-AAG prepared according to the procedure described in Example 7.
Figure 14:
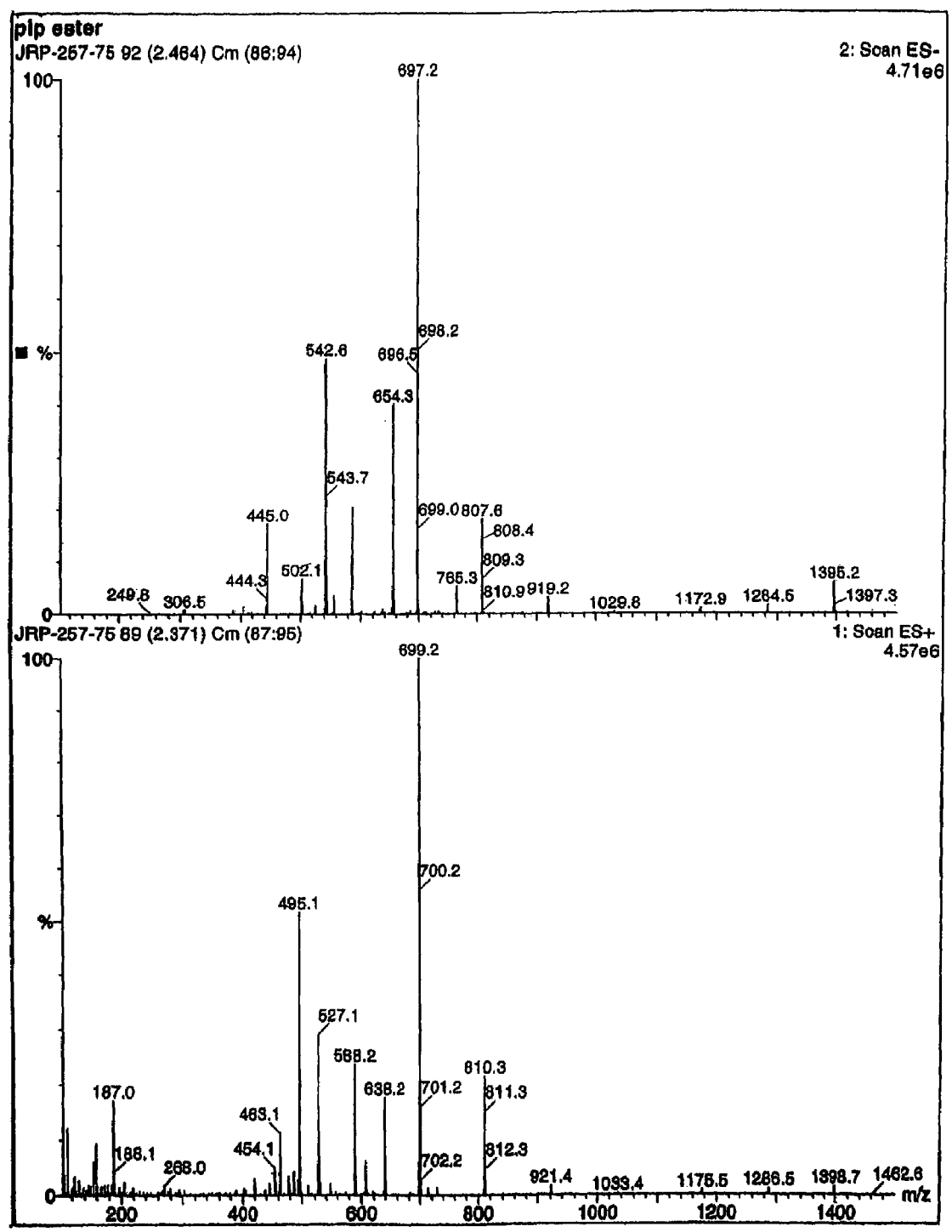
FIG. 14 depicts mass spectra from a LCMS analysis of the Piperidine Carboxylate Co-Salt of the Hydroquinone of 17-AAG prepared according to the procedure described in Example 7.
Figure 15:
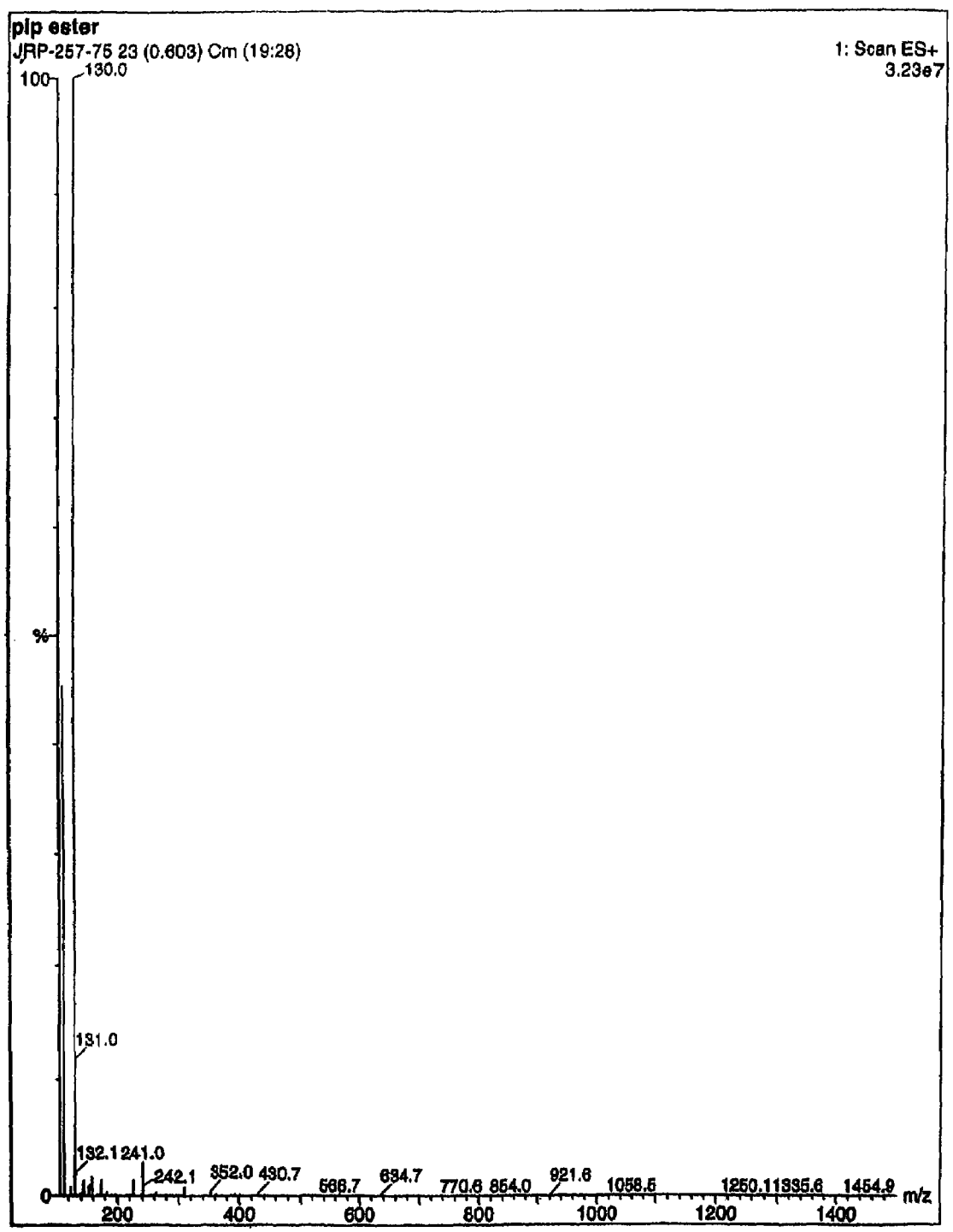
FIG. 15 depicts mass spectra from a LCMS analysis of the Piperidine Carboxylate Co-Salt of the Hydroquinone of 17-AAG prepared according to the procedure described in Example 7.
Figure 16:
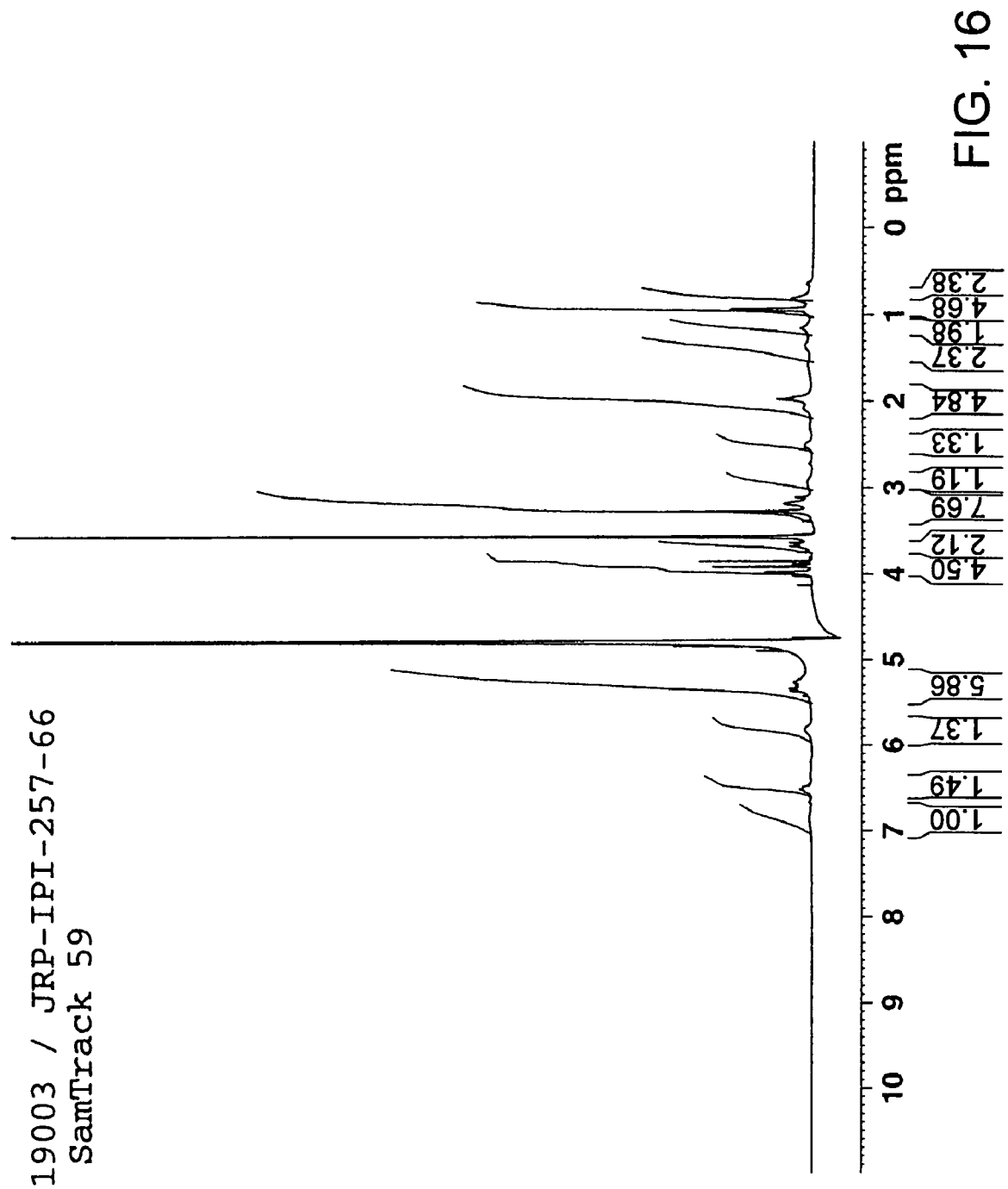
FIG. 16 depicts a $^1$H NMR spectrum of the Glycine Co-Salt of the Hydroquinone of 17-AAG prepared according to the procedure described in Example 8.
Figure 17B:
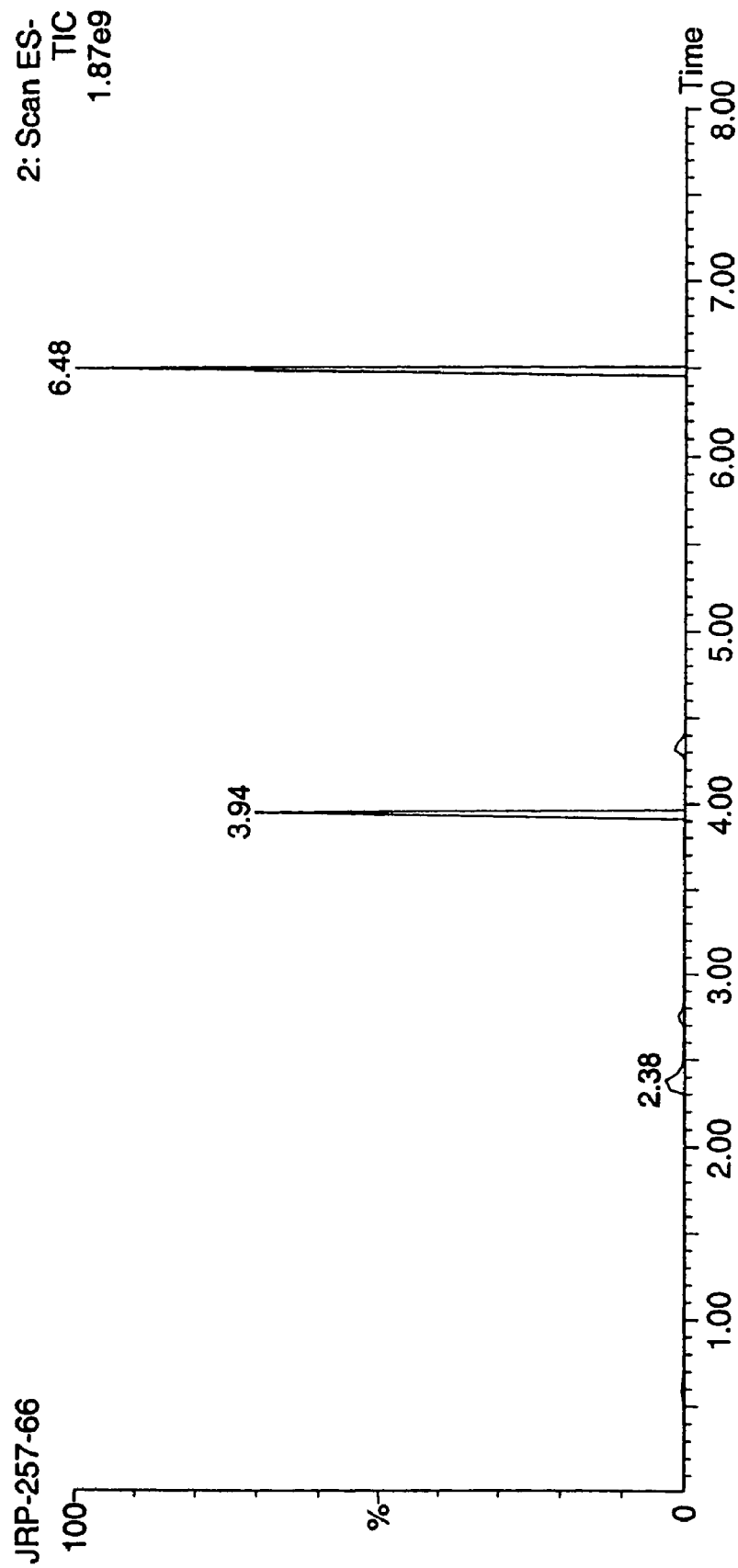
FIG. 17 depicts chromatograms from a LCMS analysis of the Glycine Co-Salt of the Hydroquinone of 17-AAG prepared according to the procedure described in Example 8.
Figure 17C:
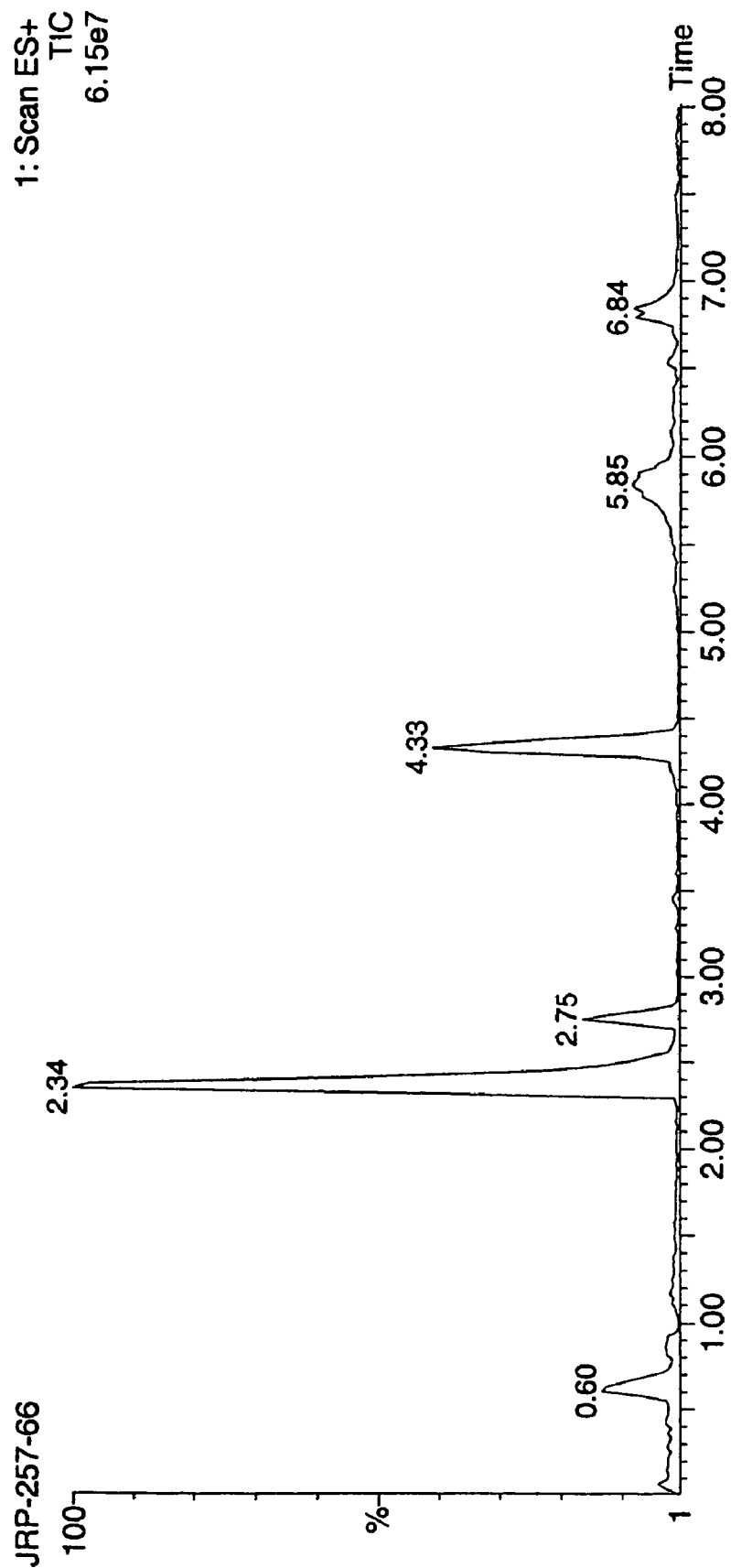
Figure 18:
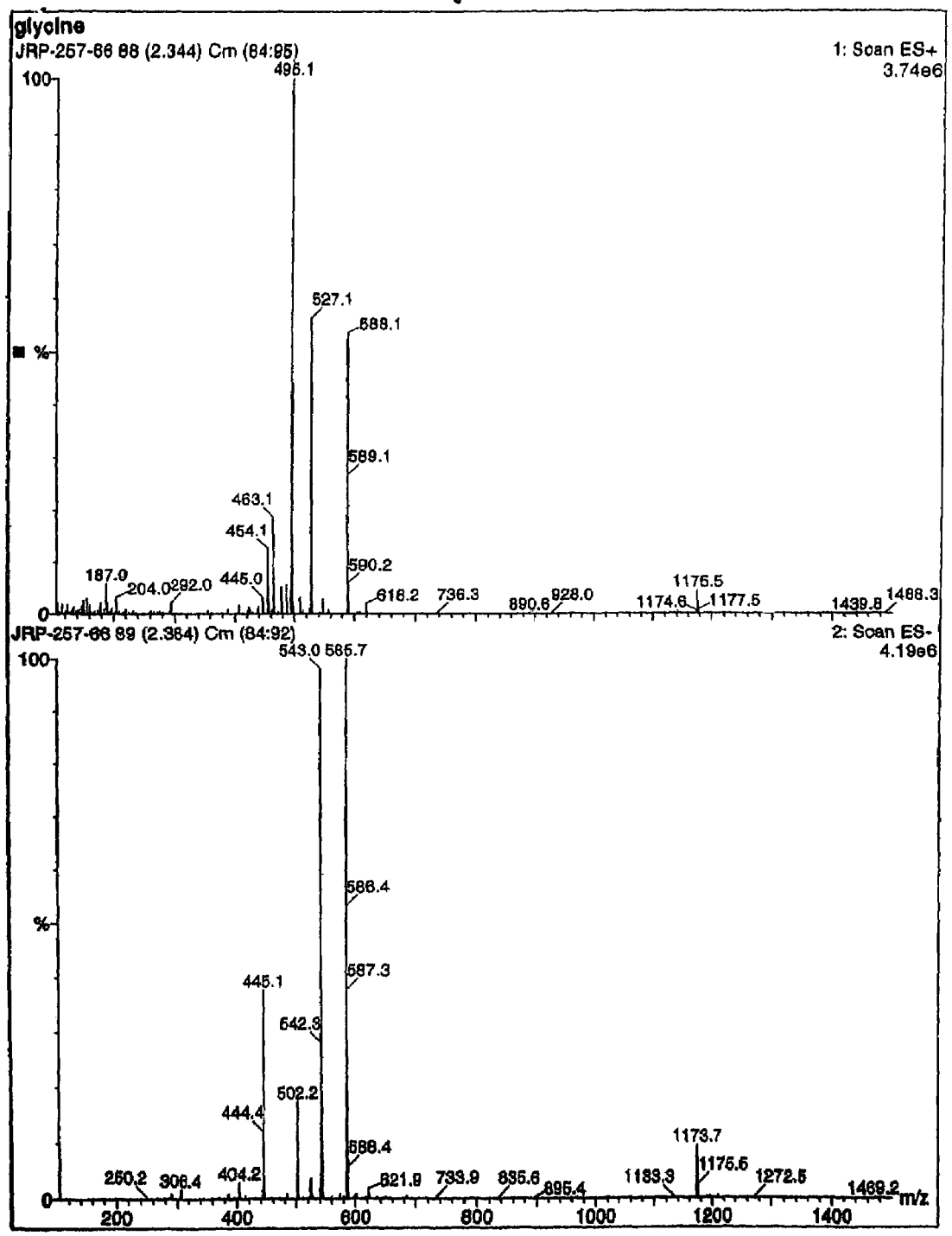
FIG. 18 depicts mass spectra from a LCMS analysis of the Glycine Co-Salt of the Hydroquinone of 17-AAG prepared according to the procedure described in Example 8.
Figure 19:
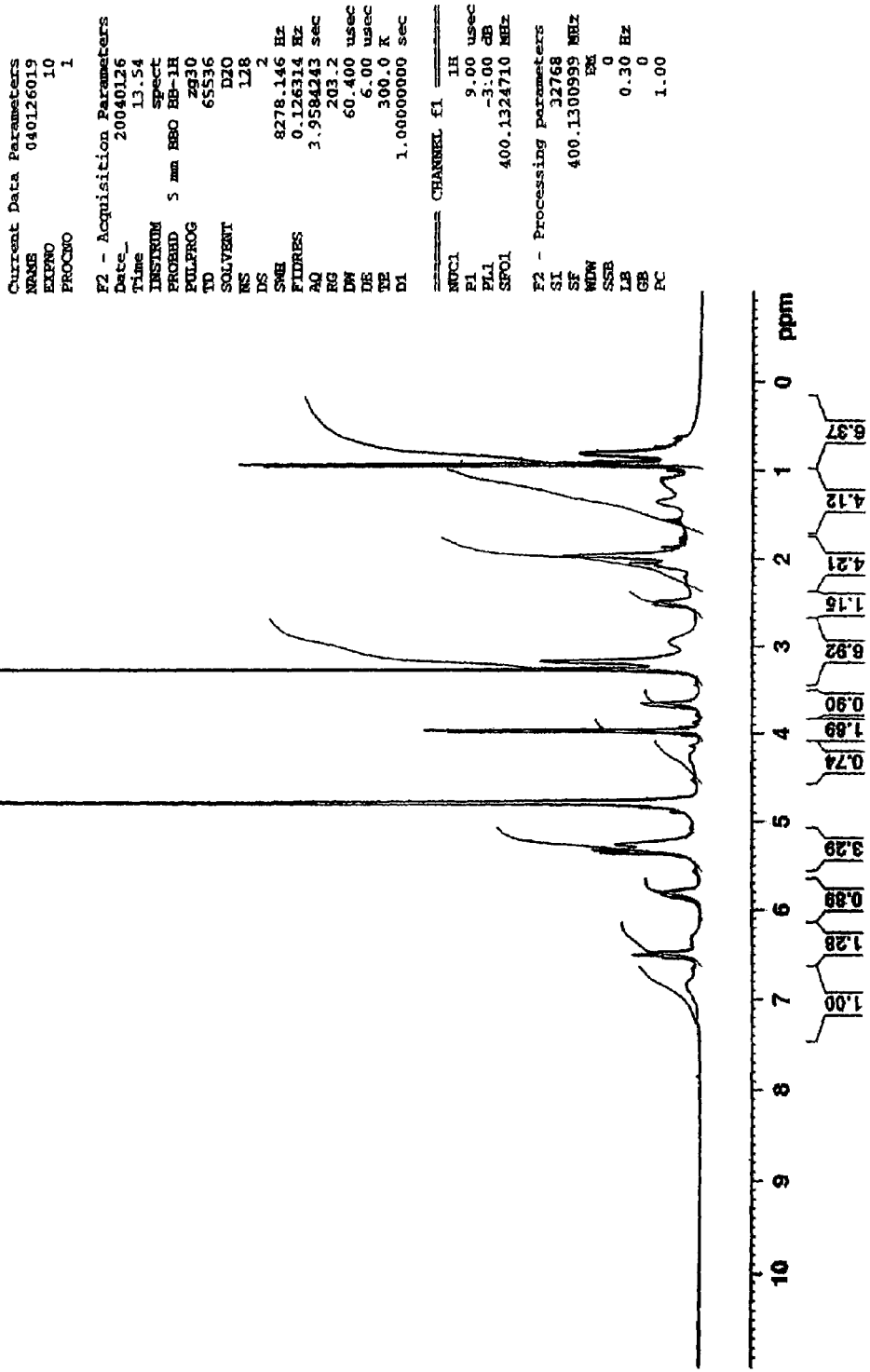
FIG. 19 depicts a $^1$H NMR spectrum of the 2-Amino-2-ethyl-butyrate Co-Salt of the Hydroquinone of 17-AAG prepared according to the procedure described in Example 9.
Figure 20:
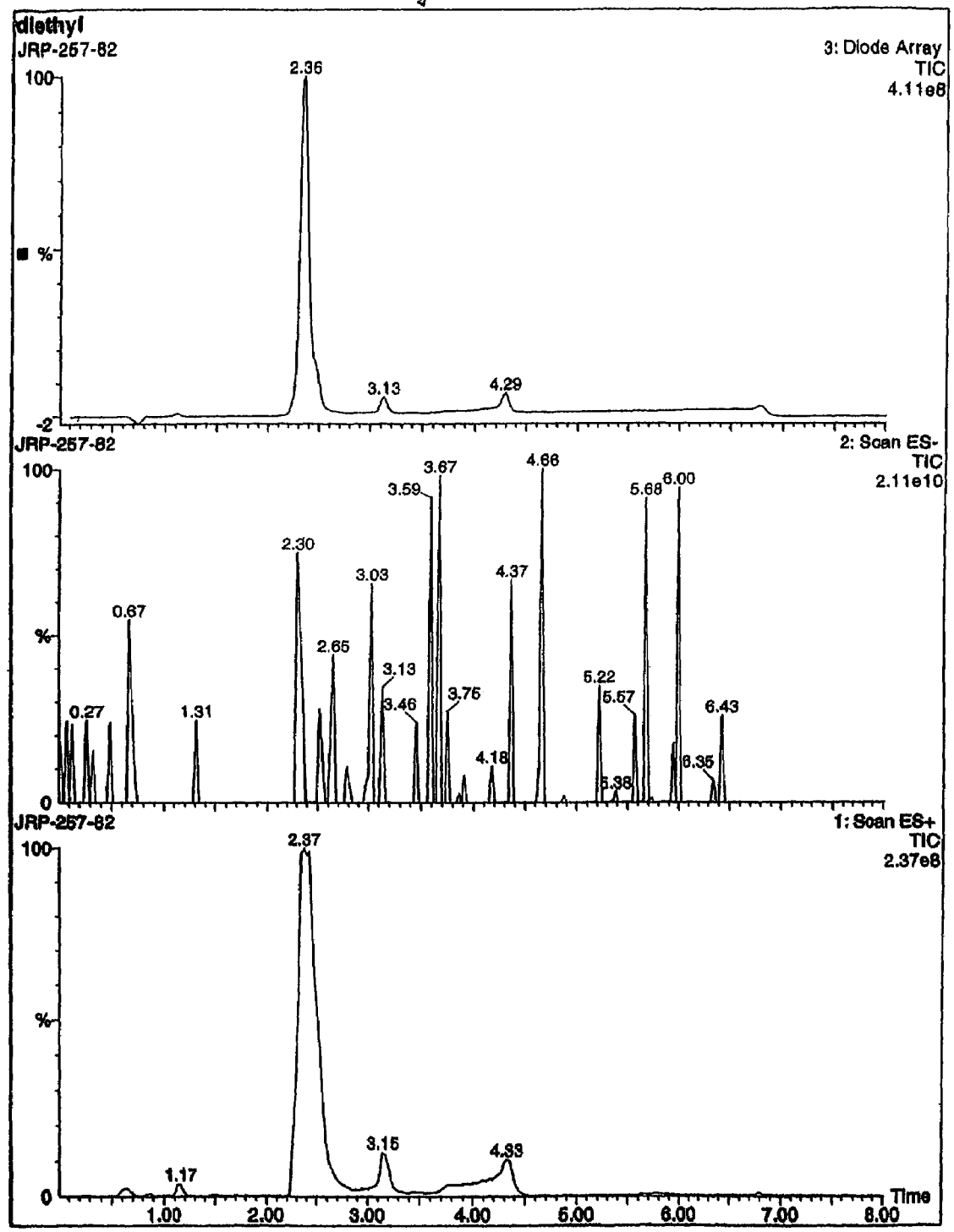
FIG. 20 depicts chromatograms from a LCMS analysis of the 2-Amino-2-ethyl-butyrate Co-Salt of the Hydroquinone of 17-AAG prepared according to the procedure described in Example 9.
Figure 21:
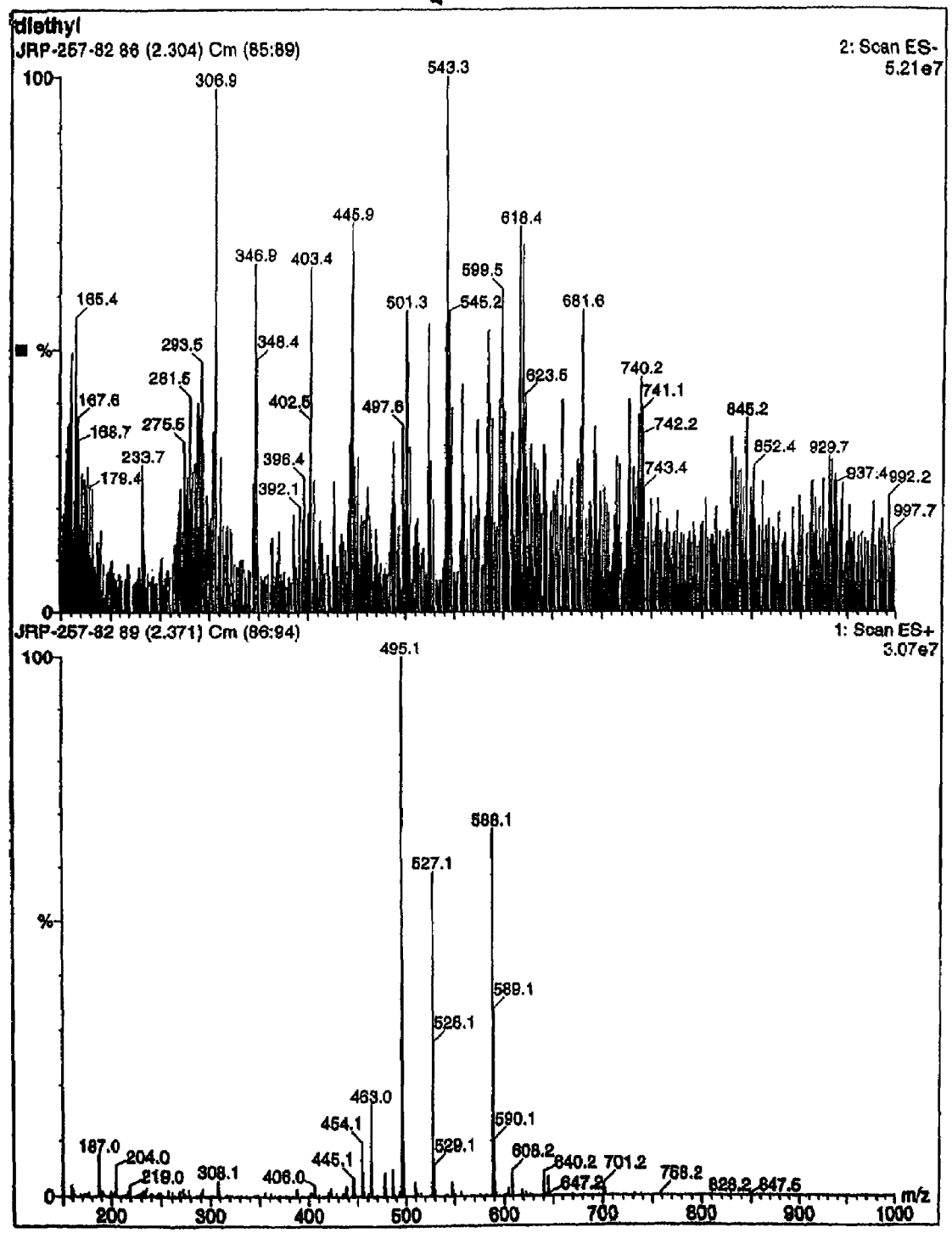
FIG. 21 depicts mass spectra from a LCMS analysis of the 2-Amino-2-ethyl-butyrate Co-Salt of the Hydroquinone of 17-AAG prepared according to the procedure described in Example 9.
Figure 22:
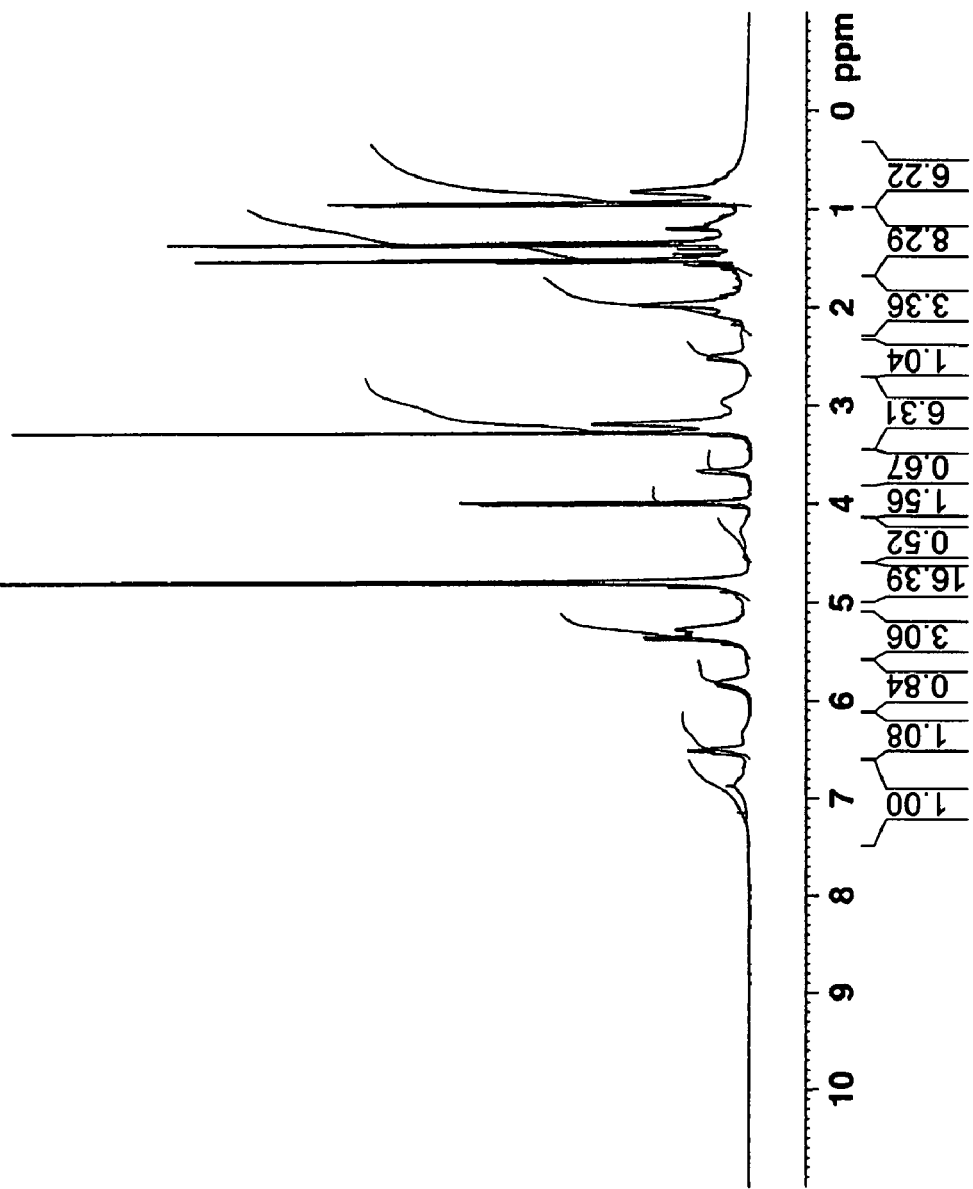
FIG. 22 depicts a $^1$H NMR spectrum of the 1-Amino-Cyclopropanecarboxylate Co-Salt of the Hydroquinone of 17-AAG prepared according to the procedure described in Example 10.
Figure 23:
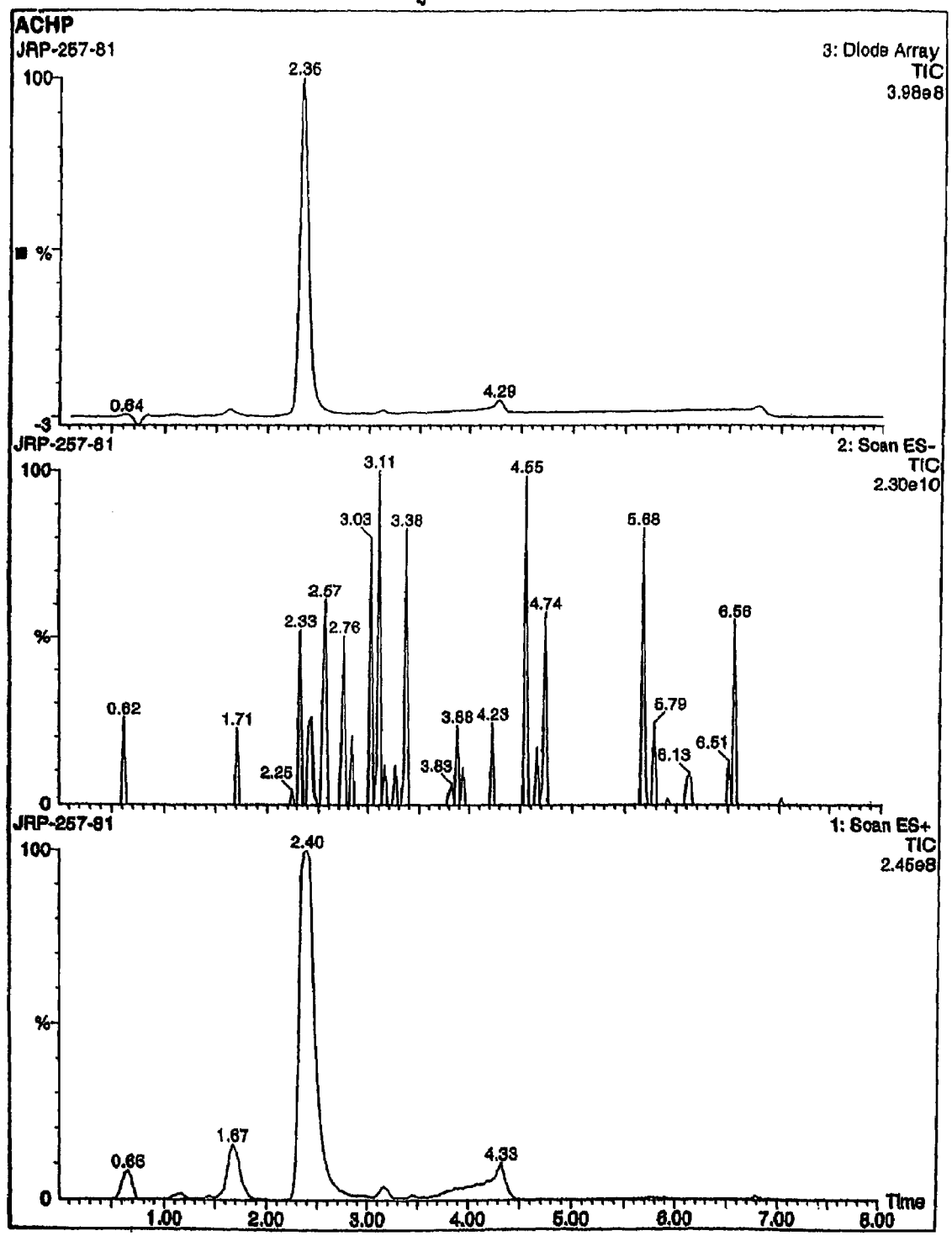
FIG. 23 depicts chromatograms from a LCMS analysis of the 1-Amino-Cyclopropanecarboxylate Co-Salt of the Hydroquinone of 17-AAG prepared according to the procedure described in Example 10.
Figure 24:
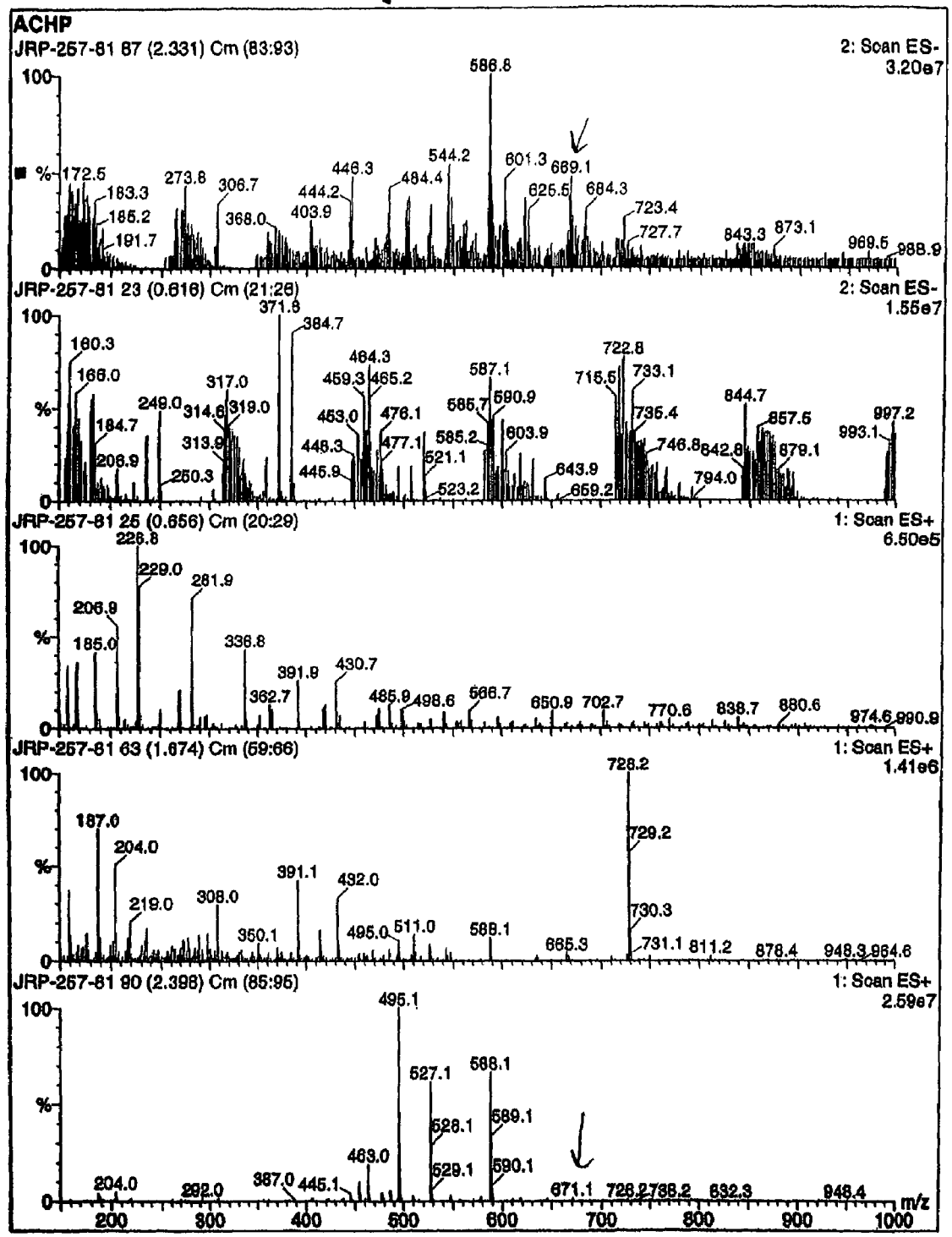
FIG. 24 depicts mass spectra from a LCMS analysis of the 1-Amino-Cyclopropanecarboxylate Co-Salt of the Hydroquinone of 17-AAG prepared according to the procedure described in Example 10.
Figure 25:
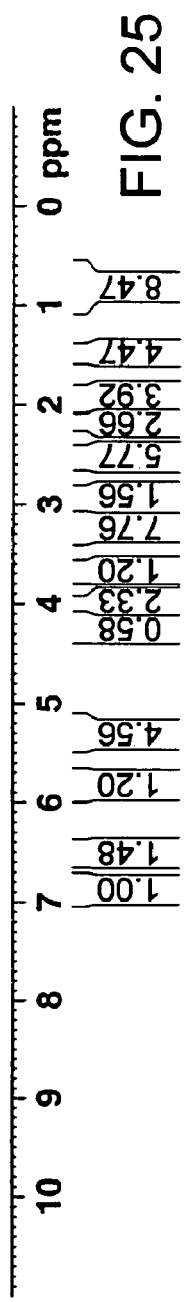
FIG. 25 depicts a $^1$H NMR spectrum of the Carboxylate Co-Salt of the Hydroquinone of 17-AAG prepared according to the procedure described in Example 11.
Figure 26:
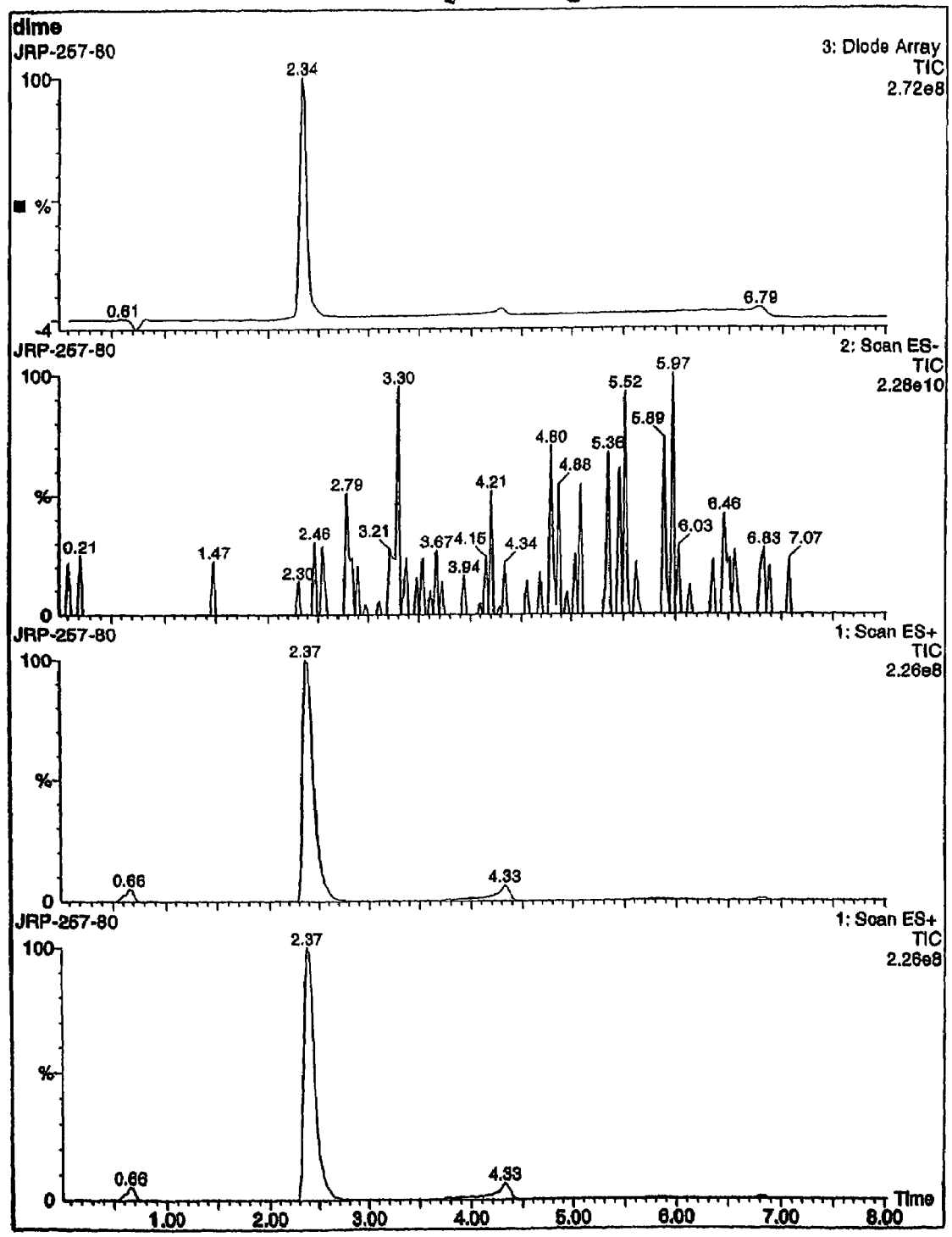
FIG. 26 depicts chromatograms from a LCMS analysis of the Carboxylate Co-Salt of the Hydroquinone of 17-AAG prepared according to the procedure described in Example 11.
Figure 27:
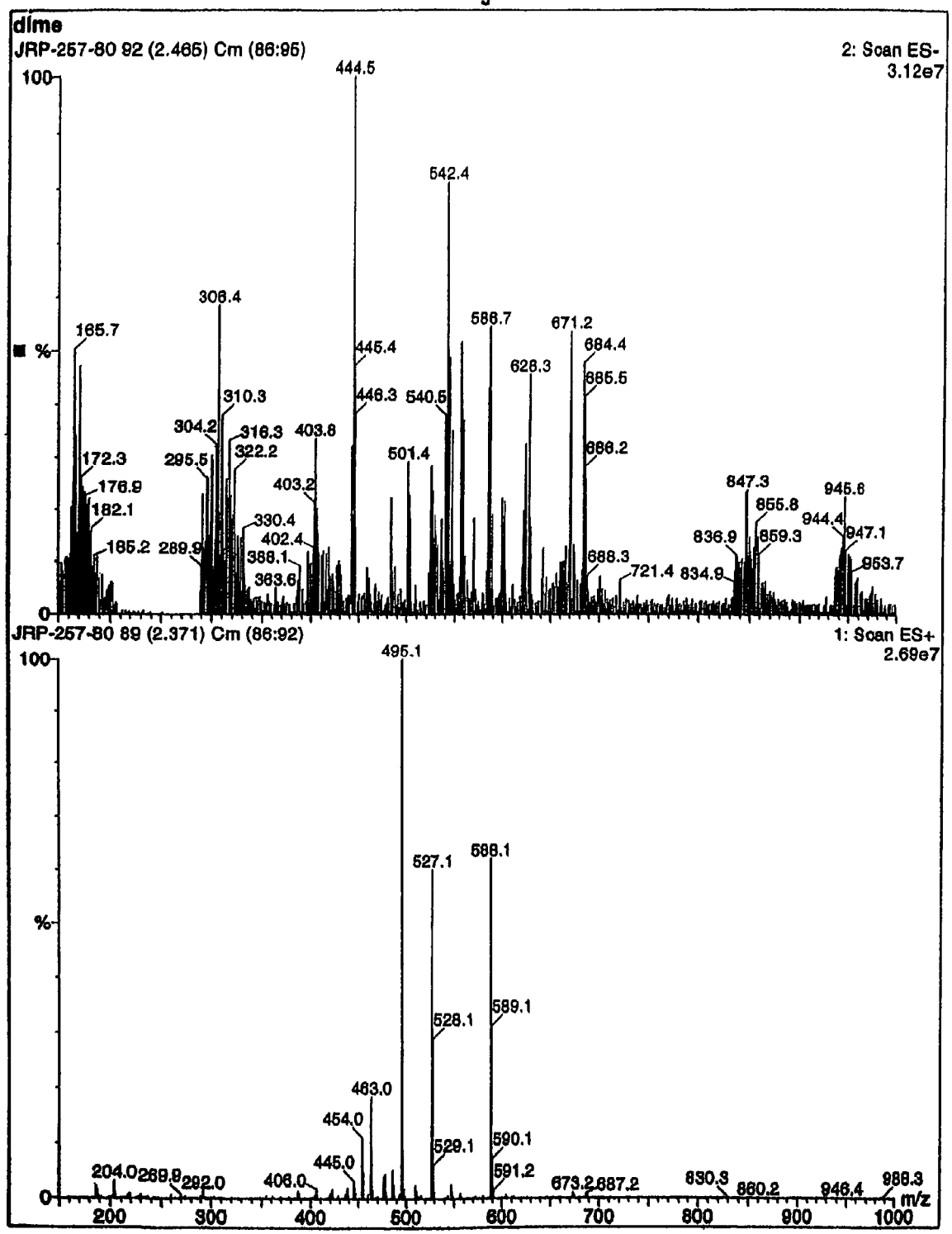
FIG. 27 depicts mass spectra from a LCMS analysis of the Carboxylate Co-Salt of the Hydroquinone of 17-AAG prepared according to the procedure described in Example 11.
Figure 28:
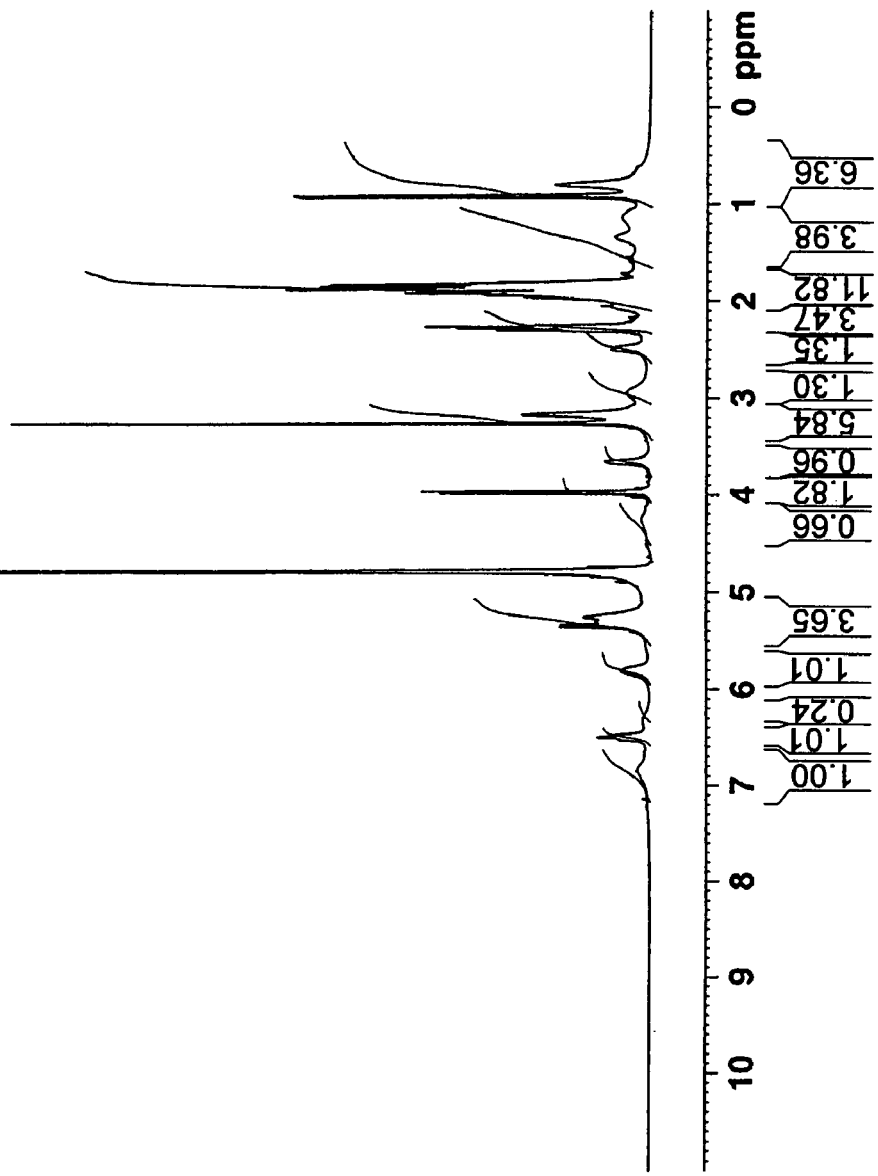
FIG. 28 depicts a $^1$H NMR spectrum of the 1-Amino-cyclopentanecarboxylate Co-Salt of the Hydroquinone of 17-AAG prepared according to the procedure described in Example 12.
Figure 29:
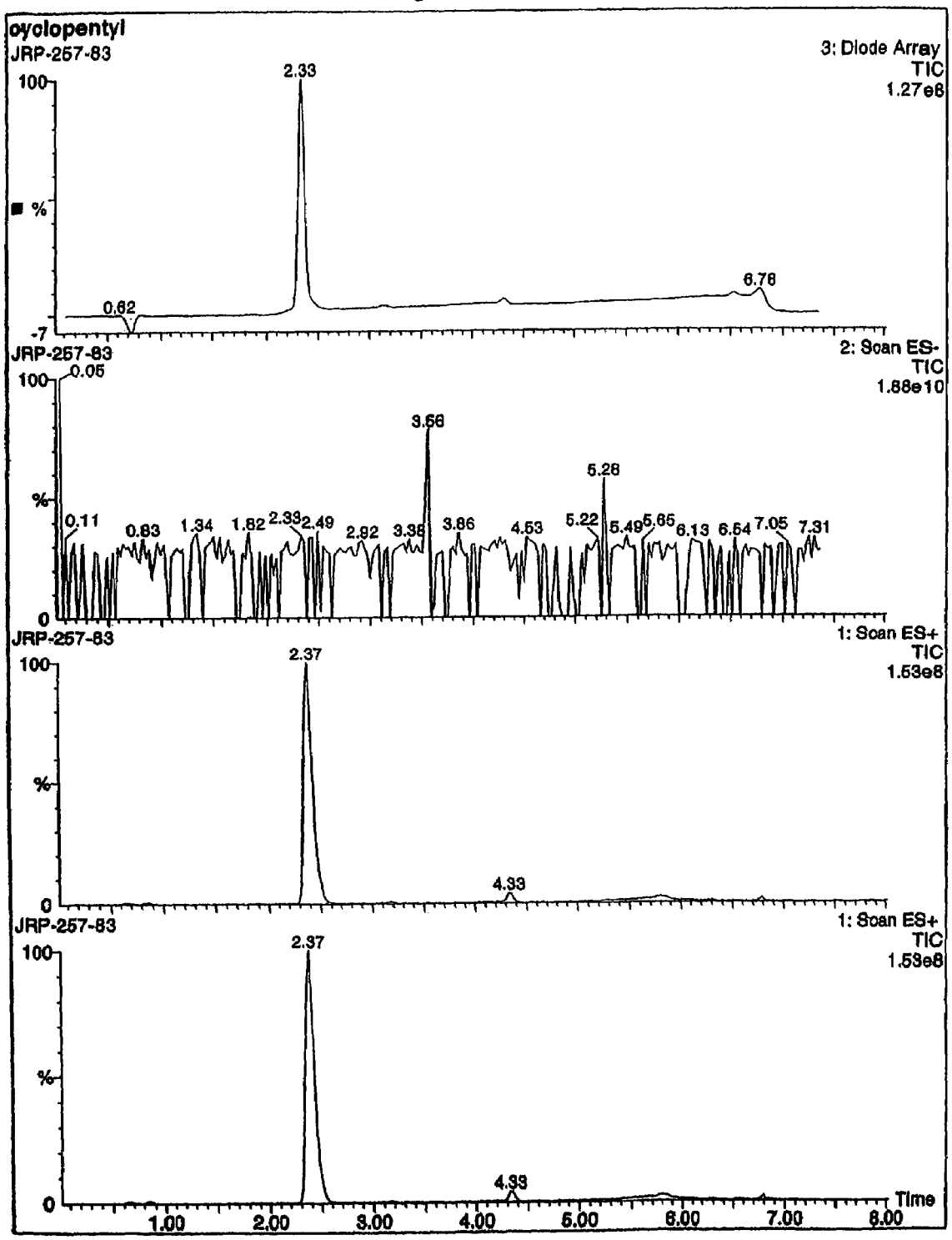
FIG. 29 depicts chromatograms from a LCMS analysis of the 1-Amino-cyclopentanecarboxylate Co-Salt of the Hydroquinone of 17-AAG prepared according to the procedure described in Example 12.
Figure 30:
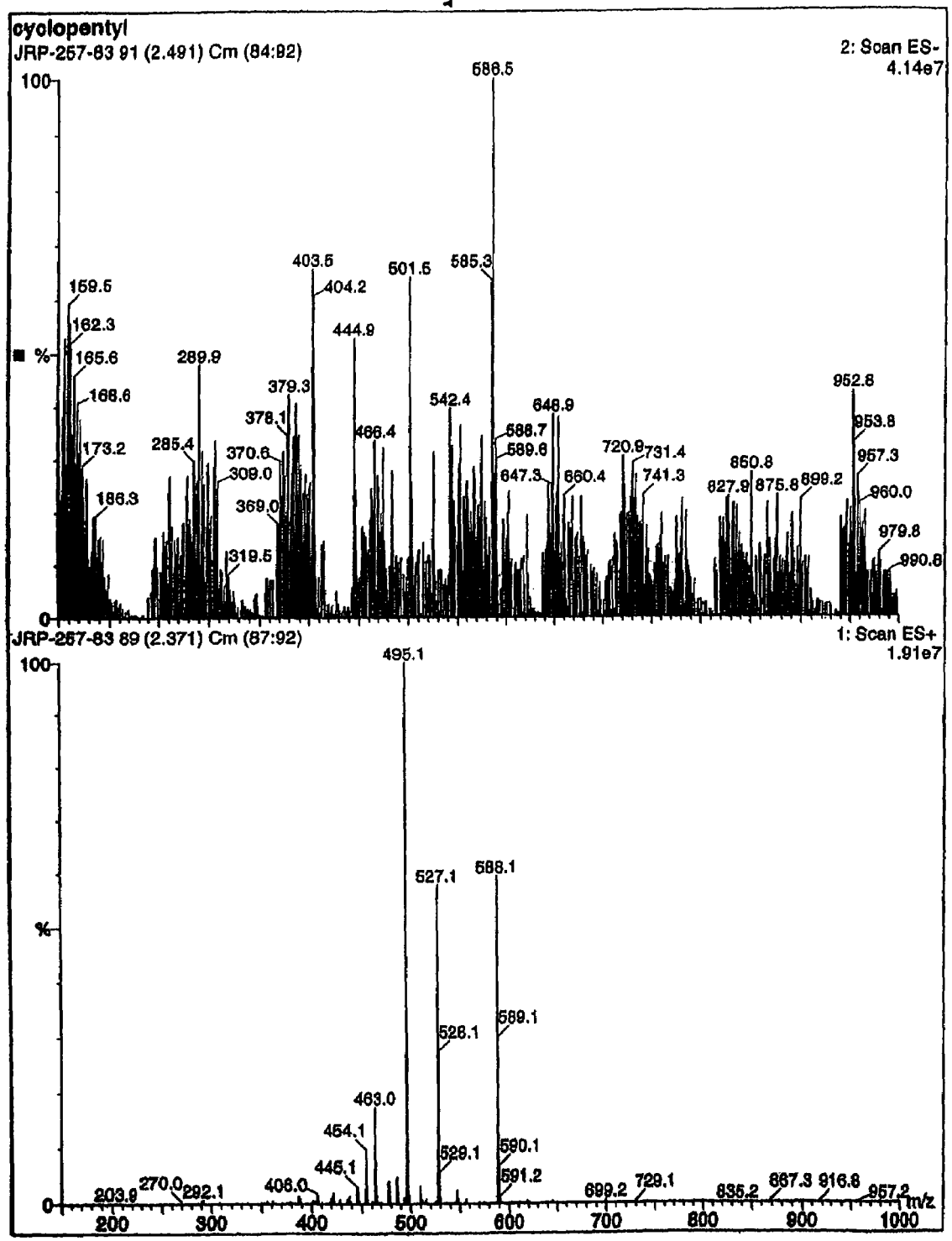
FIG. 30 depicts mass spectra from a LCMS analysis of the 1-Amino-cyclopentanecarboxylate Co-Salt of the Hydroquinone of 17-AAG prepared according to the procedure described in Example 12.
Figure 31:
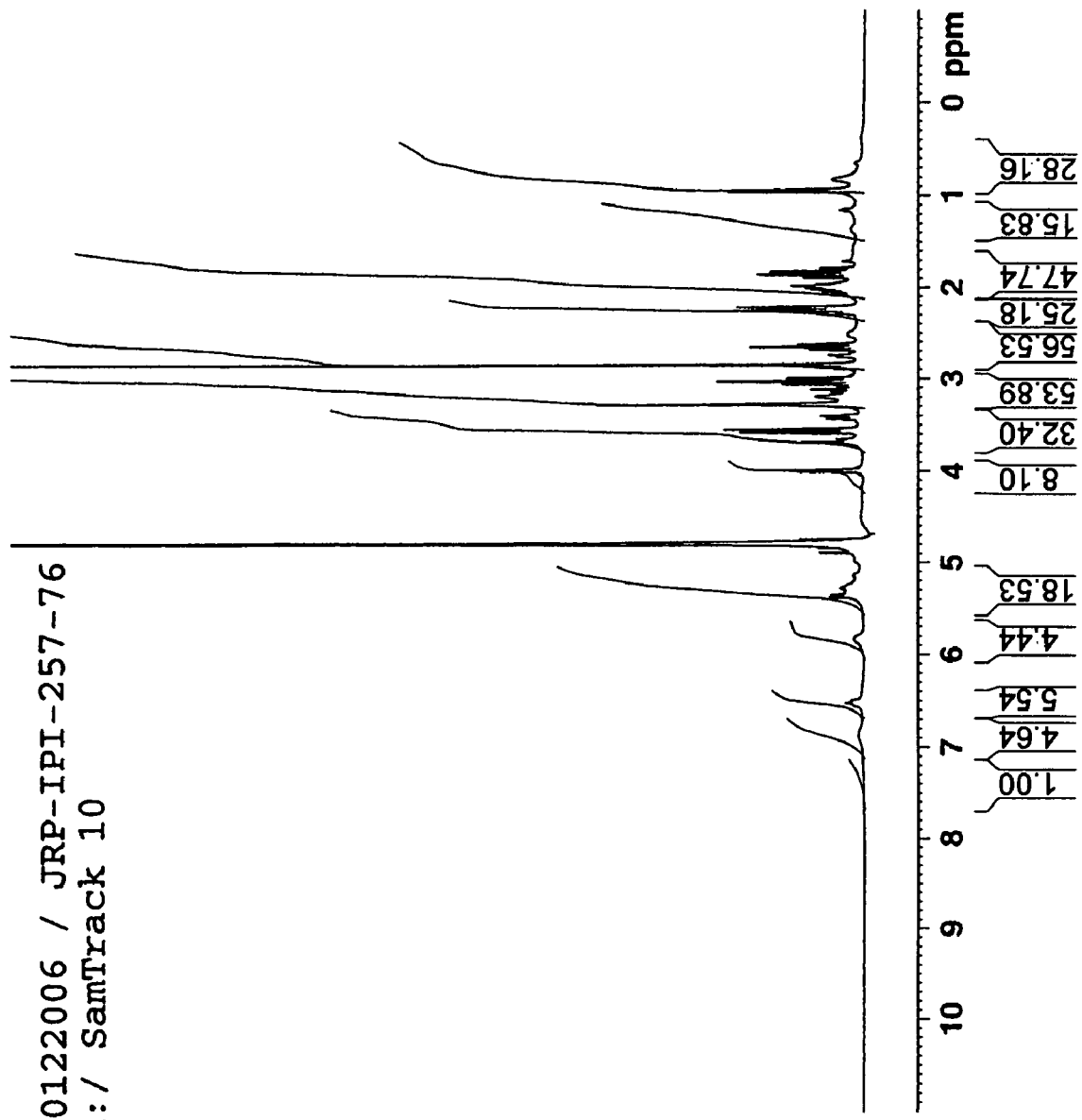
FIG. 31 depicts a $^1$H NMR spectrum of the N-Methyl Piperidinecarboxylate Co-Salt of the Hydroquinone of 17-AAG prepared according to the procedure described in Example 13.
Figure 32B:
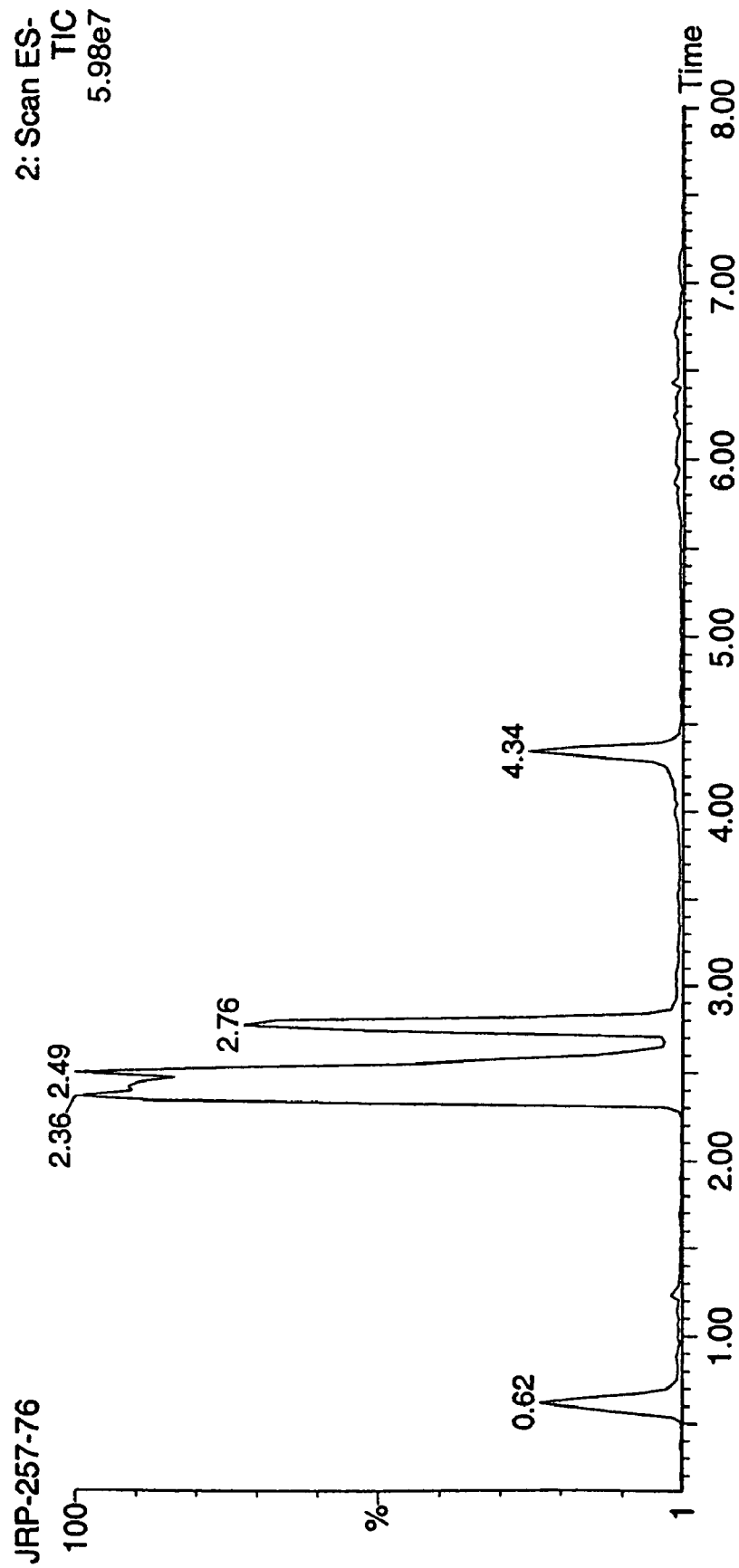
FIG. 32 depicts chromatograms from a LCMS analysis of the N-Methyl Piperidinecarboxylate Co-Salt of the Hydroquinone of 17-AAG prepared according to the procedure described in Example 13.
Figure 32C:
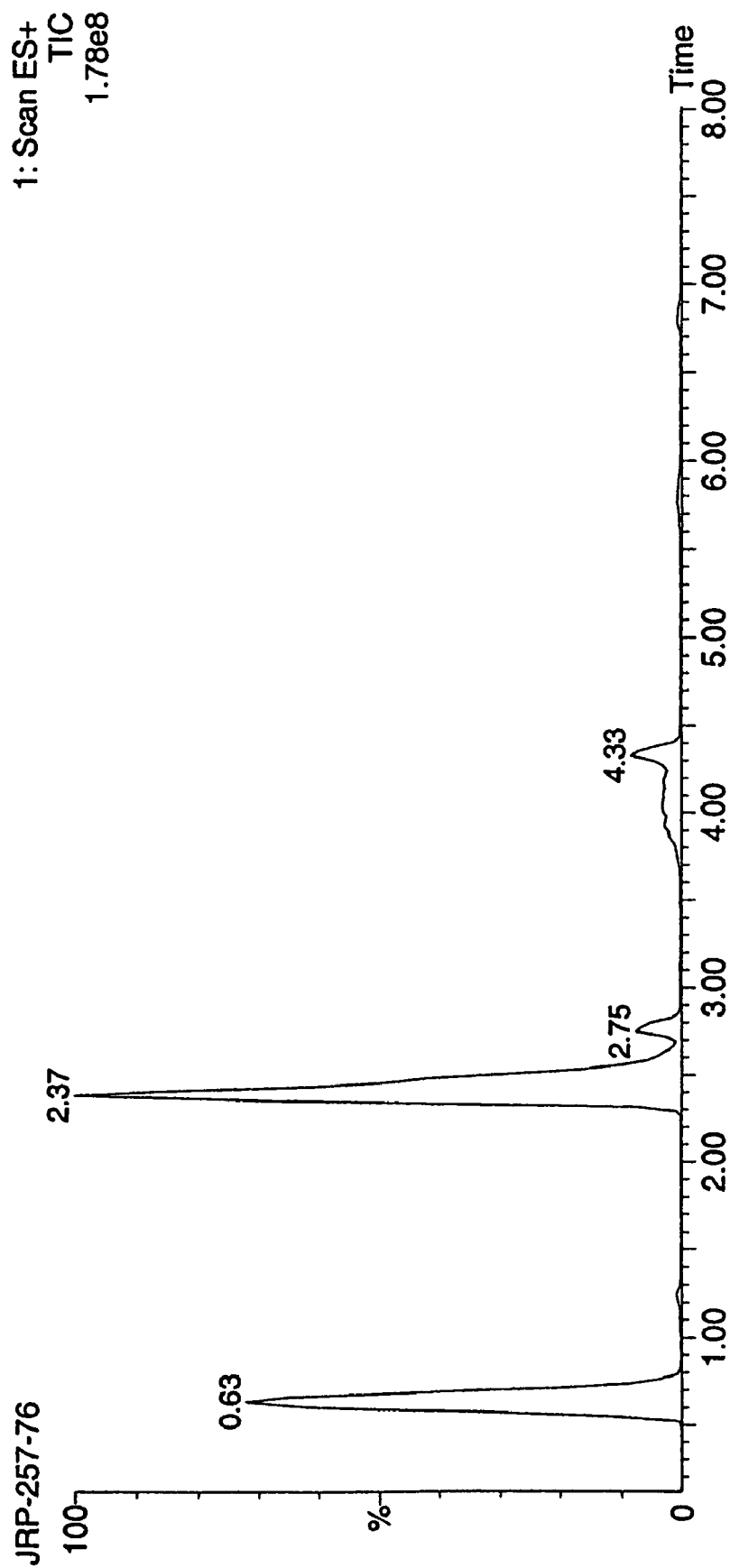
Figure 33:
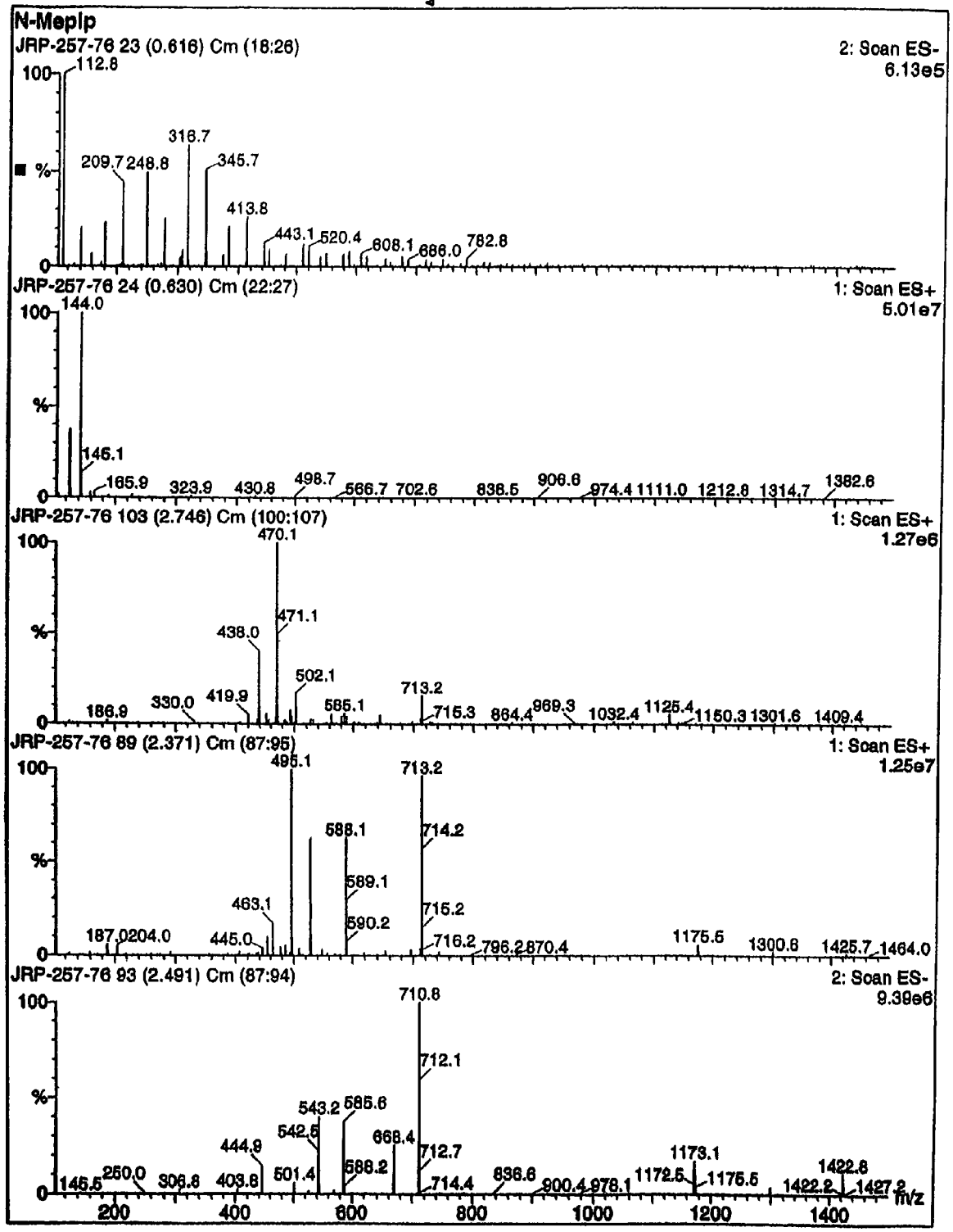
FIG. 33 depicts mass spectra from a LCMS analysis of the N-Methyl Piperidinecarboxylate Co-Salt of the Hydroquinone of 17-AAG prepared according to the procedure described in Example 13.
Figure 34:
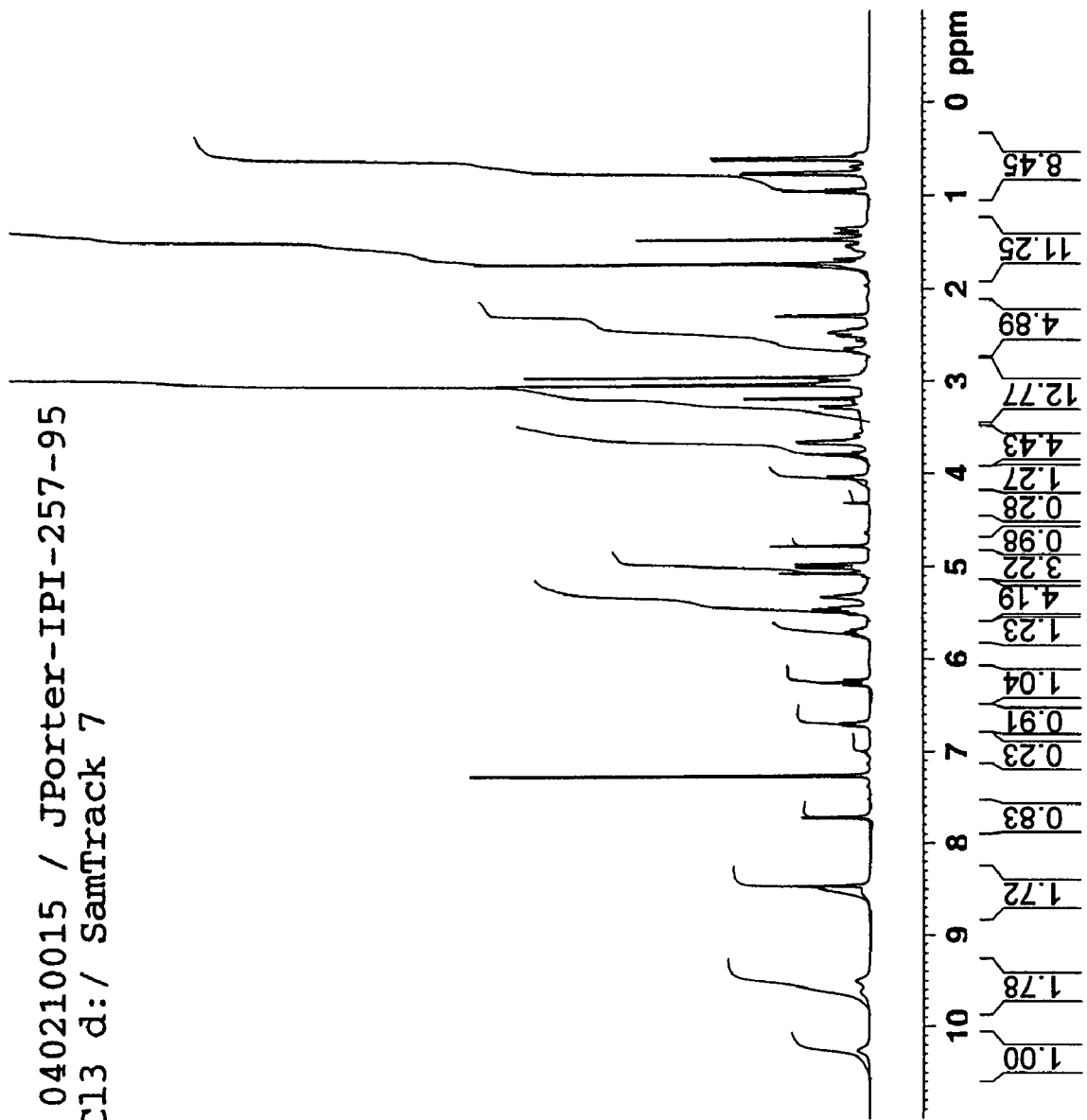
FIG. 34 depicts a $^1$H NMR spectrum of the N,N,N-Trimethylammonium Acetate Co-Salt of the Hydroquinone of 17-AAG prepared according to the procedure described in Example 14.
Figure 35:
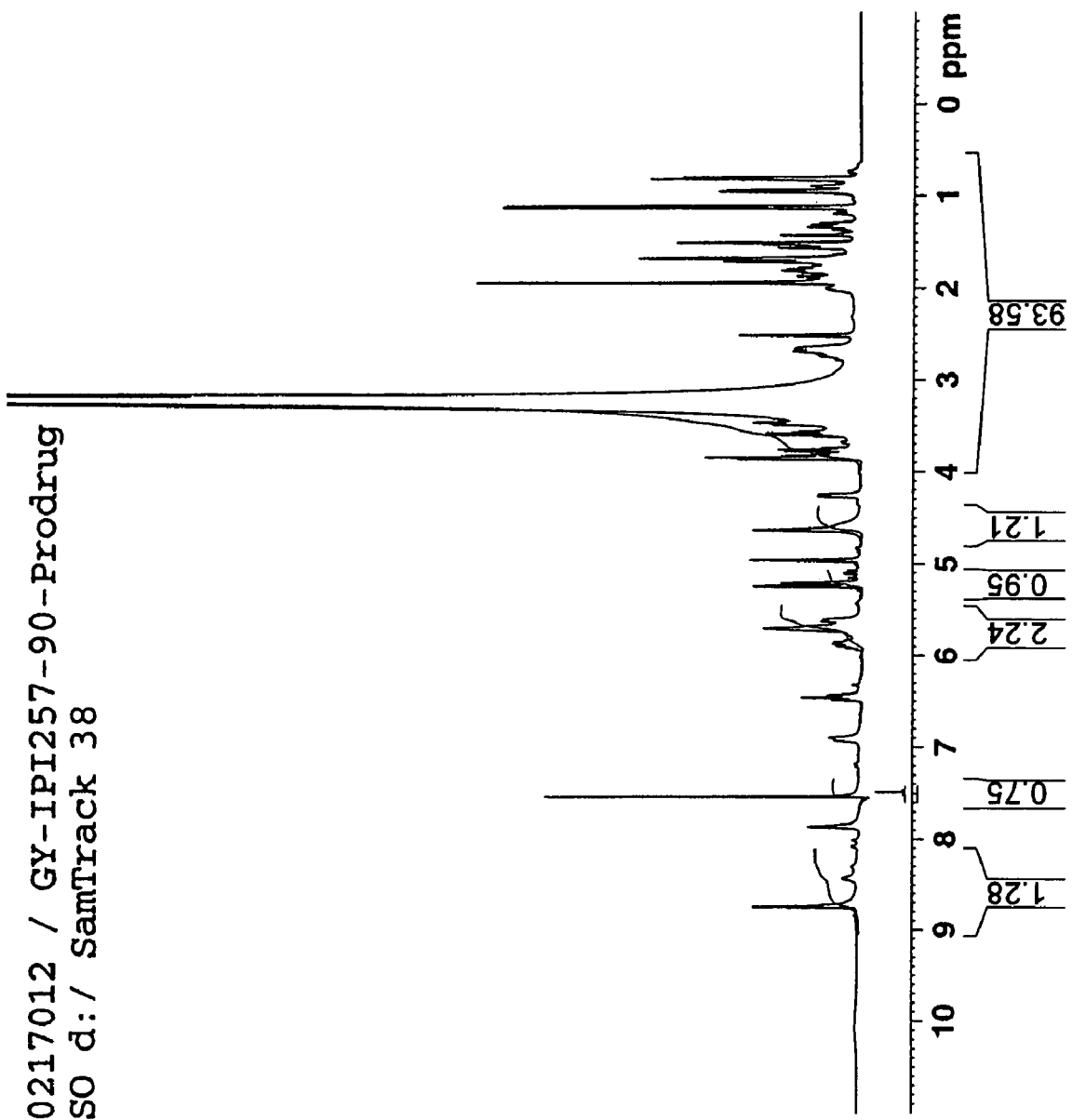
FIG. 35 depicts a $^1$H NMR spectrum of the Air-stable Hydroquinone Derivatives of 17-AAG Geldanamycin prepared according to the procedure described in Example 15.
Figure 36:
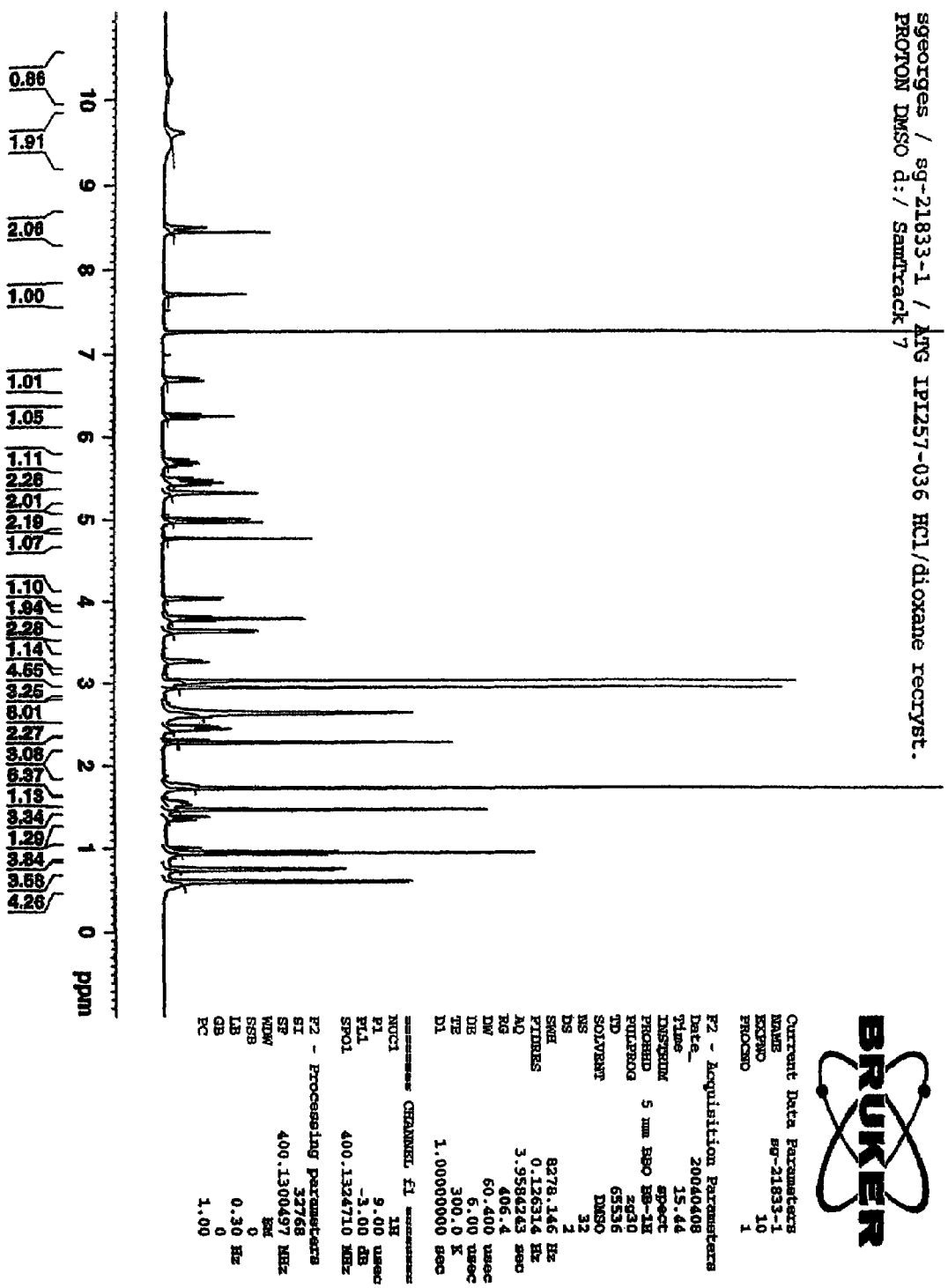
FIG. 36 depicts a $^1$H NMR spectrum of the HCl salt of the Hydroquinone Derivative of 17-AAG Geldanamycin prepared according to the procedure described in Example 17.
Figure 37:
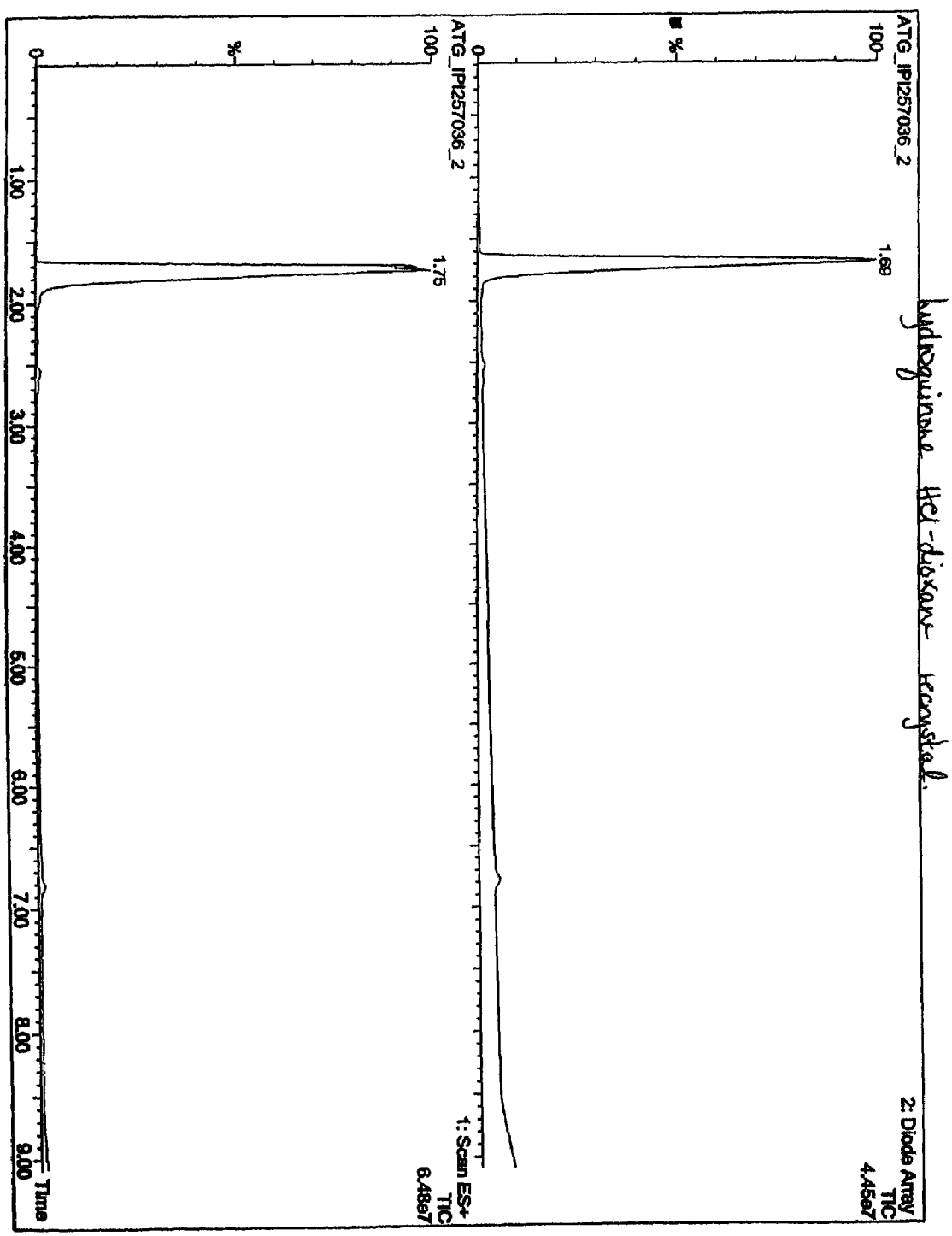
FIG. 37 depicts chromatograms from a LCMS analysis of the HCl Salt of the Hydroquinone of 17-AAG prepared according to the procedure described in Example 17.
Figure 38:
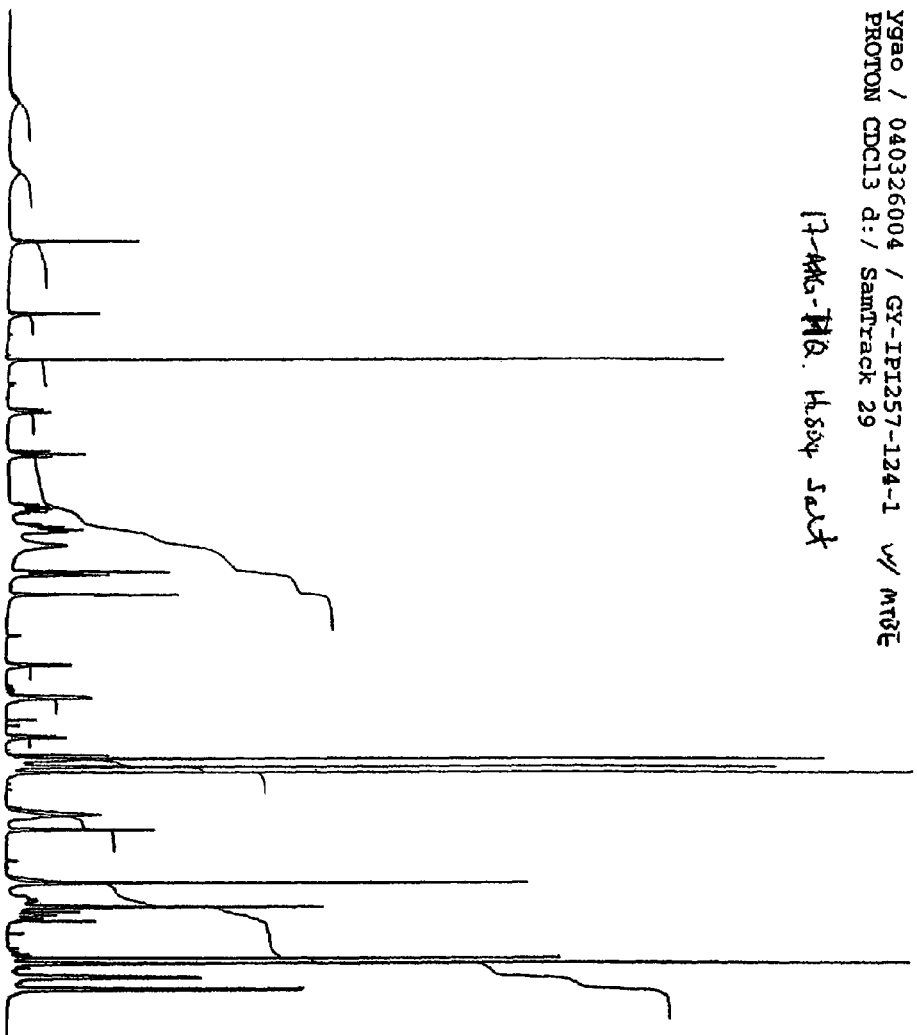
FIG. 38 depicts a $^1$H NMR spectrum of the $H_2SO_4$ salt of the Hydroquinone Derivative of 17-AAG Geldanamycin prepared according to the procedure described in Example 18.
Figure 39A:
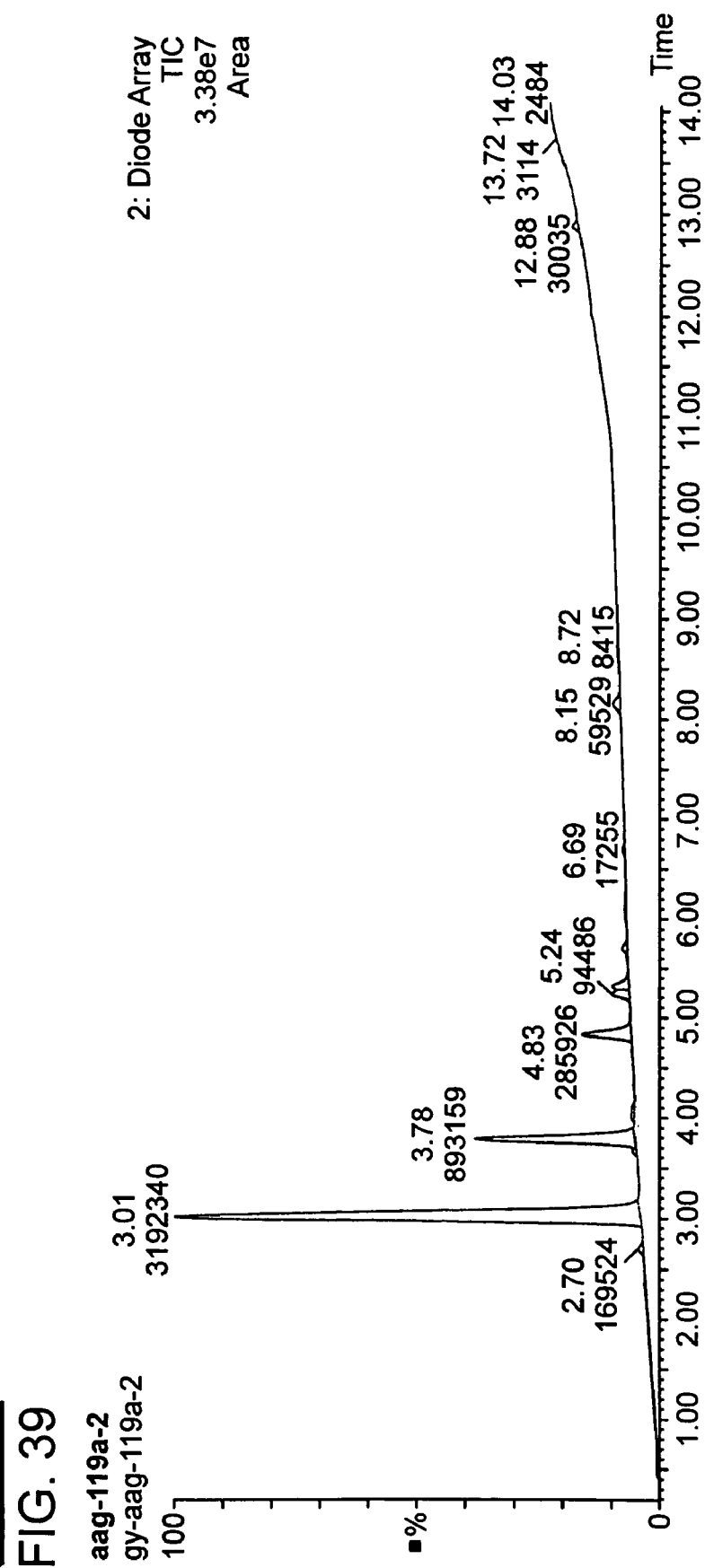
FIG. 39 depicts chromatograms from a LCMS analysis of the $H_2SO_4$ Salt of the Hydroquinone of 17-AAG prepared according to the procedure described in Example 18.
Figure 39B:
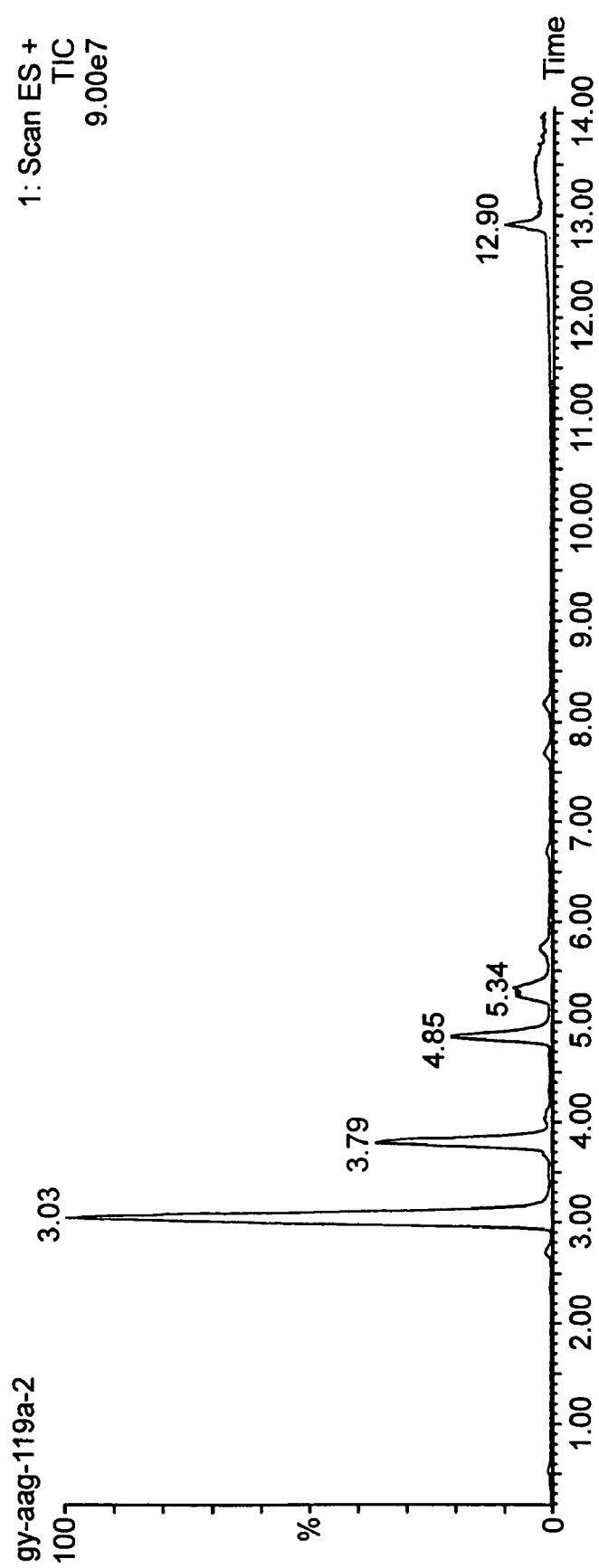
Figure 40:
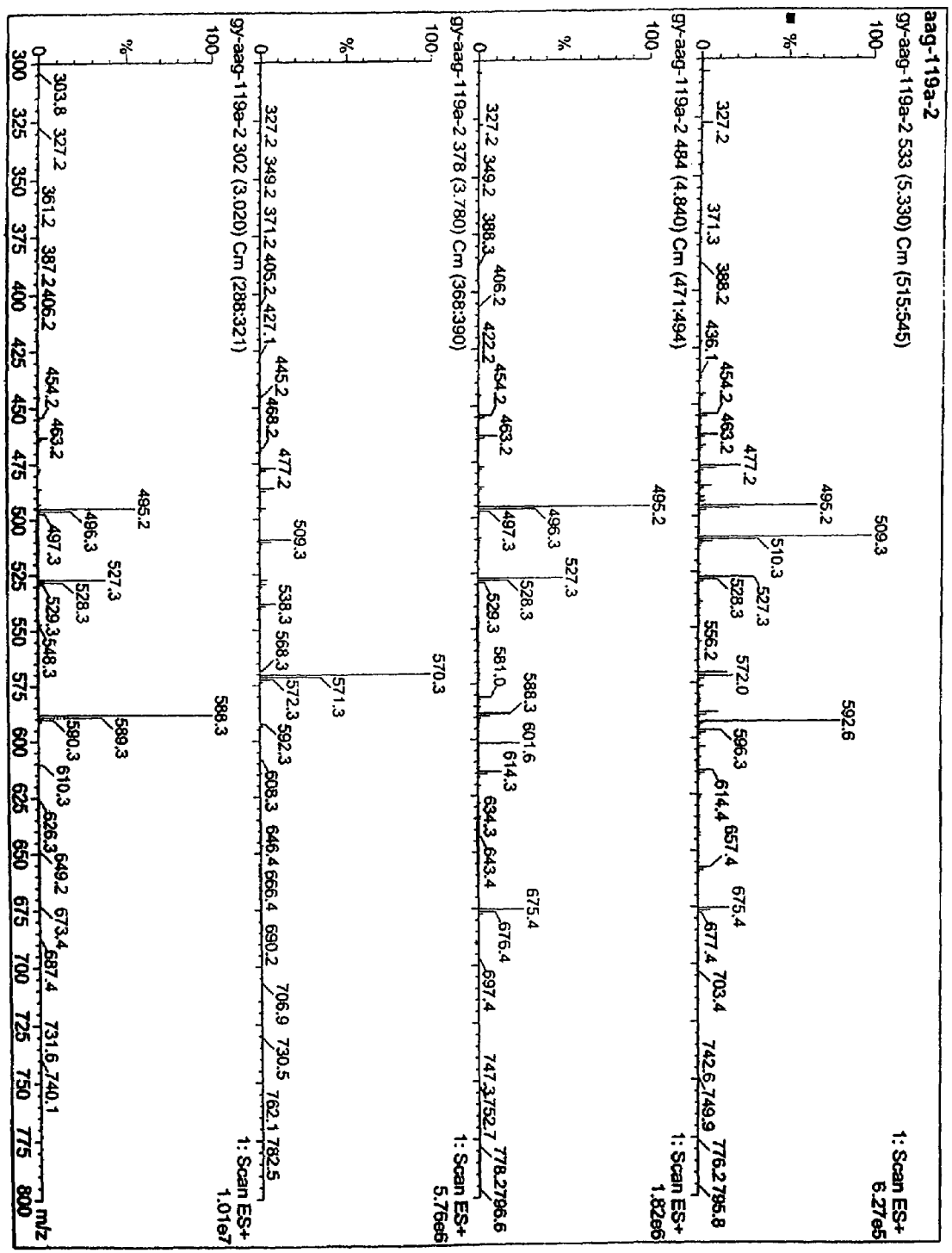
FIG. 40 depicts mass spectra from a LCMS analysis of the $H_2SO_4$ Salt of the Hydroquinone of 17-AAG prepared according to the procedure described in Example 18.
Figure 41:
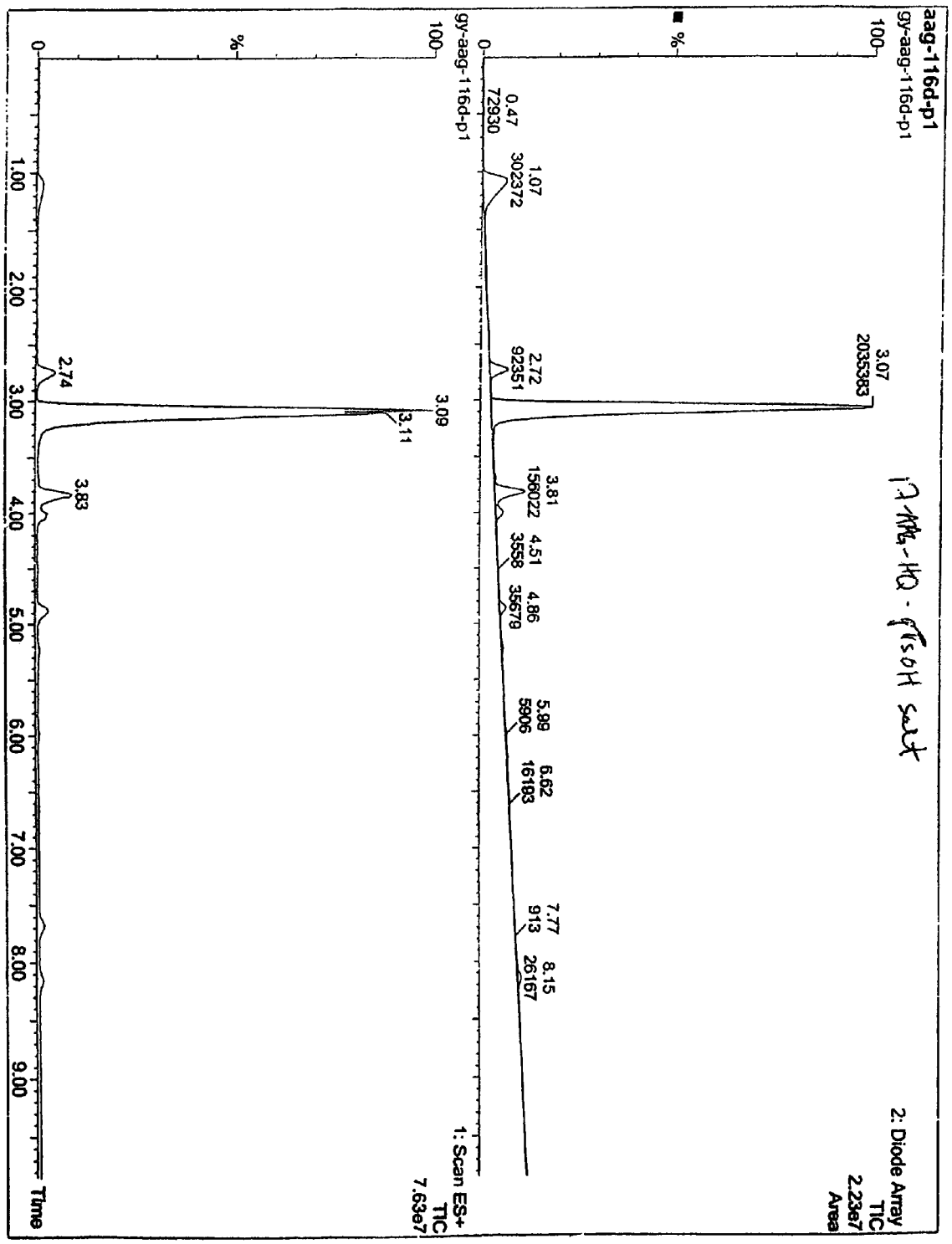
FIG. 41 depicts chromatograms from a LCMS analysis of the p-Toluenesulfonic Salt of the Hydroquinone of 17-AAG prepared according to the procedure described in Example 19.
Figure 42:
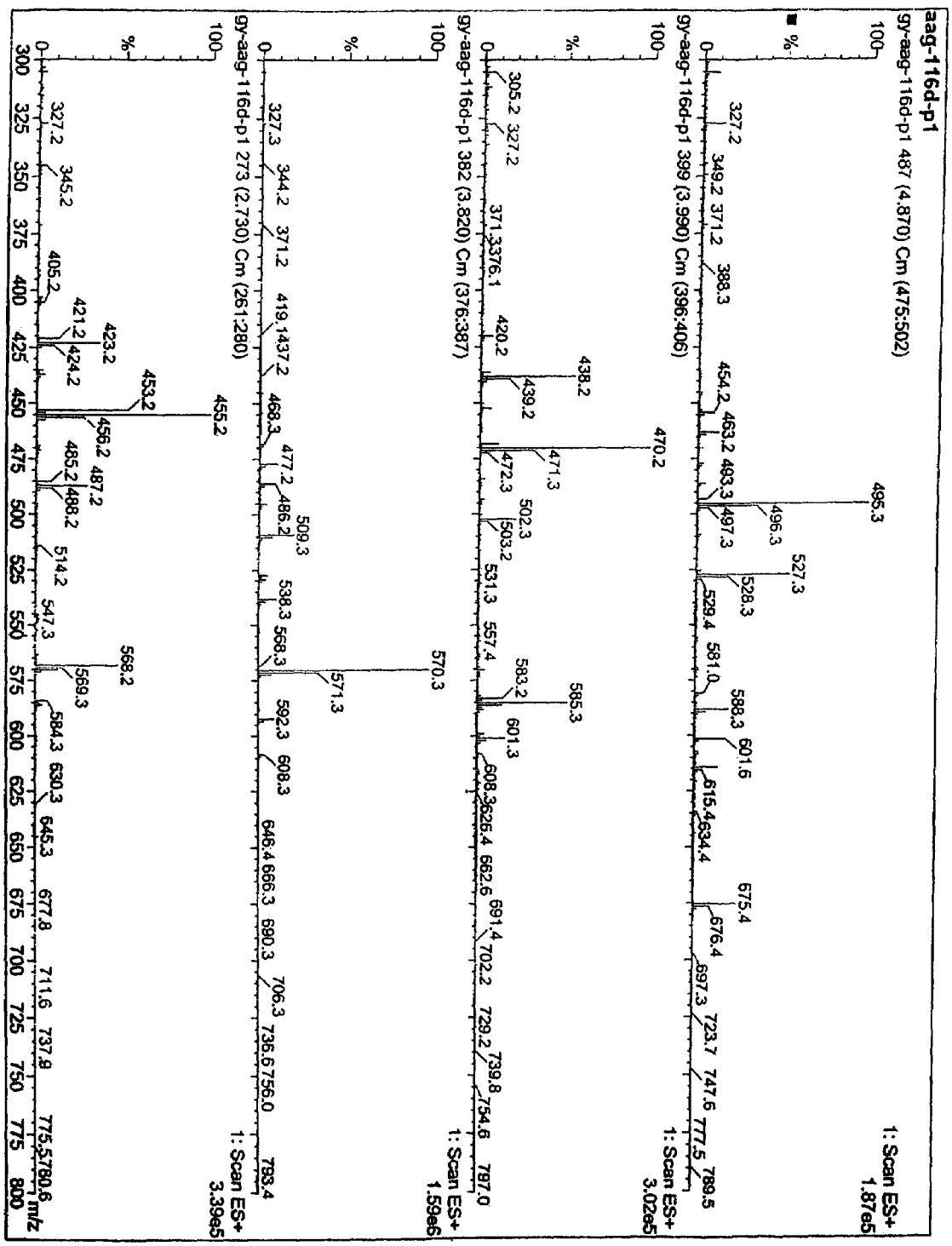
FIG. 42 depicts mass spectra from a LCMS analysis of the p-Toluenesulfonic Salt of the Hydroquinone of 17-AAG prepared according to the procedure described in Example 19.
Figure 43:
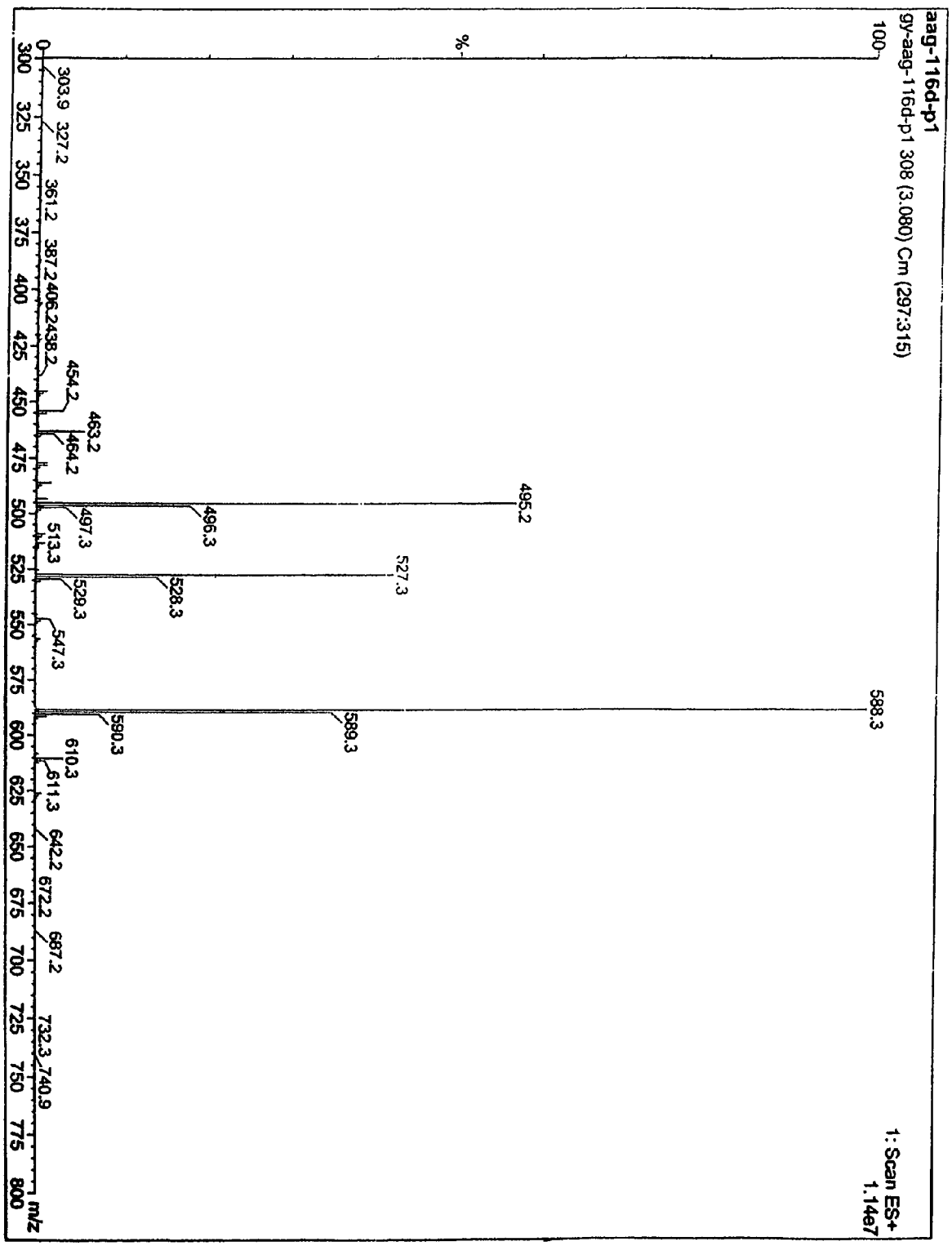
FIG. 43 depicts mass spectra from a LCMS analysis of the p-Toluenesulfonic Salt of the Hydroquinone of 17-AAG prepared according to the procedure described in Example 19.
Figure 44:
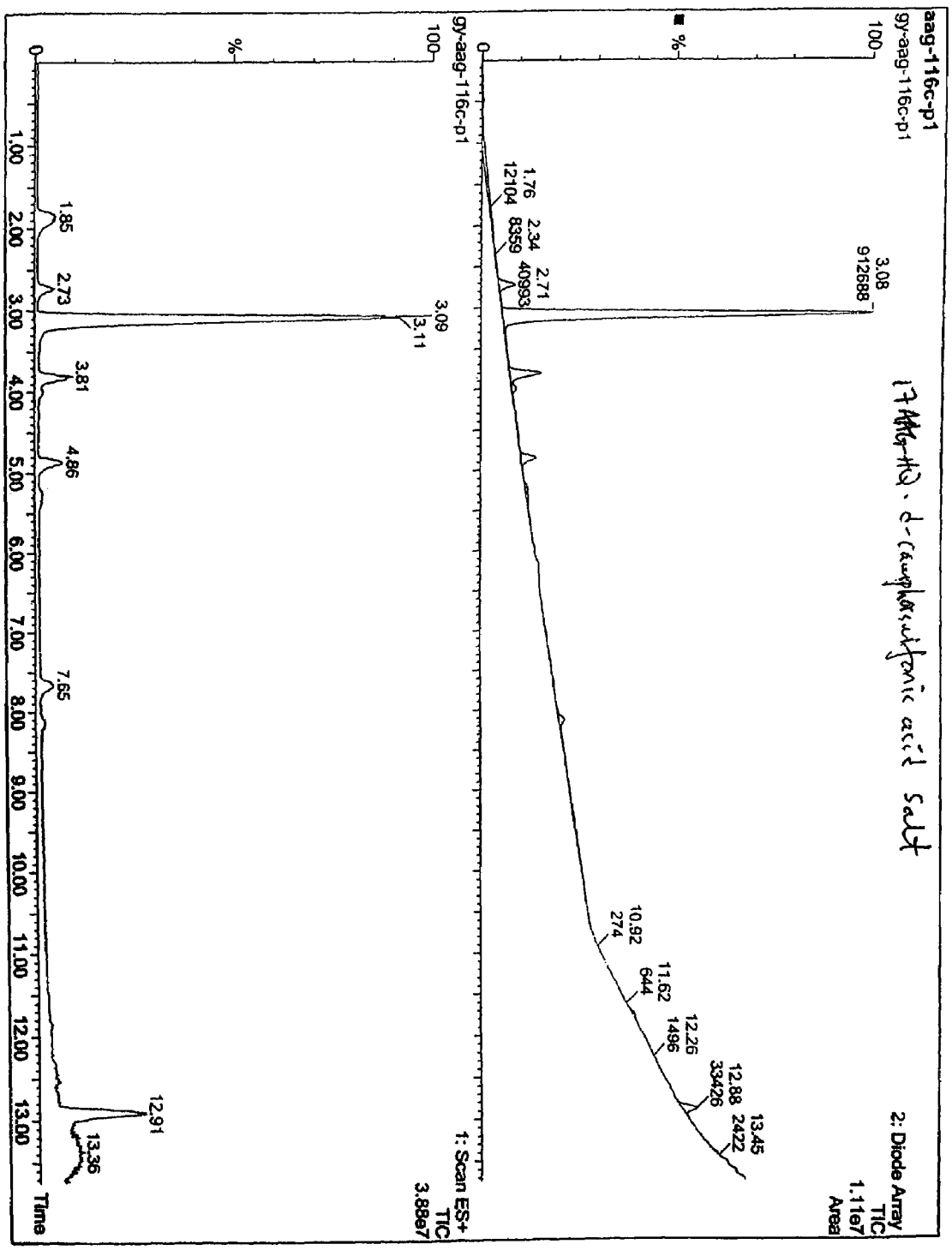
FIG. 44 depicts chromatograms from a LCMS analysis of the d-Camphorsulfonic Salt of the Hydroquinone of 17-AAG prepared according to the procedure described in Example 20.
Figure 45:
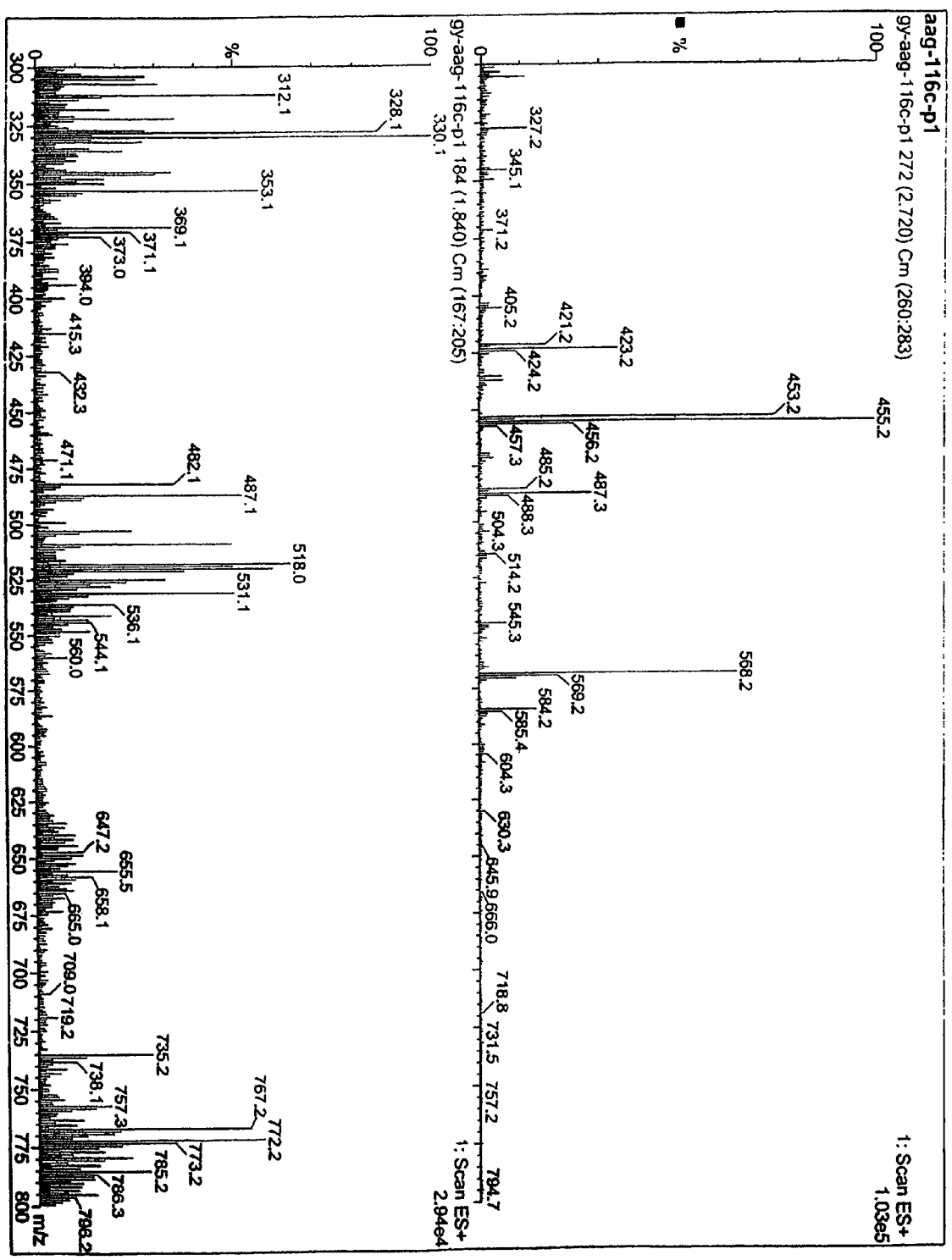
FIG. 45 depicts mass spectra from a LCMS analysis of the d-Camphorsulfonic Salt of the Hydroquinone of 17-AAG prepared according to the procedure described in Example 20.
Figure 46:
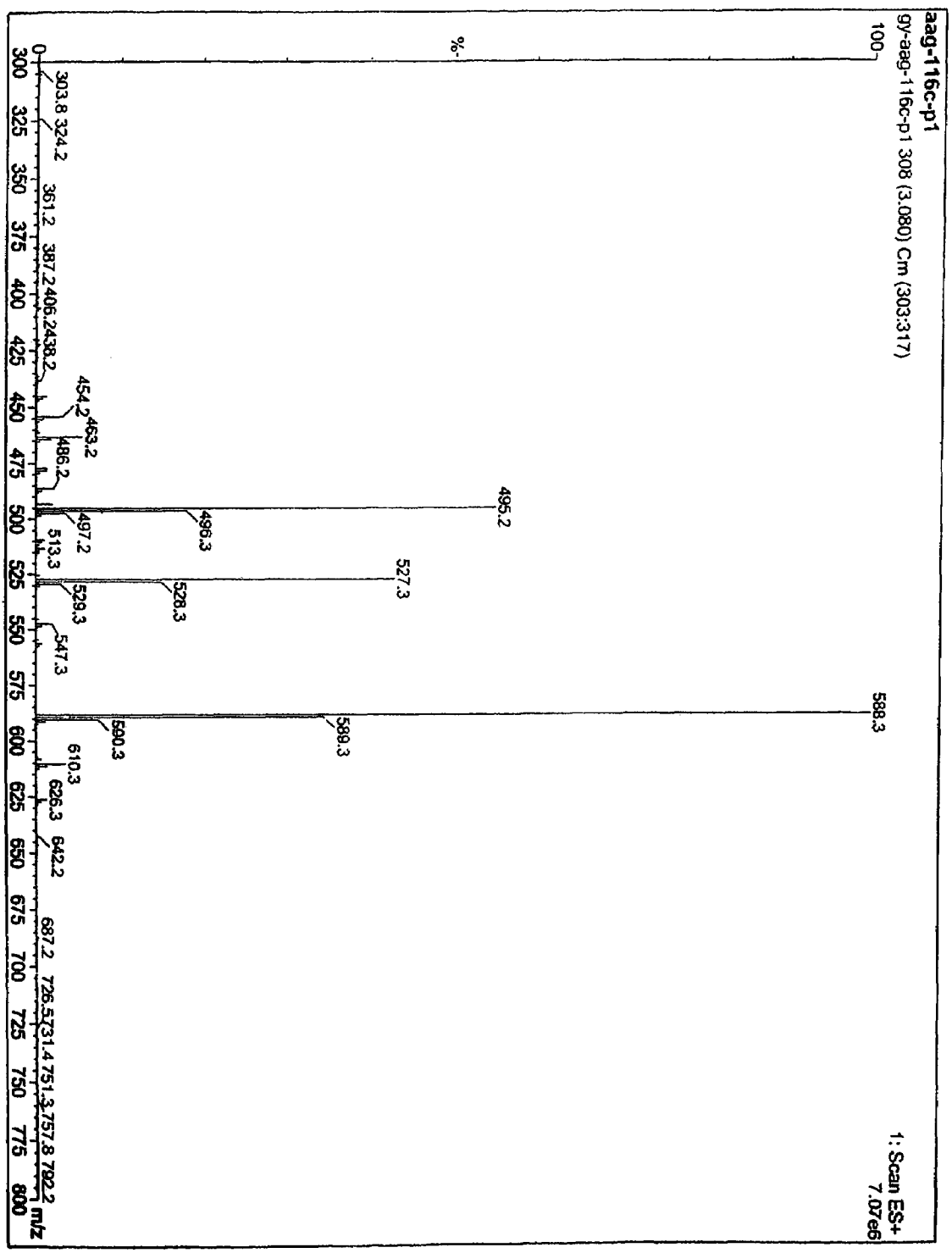
FIG. 46 depicts mass spectra from a LCMS analysis of the d-Camphorsulfonic Salt of the Hydroquinone of 17-AAG prepared according to the procedure described in Example 20.
Figure 47:
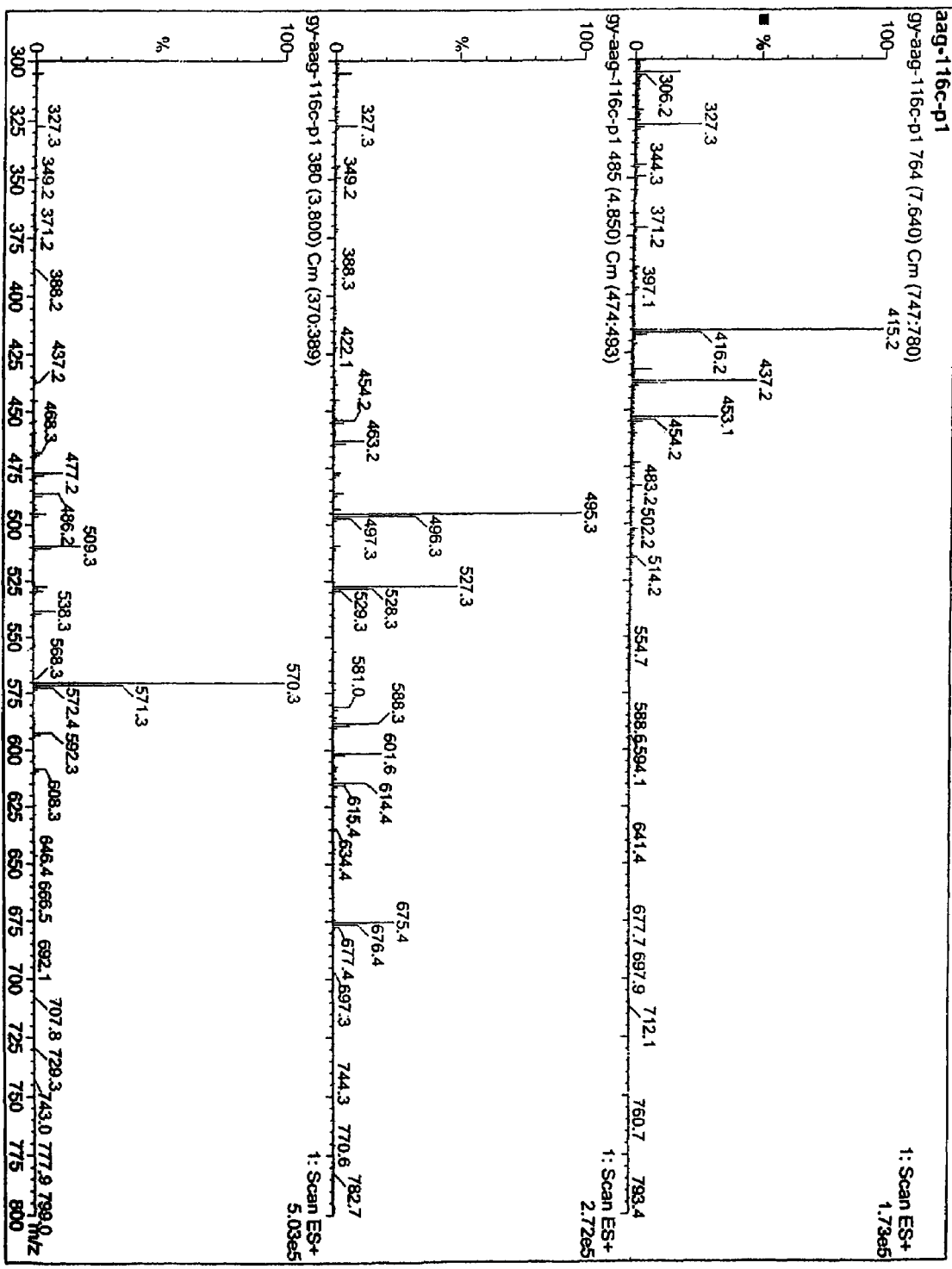
FIG. 47 depicts mass spectra from a LCMS analysis of the d-Camphorsulfonic Salt of the Hydroquinone of 17-AAG prepared according to the procedure described in Example 20.
Figure 48:
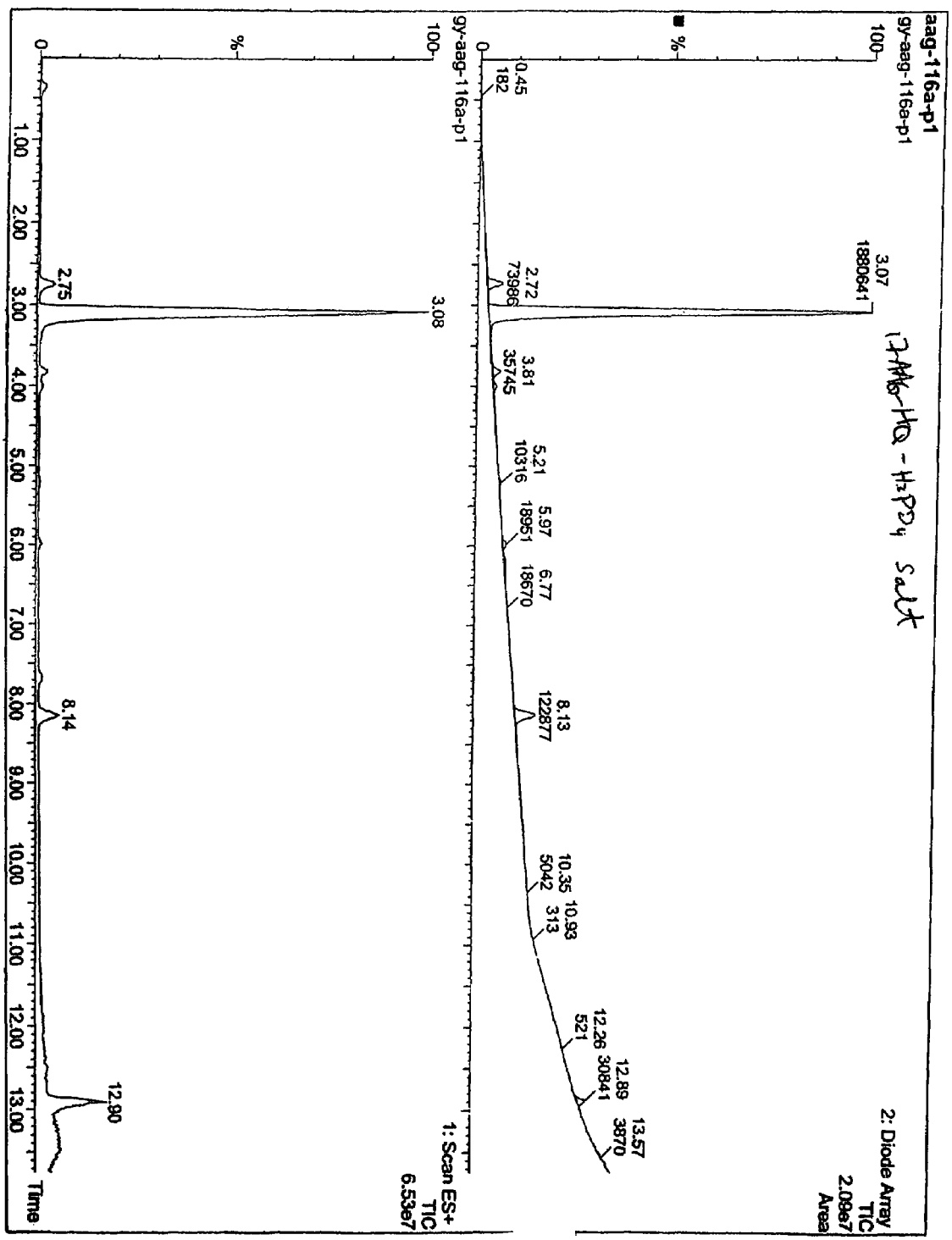
FIG. 48 depicts chromatograms from a LCMS analysis of the $H_3PO_4$ Salt of the Hydroquinone of 17-AAG prepared according to the procedure described in Example 21.
Figure 49:
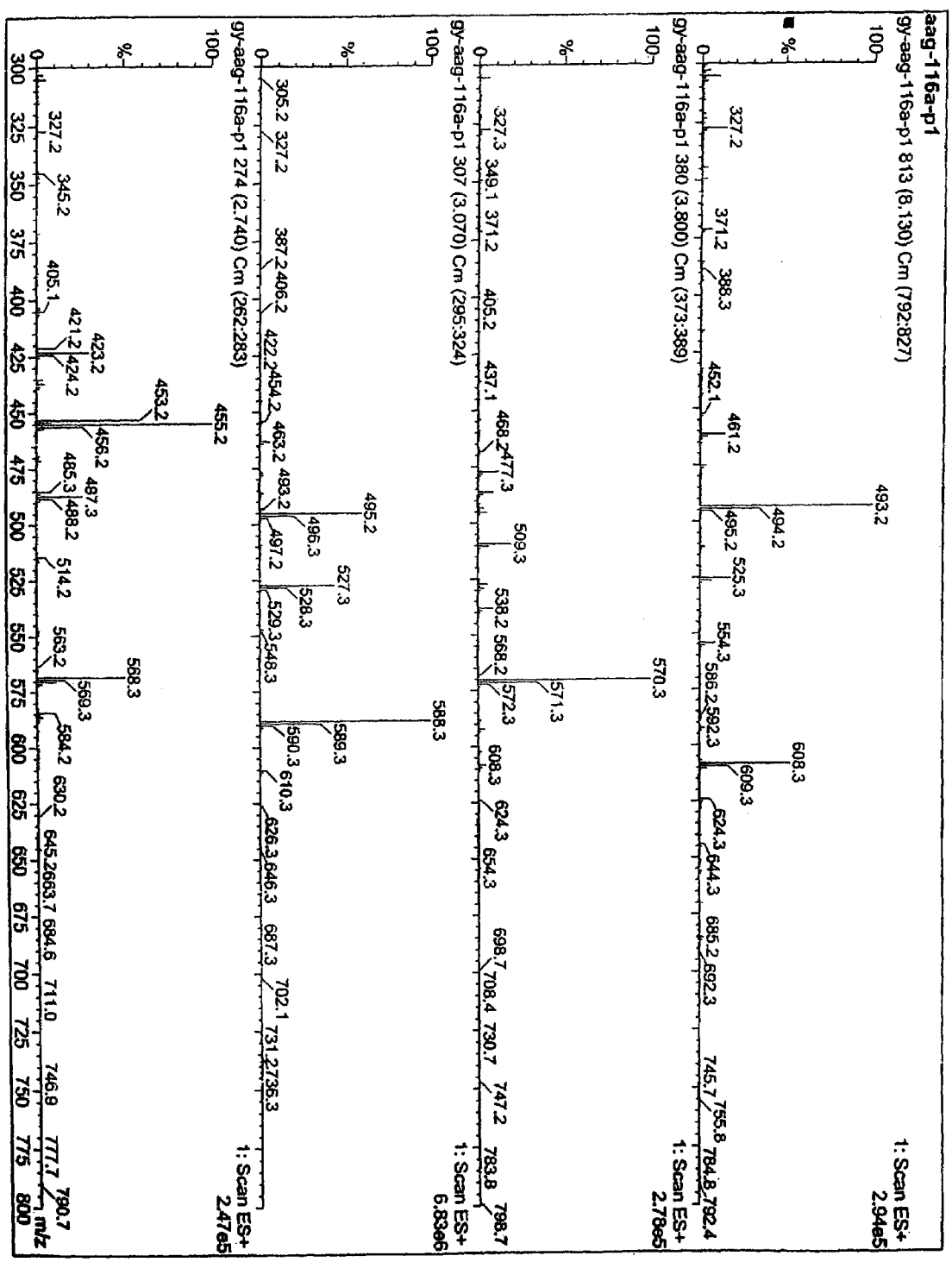
FIG. 49 depicts mass spectra from a LCMS analysis of the $H_3PO_4$ Salt of the Hydroquinone of 17-AAG prepared according to the procedure described in Example 21.
Figure 50:
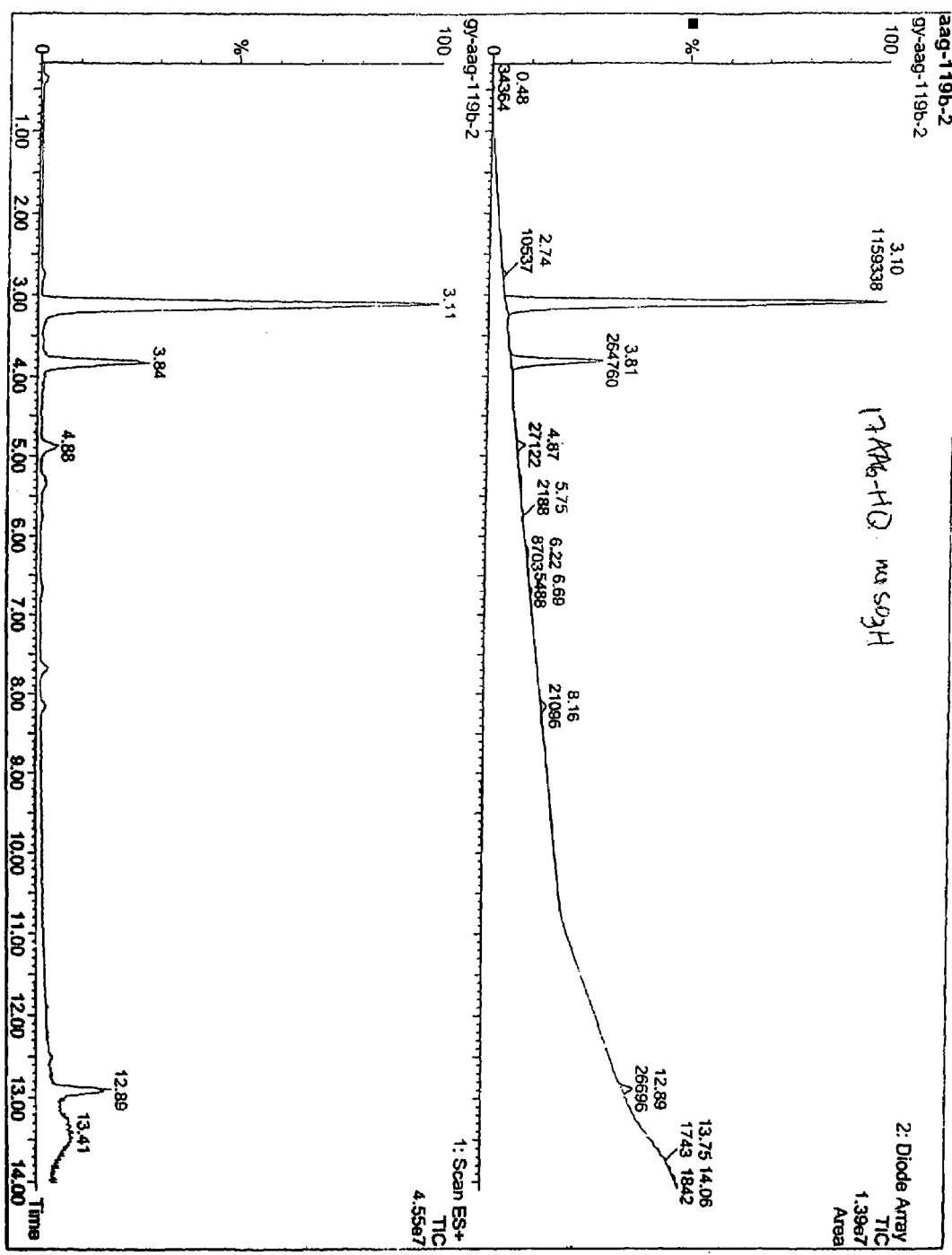
FIG. 50 depicts chromatograms from a LCMS analysis of the $MeSO_3H$ Salt of the Hydroquinone of 17-AAG prepared according to the procedure described in Example 22.
Figure 51:
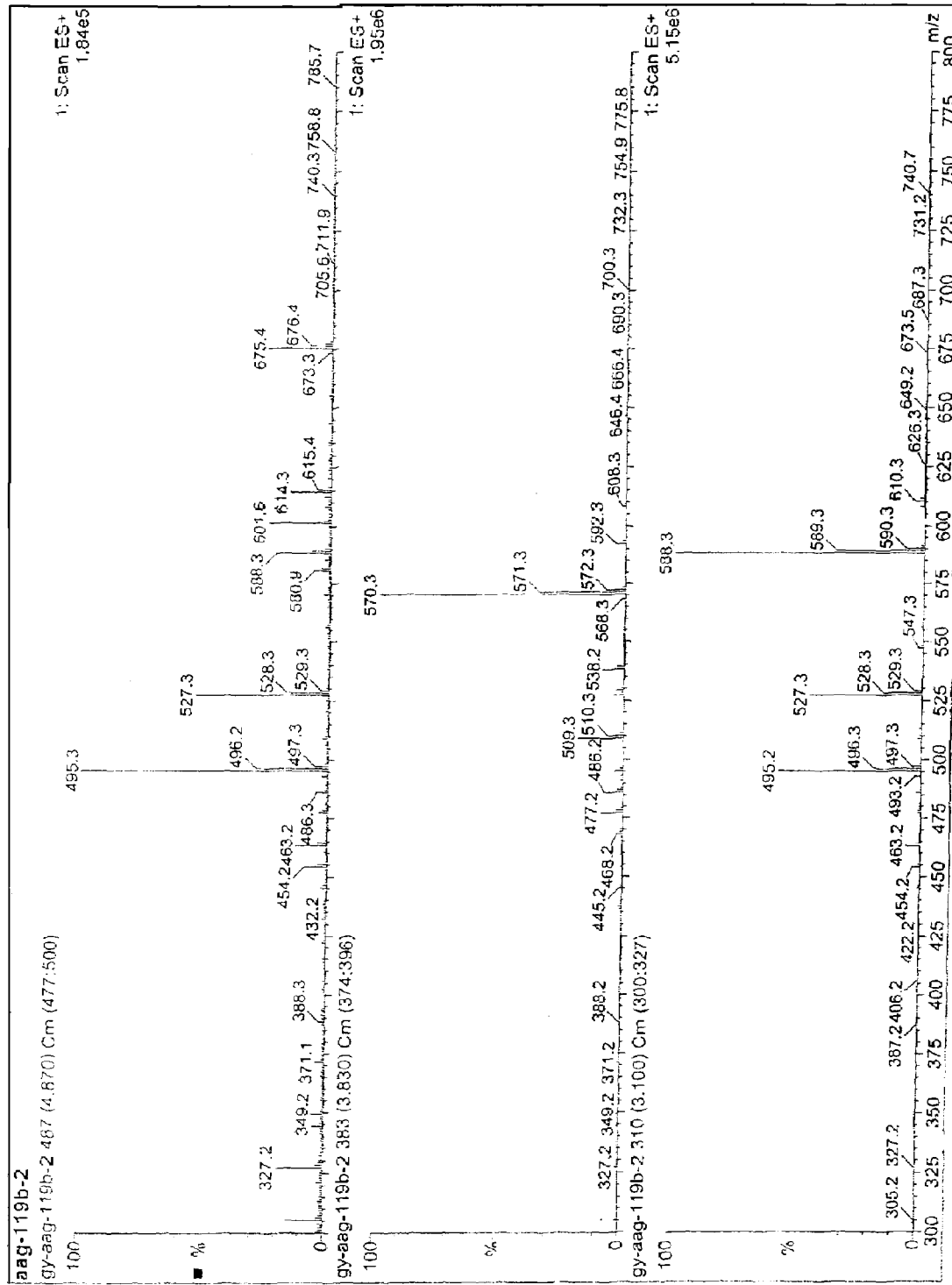
FIG. 51 depicts mass spectra from a LCMS analysis of the $MeSO_3H$ Salt of the Hydroquinone of 17-AAG prepared according to the procedure described in Example 22.
Figure 52:
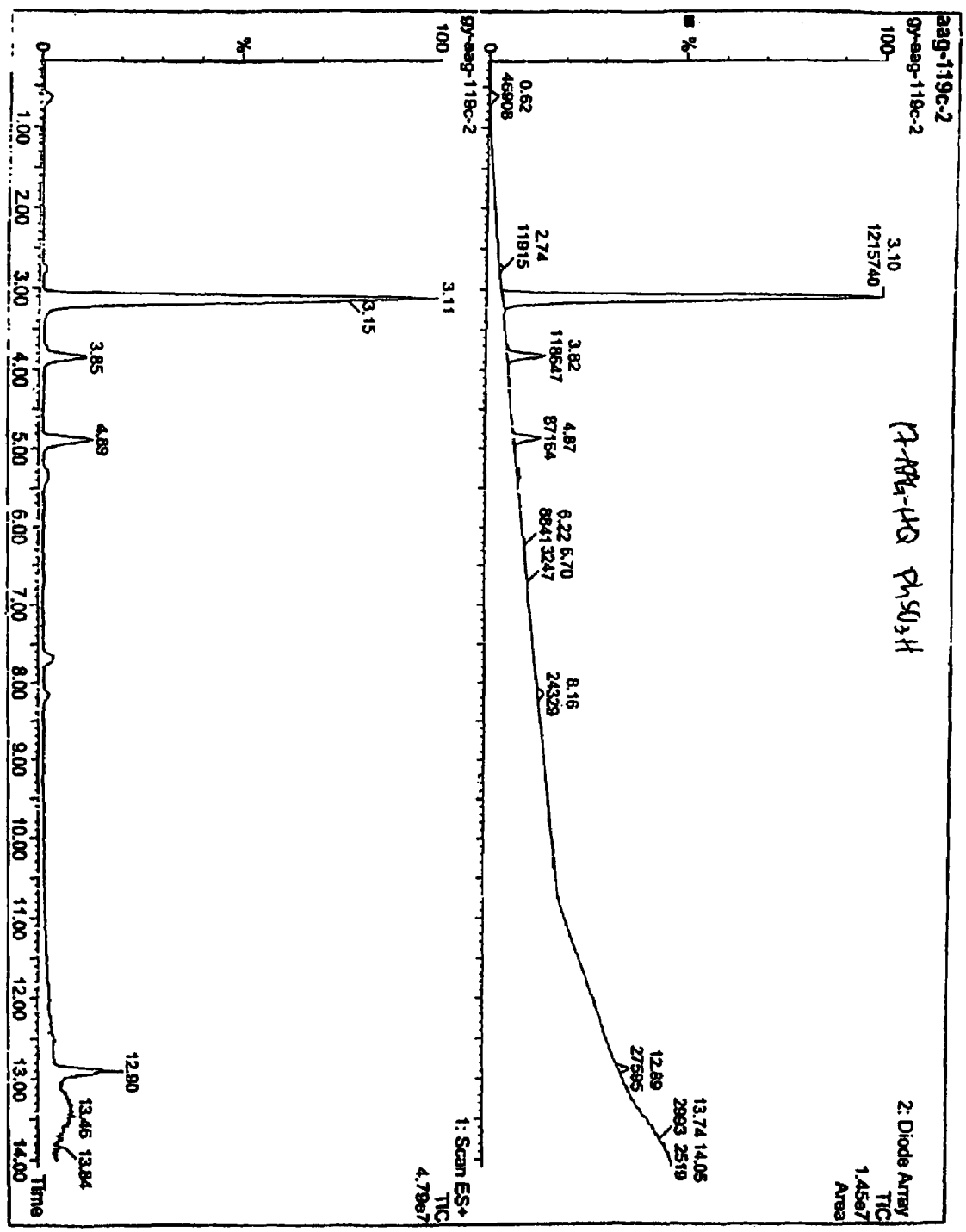
FIG. 52 depicts chromatograms from a LCMS analysis of the $PhSO_3H$ Salt of the Hydroquinone of 17-AAG prepared according to the procedure described in Example 23.
Figure 53:
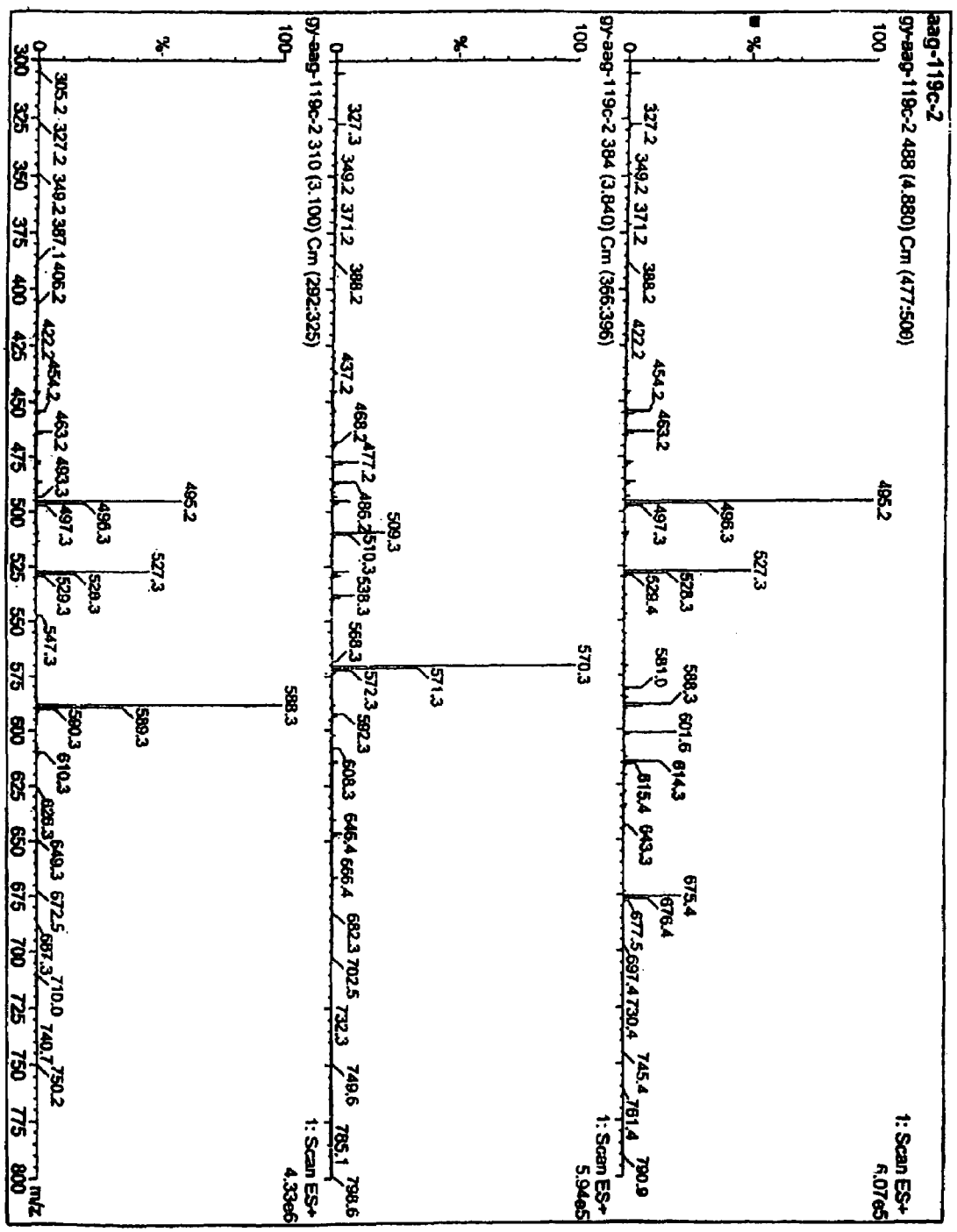
FIG. 53 depicts mass spectra from a LCMS analysis of the $PhSO_3H$ Salt of the Hydroquinone of 17-AAG prepared according to the procedure described in Example 23.
Figure 54:
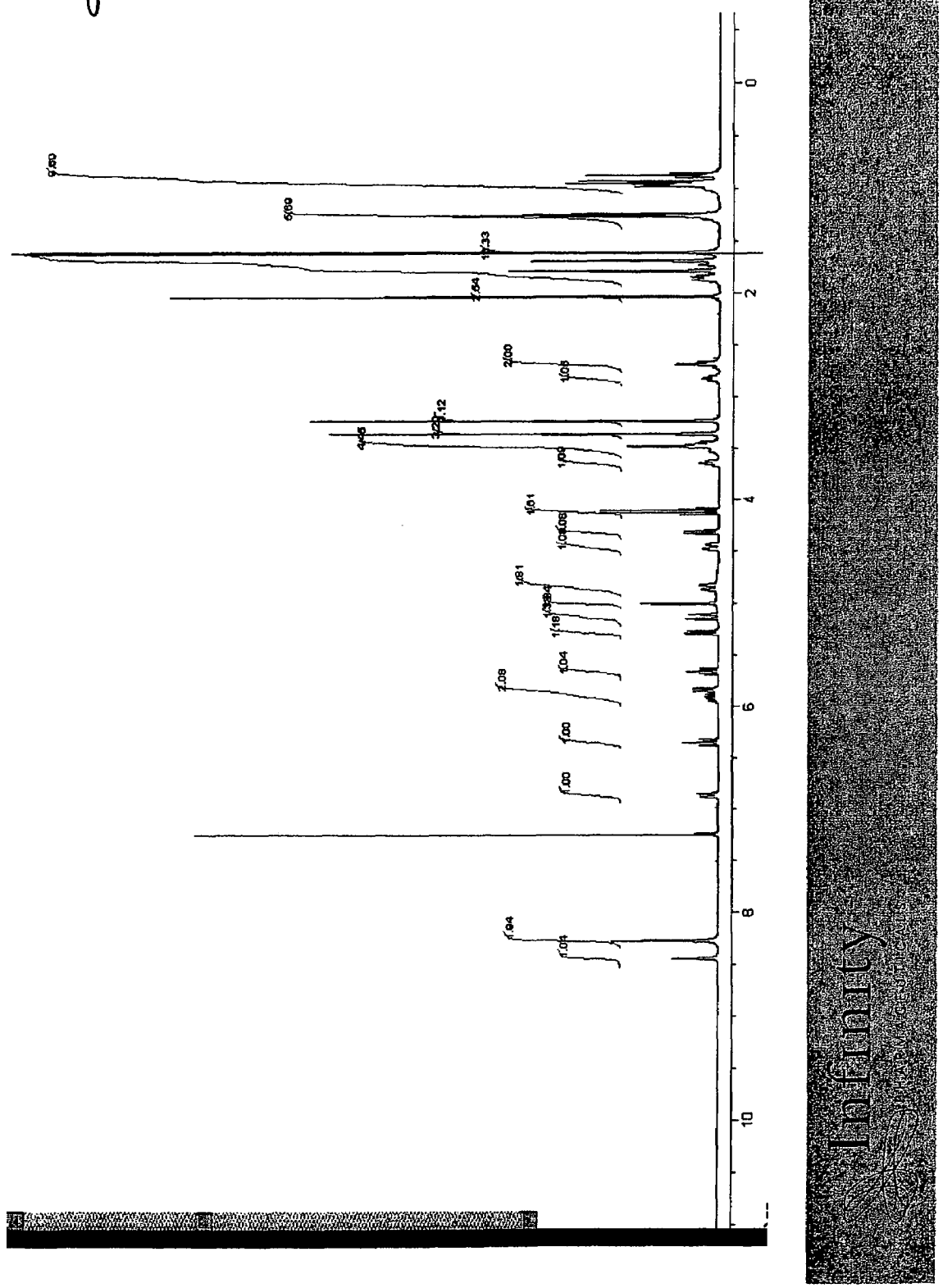
FIG. 54 depicts a $^1H$ NMR spectrum of the cyclic carbamate of the Hydroquinone of 17-AAG prepared according to the procedure described in Example 25.
Figure 55:
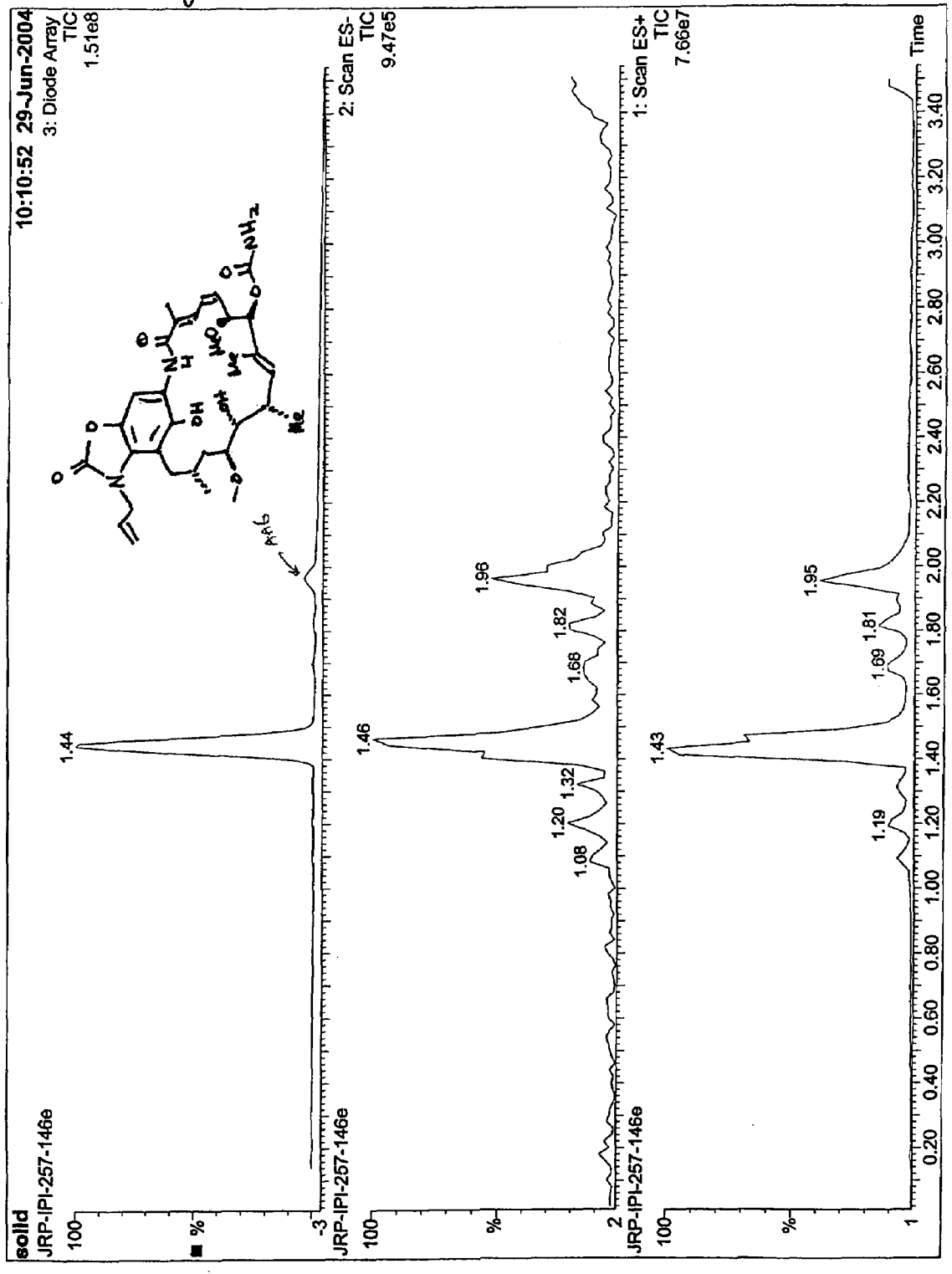
FIG. 55 depicts chromatograms from a LCMS analysis of the cyclic carbamate of the Hydroquinone of 17-AAG prepared according to the procedure described in Example 25.
Figure 56:
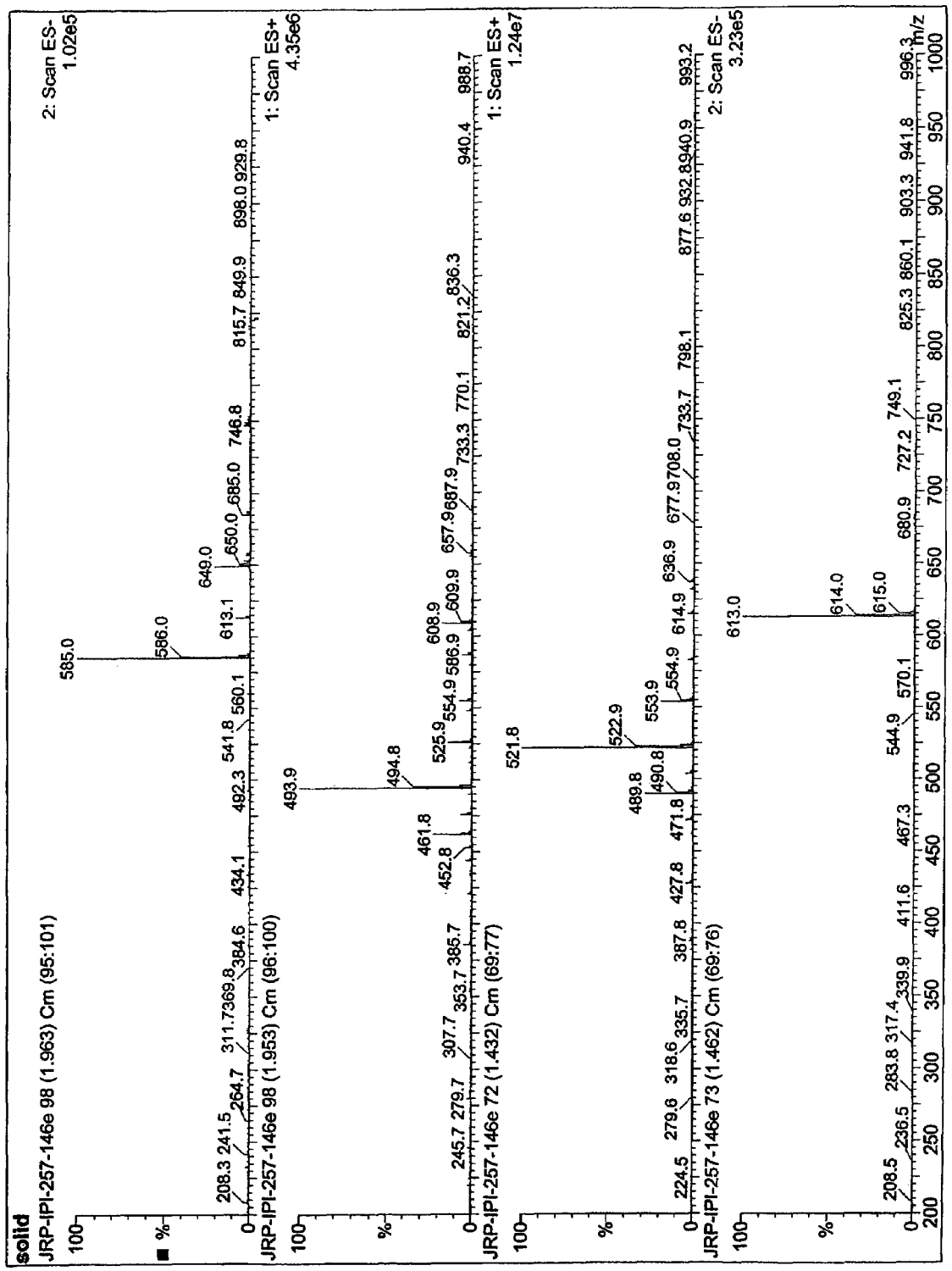
FIG. 56 depicts a mass spectrum from a LCMS analysis of the cyclic carbamate of the Hydroquinone of 17-AAG prepared according to the procedure described in Example 25.
Figure 57:
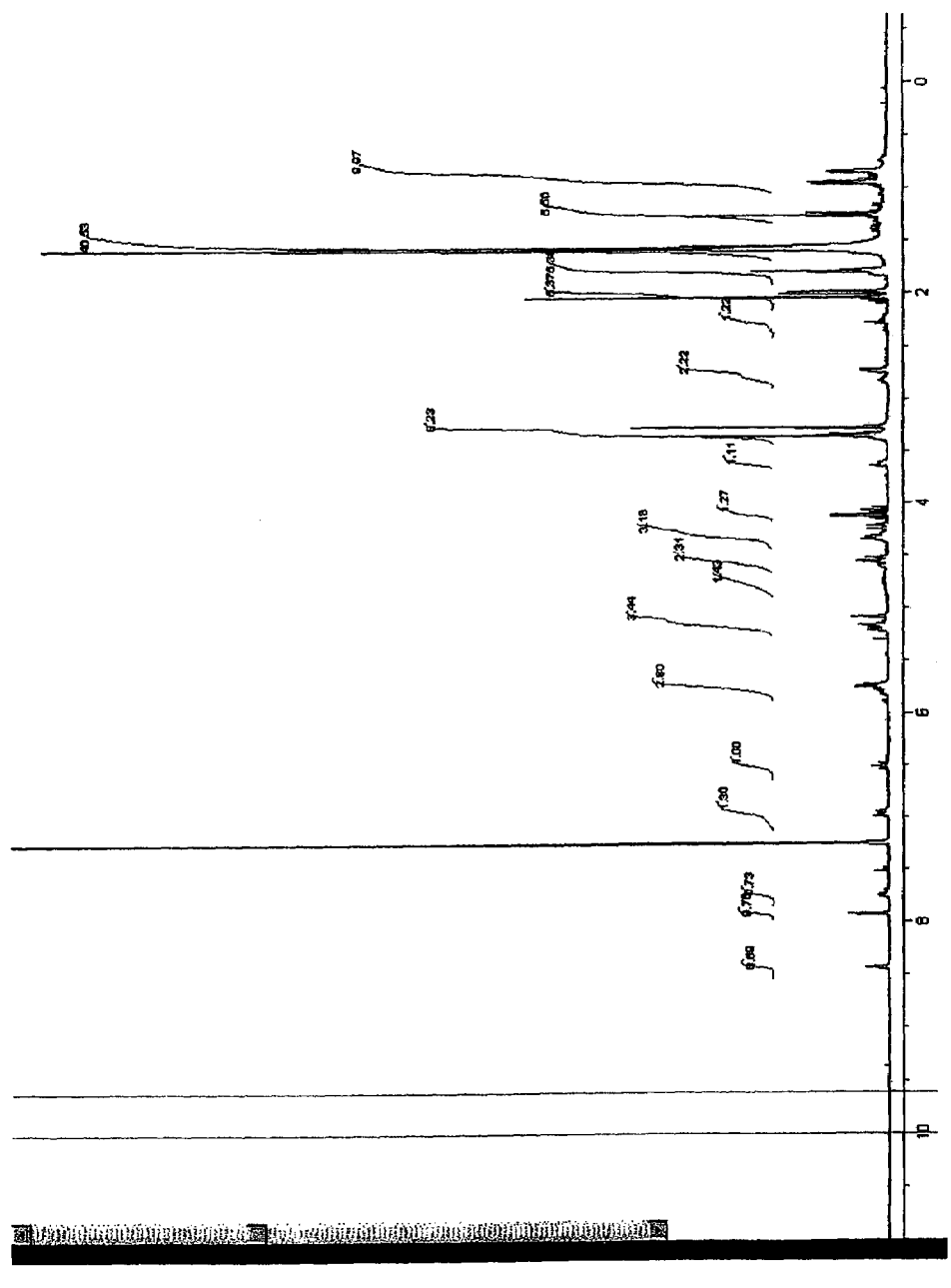
FIG. 57 depicts a $^1H$ NMR spectrum of the lactam of the Hydroquinone of 17-AAG prepared according to the procedure described in Example 26.
Figures 58, 58A:
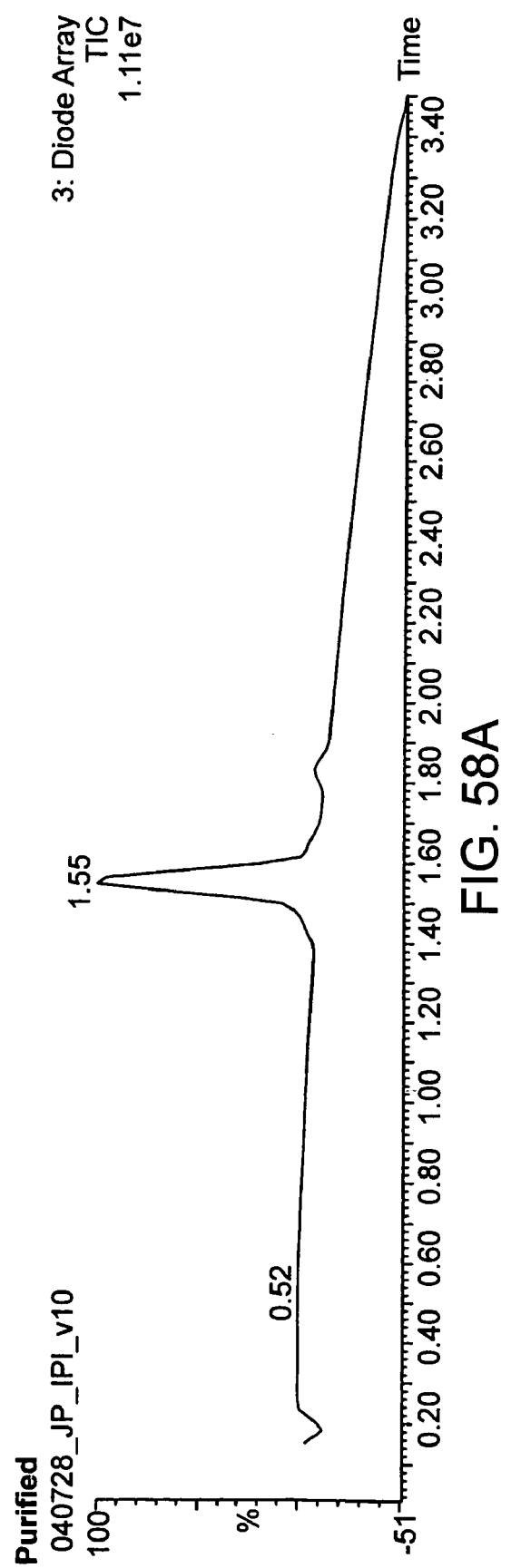
FIG. 58 depicts chromatograms from a LCMS analysis of the lactam of the Hydroquinone of 17-AAG prepared according to the procedure described in Example 26.
Figure 58B:
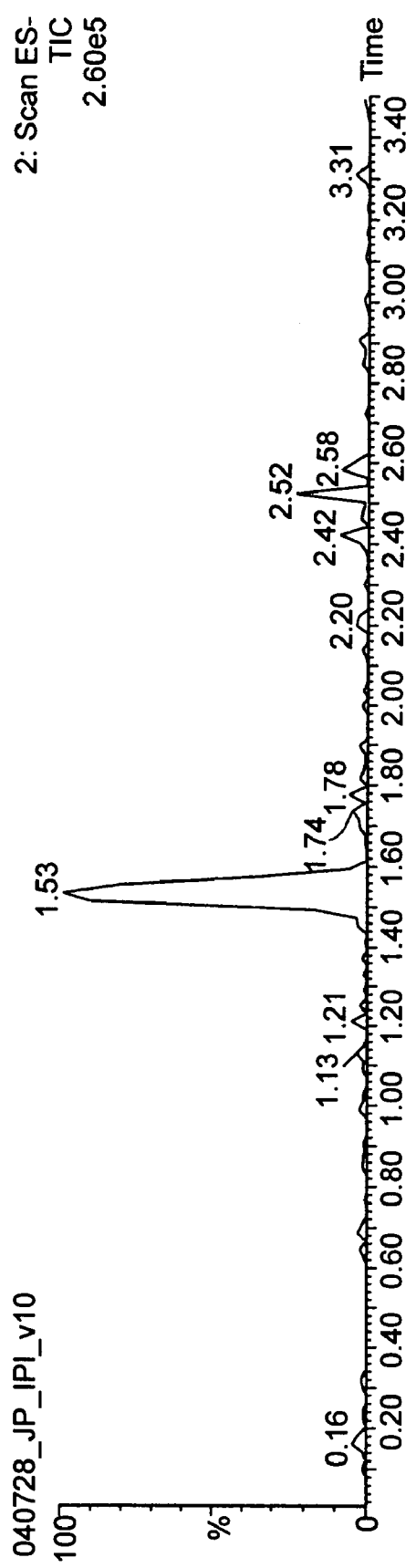
Figure 58C:
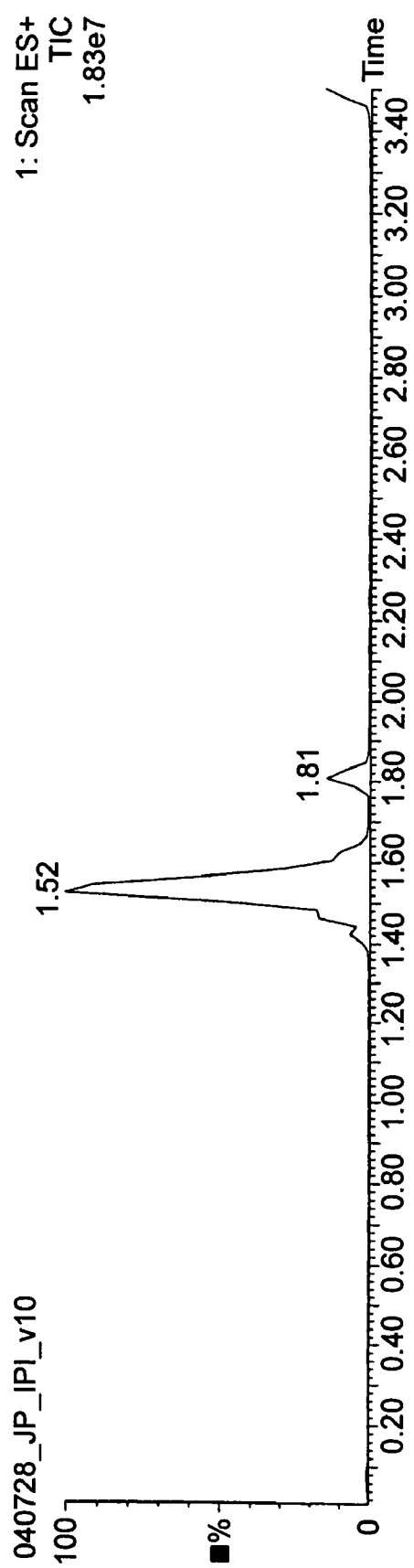
Figure 59B:
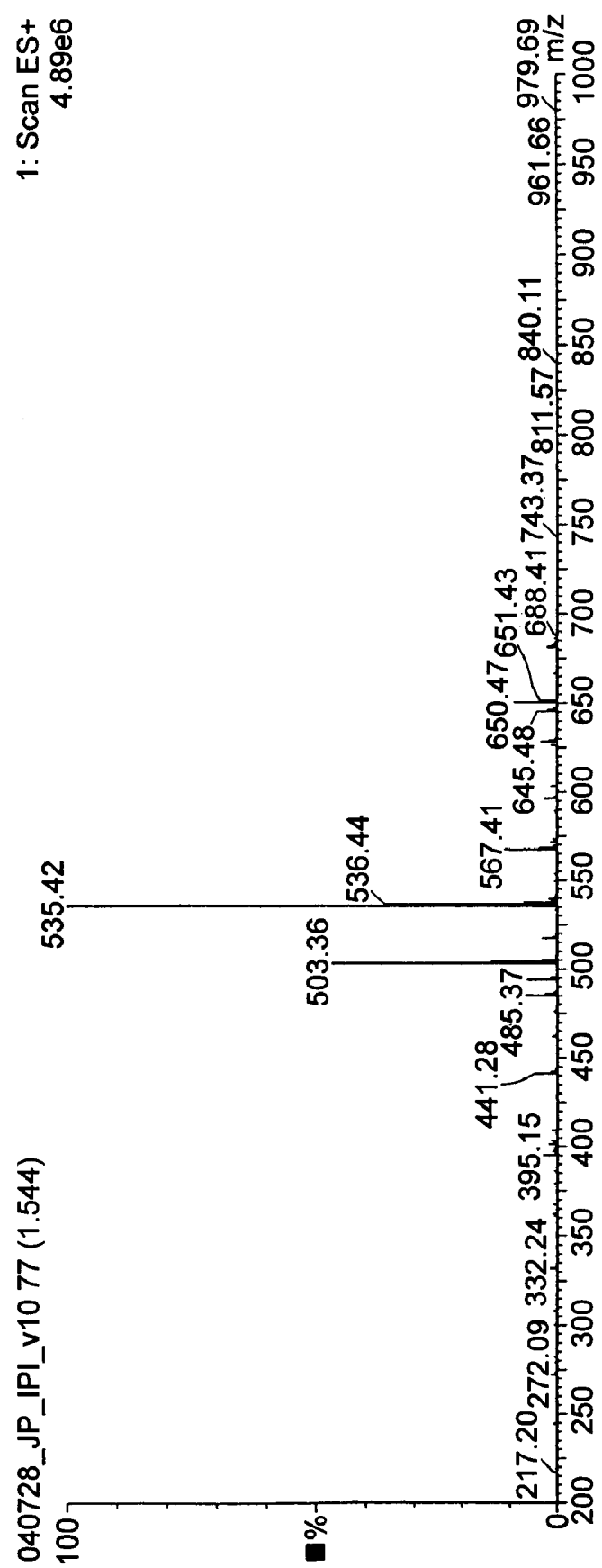
FIG. 59 depicts a mass spectrum from a LCMS analysis of the lactam of the Hydroquinone of 17-AAG prepared according to the procedure described in Example 26.
Figure 60:
FIG. 60 depicts a $^1H$ NMR spectrum of a 17-amino derivative of the Hydroquinone of 17-AAG prepared according to the procedure described in Example 27.
Figure 61:
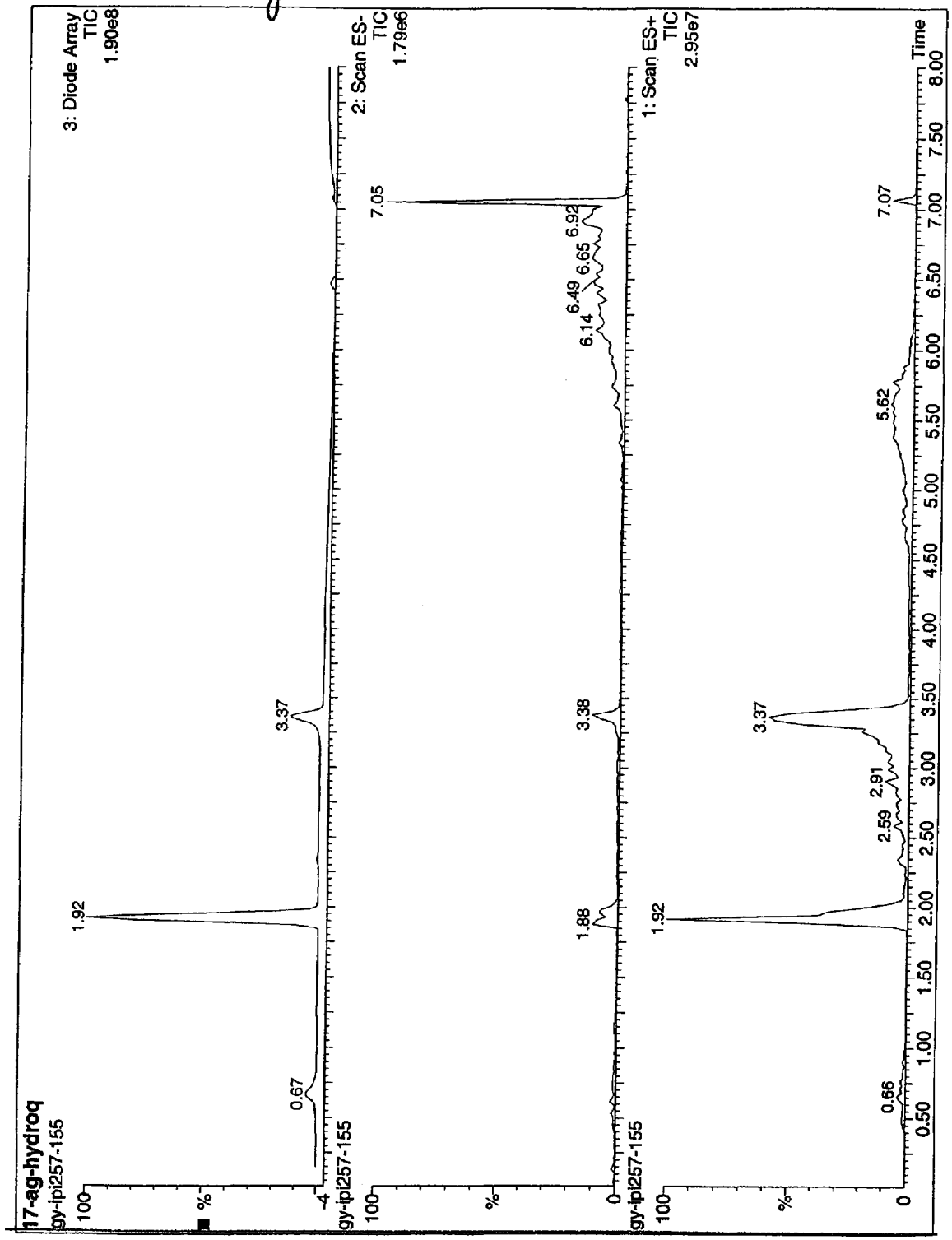
FIG. 61 depicts chromatograms from a LCMS analysis of a 17-amino derivative of the Hydroquinone of 17-AAG prepared according to the procedure described in Example 27.
Figure 62:
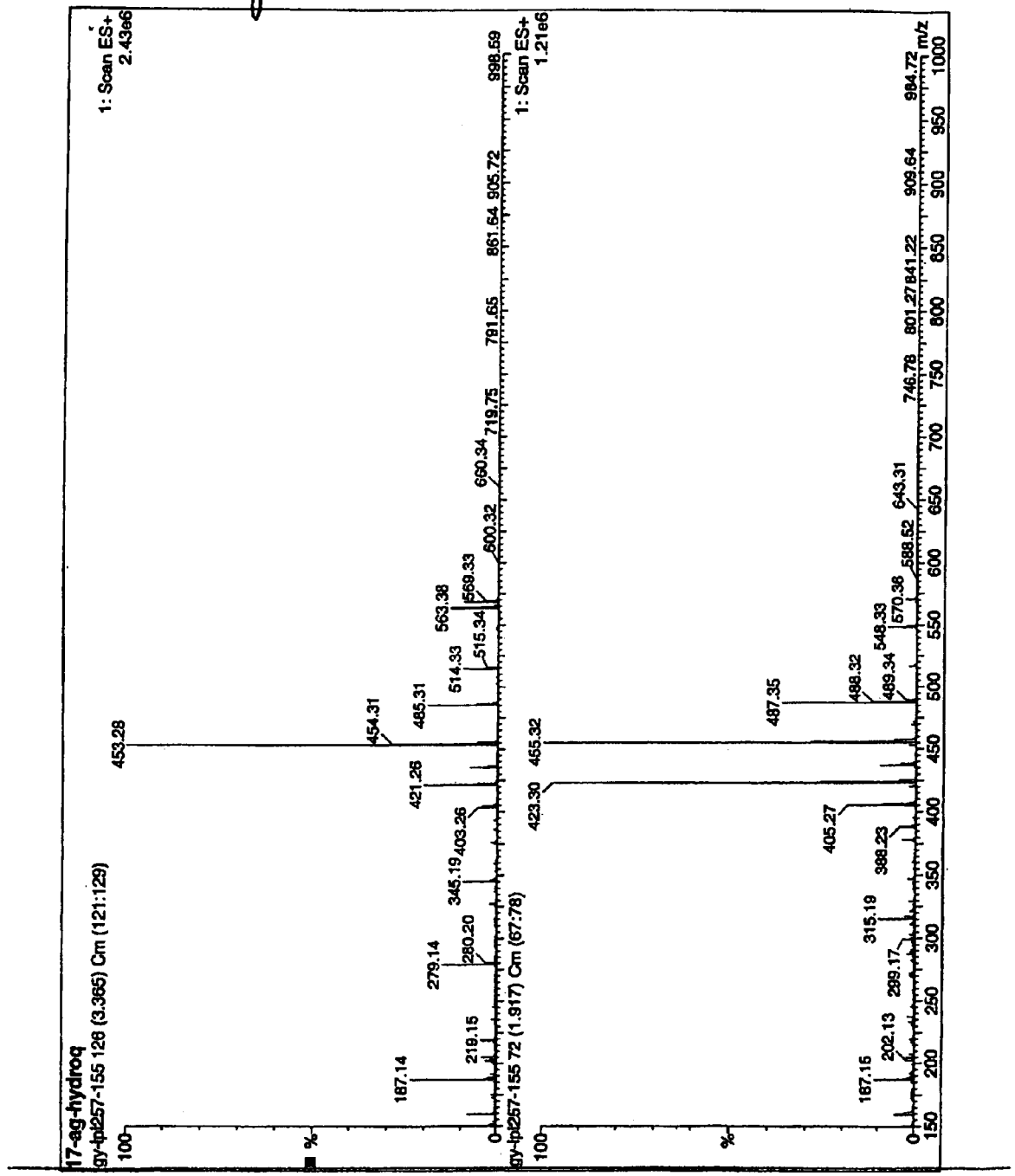
FIG. 62 depicts a mass spectrum from a LCMS analysis of a 17-amino derivative of the Hydroquinone of 17-AAG prepared according to the procedure described in Example 27.
Figure 63:
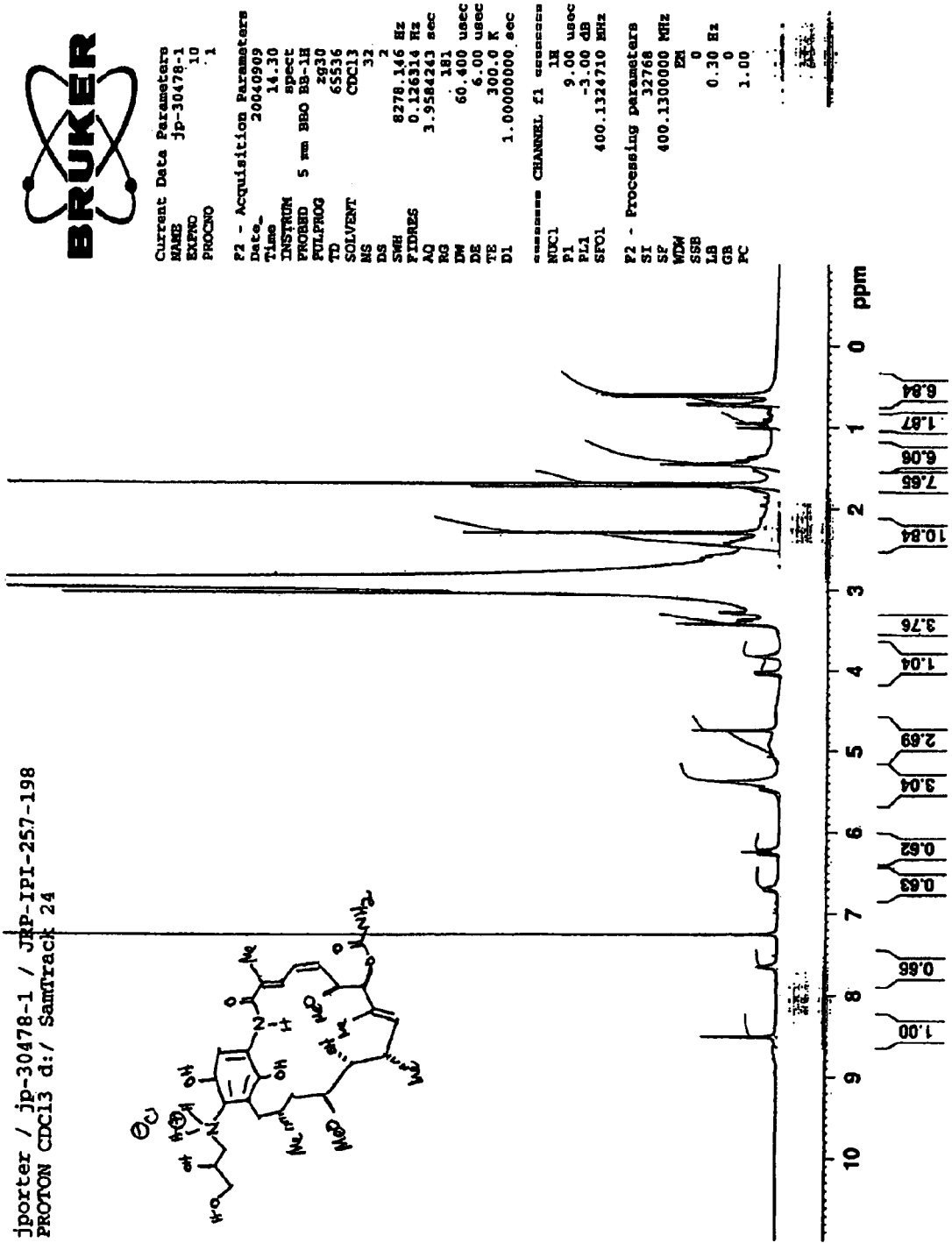
FIG. 63 depicts a $^1H$ NMR spectrum of a 17-(3-amino-propane-1,2-diol) derivative of the Hydroquinone of 17-AAG prepared according to the procedure described in Example 28.
Figure 64A:
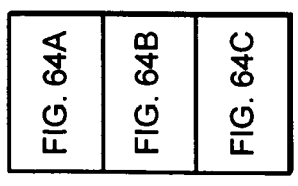
FIG. 64 depicts chromatograms from a LCMS analysis of a 17-(3-amino-propane-1,2-diol) derivative of the Hydroquinone of 17-AAG prepared according to the procedure described in Example 28.
Figure 64A:
Figure 64A:
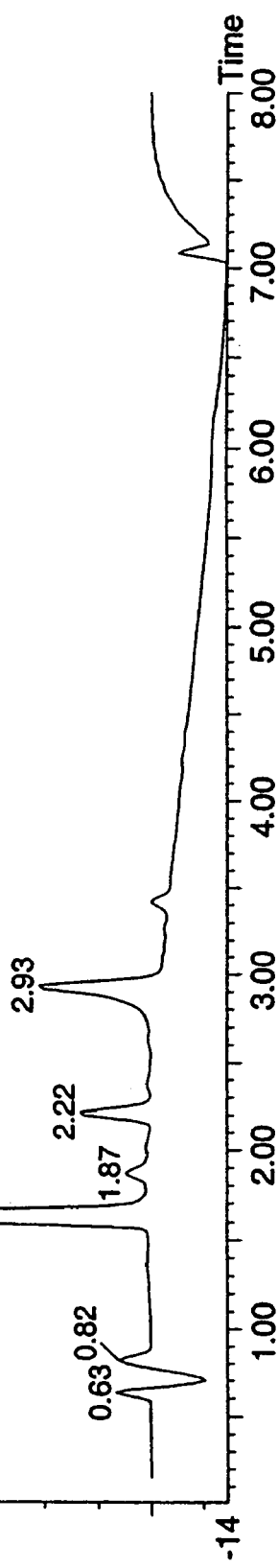
Figure 64B:
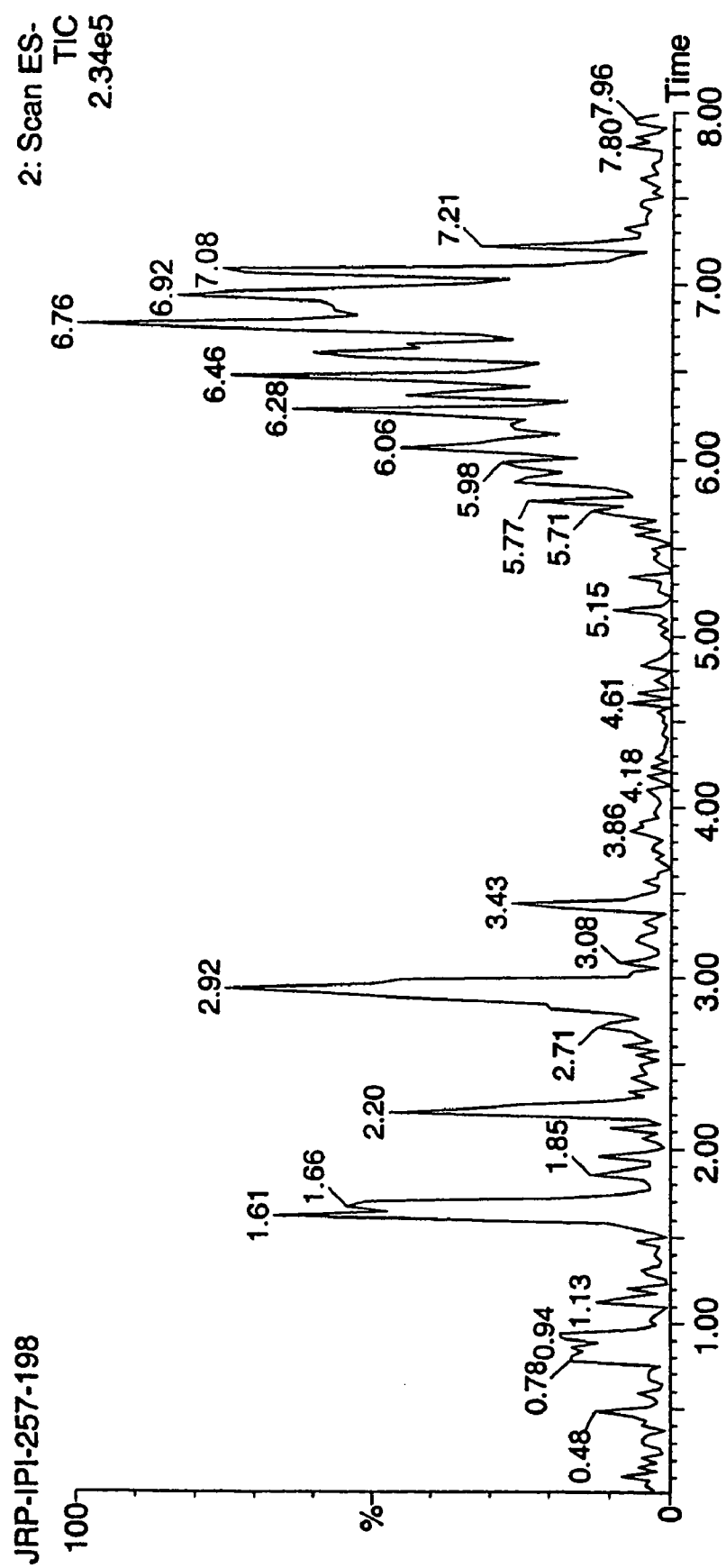
Figure 64C:
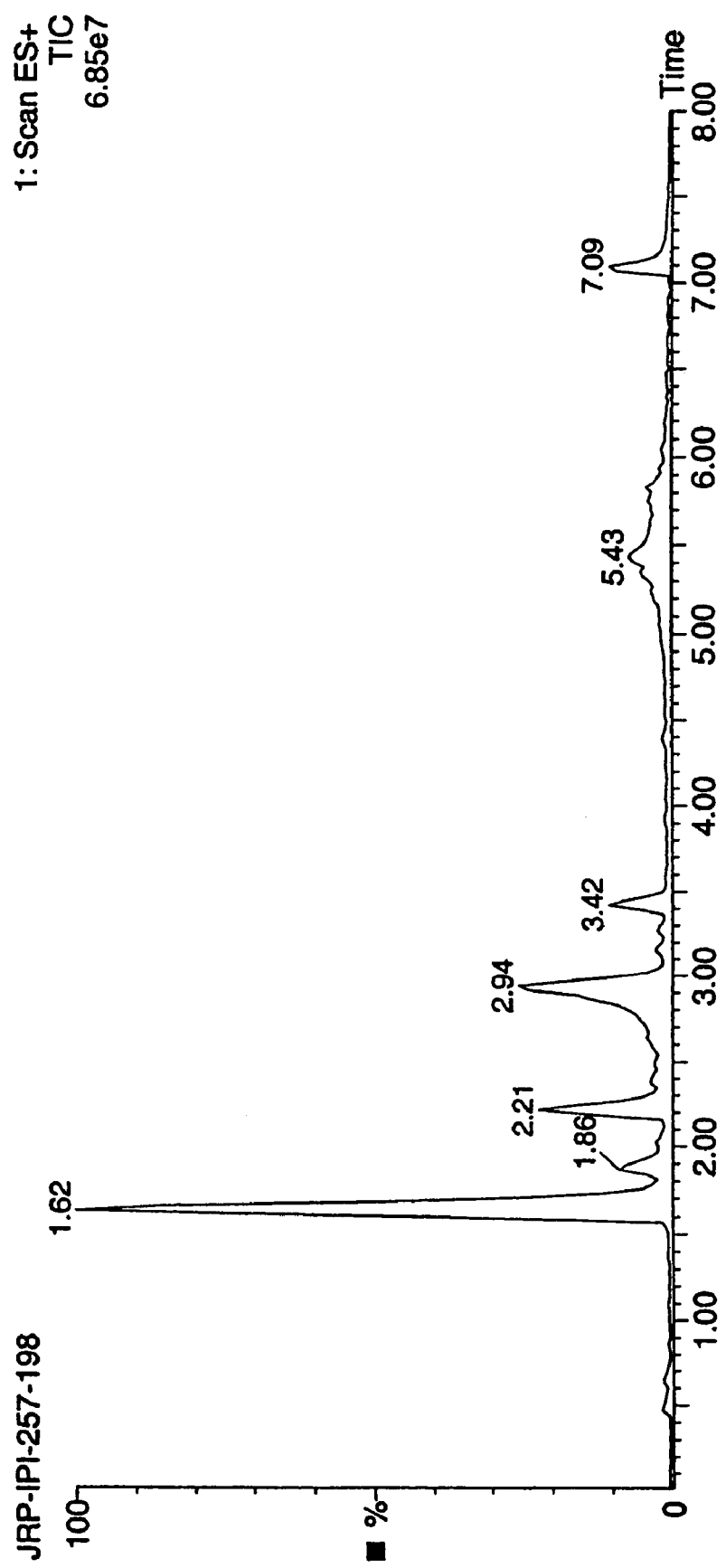
Figure 65A:
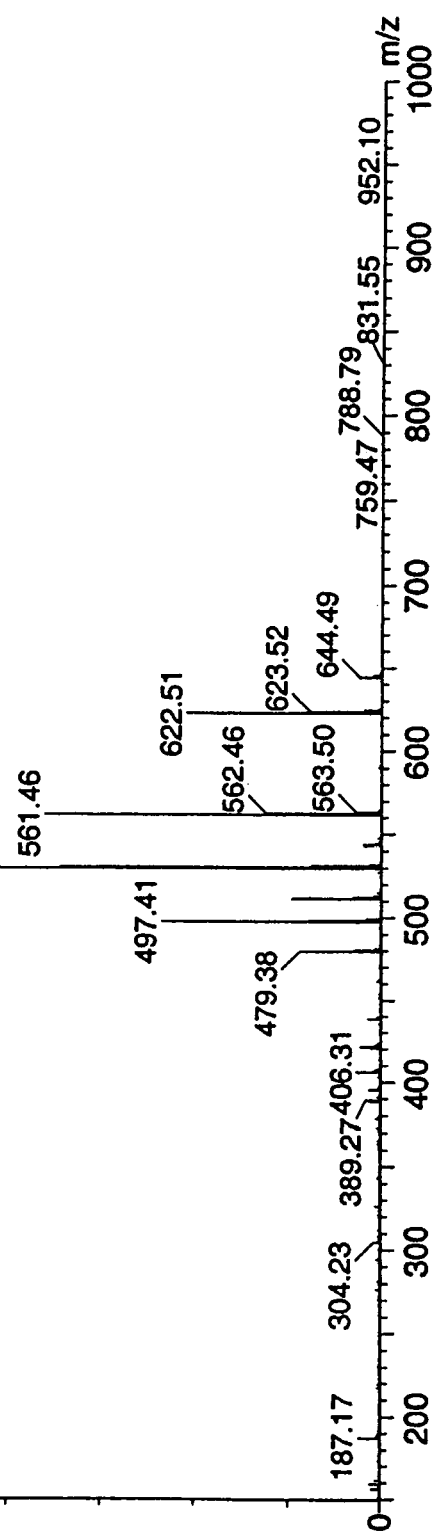
FIG. 65 depicts a mass spectrum from a LCMS analysis of a 17-(3-amino-propane-1,2-diol) derivative of the Hydroquinone of 17-AAG prepared according to the procedure described in Example 28.
Figure 66:
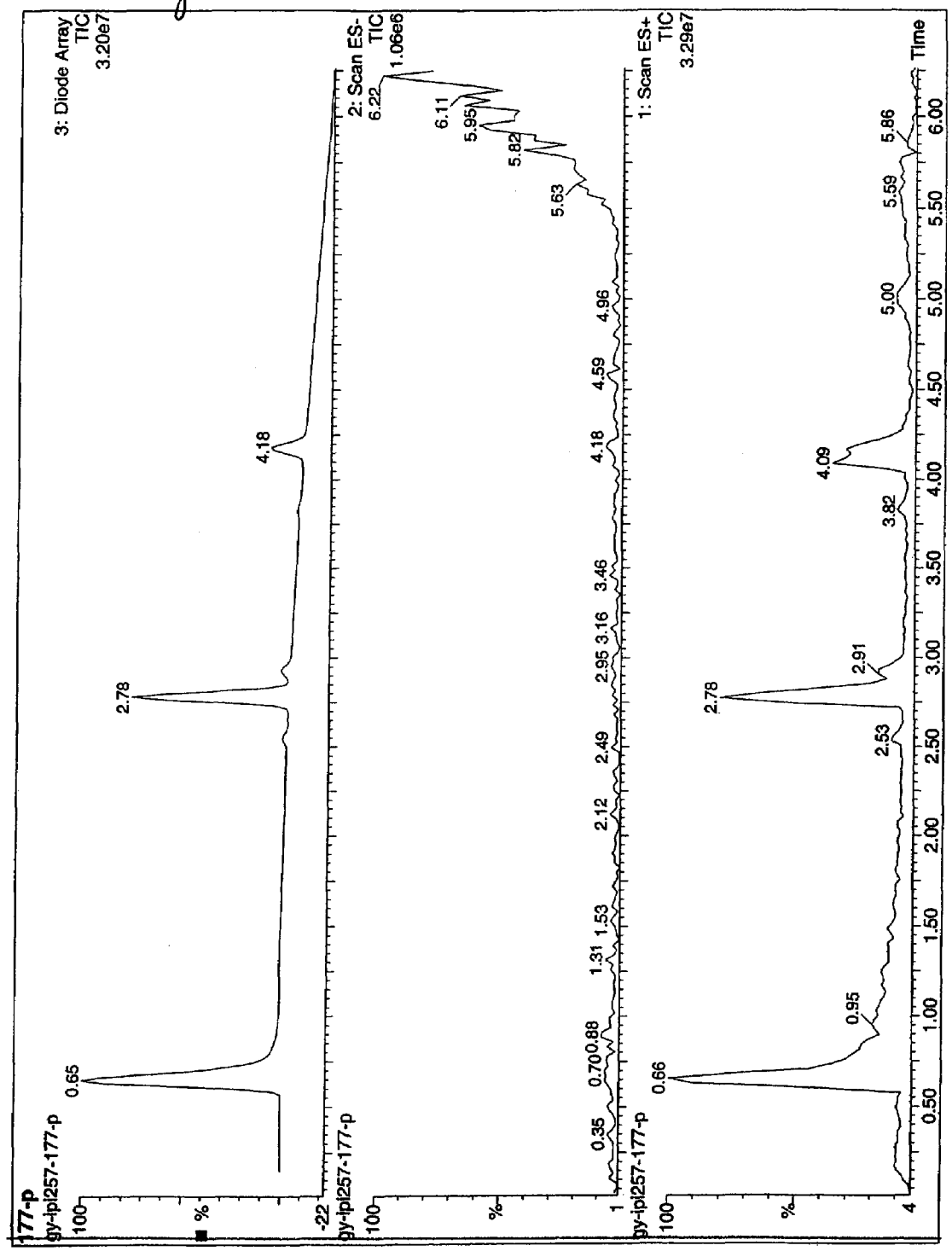
FIG. 66 depicts chromatograms from a LCMS analysis of a BODIPY derivative of the Hydroquinone of 17-AAG prepared according to the procedure described in Example 29.
Figure 67:
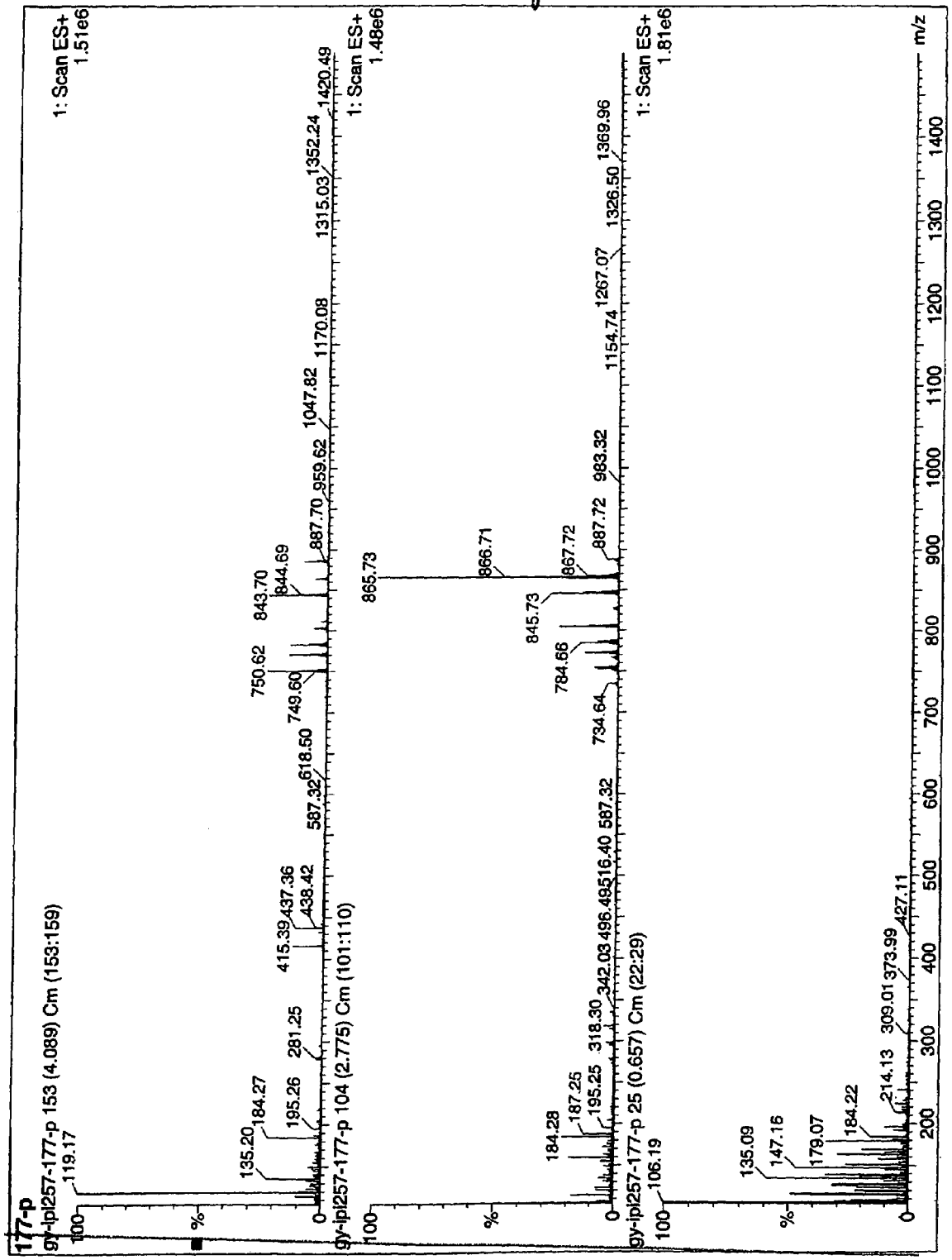
FIG. 67 depicts a mass spectrum from a LCMS analysis of a BODIPY derivative of the Hydroquinone of 17-AAG prepared according to the procedure described in Example 29.
Figure 68:
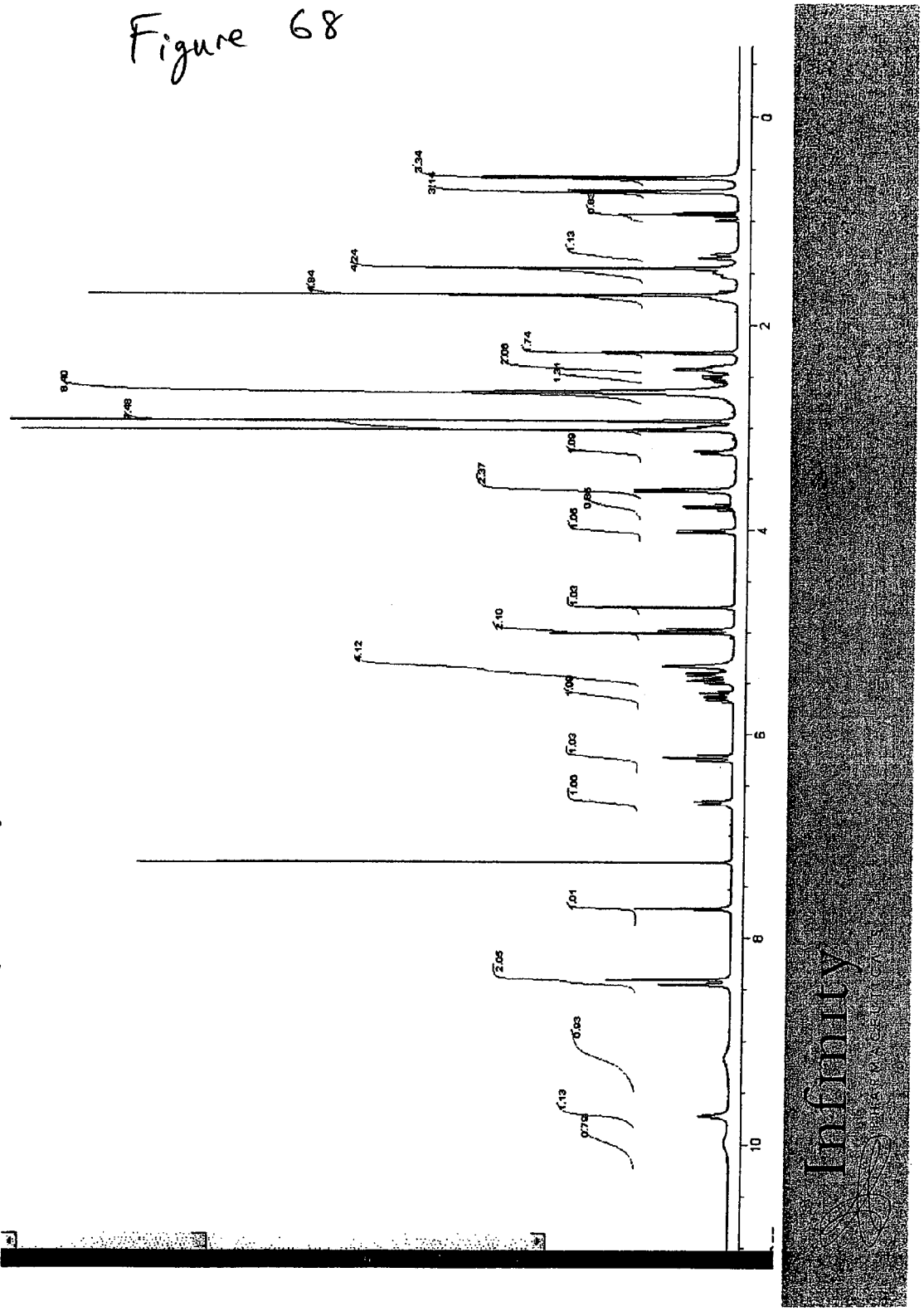
FIG. 68 depicts a $^1H$ NMR spectrum of the HBr Salt of the Hydroquinone of 17-AAG prepared according to the procedure described in Example 31.
Figure 69:
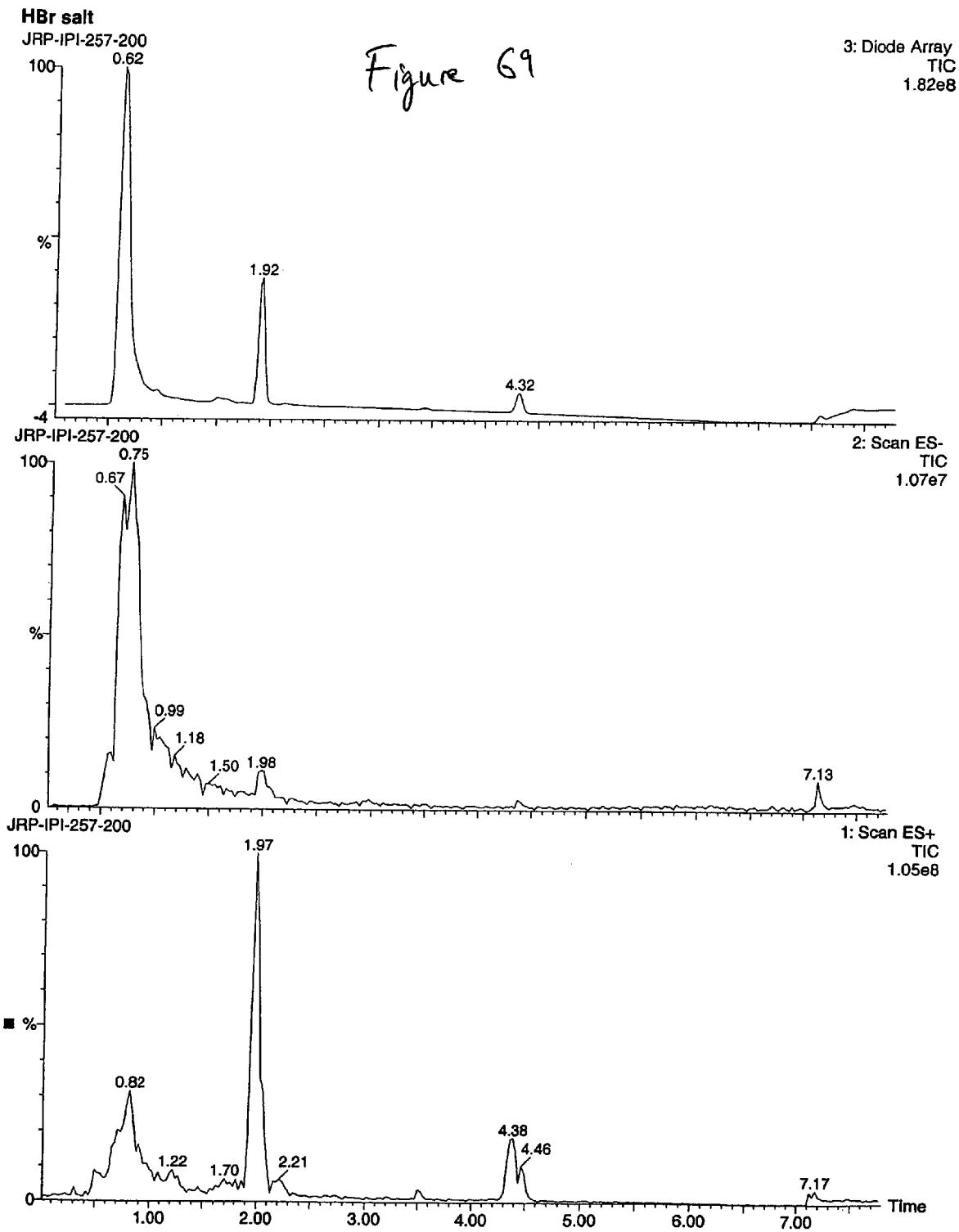
FIG. 69 depicts chromatograms from a LCMS analysis of the HBr Salt of the Hydroquinone of 17-AAG prepared according to the procedure described in Example 31.

The present invention provides pure and isolated, reduced forms of analogs of benzoquinone-containing ansamycins, salts and intermediates thereto. The present invention also provides methods for the use of these compounds in the treatment of diseases or conditions characterized by undesired cellular hyperproliferation, such as cancers, as well as other conditions and disorders associated with unwanted HSP90 activity or in which HSP90 plays a role in the cells involved in causing the disorder. The present invention provides reduced analogs of benzoquinone-containing ansamycins where the benzoquinone is reduced to a hydroquinone, and preferably isolated and purified as a salt form. In an alternative embodiment a compound of the present invention is co-crystallized with an amino acid salt. Such analogs, either with or without the amino acid salt, are remarkably water soluble (1-3 orders of magnitude greater solubility than the non-reduced form, e.g., 35 µg/mL 17-AAG vs. 1-3 mg/mL for the hydroquinone of 17-AAG and >200 mg/mL for the salt of the hydroquinone), and stable at room temperature; and they can be isolated and formulated for human administration without the problems associated with the formulation, storage and instability of the non-reduced parent forms and other formulations of ansamycins.

Definitions

The definitions of terms used herein are meant to incorporate the present state-of-the-art definitions recognized for each term in the chemical and pharmaceutical fields. Where appropriate, exemplification is provided. The definitions apply to the terms as they are used throughout this specification, unless otherwise limited in specific instances, either individually or as part of a larger group.

Where stereochemistry is not specifically indicated, all stereoisomers of the inventive compounds are included within the scope of the invention, as pure compounds as well as mixtures thereof. Unless otherwise indicated, individual enantiomers, diastereomers, geometrical isomers, and combinations and mixtures thereof are all encompassed by the present invention. Polymorphic crystalline forms and solvates are also encompassed within the scope of this invention.

As used herein, the term "amino acid" refers to molecules containing both a carboxylic acid moiety and an amino moiety. The carboxylic acid and amino moeities are as defined below. Both naturally occurring and synthetically derived amino acids are encompassed in the scope of this invention.

As used herein, the term "benzoquinone ansamycin" refers to a compound comprising a macrocyclic lactam, further comprising only one lactam in the ring and a benzoquinone moiety in the lactam ring, wherein said benzoquinone moiety has at least one nitrogen substituent, wherein one of said at least one nitrogen substitutents is part of said only one amide moiety in the lactam ring. Specific examples of naturally-occurring benzoquinone ansamycins that can be used in the present invention include, but are not limited to, geldanamycin and herbimycin. The term "geldanamycin analog" refers to a benzoquinone ansamycin that can be derived from geldanamycin e.g., by chemical manipulation; for example 17-allylamino-17-demethoxygeldanamycin (17-AAG) or 17-(2-dimethylaminoethy)amino-17-demethoxygeldanamycin (17-DMAG).

As used herein, the term "isolated" in connection with a compound of the present invention means the compound is not in a cell or organism and the compound is separated from some or all of the components that typically accompany it in nature.

As used herein, the term "pure" in connection with an isolated sample of a compound of the present invention means the isolated sample contains at least 60% by weight of the compound. Preferably, the isolated sample contains at least 70% by weight of the compound. More preferably, the isolated sample contains at least 80% by weight of the compound. Even more preferably, the isolated sample contains at least 90% by weight of the compound. Most preferably, the isolated sample contains at least 95% by weight of the compound. The purity of an isolated sample of a compound of the present invention may be assessed by a number of methods or a combination of them; e.g., thin-layer, preparative or flash chromatography, mass spectrometry, HPLC, NMR analysis, and the like.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "optionally substituted" refers to a chemical group, such as alkyl, cycloalkyl aryl, and the like, wherein one or more hydrogen may be replaced with a with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2$—. "Halide" designates the corresponding anion of the halogens, and "pseudohalide" has the definition set forth on 560 of "*Advanced Inorganic Chemistry*" by Cotton and Wilkinson.

The terms "amine" and "amino" are art-recognized and refer to both unsubstituted and substituted amines, e.g., a moiety that may be represented by the general formulas:

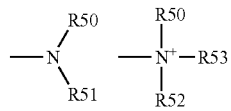

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

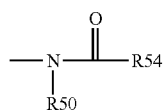

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

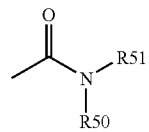

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carboxyl" is art recognized and includes such moieties as may be represented by the general formulas:

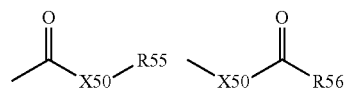

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "oxime" and "oxime ether" are art-recognized and refer to moieties that may be represented by the general formula:

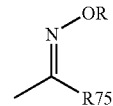

wherein R75 is hydrogen, alkyl, cycloalkyl, alkenyl, alkynyl, aryl, aralkyl, or —(CH$_2$)$_m$—R61. The moiety is an "oxime"

when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$-R61, where m and R61 are described above.

The term "sulfonate" is art recognized and refers to a moiety that may be represented by the general formula:

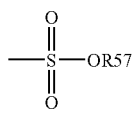

in which R57 is an electron pair, hydrogen, alkyl, cycloalkyl, or aryl.

The term "sulfate" is art recognized and includes a moiety that may be represented by the general formula:

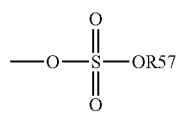

in which R57 is as defined above.

The term "sulfonamido" is art recognized and includes a moiety that may be represented by the general formula:

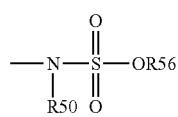

in which R50 and R56 are as defined above.

The term "sulfamoyl" is art-recognized and refers to a moiety that may be represented by the general formula:

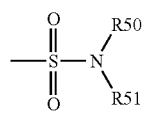

in which R50 and R51 are as defined above.

The term "sulfonyl" is art-recognized and refers to a moiety that may be represented by the general formula:

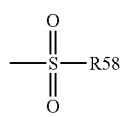

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

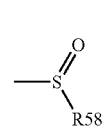

The term "phosphoryl" is art-recognized and may in general be represented by the formula:

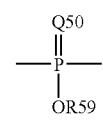

wherein Q50 represents S or O, and R59 represents hydrogen, a lower alkyl or an aryl. When used to substitute, e.g., an alkyl, the phosphoryl group of the phosphorylalkyl may be represented by the general formulas:

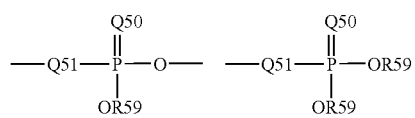

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

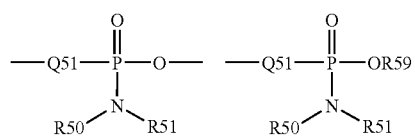

wherein Q51, R50, R51 and R59 are as defined above.

The term "phosphonamidite" is art-recognized and may be represented in the general formulas:

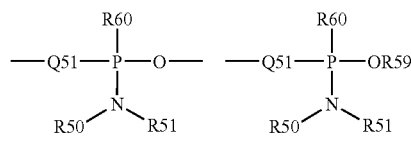

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—(CH$_2$)$_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization and chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991). Protected forms of the inventive compounds are included within the scope of this invention.

For purposes of this invention, the chemical elements are identified in accordance with the Periodic Table of the Elements, CAS version, *Handbook of Chemistry and Physics*, 67th Ed., 1986-87, inside cover.

The term "pharmaceutically acceptable salt" or "salt" refers to a salt of one or more compounds. Suitable pharmaceutically acceptable salts of compounds include acid addition salts which may, for example, be formed by mixing a solution of the compound with a solution of a pharmaceutically acceptable acid, such as hydrochloric acid, hydrobromic acid, sulfuric acid, fumaric acid, maleic acid, succinic acid, benzoic acid, acetic acid, citric acid, tartaric acid, phosphoric acid, carbonic acid, or the like. Where the compounds carry one or more acidic moieties, pharmaceutically acceptable salts may be formed by treatment of a solution of the compound with a solution of a pharmaceutically acceptable base, such as lithium hydroxide, sodium hydroxide, potassium hydroxide, tetraalkylammonium hydroxide, lithium carbonate, sodium carbonate, potassium carbonate, ammonia, alkylamines, or the like.

The term "pharmaceutically acceptable acid" refers to inorganic or organic acids that exhibit no substantial toxicity. Examples of pharmaceutically acceptable acids include, but are not limited to hydrochloric acid, hydrobromic acid, sulfuric acid, nitric acid, phenylsulfonic acid, methanesulfonic acid, fumaric acid, maleic acid, succinic acid, benzoic acid, acetic acid, citric acid, tartaric acid, phosphoric acid, carbonic acid, and the like.

The term "co-salt" or "co-crystal" refers to compositions in which the reduced salt form of the ansamycin is present with at least one other salt, such as a salt of an amino acid.

The term "subject" as used herein, refers to an animal, typically a mammal or a human, that will be or has been the object of treatment, observation, and/or experiment. When the term is used in conjunction with administration of a compound or drug, then the subject has been the object of treatment, observation, and/or administration of the compound or drug.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "therapeutically effective amount" as used herein, means that amount of active compound or pharmaceutical agent that elicits a biological or medicinal response in a cell culture, tissue system, animal, or human that is being sought by a researcher, veterinarian, clinician, or physician, which includes alleviation of the symptoms of the disease, condition, or disorder being treated.

The term "composition" is intended to encompass a product comprising the specified ingredients in the specified amounts, as well as any product that results, directly or indirectly, from combinations of the specified ingredients in the specified amounts, particularly co-salts such as the reduced ansamycin salt (e.g., sulfate) with a salt of an amino acid (e.g., glycine).

The term "HSP90 mediated disorder" or "disorder mediated by cells expressing HSP90" refers to pathological and disease conditions in which HSP90 plays a role. Such roles can be directly related to the pathological condition or can be indirectly related to the condition. The common feature to this class of conditions is that the condition can be ameliorated by inhibiting the activity, function, or association with other proteins of HSP90.

The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

Description of Certain Preferred Embodiments

The present invention addresses the need to generate soluble forms of ansamycins, particularly members of the benzoquinone-containing families, such as geldanamycin. Members of these classes of macrocyclic molecules tend to be very insoluble, leading to poor profiles as potential drugs (for example, 17-AAG has a solubility of only 100 µg/mL in an aqueous solution). The present invention solves these problems by providing general reaction schemes that can be used to create analogs of these molecules that have improved solubility. The reaction schemes include reducing the quinone of such molecules to form a hydroquinone, and trapping it as a salt, such as HCl or $H_2SO_4$ salt. Remarkably, for example, the hydroquinone HCl salt of 17-AAG has a solubility>about 200 mg/mL.

Compounds

The present invention also provides the isolated analogs of benzoquinone-containing ansamycins, wherein the benzoquinone is reduced to a hydroquinone and trapped as the ammonium salt by reaction of the hydroquinone with a suitable organic or inorganic acid.

In one embodiment, the present invention provides a pure and isolated compound of formula 1:

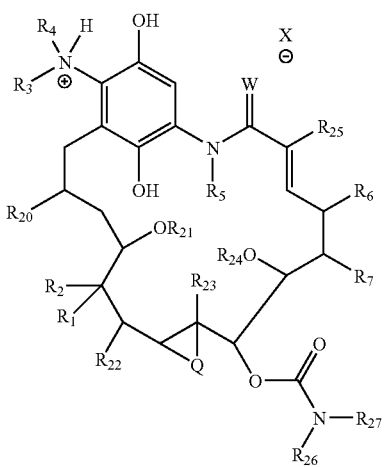

1 or the free base thereof;
wherein independently for each occurrence:
W is oxygen or sulfur;
Q is oxygen, NR, N(acyl) or a bond;
$X^-$ is a conjugate base of a pharmaceutically acceptable acid;

R for each occurrence is independently selected from the group consisting of hydrogen, alkyl, cycloalkyl, heterocycloalkyl, aralkyl, heteroaryl, and heteroaralkyl;

$R_1$ is hydroxyl, alkoxyl, $-OC(O)R_8$, $-OC(O)OR_9$, $-OC(O)NR_{10}R_{11}$, $-OSO_2R_{12}$, $-OC(O)NHSO_2NR_{13}R_{14}$, $-NR_{13}R_{14}$, or halide; and $R_2$ is hydrogen, alkyl, or aralkyl; or $R_1$ and $R_2$ taken together, along with the carbon to which they are bonded, represent $-(C=O)-$, $-(C=N-OR)-$, $-(C=N-NHR)-$, or $-(C=N-R)-$;

$R_3$ and $R_4$ are each independently selected from the group consisting of hydrogen, alkyl, alkenyl, alkynyl, aryl, cycloalkyl, heterocycloalkyl, aralkyl, heteroaryl, heteroaralkyl, and $-[(CR_2)_p]-R_{16}$; or $R_3$ taken together with $R_4$ represent a 4-8 membered optionally substituted heterocyclic ring;

$R_5$ is selected from the group consisting of H, alkyl, aralkyl, and a group having the formula 1a:

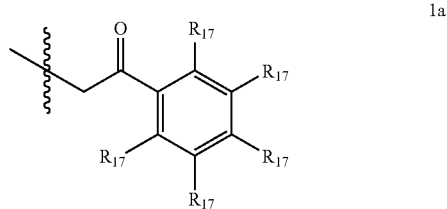

1a wherein $R_{17}$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, $-COR_{18}$, $-CO_2R_{18}$, $-N(R_{18})CO_2R_{19}$, $-OC(O)N(R_{18})(R_{19})$, $-N(R_{18})SO_2R_{19}$, $-N(R_{18})C(O)N(R_{18})(R_{19})$, and $-CH_2O$-heterocyclyl;

$R_6$ and $R_7$ are both hydrogen; or $R_6$ and $R_7$ taken together form a bond;

$R_8$ is hydrogen, alkyl, alkenyl, alkynyl, aryl, cycloalkyl, heterocycloalkyl, aralkyl, heteroaryl, heteroaralkyl, or $-[(CR_2)_p]-R_{16}$;

$R_9$ is alkyl, alkenyl, alkynyl, aryl, cycloalkyl, heterocycloalkyl, aralkyl, heteroaryl, heteroaralkyl, or $-[(CR_2)_p]-R_{16}$;

$R_{10}$ and $R_{11}$ are each independently selected from the group consisting of hydrogen, alkyl, alkenyl, alkynyl, aryl, cycloalkyl, heterocycloalkyl, aralkyl, heteroaryl, heteroaralkyl, and $-[(CR_2)_p]-R_{16}$; or $R_{10}$ and $R_{11}$ taken together with the nitrogen to which they are bonded represent a 4-8 membered optionally substituted heterocyclic ring;

$R_{12}$ is alkyl, alkenyl, alkynyl, aryl, cycloalkyl, heterocycloalkyl, aralkyl, heteroaryl, heteroaralkyl, or $-[(CR_2)_p]-R_{16}$;

$R_{13}$ and $R_{14}$ are each independently selected from the group consisting of hydrogen, alkyl, alkenyl, alkynyl, aryl, cycloalkyl, heterocycloalkyl, aralkyl, heteroaryl, heteroaralkyl, and $-[(CR_2)_p]-R_{16}$; or $R_{13}$ and $R_{14}$ taken together with the nitrogen to which they are bonded represent a 4-8 membered optionally substituted heterocyclic ring;

$R_{16}$ for each occurrence is independently selected from the group consisting of hydrogen, hydroxyl, acylamino, $-N(R_{18})COR_{19}$, $-N(R_{18})C(O)OR_{19}$, $-N(R_{18})SO_2(R_{19})$, $-CON(R_{18})(R_{19})$, $-OC(O)N(R_{18})(R_{19})$, $-SO_2N(R_{18})(R_{19})$, $-N(R_{18})(R_{19})$, $-OC(O)OR_{18}$, $-COOR_{18}$, $-C(O)N(OH)(R_{18})$, $-OS(O)_2OR_{18}$, $-S(O)_2OR_{18}$, $-OP(O)(OR_{18})(OR_{19})$, $-N(R_{18})P(O)(OR_{18})(OR_{19})$, and $-P(O)(OR_{18})(OR_{19})$;

p is 1, 2, 3, 4, 5, or 6;

$R_{18}$ for each occurrence is independently selected from the group consisting of hydrogen, alkyl, aryl, cycloalkyl, heterocycloalkyl, aralkyl, heteroaryl, and heteroaralkyl;

$R_{19}$ for each occurrence is independently selected from the group consisting of hydrogen, alkyl, aryl, cycloalkyl, heterocycloalkyl, aralkyl, heteroaryl, and heteroaralkyl; or $R_{18}$ taken together with $R_{19}$ represent a 4-8 membered optionally substituted ring;

$R_{20}$, $R_{21}$, $R_{22}$, $R_{24}$, and $R_{25}$, for each occurrence are independently alkyl;

$R_{23}$ is alkyl, —$CH_2OH$, —CHO, —$COOR_{18}$, or —CH$(OR_{18})_2$;

$R_{26}$ and $R_{27}$ for each occurrence are independently selected from the group consisting of hydrogen, alkyl, aryl, cycloalkyl, heterocycloalkyl, aralkyl, heteroaryl, and heteroaralkyl;

provided that when $R_1$ is hydroxyl, $R_2$ is hydrogen, $R_6$ and $R_7$ taken together form a double bond, $R_{20}$ is methyl, $R_{21}$ is methyl, $R_{22}$ is methyl, $R_{23}$ is methyl, $R_{24}$ is methyl, $R_{25}$ is methyl, $R_{26}$ is hydrogen, $R_{27}$ is hydrogen, Q is a bond, and W is oxygen; $R_3$ and $R_4$ are not both hydrogen nor when taken together represent an unsubstituted azetidine; and the absolute stereochemistry at a stereogenic center of formula 1 may be R or S or a mixture thereof and the stereochemistry of a double bond may be E or Z or a mixture thereof.

In certain embodiments, the present invention relates to the aforementioned compound and the attendant definitions, provided that when RI is hydroxyl, $R_2$ is hydrogen, $R_5$ is hydrogen, $R_6$ and $R_7$ taken together form a double bond, $R_{20}$ is methyl, $R_{21}$ is methyl, $R_{22}$ is methyl, $R_{23}$ is methyl, $R_{24}$ is methyl, $R_{25}$ is methyl, $R_{26}$ is hydrogen, $R_{27}$ is hydrogen, Q is a bond, and W is oxygen; $R_3$ and $R_4$ are not both hydrogen nor when taken together represent an unsubstituted azetidine.

In certain embodiments, the present invention relates to the aforementioned compound and the attendant definitions, wherein $R_{20}$, $R_{21}$, $R_{22}$, $R_{23}$, $R_{24}$, and $R_{25}$ are methyl; $R_{26}$ is hydrogen, Q is a bond; and W is oxygen.

In certain embodiments, the present invention relates to the aforementioned compound and the attendant definitions, wherein said pharmaceutically acceptable acid has a pKa between about −10 and about 7 in water.

In certain embodiments, the present invention relates to the aforementioned compound and the attendant definitions, wherein said pharmaceutically acceptable acid has a pKa between about −10 and about 4 in water.

In certain embodiments, the present invention relates to the aforementioned compound and the attendant definitions, wherein said pharmaceutically acceptable acid has a pKa between about −10 and about 1 in water.

In certain embodiments, the present invention relates to the aforementioned compound and the attendant definitions, wherein said pharmaceutically acceptable acid has a pKa between about −10 and about -3 in water.

In certain embodiments, the present invention relates to the aforementioned compound and the attendant definitions, wherein $X^-$ is selected from the group consisting of chloride, bromide, iodide, $H_2PO_4^-$, $HSO_4^-$, methylsulfonate, benzenesulfonate, p-toluenesulfonate, trifluoromethylsulfonate, 10-camphorsulfonate, naphthalene-1-sulfonic acid-5-sulfonate, ethan-1-sulfonic acid-2-sulfonate, cyclamic acid salt, thiocyanic acid salt, naphthalene-2-sulfonate, and oxalate.

In certain embodiments, the present invention relates to the aforementioned compound and the attendant definitions, wherein RI is hydroxyl or —$OC(O)R_8$.

In certain embodiments, the present invention relates to the aforementioned compound and the attendant definitions, wherein $R_2$ is hydrogen.

In certain embodiments, the present invention relates to the aforementioned compound and the attendant definitions, wherein $R_3$ and $R_4$ are independently hydrogen, alkyl, alkenyl, alkynyl, cycloalkyl, aralkyl, heteroaralkyl, or —$[(CR_2)_p]$—$R_{16}$.

In certain embodiments, the present invention relates to the aforementioned compound and the attendant definitions, wherein $R_5$ is hydrogen or has a formula 1a:

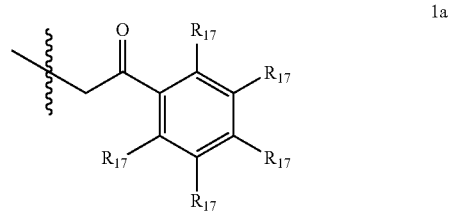

wherein $R_{17}$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —$COR_{18}$, —$CO_2R_{18}$, —$N(R_{18})CO_2R_{19}$, —$OC(O)N(R_{18})(R_{19})$, —$N(R_{18})SO_2R_{19}$, —$N(R_{18})C(O)N(R_{18})(R_{19})$, and —$CH_2O$-heterocyclyl.

In certain embodiments, the present invention relates to the aforementioned compound and the attendant definitions, wherein $R_6$ and $R_7$ taken together form a double bond.

In certain embodiments, the present invention relates to the aforementioned compound and the attendant definitions, wherein $R_{27}$ is hydrogen.

In certain embodiments, the present invention relates to the aforementioned compound and the attendant definitions, wherein $R_1$ is hydroxyl or —$OC(O)R_8$; and $R_2$ is hydrogen.

In certain embodiments, the present invention relates to the aforementioned compound and the attendant definitions, wherein $R_1$ is hydroxyl or —$OC(O)R_8$; $R_2$ is hydrogen; and $R_3$ and $R_4$ are independently hydrogen, alkyl, alkenyl, alkynyl, cycloalkyl, aralkyl, heteroaralkyl, or —$[(CR_2)_p]$—$R_{16}$.

In certain embodiments, the present invention relates to the aforementioned compound and the attendant definitions, wherein RI is hydroxyl or —$OC(O)R_8$; $R_2$ is hydrogen; $R_3$ and $R_4$ are independently hydrogen, alkyl, alkenyl, alkynyl, cycloalkyl, aralkyl, heteroaralkyl, or —$[(CR_2)_p]$—$R_{16}$; and $R_5$ is hydrogen or has a formula 1a:

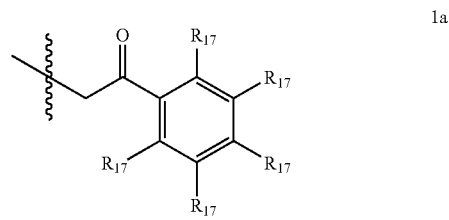

wherein $R_{17}$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —$COR_{18}$, —$CO_2R_{18}$, —$N(R_{18})CO_2R_{19}$, —$OC(O)N(R_{18})(R_{19})$, —$N(R_{18})SO_2R_{19}$, —$N(R_{18})C(O)N(R_{18})(R_{19})$, and —$CH_2O$-heterocyclyl.

In certain embodiments, the present invention relates to the aforementioned compound and the attendant definitions, wherein $R_1$ is hydroxyl or —OC(O)$R_8$; $R_2$ is hydrogen; $R_3$ and $R_4$ are independently hydrogen, alkyl, alkenyl, alkynyl, cycloalkyl, aralkyl, heteroaralkyl, or —[(CR$_2$)$_p$]—$R_{16}$; $R_5$ is hydrogen or has a formula 1a:

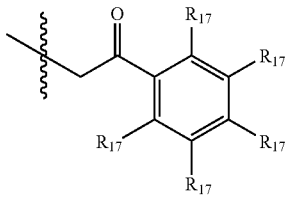

wherein $R_{17}$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —COR$_{18}$, —CO$_2$R$_{18}$, —N(R$_{18}$)CO$_2$R$_{19}$, —OC(O)N(R$_{18}$) (R$_{19}$), —N(R$_{18}$)SO$_2$R$_{19}$, —N(R$_{18}$)C(O)N(R$_{18}$)(R$_{19}$), and —CH$_2$O-heterocyclyl; and $R_6$ and $R_7$ taken together form a double bond.

In certain embodiments, the present invention relates to the aforementioned compound and the attendant definitions, wherein $R_1$ is hydroxyl or —OC(O)$R_8$; $R_2$ is hydrogen; $R_3$ and $R_4$ are independently hydrogen, alkyl, alkenyl, alkynyl, cycloalkyl, aralkyl, heteroaralkyl, or —[(CR$_2$)$_p$]—$R_{16}$; $R_5$ is hydrogen or has a formula 1a:

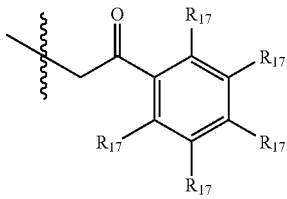

wherein $R_{17}$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —COR$_{18}$, —CO$_2$R$_{18}$, —N(R$_{18}$)CO$_2$R$_{19}$, —OC(O)N(R$_{18}$) (R$_{19}$), —N(R$_{18}$)SO$_2$R$_{19}$, —N(R$_{18}$)C(O)N(R$_{18}$)(R$_{19}$), and —CH$_2$O-heterocyclyl; $R_6$ and $R_7$ taken together form a double bond; and $R_{27}$ is hydrogen.

In certain embodiments, the present invention relates to the aforementioned compound and the attendant definitions, wherein $R_1$ is hydroxyl or —OC(O)$R_8$; $R_2$ is hydrogen; $R_3$ and $R_4$ are independently hydrogen, alkyl, alkenyl, alkynyl, cycloalkyl, aralkyl, heteroaralkyl, or —[(CR$_2$)$_p$]—$R_{16}$; $R_5$ is hydrogen or has a formula 1a:

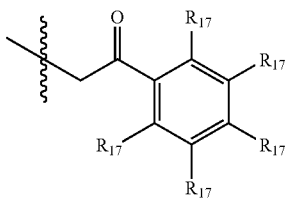

wherein $R_{17}$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —COR$_{18}$, —CO$_2$R$_{18}$, —N(R$_{18}$)CO$_2$R$_{19}$, —OC(O)N(R$_{18}$) (R$_{19}$), —N(R$_{18}$)SO$_2$R$_{19}$, —N(R$_{18}$)C(O)N(R$_{18}$)(R$_{19}$), and —CH$_2$O-heterocyclyl; $R_6$ and $R_7$ taken together form a double bond; $R_{27}$ is hydrogen; and X$^-$ is selected from the group consisting of chloride, bromide, iodide, H$_2$PO$_4^-$, HSO$_4^-$, methylsulfonate, benzenesulfonate, p-toluenesulfonate, trifluoromethylsulfonate, 10-camphorsulfonate, naphthalene-1-sulfonic acid-5-sulfonate, ethan-1-sulfonic acid-2-sulfonate, cyclamic acid salt, thiocyanic acid salt, naphthalene-2-sulfonate, and oxalate.

In certain embodiments, the present invention relates to the aforementioned compound and the attendant definitions, wherein $R_1$ is hydroxyl or —OC(O)$R_8$; $R_2$ is hydrogen; $R_3$ and $R_4$ are independently hydrogen, alkyl, alkenyl, alkynyl, cycloalkyl, aralkyl, heteroaralkyl, or —[(CR$_2$)$_p$]—$R_{16}$; $R_5$ is hydrogen or has a formula 1a:

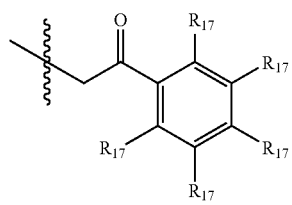

wherein $R_{17}$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —COR$_{18}$, —CO$_2$R$_{18}$, —N(R$_{18}$)CO$_2$R$_{19}$, —OC(O)N(R$_{18}$) (R$_{19}$), —N(R$_{18}$)SO$_2$R$_{19}$, —N(R$_{18}$)C(O)N(R$_{18}$)(R$_{19}$), and —CH$_2$O-heterocyclyl; $R_6$ and $R_7$ taken together form a double bond; $R_{27}$ is hydrogen; and X$^-$ is selected from the group consisting of chloride and bromide.

In one embodiment the present invention provides a pure and isolated compound with absolute sterochemistry as shown in formula 2:

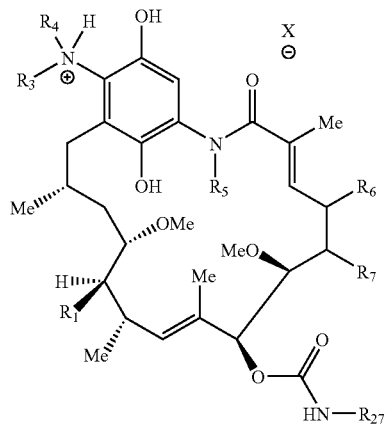

or the free base thereof;
wherein independently for each occurrence:

X⁻ is selected from the group consisting of chloride, bromide, iodide, $H_2PO_4^-$, $HSO_4^-$, methylsulfonate, benzenesulfonate, p-toluenesulfonate, trifluoromethylsulfonate, 10-camphorsulfonate, naphthalene-1-sulfonic acid-5-sulfonate, ethan-1-sulfonic acid-2-sulfonate, cyclamic acid salt, thiocyanic acid salt, naphthalene-2-sulfonate, and oxalate.

$R_1$ is hydroxyl or —OC(O)$R_8$;

$R_3$ and $R_4$ are hydrogen, alkyl, alkenyl, alkynyl, cycloalkyl, aralkyl, heteroaralkyl, or —[(CR$_2$)$_p$]—$R_{16}$; or $R_3$ taken together with $R_4$ represent a 4-8 membered optionally substituted heterocyclic ring;

$R_5$ is hydrogen or has a formula 1a:

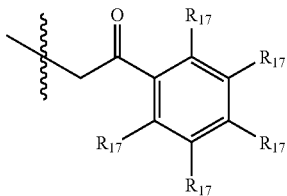

1a wherein $R_{17}$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —COR$_{18}$, —CO$_2$R$_{18}$, —N(R$_{18}$)CO$_2$R$_{19}$, —OC(O)N(R$_{18}$)(R$_{19}$), —N(R$_{18}$)SO$_2$R$_{19}$, —N(R$_{18}$)C(O)N(R$_{18}$)(R$_{19}$), and —CH$_2$O-heterocyclyl;

$R_6$ and $R_7$ are both hydrogen; or $R_6$ and $R_7$ taken together form a bond;

$R_8$ is hydrogen, alkyl, alkenyl, alkynyl, aryl, cycloalkyl, heterocycloalkyl, aralkyl, heteroaryl, heteroaralkyl, or —[(CR$_2$)$_p$]—$R_{16}$;

$R_{16}$ for each occurrence is independently selected from the group consisting of hydrogen, hydroxyl, acylamino, —N(R$_{18}$)COR$_{19}$, —N(R$_{18}$)C(O)OR$_{19}$, —N(R$_{18}$)SO$_2$(R$_{19}$), —CON(R$_{18}$)(R$_{19}$), —OC(O)N(R$_{18}$)(R$_{19}$), —SO$_2$N(R$_{18}$)(R$_{19}$), —N(R$_{18}$)(R$_{19}$), —OC(O)OR$_{18}$, —COOR$_{18}$, —C(O)N(OH)(R$_{18}$), —OS(O)$_2$OR$_{18}$, —S(O)$_2$OR$_{18}$, —OP(O)(OR$_{18}$)(OR$_{19}$), —N(R$_{18}$)P(O)(OR$_{18}$)(OR$_{19}$), and —P(O)(OR$_{18}$)(OR$_{19}$);

p is 1, 2, 3, 4, 5, or 6;

$R_{18}$ for each occurrence is independently selected from the group consisting of hydrogen, alkyl, aryl, cycloalkyl, heterocycloalkyl, aralkyl, heteroaryl, and heteroaralkyl;

$R_{19}$ for each occurrence is independently selected from the group consisting of hydrogen, alkyl, aryl, cycloalkyl, heterocycloalkyl, aralkyl, heteroaryl, and heteroaralkyl; or $R_{18}$ taken together with $R_{19}$ represent a 4-8 membered optionally substituted ring;

$R_{27}$ is hydrogen, alkyl, aryl, cycloalkyl, heterocycloalkyl, aralkyl, heteroaryl, or heteroaralkyl;

provided that when $R_1$ is hydroxyl, $R_2$ is hydrogen, $R_6$ and $R_7$ taken together form a double bond, $R_{27}$ is hydrogen; $R_3$ and $R_4$ are not both hydrogen nor when taken together represent an unsubstituted azetidine; and the stereochemistry of a double bond may be E or Z or a mixture thereof.

In certain embodiments, the present invention relates to the aforementioned compound and the attendant definitions, provided that when $R_1$ is hydroxyl, $R_5$ is hydrogen, $R_6$ and $R_7$ taken together form a double bond, $R_{27}$ is hydrogen; $R_3$ and $R_4$ are not both hydrogen nor when taken together represent an unsubstituted azetidine.

In certain embodiments, the present invention relates to the aforementioned compound and the attendant definitions, wherein $R_1$ is hydroxyl.

In certain embodiments, the present invention relates to the aforementioned compound and the attendant definitions, wherein $R_3$ is allyl.

In certain embodiments, the present invention relates to the aforementioned compound and the attendant definitions, wherein $R_3$ has formula 9

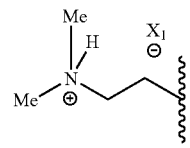

9 or the free base thereof;

wherein $X_1^-$ is selected from the group consisting of chloride, bromide, iodide, $H_2PO_4^-$, $HSO_4^-$, methylsulfonate, benzenesulfonate, p-toluenesulfonate, trifluoromethylsulfonate, and 10-camphorsulfonate, naphthalene-1-sulfonic acid-5-sulfonate, ethan-1-sulfonic acid-2-sulfonate, cyclamic acid salt, thiocyanic acid salt, naphthalene-2-sulfonate, and oxalate.

In certain embodiments, the present invention relates to the aforementioned compound and the attendant definitions, wherein $R_4$ is hydrogen.

In certain embodiments, the present invention relates to the aforementioned compound and the attendant definitions, wherein $R_5$ is hydrogen.

In certain embodiments, the present invention relates to the aforementioned compound and the attendant definitions, wherein $R_6$ and $R_7$ taken together form a bond.

In certain embodiments, the present invention relates to the aforementioned compound and the attendant definitions, wherein $R_{27}$ is hydrogen.

In certain embodiments, the present invention relates to the aforementioned compound and the attendant definitions, wherein $R_1$ is hydroxyl; $R_3$ is allyl; and $R_4$ is hydrogen.

In certain embodiments, the present invention relates to the aforementioned compound and the attendant definitions, wherein $R_1$ is hydroxyl; $R_3$ has formula 9

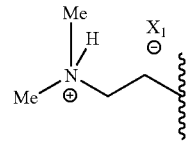

9 or the free base thereof;

wherein $X_1^-$ is selected from the group consisting of chloride, bromide, iodide, $H_2PO_4^-$, $HSO_4^-$, methylsulfonate, benzenesulfonate, p-toluenesulfonate, trifluoromethylsulfonate, and 10-camphorsulfonate, naphthalene-1-sulfonic acid-5-sulfonate, ethan-1-sulfonic acid-2-sulfonate, cyclamic acid salt, thiocyanic acid salt, naphthalene-2-sulfonate, and oxalate; and $R_4$ is hydrogen.

In certain embodiments, the present invention relates to the aforementioned compound and the attendant definitions, wherein $R_1$ is hydroxyl; $R_3$ is allyl; $R_4$ is hydrogen; and $R_5$ is hydrogen.

In certain embodiments, the present invention relates to the aforementioned compound and the attendant definitions, wherein $R_1$ is hydroxyl; $R_3$ has formula 9

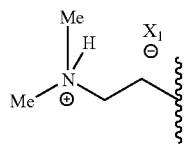

9 or the free base thereof;
wherein $X_1^-$ is selected from the group consisting of chloride, bromide, iodide, $H_2PO_4^-$, $HSO_4^-$, methylsulfonate, benzenesulfonate, p-toluenesulfonate, trifluoromethylsulfonate, and 10-camphorsulfonate, naphthalene-1-sulfonic acid-5-sulfonate, ethan-1-sulfonic acid-2-sulfonate, cyclamic acid salt, thiocyanic acid salt, naphthalene-2-sulfonate, and oxalate; $R_4$ is hydrogen; and $R_5$ is hydrogen.

In certain embodiments, the present invention relates to the aforementioned compound and the attendant definitions, wherein $R_1$ is hydroxyl; $R_3$ is allyl; $R_4$ is hydrogen; $R_5$ is hydrogen; and $R_6$ and $R_7$ taken together form a bond.

In certain embodiments, the present invention relates to the aforementioned compound and the attendant definitions, wherein $R_1$ is hydroxyl; $R_3$ has formula 9

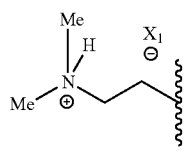

9 the free base thereof;
wherein $X_1^-$ is selected from the group consisting of chloride, bromide, iodide, $H_2PO_4^-$, $HSO_4^-$, methylsulfonate, benzenesulfonate,p-toluenesulfonate, trifluoromethylsulfonate, and 10-camphorsulfonate, naphthalene-1-sulfonic acid-5-sulfonate, ethan-1-sulfonic acid-2-sulfonate, cyclamic acid salt, thiocyanic acid salt, naphthalene-2-sulfonate, and oxalate; $R_4$ is hydrogen; $R_5$ is hydrogen; and $R_6$ and $R_7$ taken together form a bond.

In certain embodiments, the present invention relates to the aforementioned compound and the attendant definitions, wherein $R_1$ is hydroxyl; $R_3$ is allyl; $R_4$ is hydrogen; $R_5$ is hydrogen; $R_6$ and $R_7$ taken together form a bond; and $R_{27}$ is hydrogen.

In certain embodiments, the present invention relates to the aforementioned compound and the attendant definitions, wherein $R_1$ is hydroxyl; $R_3$ has formula 9

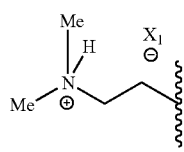

9 or the free base thereof;
wherein $X_1^-$ is selected from the group consisting of chloride, bromide, iodide, $H_2PO_4^-$, $HSO_4^-$, methylsulfonate, benzenesulfonate, p-toluenesulfonate, trifluoromethylsulfonate, and 10-camphorsulfonate, naphthalene-1-sulfonic acid-5-sulfonate, ethan-1-sulfonic acid-2-sulfonate, cyclamic acid salt, thiocyanic acid salt, naphthalene-2-sulfonate, and oxalate; $R_4$ is hydrogen; $R_5$ is hydrogen; $R_6$ and $R_7$ taken together form a bond; and $R_{27}$ is hydrogen.

In one embodiment the present invention provides a pure and isolated compound with absolute sterochemistry as shown in formula 3:

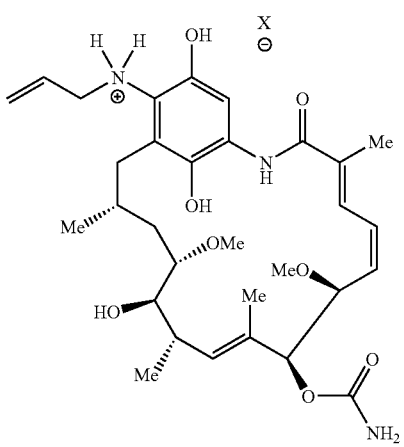

3 wherein $X^-$ is selected from the group consisting of chloride, bromide, iodide, $H_2PO_4^-$, $HSO_4^-$, methylsulfonate, benzenesulfonate, p-toluenesulfonate, trifluoromethylsulfonate, and 10-camphorsulfonate, naphthalene-1-sulfonic acid-5-sulfonate, ethan-1-sulfonic acid-2-sulfonate, cyclamic acid salt, thiocyanic acid salt, naphthalene-2-sulfonate, and oxalate.

In certain embodiments, the present invention relates to the aforementioned compound and the attendant definitions, wherein $X^-$ is chloride.

In certain embodiments, the present invention relates to the aforementioned compound and the attendant definitions, wherein $X^-$ is bromide.

In one embodiment, the present invention relates to a composition comprising a compound of any one of the aforementioned compounds and an amino acid.

In certain embodiments, the present invention relates to the aforementioned composition and the attendant definitions, wherein the amino acid is selected from the group consisting of:

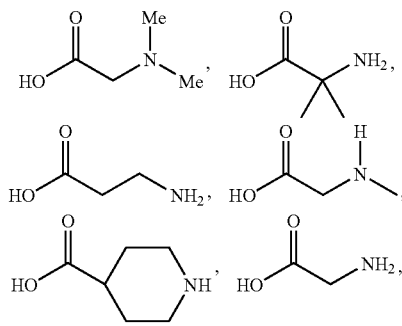

-continued

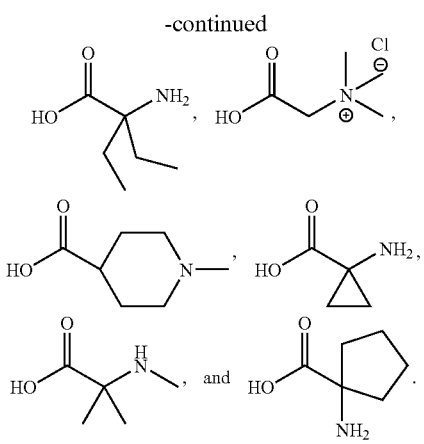

In one embodiment the present invention provides a compound of formula 4:

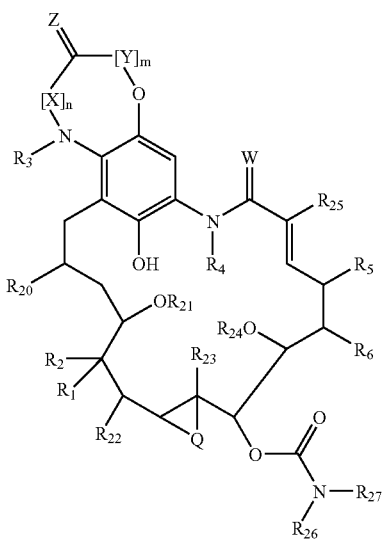

or a pharmaceutically acceptable salt thereof;
wherein, independently for each occurrence,
W is oxygen or sulfur;
Z is oxygen or sulfur;
Q is oxygen, NR, N(acyl) or a bond;
n is equal to 0, 1, or 2;
m is equal to 0, 1, or 2;
X and Y are independently $C(R_{30})_2$; wherein $R_{30}$ for each occurrence is independently selected from the group consisting of hydrogen, alkyl, cycloalkyl, heterocycloalkyl, aralkyl, heteroaryl, and heteroaralkyl; or $—[(CR_2)_p]—R_{16}$;

R for each occurrence is independently selected from the group consisting of hydrogen, alkyl, cycloalkyl, heterocycloalkyl, aralkyl, heteroaryl, and heteroaralkyl;

$R_1$ is hydroxyl, alkoxyl, $—OC(O)R_8$, $—OC(O)OR_9$, $—OC(O)NR_{10}R_{11}$, $—OSO_2R_{12}$, $—OC(O)NHSO_2NR_{13}R_{14}$, $NR_{13}R_{14}$, or halide; and $R_2$ is hydrogen, alkyl, or aralkyl; or $R_1$ and $R_2$ taken together, along with the carbon to which they are bonded, represent $—(C=O)—$, $—(C=N—OR)—$, $—(C=N—NHR)—$, or $—(C=N—R)—$;

$R_3$ are each independently selected from the group consisting of hydrogen, alkyl, alkenyl, alkynyl, aryl, cycloalkyl, heterocycloalkyl, aralkyl, heteroaryl, heteroaralkyl, and $—[(CR_2)_p]—R_{16}$;

$R_4$ is selected from the group consisting of H, alkyl, aralkyl, and a group having the Formula 4a:

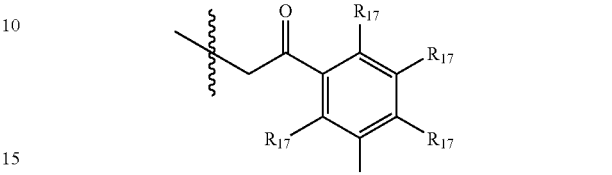

wherein $R_7$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, $—COR_{18}$, $—CO_2R_{18}$, $—N(R_{18})CO_2R_{19}$, $—OC(O)N(R_{18})(R_{19})$, $—N(R_{18})SO_2R_{19}$, $—N(R_{18})C(O)N(R_{18})(R_{19})$, and $—CH_2O$-heterocyclyl;

$R_5$ and $R_6$ are both hydrogen; or $R_5$ and $R_6$ taken together form a bond;

$R_8$ is hydrogen, alkyl, alkenyl, alkynyl, aryl, cycloalkyl, heterocycloalkyl, aralkyl, heteroaryl, heteroaralkyl, or $—[(CR_2)_p]—R_{16}$;

$R_9$ is alkyl, alkenyl, alkynyl, aryl, cycloalkyl, heterocycloalkyl, aralkyl, heteroaryl, heteroaralkyl, or $—[(CR_2)_p]—R_{16}$;

$R_{10}$ and $R_{11}$ are each independently selected from the group consisting of hydrogen, alkyl, alkenyl, alkynyl, aryl, cycloalkyl, heterocycloalkyl, aralkyl, heteroaryl, heteroaralkyl, and $—[(CR_2)_p]—R_{16}$; or $R_{10}$ and $R_{11}$ taken together with the nitrogen to which they are bonded represent a 4-8 membered optionally substituted heterocyclic ring;

$R_{12}$ is alkyl, alkenyl, alkynyl, aryl, cycloalkyl, heterocycloalkyl, aralkyl, heteroaryl, heteroaralkyl, or $—[(CR_2)_p]—R_{16}$;

$R_{13}$ and $R_{14}$ are each independently selected from the group consisting of hydrogen, alkyl, alkenyl, alkynyl, aryl, cycloalkyl, heterocycloalkyl, aralkyl, heteroaryl, heteroaralkyl, and $—[(CR_2)_p]—R_{16}$; or $R_{13}$ and $R_{14}$ taken together with the nitrogen to which they are bonded represent a 4-8 membered optionally substituted heterocyclic ring;

$R_{16}$ for each occurrence is independently selected from the group consisting of hydrogen, hydroxyl, acylamino, $—N(R_{18})COR_{19}$, $—N(R_{18})C(O)OR_{19}$, $—N(R_{18})SO_2(R_{19})$, $—CON(R_{18})(R_{19})$, $—OC(O)N(R_{18})(R_{19})$, $—SO_2N(R_{18})(R_{19})$, $—N(R_{18})(R_{19})$, $—OC(O)OR_{18}$, $—COOR_{18}$, $—C(O)N(OH)(R_{18})$, $—OS(O)_2OR_{18}$, $—S(O)_2OR_{18}$, $—OP(O)(OR_{18})(R_{19})$, $—N(R_{18})P(O)(OR_{18})(OR_{19})$, and $—P(O)(OR_{18})(OR_{19})$;

p is 1, 2, 3, 4, 5, or 6;

$R_{18}$ for each occurrence is independently selected from the group consisting of hydrogen, alkyl, aryl, cycloalkyl, heterocycloalkyl, aralkyl, heteroaryl, and heteroaralkyl;

$R_{19}$ for each occurrence is independently selected from the group consisting of hydrogen, alkyl, aryl, cycloalkyl, heterocycloalkyl, aralkyl, heteroaryl, and heteroaralkyl; or $R_{18}$ taken together with $R_{19}$ represent a 4-8 membered optionally substituted ring;

$R_{20}$, $R_{21}$, $R_{22}$, $R_{24}$, and $R_{25}$, for each occurrence are independently alkyl;

$R_{23}$ is alkyl, —CH$_2$OH, —CHO, —COOR$_{18}$, or —CH(OR$_{18}$)$_2$;

$R_{26}$ and $R_{27}$ for each occurrence are independently selected from the group consisting of hydrogen, alkyl, aryl, cycloalkyl, heterocycloalkyl, aralkyl, heteroaryl, and heteroaralkyl; and the absolute stereochemistry at a stereogenic center of formula 4 may be R or S or a mixture thereof and the stereochemistry of a double bond may be E or Z or a mixture thereof.

In certain embodiments, the present invention relates to the aforementioned compound and the attendant definitions, wherein $R_{20}$, $R_{21}$, $R_{22}$, $R_{23}$, $R_{24}$, $R_{25}$ are methyl; $R_{26}$ is hydrogen; Q is a bond; and Z and W are oxygen.

In certain embodiments, the present invention relates to the aforementioned compound and the attendant definitions, wherein $R_1$ is hydroxyl or —OC(O)R$_8$.

In certain embodiments, the present invention relates to the aforementioned compound and the attendant definitions, wherein $R_2$ is hydrogen.

In certain embodiments, the present invention relates to the aforementioned compound and the attendant definitions, wherein $R_3$ is hydrogen, alkyl, alkenyl, cycloalkyl, aralkyl, heteroaralkyl, or —[(CR$_2$)$_p$]—R$_{16}$.

In certain embodiments, the present invention relates to the aforementioned compound and the attendant definitions, wherein $R_4$ is hydrogen or has a formula 1a:

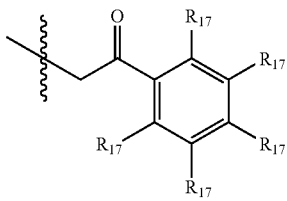

1a wherein $R_{17}$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —COR$_{18}$, —CO$_2$R$_{18}$, —N(R$_{18}$)CO$_2$R$_{19}$, —OC(O)N(R$_{18}$)(R$_{19}$), —N(R$_{18}$)SO$_2$R$_{19}$, —N(R$_{18}$)C(O)N(R$_{18}$)(R$_{19}$), and —CH$_2$O-heterocyclyl.

In certain embodiments, the present invention relates to the aforementioned compound and the attendant definitions, wherein $R_5$ and $R_6$ taken together form a bond.

In certain embodiments, the present invention relates to the aforementioned compound and the attendant definitions, wherein X and Y are —CH$_2$—.

In certain embodiments, the present invention relates to the aforementioned compound and the attendant definitions, wherein n is equal to 0; and m is equal to 0 or 1.

In certain embodiments, the present invention relates to the aforementioned compound and the attendant definitions, wherein $R_1$ is hydroxyl or —OC(O)R$_8$; and $R_2$ is hydrogen.

In certain embodiments, the present invention relates to the aforementioned compound and the attendant definitions, wherein $R_1$ is hydroxyl or —OC(O)R$_8$; $R_2$ is hydrogen; and $R_3$ is hydrogen, alkyl, alkenyl, cycloalkyl, aralkyl, heteroaralkyl, or —[(CR$_2$)$_p$]—R$_{16}$.

In certain embodiments, the present invention relates to the aforementioned compound and the attendant definitions, wherein $R_1$ is hydroxyl or —OC(O)R$_8$; $R_2$ is hydrogen; $R_3$ is hydrogen, alkyl, alkenyl, cycloalkyl, aralkyl, heteroaralkyl, or —[(CR$_2$)$_p$]—R$_{16}$; and $R_4$ is hydrogen or has a formula 1a:

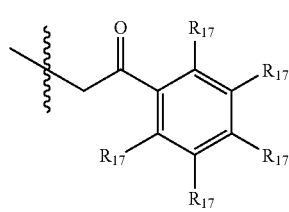

1a wherein $R_7$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —COR$_{18}$, —CO$_2$R$_{18}$, —N(R$_{18}$)CO$_2$R$_{19}$, —OC(O)N(R$_{18}$)(R$_{19}$), —N(R$_{18}$)SO$_2$R$_{19}$, —N(R$_{18}$)C(O)N(R$_{18}$)(R$_{19}$), and —CH$_2$O-heterocyclyl.

In certain embodiments, the present invention relates to the aforementioned compound and the attendant definitions, wherein $R_1$ is hydroxyl or —OC(O)R$_8$; $R_2$ is hydrogen; $R_3$ is hydrogen, alkyl, alkenyl, cycloalkyl, aralkyl, heteroaralkyl, or —[(CR$_2$)$_p$]—R$_{16}$; $R_4$ is hydrogen or has a formula 1a:

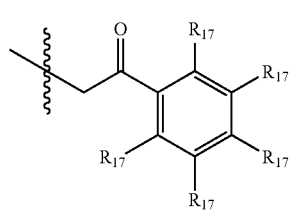

1a wherein $R_7$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —COR$_{18}$, —CO$_2$R$_{18}$, —N(R$_{18}$)CO$_2$R$_{19}$, —OC(O)N(R$_{18}$)(R$_{19}$), —N(R$_{18}$)SO$_2$R$_{19}$, —N(R$_{18}$)C(O)N(R$_{18}$)(R$_{19}$), and —CH$_2$O-heterocyclyl; and $R_5$ and $R_6$ taken together form a bond.

In certain embodiments, the present invention relates to the aforementioned compound and the attendant definitions, wherein $R_1$ is hydroxyl or —OC(O)R$_8$; $R_2$ is hydrogen; $R_3$ is hydrogen, alkyl, alkenyl, cycloalkyl, aralkyl, heteroaralkyl, or —[(CR$_2$)$_p$]—R$_{16}$; $R_4$ is hydrogen or has a formula 1a:

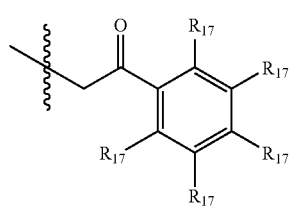

1a wherein $R_{17}$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —COR$_{18}$, —CO$_2$R$_{18}$, —N(R$_{18}$)CO$_2$R$_{19}$, —OC(O)N(R$_{18}$)

($R_{19}$), —N($R_{18}$)SO$_2R_{19}$, —N($R_{18}$)C(O)N($R_{18}$)($R_{19}$), and —CH$_2$O-heterocyclyl; $R_5$ and $R_6$ taken together form a bond; and X and Y are —CH$_2$—.

In certain embodiments, the present invention relates to the aforementioned compound and the attendant definitions, wherein $R_1$ is hydroxyl or —OC(O)$R_8$; $R_2$ is hydrogen; $R_3$ is hydrogen, alkyl, alkenyl, cycloalkyl, aralkyl, heteroaralkyl, or —[(CR$_2$)$_p$]—$R_{16}$; $R_4$ is hydrogen or has a formula 1a:

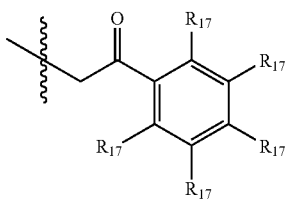

wherein $R_7$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —COR$_{18}$, —CO$_2R_{18}$, —N($R_{18}$)CO$_2R_{19}$, —OC(O)N($R_{18}$)($R_{19}$), —N($R_{18}$)SO$_2R_{19}$, —N($R_{18}$)C(O)N($R_{18}$)($R_{19}$), and —CH$_2$O-heterocyclyl; $R_5$ and $R_6$ taken together form a bond; X and Y are —CH$_2$—; n is equal to 0; and m is equal to 0 or 1.

In one embodiment the present invention provides a compound with absolute sterochemistry as shown in formula 5:

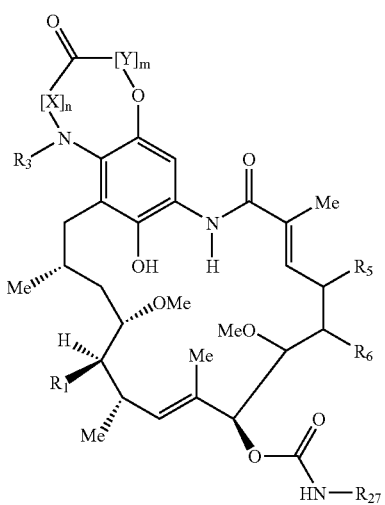

wherein independently for each occurrence:
n is equal to 0, 1, or 2;
m is equal to 0, 1, or 2;
X and Y are independently C($R_{30}$)$_2$; wherein $R_{30}$ for each occurrence is independently selected from the group consisting of hydrogen, alkyl, cycloalkyl, heterocycloalkyl, aralkyl, heteroaryl, and heteroaralkyl; or —[(CR$_2$)$_p$]—$R_{16}$;

$R_1$ is hydroxyl or —OC(O)$R_8$;

$R_3$ is hydrogen, alkyl, alkenyl, alkynyl, cycloalkyl, aralkyl, heteroaralkyl, or —[(CR$_2$)$_p$]—$R_{16}$;

$R_5$ and $R_6$ are both hydrogen; or $R_5$ and $R_6$ taken together form a bond;

$R_8$ is hydrogen, alkyl, alkenyl, alkynyl, aryl, cycloalkyl, heterocycloalkyl, aralkyl, heteroaryl, heteroaralkyl, or —[(CR$_2$)$_p$]—$R_{16}$;

$R_{16}$ for each occurrence is independently selected from the group consisting of hydrogen, hydroxyl, acylamino, —N($R_{18}$)COR$_{19}$, —N($R_{18}$)C(O)OR$_{19}$, —N($R_{18}$)SO$_2$($R_{19}$), —CON($R_{18}$)($R_{19}$), —OC(O)N($R_{18}$)($R_{19}$), —SO$_2$N($R_{18}$)($R_{19}$), —N($R_{18}$)($R_{19}$), —OC(O)OR$_{18}$, —COOR$_{18}$, —C(O)N(OH)($R_{18}$), —OS(O)$_2$OR$_{18}$, —S(O)$_2$OR$_{18}$, —OP(O)(OR$_{18}$)(OR$_{19}$), —N($R_{18}$)P(O)(OR$_{18}$)(OR$_{19}$), and —P(O)(OR$_{18}$)(OR$_{19}$);

p is 1, 2, 3, 4, 5, or 6;

$R_{18}$ for each occurrence is independently selected from the group consisting of hydrogen, alkyl, aryl, cycloalkyl, heterocycloalkyl, aralkyl, heteroaryl, and heteroaralkyl;

$R_{19}$ for each occurrence is independently selected from the group consisting of hydrogen, alkyl, aryl, cycloalkyl, heterocycloalkyl, aralkyl, heteroaryl, and heteroaralkyl; or $R_{18}$ taken together with $R_{19}$ represent a 4-8 membered optionally substituted ring;

$R_{27}$ is hydrogen, alkyl, aryl, cycloalkyl, heterocycloalkyl, aralkyl, heteroaryl, or heteroaralkyl; and the stereochemistry of a double bond may be E or Z or a mixture thereof.

In certain embodiments, the present invention relates to the aforementioned compound and the attendant definitions, wherein $R_1$ is hydroxyl.

In certain embodiments, the present invention relates to the aforementioned compound and the attendant definitions, wherein $R_3$ is allyl.

In certain embodiments, the present invention relates to the aforementioned compound and the attendant definitions, wherein $R_5$ and $R_6$ taken together form a bond.

In certain embodiments, the present invention relates to the aforementioned compound and the attendant definitions, wherein $R_{27}$ is hydrogen.

In certain embodiments, the present invention relates to the aforementioned compound and the attendant definitions, wherein X and Y are —CH$_2$—.

In certain embodiments, the present invention relates to the aforementioned compound and the attendant definitions, wherein n is equal to 0; and m is equal to 0 or 1.

In certain embodiments, the present invention relates to the aforementioned compound and the attendant definitions, wherein $R_1$ is hydroxyl; and $R_3$ is allyl.

In certain embodiments, the present invention relates to the aforementioned compound and the attendant definitions, wherein $R_1$ is hydroxyl; $R_3$ is allyl; and $R_5$ and $R_6$ taken together form a bond.

In certain embodiments, the present invention relates to the aforementioned compound and the attendant definitions, wherein $R_1$ is hydroxyl; $R_3$ is allyl; $R_5$ and $R_6$ taken together form a bond; and $R_{27}$ is hydrogen.

In certain embodiments, the present invention relates to the aforementioned compound and the attendant definitions, wherein $R_1$ is hydroxyl; $R_3$ is allyl; $R_5$ and $R_6$ taken together form a bond; $R_{27}$ is hydrogen; and X and Y are —CH$_2$—.

In certain embodiments, the present invention relates to the aforementioned compound and the attendant definitions, wherein $R_1$ is hydroxyl; $R_3$ is allyl; $R_5$ and $R_6$ taken together form a bond; $R_{27}$ is hydrogen; X and Y are —CH$_2$—; n is equal to 0; and m is equal to 0 or 1.

In one embodiment the present invention provides a compound selected from the group consisting of:

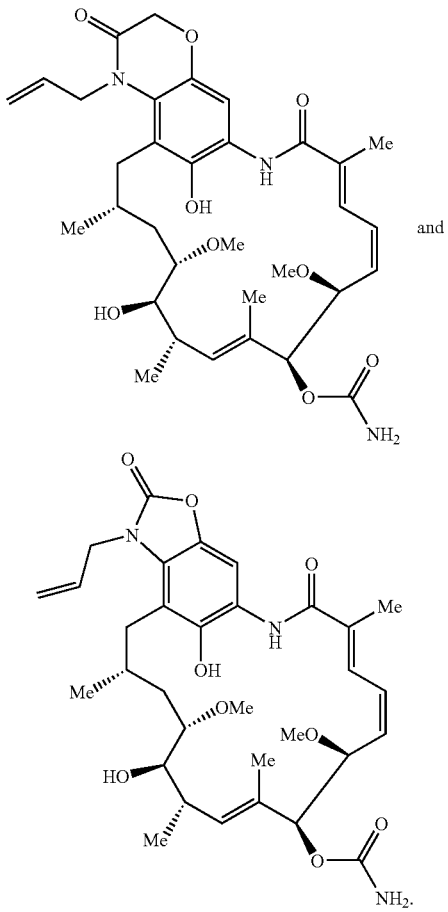

and

The embodiments described above and in the following sections encompass hydroquinone analogs of the geldanamycin family of molecules. In addition to reduced forms of 17-AAG (17-allylamino-18,21-dihydro-17-demethoxygeldanamycin), other preferred compounds of the present invention relates to 18,21-dihydro-geldanamycin family including, but not limited to, 18,21-dihydro analogs of 17-Amino-4,5-dihydro-17-demethoxy-geldanamycin; 17-Methylamino-4,5-dihydro-17-demethoxygeldanamycin; 17-Cyclopropylamino-4,5-dihydro-17-demethoxygeldanarnycin; 17-(2'-Hydroxyethylamino)-4,5-dihydro-17-demethoxygelclanamycin; 17-(2-Methoxyethylamino)-4,5-dihydro-17-demethoxygeldanamycin; 17-(2'-Fluoroethylamino)-4,5-dihydro-17-demethoxygeldanamycin; 17-(S)-(+)-2-Hydroxypropylamino-4,5-dihydro-17-demethoxygeldanamycin; 17-Azetidin-1-yl-4,5-dihydro-17-demethoxygeldanamycin; 17-(3-Hydroxyazetidin-1-yl)-4,5-dihydro-17-demethoxygeldanamycin; 17-Azetidin-1-yl-4,5-dihydro-11-alpha-fluoro-17-demethoxygeldanamycin; 17-(2'-Cyanoethylamino)-17-demethoxygeldanamycin; 17-(2'-Fluoroethylamino)-17-demethoxygeldanamycin; 17-Amino-22-(2'-methoxyphenacyl)-17-demethoxygeldanamycin; 17-Amino-22-(3'-methoxyphenacyl)-17-demethoxygeldanetmycin; 17-Amino-22-(4'-chlorophenacyl)-17-demethoxygeldanamycin; 17-Amino-22-(3',4'-dichlorophenacyl)-17-demethoxygeldanamycin; 17-Amino-22-(4'-amino-3'-iodophenacyl)-17-demethoxygeldanamycin; 17-Amino-22-(4'-azido-3'-iodophenacyl)-17-demethoxygeldanamycin; 17-Amino-11-alpha-fluoro-17-demethoxygeldanamycin; 17-Allylamino-11-alpha-fluoro-17-demethoxygeldanamycin; 17-Propargylamino-11-alpha-fluoro-17-demethoxygeldanamycin; 17-(2'-Fluoroethylamino)-11-alpha-fluoro-17-demethoxygeldanamycin; 17-Azetidin-1-yl-11-(4'-azidophenyl)sulfamylcarbonyl-17-demethoxygeldanamycin; 17-(2'-Fluoroethylamino)-11-keto-17-demethoxygeldanamycin; 17-Azetidin-1-yl-11-keto-17-demethoxygeldanamycin; and 17-(3'-Hydroxyazetidin-1-yl)-11-keto-17-demethoxygeldanamycin.

It will be understood by one skilled in the art that the methodology outlined herein can be used with any amino substituted benzoquinone ansamycin.

The compositions of the present invention exists as salts of the reduced ansamycin, e.g., HCl or $H_2SO_4$ salts. In another embodiment the compounds are co-crystallized with another salt, such as an amino acid, e.g., glycine. In general, in these embodiments, the ratio of amino acid to ansamycin can vary, but is preferably from 2:1 to 1:2 amino acid:ansamycin.

Compositions & Formulations

The present invention also provides a pharmaceutical composition comprising any one of the aforementioned compounds and at least one pharmaceutically acceptable excipient.

In one embodiment, the present invention provides a pharmaceutical composition comprising: at least one pharmaceutically acceptable excipient; and a compound of formula 6:

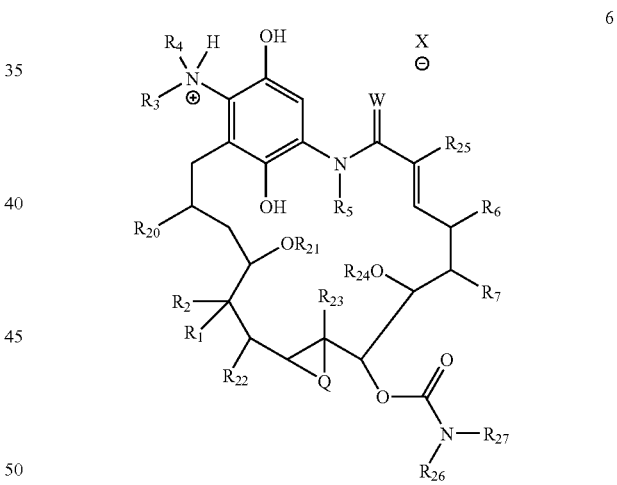

6 or the free base thereof,
wherein independently for each occurrence:
W is oxygen or sulfur;
Q is oxygen, NR, N(acyl) or a bond;
$X^-$ is a conjugate base of a pharmaceutically acceptable acid;
R for each occurrence is independently selected from the group consisting of hydrogen, alkyl, cycloalkyl, heterocycloalkyl, aralkyl, heteroaryl, and heteroaralkyl;
$R_1$ is hydroxyl, alkoxyl, —OC(O)$R_8$, —OC(O)O$R_9$, —OC(O)N$R_{10}R_{11}$, —OSO$_2R_{12}$, —OC(O)NHSO$_2$N$R_{13}R_{14}$, —N$R_{13}R_{14}$, or halide; and $R_2$ is hydrogen, alkyl, or aralkyl; or $R_1$ and $R_2$ taken together, along with the carbon to which they are bonded, represent —(C═O)—, —(C═N—OR)—, —(C═N—N—HR)—, or —(C═N—R)—;

$R_3$ and $R_4$ are each independently selected from the group consisting of hydrogen, alkyl, alkenyl, alkynyl, aryl, cycloalkyl, heterocycloalkyl, aralkyl, heteroaryl, heteroaralkyl, and —$[(CR_2)_p]$—$R_{16}$; or $R_3$ taken together with $R_4$ represent a 4-8 membered optionally substituted heterocyclic ring;

$R_5$ is selected from the group consisting of H, alkyl, aralkyl, and a group having the formula 6a:

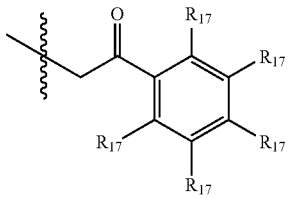

6a wherein $R_{17}$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —$COR_{18}$, —$CO_2R_{18}$, —$N(R_{18})CO_2R_{19}$, —$OC(O)N(R_{18})(R_{19})$, —$N(R_{18})SO_2R_{19}$, —$N(R_{18})C(O)N(R_{18})(R_{19})$, and —$CH_2O$-heterocyclyl;

$R_6$ and $R_7$ are both hydrogen; or $R_6$ and $R_7$ taken together form a bond;

$R_8$ is hydrogen, alkyl, alkenyl, alkynyl, aryl, cycloalkyl, heterocycloalkyl, aralkyl, heteroaryl, heteroaralkyl, or —$[(CR_2)_p]$—$R_{16}$;

$R_9$ is alkyl, alkenyl, alkynyl, aryl, cycloalkyl, heterocycloalkyl, aralkyl, heteroaryl, heteroaralkyl, or —$[(CR_2)_p]$—$R_{16}$;

$R_{10}$ and $R_{11}$ are each independently selected from the group consisting of hydrogen, alkyl, alkenyl, alkynyl, aryl, cycloalkyl, heterocycloalkyl, aralkyl, heteroaryl, heteroaralkyl, and —$[(CR_2)_p]$—$R_{16}$; or $R_{10}$ and $R_{11}$ taken together with the nitrogen to which they are bonded represent a 4-8 membered optionally substituted heterocyclic ring;

$R_{12}$ is alkyl, alkenyl, alkynyl, aryl, cycloalkyl, heterocycloalkyl, aralkyl, heteroaryl, heteroaralkyl, or —$[(CR_2)_p]$—$R_{16}$;

$R_{13}$ and $R_{14}$ are each independently selected from the group consisting of hydrogen, alkyl, alkenyl, alkynyl, aryl, cycloalkyl, heterocycloalkyl, aralkyl, heteroaryl, heteroaralkyl, and —$[(CR_2)_p]$—$R_{16}$; or $R_{13}$ and $R_{14}$ taken together with the nitrogen to which they are bonded represent a 4-8 membered optionally substituted heterocyclic ring;

$R_{16}$ for each occurrence is independently selected from the group consisting of hydrogen, hydroxyl, acylamino, —$N(R_{18})COR_{19}$, —$N(R_{18})C(O)OR_{19}$, —$N(R_{18})SO_2(R_{19})$, —$CON(R_{18})(R_{19})$, —$OC(O)N(R_{18})(R_{19})$, —$SO_2N(R_{18})(R_{19})$, —$N(R_{18})(R_{19})$, —$OC(O)OR_{18}$, —$COOR_{18}$, —$C(O)N(OH)(R_{18})$, —$OS(O)OR_{18}$, —$S(O)_2OR_{18}$, —$OP(O)(OR_{18})(OR_{19})$, —$N(R_{18})P(O)(OR_{18})(OR_{19})$, and —$P(O)(OR_{18})(OR_{19})$;

p is 1, 2, 3, 4, 5, or 6;

$R_{18}$ for each occurrence is independently selected from the group consisting of hydrogen, alkyl, aryl, cycloalkyl, heterocycloalkyl, aralkyl, heteroaryl, and heteroaralkyl;

$R_{19}$ for each occurrence is independently selected from the group consisting of hydrogen, alkyl, aryl, cycloalkyl, heterocycloalkyl, aralkyl, heteroaryl, and heteroaralkyl; or $R_{18}$ taken together with $R_{19}$ represent a 4-8 membered optionally substituted ring;

$R_{20}$, $R_{21}$, $R_{22}$, $R_{24}$, and $R_{25}$, for each occurrence are independently alkyl;

$R_{23}$ is alkyl, —$CH_2OH$, —$CHO$, —$COOR_{18}$, or —$CH(OR_{18})_2$;

$R_{26}$ and $R_{27}$ for each occurrence are independently selected from the group consisting of hydrogen, alkyl, aryl, cycloalkyl, heterocycloalkyl, aralkyl, heteroaryl, and heteroaralkyl;

provided that when $R_1$ is hydroxyl, $R_2$ is hydrogen, $R_6$ and $R_7$ taken together form a double bond, $R_{20}$ is methyl, $R_{21}$ is methyl, $R_{22}$ is methyl, $R_{23}$ is methyl, $R_{24}$ is methyl, $R_{25}$ is methyl, $R_{26}$ is hydrogen, $R_{27}$ is hydrogen, Q is a bond, and W is oxygen; $R_3$ and $R_4$ are not both hydrogen nor when taken together represent an unsubstituted azetidine; and the absolute stereochemistry at a stereogenic center of formula 6 may be R or S or a mixture thereof and the stereochemistry of a double bond may be E or Z or a mixture thereof.

In certain embodiments, the present invention relates to the aforementioned composition and the attendant definitions, provided that when $R_1$ is hydroxyl, $R_2$ is hydrogen, $R_5$ is hydrogen, $R_6$ and $R_7$ taken together form a double bond, $R_{20}$ is methyl, $R_{21}$ is methyl, $R_{22}$ is methyl, $R_{23}$ is methyl, $R_{24}$ is methyl, $R_{25}$ is methyl, $R_{26}$ is hydrogen, $R_{27}$ is hydrogen, Q is a bond, and W is oxygen; $R_3$ and $R_4$ are not both hydrogen nor when taken together represent an unsubstituted azetidine.

In certain embodiments, the present invention relates to the aforementioned composition and the attendant definitions, further comprising an antioxidant.

In certain embodiments, the present invention relates to the aforementioned composition and the attendant definitions, further comprising a buffering agent.

In certain embodiments, the present invention relates to the aforementioned composition and the attendant definitions, further comprising a metal chelator.

In certain embodiments, the present invention relates to the aforementioned composition and the attendant definitions, further comprising an antioxidant; and a buffering agent.

In certain embodiments, the present invention relates to the aforementioned composition and the attendant definitions, further comprising an antioxidant; and a metal chelator.

In certain embodiments, the present invention relates to the aforementioned composition and the attendant definitions, further comprising a buffering agent; and a metal chelator.

In certain embodiments, the present invention relates to the aforementioned composition and the attendant definitions, further comprising an antioxidant; a buffering agent; and a metal chelator.

In certain embodiments, the present invention relates to the aforementioned composition and the attendant definitions, wherein said antioxidant is ascorbate, cysteine hydrochloride, sodium bisulfate, sodium metabisulfite, sodium sulfite, thioglycerol, sodium mercaptoacetate, sodium formaldehyde sulfoxylate, ascorbyl palmitate, butylated hydroxyanisole, butylated hydroxytoluene, lecithin, propyl gallate, or alpha-tocopherol.

In certain embodiments, the present invention relates to the aforementioned composition and the attendant definitions, wherein said antioxidant is ascorbate.

In certain embodiments, the present invention relates to the aforementioned composition and the attendant definitions, wherein said buffering agent is citrate, ascorbate, phosphate, bicarbonate, carbonate, fumarate, acetate, tartarate, malate, succinate, lactate, maleate, glycine, or other naturally-occurring α- or, β-amino acids.

In certain embodiments, the present invention relates to the aforementioned composition and the attendant definitions, wherein said buffering agent is citrate.

In certain embodiments, the present invention relates to the aforementioned composition and the attendant definitions, wherein said metal chelator is citric acid, ethylenediamine tetraacetic acid (EDTA) and its salt, DTPA (diethylene-tri-amine-penta-acetic acid) and its salt, EGTA and its salt, NTA (nitriloacetic acid) and its salt, sorbitol and its salt, tartaric acid and its salt, N-hydroxy iminodiacetate and its salt, hydroxyethyl-ethylene diamine-tetraacetic acid and its salt, 1- and 3-propanediamine tetra acetic acid and their salts, 1- and 3-diamino-2-hydroxy propane tetra-acetic acid and their salts, sodium gluconate, hydroxy ethane diphosphonic acid and its salt, or phosphoric acid and its salt.

In certain embodiments, the present invention relates to the aforementioned composition and the attendant definitions, wherein said metal chelator is EDTA.

In certain embodiments, the present invention relates to the aforementioned composition and the attendant definitions, wherein said buffering agent is citrate, said antioxidant is ascorbate, and said metal chelator is EDTA.

In certain embodiments, the present invention relates to the aforementioned composition and the attendant definitions, wherein the molar ratio of said EDTA to said compound of formula 6 is in the range from about 0.001 to about 0.1.

In certain embodiments, the present invention relates to the aforementioned composition and the attendant definitions, wherein the molar ratio of said EDTA to said compound of formula 6 is in the range from about 0.01 to about 0.05.

In certain embodiments, the present invention relates to the aforementioned composition and the attendant definitions, wherein the molar ratio of said ascorbic acid to said compound of formula 6 is in the range from about 0.001 to about 1.

In certain embodiments, the present invention relates to the aforementioned composition and the attendant definitions, wherein the molar ratio of said ascorbic acid to said compound of formula 6 is in the range from about present 0.01 to about 1.

In certain embodiments, the present invention relates to the aforementioned composition and the attendant definitions, wherein the molar ratio of said citrate to said compound of formula 6 is in the range of about 0.05 to about 2.

In certain embodiments, the present invention relates to the aforementioned composition and the attendant definitions, wherein the molar ratio of said citrate to said compound of formula 6 is in the range of about 0.2 to about 1.

In certain embodiments, the present invention relates to the aforementioned composition and the attendant definitions, wherein the molar ratio of said EDTA to said compound of formula 6 is in the range from about 0.001 to about 0. 1; and the molar ratio of said ascorbic acid to said compound of formula 6 is in the range from about 0.001 to about 1.

In certain embodiments, the present invention relates to the aforementioned composition and the attendant definitions, wherein the molar ratio of said EDTA to said compound of formula 6 is in the range from about 0.01 to about 0.05; and the molar ratio of said ascorbic acid to said compound of formula 6 is in the range from about present 0.01 to about 1.

In certain embodiments, the present invention relates to the aforementioned composition and the attendant definitions, wherein the molar ratio of said EDTA to said compound of formula 6 is in the range from about 0.001 to about 0.1; the molar ratio of said ascorbic acid to said compound of formula 6 is in the range from about 0.001 to about 1; the molar ratio of said citrate to said compound of formula 6 is in the range of about 0.05 to about 2.

In certain embodiments, the present invention relates to the aforementioned composition and the attendant definitions, wherein the molar ratio of said EDTA to said compound of formula 6 is in the range from about 0.01 to about 0.05; the molar ratio of said ascorbic acid to said compound of formula 6 is in the range from about present 0.01 to about 1; the molar ratio of said citrate to said compound of formula 6 is in the range of about 0.2 to about 1.

In certain embodiments, the present invention relates to a pharmaceutical composition of any one of the aforementioned compositions, further comprising a solubilizing agent.

In certain embodiments, the present invention relates to the aforementioned composition and the attendant definitions, wherein said solubilizing agent is polyoxyethylene sorbitan fatty acid esters, polyoxyethylene stearates, benzyl alcohol, ethyl alcohol, polyethylene glycols, propylene glycol, glycerin, cyclodextrin, or poloxamers.

In one embodiment, the present invention provides a pharmaceutical composition comprising: at least one pharmaceutically acceptable excipient; a compound of formula 6:

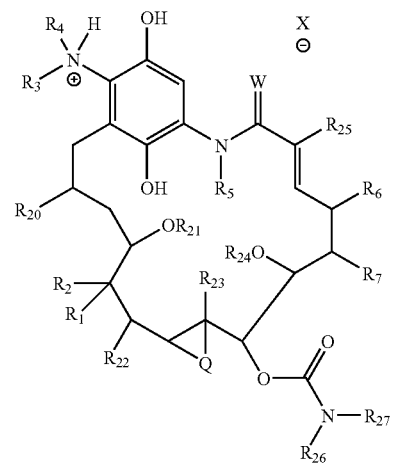

or the free base thereof; and a compound of formula 10, wherein said compound of formula 10 is present in the range of about 0.00001% to about 5% (m/v):

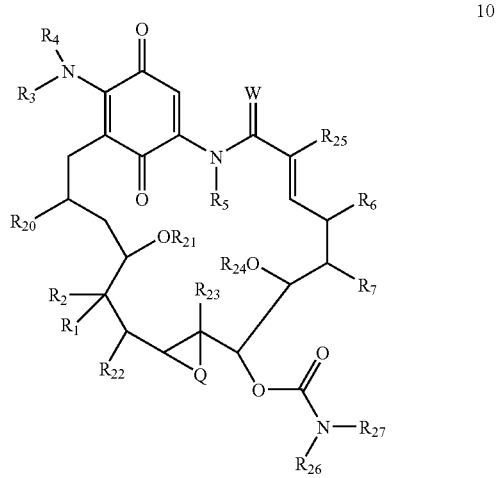

or pharmaceutically acceptable salt thereof;

wherein independently for each occurrence:

W is oxygen or sulfur;

Q is oxygen, NR, N(acyl) or a bond;

$X^-$ is a conjugate base of a pharmaceutically acceptable acid;

R for each occurrence is independently selected from the group consisting of hydrogen, alkyl, cycloalkyl, heterocycloalkyl, aralkyl, heteroaryl, and heteroaralkyl;

$R^1$ is hydroxyl, alkoxyl, —OC(O)$R_8$, —OC(O)O$R_9$, —OC(O)N$R_{10}R_{11}$, —OSO$_2R_{12}$, —OC(O)NHSO$_2$N$R_{13}R_{14}$, —N$R_{13}R_{14}$, or halide; and $R_2$ is hydrogen, alkyl, or aralkyl; or $R_1$ and $R_2$ taken together, along with the carbon to which they are bonded, represent —(C=O)—, —(C=N—OR)—, —(C=N—NHR)—, or —(C=N—R)—;

$R_3$ and $R_4$ are each independently selected from the group consisting of hydrogen, alkyl, alkenyl, alkynyl, aryl, cycloalkyl, heterocycloalkyl, aralkyl, heteroaryl, heteroaralkyl, and —[(CR$_2$)$_p$]—$R_{16}$; or $R_3$ taken together with $R_4$ represent a 4-8 membered optionally substituted heterocyclic ring;

$R_5$ is selected from the group consisting of H, alkyl, aralkyl, and a group having the formula 6a:

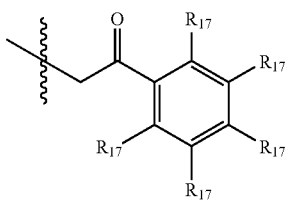

6a wherein $R_{17}$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —CO$R_{18}$, —CO$_2R_{18}$, —N(R$_{18}$)CO$_2R_{19}$, —OC(O)N(R$_{18}$)(R$_{19}$), —N(R$_{18}$)SO$_2R_{19}$, —N(R$_{18}$)C(O)N(R$_{18}$)(R$_{19}$), and —CH$_2$O-heterocyclyl;

$R_6$ and $R_7$ are both hydrogen; or $R_6$ and $R_7$ taken together form a bond;

$R_8$ is hydrogen, alkyl, alkenyl, alkynyl, aryl, cycloalkyl, heterocycloalkyl, aralkyl, heteroaryl, heteroaralkyl, or —[(CR$_2$)$_p$]—$R_{16}$;

$R_9$ is alkyl, alkenyl, alkynyl, aryl, cycloalkyl, heterocycloalkyl, aralkyl, heteroaryl, heteroaralkyl, or —[(CR$_2$)$_p$]—$R_{16}$;

$R_{10}$ and $R_{11}$ are each independently selected from the group consisting of hydrogen, alkyl, alkenyl, alkynyl, aryl, cycloalkyl, heterocycloalkyl, aralkyl, heteroaryl, heteroaralkyl, and —[(CR$_2$)$_p$]—$R_{16}$; or $R_{10}$ and $R_{11}$ taken together with the nitrogen to which they are bonded represent a 4-8 membered optionally substituted heterocyclic ring;

$R_{12}$ is alkyl, alkenyl, alkynyl, aryl, cycloalkyl, heterocycloalkyl, aralkyl, heteroaryl, heteroaralkyl, or —[(CR$_2$)$_p$]—$R_{16}$;

$R_{13}$ and $R_{14}$ are each independently selected from the group consisting of hydrogen, alkyl, alkenyl, alkynyl, aryl, cycloalkyl, heterocycloalkyl, aralkyl, heteroaryl, heteroaralkyl, and —[(CR$_2$)$_p$]—$R_{16}$; or $R_{13}$ and $R_{14}$ taken together with the nitrogen to which they are bonded represent a 4-8 membered optionally substituted heterocyclic ring;

$R_{16}$ for each occurrence is independently selected from the group consisting of hydrogen, hydroxyl, acylamino, —N(R$_{18}$)COR$_{19}$, —N(R$_{18}$)C(O)OR$_{19}$, —N(R$_{18}$)SO$_2$(R$_{19}$), —CON(R$_{18}$)(R$_{19}$), —OC(O)N(R$_{18}$)(R$_{19}$), —SO$_2$N(R$_{18}$)(R$_{19}$), —N(R$_{18}$)(R$_{19}$), —OC(O)OR$_{18}$, —COOR$_{18}$, —C(O)N(OH)(R$_{18}$), —OS(O)$_2$OR$_{18}$, —S(O)$_2$OR$_{18}$, —OP(O)(OR$_{18}$)(OR$_{19}$), —N(R$_{18}$)P(O)(OR$_{18}$)(OR$_{19}$), and —P(O)(OR$_{18}$)(OR$_{19}$);

p is 1, 2, 3, 4, 5, or 6;

$R_{18}$ for each occurrence is independently selected from the group consisting of hydrogen, alkyl, aryl, cycloalkyl, heterocycloalkyl, aralkyl, heteroaryl, and heteroaralkyl;

$R_{19}$ for each occurrence is independently selected from the group consisting of hydrogen, alkyl, aryl, cycloalkyl, heterocycloalkyl, aralkyl, heteroaryl, and heteroaralkyl; or $R_{18}$ taken together with RI represent a 4-8 membered optionally substituted ring;

$R_{20}$, $R_{21}$, $R_{22}$, $R_{24}$, and $R_{25}$, for each occurrence are independently alkyl;

$R_{23}$ is alkyl, —CH$_2$OH, —CHO, —COOR$_{18}$, or —CH(OR$_{18}$)$_2$;

$R_{26}$ and $R_{27}$ for each occurrence are independently selected from the group consisting of hydrogen, alkyl, aryl, cycloalkyl, heterocycloalkyl, aralkyl, heteroaryl, and heteroaralkyl;

provided that when $R_1$ is hydroxyl, $R_2$ is hydrogen, $R_6$ and $R_7$ taken together form a double bond, $R_{20}$ is methyl, $R_{21}$ is methyl, $R_{22}$ is methyl, $R_{23}$ is methyl, $R_{24}$ is methyl, $R_{25}$ is methyl, $R_{26}$ is hydrogen, $R_{27}$ is hydrogen, Q is a bond, and W is oxygen; $R_3$ and $R_4$ are not both hydrogen nor when taken together represent an unsubstituted azetidine; and the absolute stereochemistry at a stereogenic center of formula 6 or 10 may be R or S or a mixture thereof and the stereochemistry of a double bond may be E or Z or a mixture thereof.

In certain embodiments, the present invention relates to the aforementioned composition and the attendant definitions, provided that when $R_1$ is hydroxyl, $R_2$ is hydrogen, $R_5$ is hydrogen, $R_6$ and $R_7$ taken together form a double bond, $R_{20}$ is methyl, $R_{21}$ is methyl, $R_{22}$ is methyl, $R_{23}$ is methyl, $R_{24}$ is methyl, $R_{25}$ is methyl, $R_{26}$ is hydrogen, $R_{27}$ is hydrogen, Q is a bond, and W is oxygen; $R_3$ and $R_4$ are not both hydrogen nor when taken together represent an unsubstituted azetidine.

In certain embodiments, the present invention relates to the aforementioned composition and the attendant definitions, further comprising an antioxidant.

In certain embodiments, the present invention relates to the aforementioned composition and the attendant definitions, further comprising a buffering agent.

In certain embodiments, the present invention relates to the aforementioned composition and the attendant definitions, further comprising a metal chelator.

In certain embodiments, the present invention relates to the aforementioned composition and the attendant definitions, further comprising an antioxidant; and a buffering agent.

In certain embodiments, the present invention relates to the aforementioned composition and the attendant definitions, further comprising an antioxidant; and a metal chelator.

In certain embodiments, the present invention relates to the aforementioned composition and the attendant definitions, further comprising a buffering agent; and a metal chelator.

In certain embodiments, the present invention relates to the aforementioned composition and the attendant definitions, further comprising an antioxidant; a buffering agent; and a metal chelator.

In certain embodiments, the present invention relates to the aforementioned composition and the attendant definitions, wherein said antioxidant is ascorbate, cysteine hydrochloride, sodium bisulfate, sodium metabisulfite, sodium sulfite, thioglycerol, sodium mercaptoacetate, sodium formaldehyde sulfoxylate, ascorbyl palmitate, butylated hydroxyanisole, butylated hydroxytoluene, lecithin, propyl gallate, or alpha-tocopherol.

In certain embodiments, the present invention relates to the aforementioned composition and the attendant definitions, wherein said antioxidant is ascorbate.

In certain embodiments, the present invention relates to the aforementioned composition and the attendant definitions, wherein said buffering agent is citrate, ascorbate, phosphate, bicarbonate, carbonate, fumarate, acetate, tartarate, malate, succinate, lactate, maleate, glycine, or other naturally-occurring α- or β-amino acids.

In certain embodiments, the present invention relates to the aforementioned composition and the attendant definitions, wherein said buffering agent is citrate.

In certain embodiments, the present invention relates to the aforementioned composition and the attendant definitions, wherein said metal chelator is citric acid, ethylenediamine tetraacetic acid (EDTA) and its salt, DTPA (diethylene-tri-amine-penta-acetic acid) and its salt, EGTA and its salt, NTA (nitriloacetic acid) and its salt, sorbitol and its salt, tartaric acid and its salt, N-hydroxy iminodiacetate and its salt, hydroxyethyl-ethylene diamine-tetraacetic acid and its salt, 1- and 3-propanediamine tetra acetic acid and their salts, 1- and 3-diamino-2-hydroxy propane tetra-acetic acid and their salts, sodium gluconate, hydroxy ethane diphosphonic acid and its salt, or phosphoric acid and its salt.

In certain embodiments, the present invention relates to the aforementioned composition and the attendant definitions, wherein said metal chelator is EDTA.

In certain embodiments, the present invention relates to the aforementioned composition and the attendant definitions, wherein said buffering agent is citrate, said antioxidant is ascorbate, and said metal chelator is EDTA.

In certain embodiments, the present invention relates to the aforementioned composition and the attendant definitions, wherein the molar ratio of said EDTA to said compound of formula 6 is in the range from about 0.001 to about 0.1.

In certain embodiments, the present invention relates to the aforementioned composition and the attendant definitions, wherein the molar ratio of said EDTA to said compound of formula 6 is in the range from about 0.01 to about 0.05.

In certain embodiments, the present invention relates to the aforementioned composition and the attendant definitions, wherein the molar ratio of said ascorbic acid to said compound of formula 6 is in the range from about 0.001 to about 1.

In certain embodiments, the present invention relates to the aforementioned composition and the attendant definitions, wherein the molar ratio of said ascorbic acid to said compound of formula 6 is in the range from about present 0.01 to about 1.

In certain embodiments, the present invention relates to the aforementioned composition and the attendant definitions, wherein the molar ratio of said citrate to said compound of formula 6 is in the range of about 0.05 to about 2.

In certain embodiments, the present invention relates to the aforementioned composition and the attendant definitions, wherein the molar ratio of said citrate to said compound of formula 6 is in the range of about 0.2 to about 1.

In certain embodiments, the present invention relates to the aforementioned composition and the attendant definitions, wherein the molar ratio of said EDTA to said compound of formula 6 is in the range from about 0.001 to about 0. 1; and the molar ratio of said ascorbic acid to said compound of formula 6 is in the range from about 0.001 to about 1.

In certain embodiments, the present invention relates to the aforementioned composition and the attendant definitions, wherein the molar ratio of said EDTA to said compound of formula 6 is in the range from about 0.01 to about 0.05; and the molar ratio of said ascorbic acid to said compound of formula 6 is in the range from about present 0.01 to about 1.

In certain embodiments, the present invention relates to the aforementioned composition and the attendant definitions, wherein the molar ratio of said EDTA to said compound of formula 6 is in the range from about 0.001 to about 0.1; the molar ratio of said ascorbic acid to said compound of formula 6 is in the range from about 0.001 to about 1; the molar ratio of said citrate to said compound of formula 6 is in the range of about 0.05 to about 2.

In certain embodiments, the present invention relates to the aforementioned composition and the attendant definitions, wherein the molar ratio of said EDTA to said compound of formula 6 is in the range from about 0.01 to about 0.05; the molar ratio of said ascorbic acid to said compound of formula 6 is in the range from about present 0.01 to about 1; the molar ratio of said citrate to said compound of formula 6 is in the range of about 0.2 to about 1.

In certain embodiments, the present invention relates to the aforementioned composition and the attendant definitions, further comprising a solubilizing agent.

In certain embodiments, the present invention relates to the aforementioned composition and the attendant definitions, wherein said solubilizing agent is polyoxyethylene sorbitan fatty acid esters, polyoxyethylene stearates, benzyl alcohol, ethyl alcohol, polyethylene glycols, propylene glycol, glycerin, cyclodextrin, or poloxamers.

In certain embodiments, the present invention relates to a pharmaceutical composition of any one of the aforementioned compositions, wherein said compound of formula 6 is present at a concentration of about 0.00016 M to about 0.160 M.

In certain embodiments, the present invention relates to a pharmaceutical composition of any one of the aforementioned compositions, wherein said compound of formula 6 is present at a concentration of about 0.00032 M to about 0.080 M.

Methods of Making

A variety of methodologies can be adapted for generating the compounds of the present invention. In general, the steps involve (1) converting the ansamycin to a 17-demethoxy-17-amino analog (e.g., 17-AAG), (2) reducing the benzoquinone in the ansamycin to give a hydroquinone, and (3) treating said hydroquinone with a Bronsted acid, thereby providing a compound of the present invention.

A benzoquinone-containing macrocyclic molecule, can be obtained via fermentation of a strain producing the compound (for example, see WO 03/072794 and U.S. Pat. No. 3,595, 955). Alternatively, synthetic or semi-synthetic methodology can be used to produce the ansamycin (see U.S. Pat. No. 5,387,584 and WO 00/03737). Further, there are commercial suppliers of isolated fermentation materials, such as geldanamycin; therefore, such materials are readily available.

In preferred embodiments, synthetic methodology is used to create analogs of a natural product isolated from an organism using known methods. For example, geldanamycin is isolated from a fermentation culture of an appropriate microorganism and may be derivatized using a variety of functionalization reactions known in the art. Representative examples include metal-catalyzed coupling reactions, oxidations, reductions, reactions with nucleophiles, reactions with electrophiles, pericyclic reactions, installation of protecting groups, removal of protecting groups, and the like. Many methods are known in the art for generating analogs of the various benzoquinone ansamycins (for examples, see U.S. Pat. Nos. 4,261,989; 5,387,584; and 5,932,566 and *J. Med. Chem.* 1995, 38, 3806-3812, herein incorporated by reference). These analogs are readily reduced, using methods outlined below, to yield the 18,21-dihydro derivatives of the present invention.

Once the starting material is obtained, the benzoquinone is reduced to form a hydroquinone and then reacted with an acid, for instance HCl, to generate a C-17 ammonium hydroquinone ansamycin in an air-stable salt form. In an alternate embodiment the hydroquinone free base is reacted with an acid halide of an amino acid in place of a Bronsted acid to generate air-stable C-17 ammonium hydroquinone ansamycin co-salt derivatives. This method is exemplified in Example 3.

A variety of methods and reaction conditions can be used to reduce the benzoquinone portion of the ansamycin. Sodium hydrosulfite may be used as the reducing agent. Other reducing agents that can be used include, but are not limited to, zinc dust with acetic anhydride or acetic acid, ascorbic acid and electrochemical reductions.

Reduction of the benzoquinone moiety of the ansamycin derivative may be accomplished using sodium hydrosulfite in a biphasic reaction mixture. Typically, the geldanamycin analog is dissolved in an organic solvent, such as EtOAc. Other solvents that can be used include, but are not limited to, dichloromethane, chloroform, dichloroethane, chlorobenzene, THF, MeTHF, diethyl ether, diglyme, 1,2-dimethoxyethane, MTBE, THP, dioxane, 2-ethoxybutane, methyl butyl ether, methyl acetate, 2-butanone, water and mixtures thereof. Two or more equivalents of sodium hydrosulfite are then added as a solution in water (5-30% (m/v), preferably 10% (m/v)), to the reaction vessel at room temperature. Aqueous solutions of sodium hydrosulfite are unstable and therefore need to be freshly prepared just prior to use. Vigorous mixing of the biphasic mixture ensures reasonable reaction rates.

The reaction can readily be followed at this step by visual inspection since the starting material 17-AAG has a purple color which will disappear as the reaction proceeds to the product dihydro-17AAG, which is yellow. However, HPLC/UV or other analytical methods can be used to monitor the reaction.

Upon completion of the reduction, the crude reaction mixture product may be used in the next step without purification to minimize oxidation of the hydroquinone. However, purification, preferably by recrystallization, can be performed if the conditions are monitored to maintain the reduced form of the benzoquinone.

The hydroquinone-containing ansamyacin is unstable and, in the presence of small amounts of oxygen or other oxidants, the hydroquinone moiety may be rapidly oxidized to the quinone species. Remarkably, the hydroquinone can be converted into an air-stable species by reaction with an acid, or by reaction with an acid halide of an amino acid. In the examples, the C-17 allyl amino group is protonated to generate a variety of air-stable C-17 ammonium salt hydroquinone geldanamycin analogs. In addition, the C-17 ammonium salt hydroquinones formed have the added benefit of being highly soluble in aqueous solutions (>200 mg/mL), unlike 17-AAG (<100 µg/mL).

The ammonium salt hydroquinone is formed by the addition of a solution of an acid, such as HCl, in an organic solvent, such as EtOAc, DCM, IPA or dioxane, to the hydroquinone containing ansamycin in an organic solution; the organic solvents may be independently acetone, dichloromethane, chloroform, dichloroethane, chlorobenzene, THF, MeTHF, diethyl ether, diglyme, 1,2-dimethoxyethane, MTBE, THP, dioxane, 2-ethoxybutane, methyl butyl ether, methyl acetate, 2-butanone, under nitrogen.

The ammonium salt of the hydroquinone is collected by filtration in cases where the product precipitates from solution. In cases where the ammonium salt hydroquinone does not precipitate, the reaction solution is concentrated under reduced pressure to yield the product.

A variety of air-stable ammonium salt hydroquinone ansamycins can be synthesized by using organic or inorganic acids. Some acids that can be used include, but are not limited to HCl, HBr, $H_2SO_4$, methansulfonic acid, benzenesulfonic acid, p-toluenesulfonic acid, triflic acid, camphorsulfonic acid, naphthalene-1,5-disulfonic acid, ethan-1,2-disulfonic acid, cyclamic acid, thiocyanic acid, naphthalene-2-sulfonic acid, oxalic acid, and the like. See, for example, Berge et al. (1977) "Pharmaceutical Salts", *J. Pharm. Sci.* 66:1-19. The acid used preferably should have a pKa sufficient to protonate the aniline nitrogen. Thus, any acid with a pKa between about −10 and about 7, preferably about −10 and about 4, more preferably between about −10 and about 1, and even more preferably between about −10 and about −3 may be used to generate the ammonium salt hydroquinone.

The present invention further provides methods for recrystallizing the compounds of the present invention. In such methods, recrystallization is accomplished by dissolving the compound in the minimal amount of an inert polar organic solvent, such as MeOH, EtOH, or IPA, and slowly adding a miscible organic solvent, such as an aliphatic ether, ethyl acetate, methyl acetate, chloroform or DCM, causing the solution to become turbid. The mixture is then allowed to sit for a suitable period of time, and optionally cooled, and the resulting solid is collected by filtration, washed and dried under reduced pressure.

One aspect of the invention relates to a method of preparing a compound, comprising: combining a compound of formula 7 with a reducing agent in a reaction solvent to give a compound of formula 8; and

7

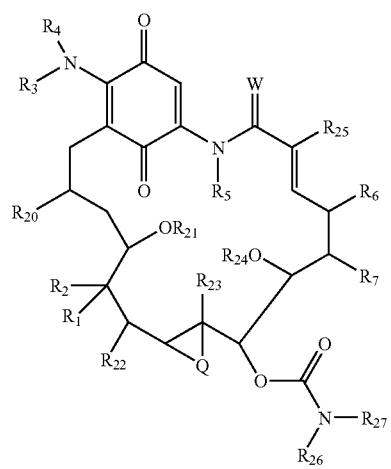

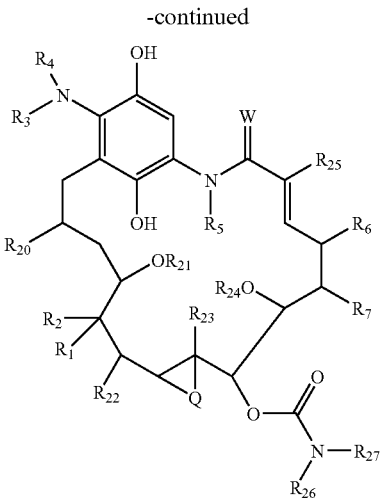

combining said compound of formula 8 with a pharmaceutically acceptable acid to give said compound of formula 1;

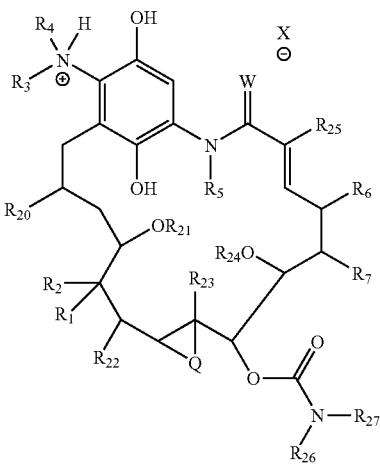

wherein independently for each occurrence:

W is oxygen or sulfur;

Q is oxygen, NR, N(acyl) or a bond;

$X^-$ is a conjugate base of a pharmaceutically acceptable acid;

R for each occurrence is independently selected from the group consisting of hydrogen, alkyl, cycloalkyl, heterocycloalkyl, aralkyl, heteroaryl, and heteroaralkyl;

$R^1$ is hydroxyl, alkoxyl, —OC(O)$R_8$, —OC(O)O$R_9$, —OC(O)N$R_{10}R_{11}$, —OSO$_2R_{12}$, —OC(O)NHSO$_2$N$R_{13}R_{14}$, —N$R_{13}R_{14}$, or halide; and $R_2$ is hydrogen, alkyl, or aralkyl; or $R_1$ and $R_2$ taken together, along with the carbon to which they are bonded, represent —(C=O)—, —(C=N—OR)—, —(C=N—NHR)—, or —(C=N—R)—;

$R_3$ and $R_4$ are each independently selected from the group consisting of hydrogen, alkyl, alkenyl, alkynyl, aryl, cycloalkyl, heterocycloalkyl, aralkyl, heteroaryl, heteroaralkyl, and —[(CR$_2$)$_p$]—R$_{16}$; or $R_3$ taken together with $R_4$ represent a 4-8 membered optionally substituted heterocyclic ring;

$R_5$ is selected from the group consisting of H, alkyl, aralkyl, and a group having the formula 1a:

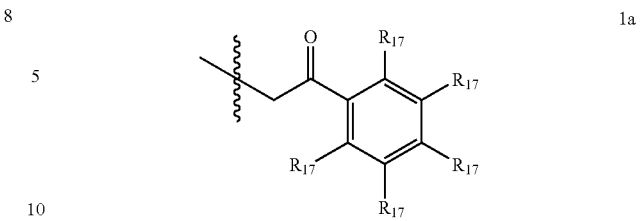

wherein $R_{17}$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —COR$_{18}$, —CO$_2$R$_{18}$, —N(R$_{18}$)CO$_2$R$_{19}$, —OC(O)N(R$_{18}$)(R$_{19}$), —N(R$_{18}$)SO$_2$R$_{19}$, —N(R$_{18}$)C(O)N(R$_{18}$)(R$_{19}$), and —CH$_2$O-heterocyclyl;

$R_6$ and $R_7$ are both hydrogen; or $R^6$ and $R_7$ taken together form a bond;

$R_8$ is hydrogen, alkyl, alkenyl, alkynyl, aryl, cycloalkyl, heterocycloalkyl, aralkyl, heteroaryl, heteroaralkyl, or —[(CR$_2$)$_p$]—R$_{16}$;

$R_9$ is alkyl, alkenyl, alkynyl, aryl, cycloalkyl, heterocycloalkyl, aralkyl, heteroaryl, heteroaralkyl, or —[(CR$_2$)$_p$]—R$_{16}$;

$R_{10}$ and $R_{11}$ are each independently selected from the group consisting of hydrogen, alkyl, alkenyl, alkynyl, aryl, cycloalkyl, heterocycloalkyl, aralkyl, heteroaryl, heteroaralkyl, and —[(CR$_2$)$_p$]—R$_{16}$; or $R_{10}$ and $R_{11}$ taken together with the nitrogen to which they are bonded represent a 4-8 membered optionally substituted heterocyclic ring;

$R_{12}$ is alkyl, alkenyl, alkynyl, aryl, cycloalkyl, heterocycloalkyl, aralkyl, heteroaryl, heteroaralkyl, or —[(CR$_2$)$_p$]—R$_{16}$;

$R_{13}$ and $R_{14}$ are each independently selected from the group consisting of hydrogen, alkyl, alkenyl, alkynyl, aryl, cycloalkyl, heterocycloalkyl, aralkyl, heteroaryl, heteroaralkyl, and —[(CR$_2$)$_p$]—R$_{16}$; or $R_{13}$ and $R_{14}$ taken together with the nitrogen to which they are bonded represent a 4-8 membered optionally substituted heterocyclic ring;

$R_{16}$ for each occurrence is independently selected from the group consisting of hydrogen, hydroxyl, acylamino, —N(R$_{18}$)COR$_{19}$, —N(R$_{18}$)C(O)OR$_{19}$, —N(R$_{18}$)SO$_2$(R$_{19}$), —CON(R$_{18}$)(R$_{19}$), —OC(O)N(R$_{18}$)(R$_{19}$), —SO$_2$N(R$_{18}$)(R$_{19}$), —N(R$_{18}$)(R$_{19}$), —OC(O)OR$_{18}$, —COOR$_{18}$, —C(O)N(OH)(R$_{18}$), —OS(O)$_2$OR$_{18}$, —S(O)$_2$OR$_{18}$, —OP(O)(OR$_{18}$)(OR$_{19}$), —N(R$_{18}$)P(O)(OR$_{18}$)(OR$_{19}$), and —P(O)(OR$_{18}$)(OR$_{19}$);

p is 1, 2, 3, 4, 5, or 6;

$R_{18}$ for each occurrence is independently selected from the group consisting of hydrogen, alkyl, aryl, cycloalkyl, heterocycloalkyl, aralkyl, heteroaryl, and heteroaralkyl;

$R_{19}$ for each occurrence is independently selected from the group consisting of hydrogen, alkyl, aryl, cycloalkyl, heterocycloalkyl, aralkyl, heteroaryl, and heteroaralkyl; or $R_{18}$ taken together with Rig represent a 4-8 membered optionally substituted ring;

$R_{20}$, $R_{21}$, $R_{22}$, $R_{24}$, and $R_{25}$, for each occurrence are independently alkyl;

$R_{23}$ is alkyl, —CH$_2$OH, —CHO, —COOR$_{18}$, or —CH(OR$_{18}$)$_2$;

$R_{26}$ and $R_{27}$ for each occurrence are independently selected from the group consisting of hydrogen, alkyl, aryl, cycloalkyl, heterocycloalkyl, aralkyl, heteroaryl, and heteroaralkyl;

provided that when $R_1$ is hydroxyl, $R_2$ is hydrogen, $R_6$ and $R_7$ taken together form a double bond, $R_{20}$ is methyl, $R_{21}$ is methyl, $R_{22}$ is methyl, $R_{23}$ is methyl, $R_{24}$ is methyl, $R_{25}$ is methyl, $R_{26}$ is hydrogen, $R_{27}$ is hydrogen, Q is a bond, and W is oxygen; $R_3$ and $R_4$ are not both hydrogen nor when taken together represent an unsubstituted azetidine; and the absolute stereochemistry at a stereogenic center of formula 1 may be R or S or a mixture thereof and the stereochemistry of a double bond may be E or Z or a mixture thereof.

In one embodiment, the present invention relates to the aforementioned method, wherein said reducing agent is sodium hydrosulfite, zinc, ascorbic acid, or an electrochemical reduction.

In one embodiment, the present invention relates to the aforementioned method, wherein said reducing agent is sodium hydrosulfite.

In one embodiment, the present invention relates to the aforementioned method, wherein said reaction solvent is dichloromethane, chloroform, dichloroethane, chlorobenzene, THF, 2-MeTHF, diethyl ether, diglyme, 1,2-dimethoxyethane, MTBE, THP, dioxane, 2-ethoxybutane, methyl butyl ether, ethyl acetate, methyl acetate, 2-butanone, water or mixtures thereof.

In one embodiment, the present invention relates to the aforementioned method, wherein said reaction solvent is a mixture of ethyl acetate and water.

In one embodiment, the present invention relates to the aforementioned method, wherein said acid has a pKa between about −10 and about 7 in water.

In one embodiment, the present invention relates to the aforementioned method, wherein said acid has a pKa between about −10 and about 4 in water.

In one embodiment, the present invention relates to the aforementioned method, wherein said acid has a pKa between about −10 and about 1 in water.

In one embodiment, the present invention relates to the aforementioned method, wherein said acid has a pKa between about −10 and about −3 in water.

In one embodiment, the present invention relates to the aforementioned method, wherein said acid is HCl, HBr, $H_2SO_4$, methansulfonic acid, benzenesulfonic acid, p-toluenesulfonic acid, triflic acid, camphorsulfonic acid, naphthalene-1,5-disulfonic acid, ethan-1,2-disulfonic acid, cyclamic acid, thiocyanic acid, naphthalene-2-sulfonic acid, or oxalic acid.

In one embodiment, the present invention relates to the aforementioned method, wherein said acid is HCl.

In one embodiment, the present invention relates to the aforementioned method, wherein said acid is HBr.

In one embodiment, the present invention relates to the aforementioned method, wherein said acid is added as a gas.

In one embodiment, the present invention relates to the aforementioned method, wherein said acid is dissolved in an organic solvent.

In one embodiment, the present invention relates to the aforementioned method, wherein said organic solvent is EtOAc, DCM, IPA or dioxane, to the hydroquinone containing ansamycin in an organic solution, such as acetone, dichloromethane, chloroform, dichloroethane, chlorobenzene, THF, 2-MeTHF, diethyl ether, diglyme, 1,2-dimethoxyethane, MTBE, THP, dioxane, 2-ethoxybutane, methyl butyl ether, methyl acetate, or 2-butanone.

In one embodiment, the present invention relates to the aforementioned method, wherein $R_1$ is hydroxyl; $R_2$ is hydrogen; $R_3$ is allyl; $R_4$ is hydrogen; $R_5$ is H; $R_6$ and $R_7$ taken together form a bond; $R_{20}$ is methyl; $R_{21}$ is methyl; $R_{22}$ is methyl; $R_{23}$ is methyl; $R_{24}$ is methyl; $R_{25}$ is methyl; $R_{26}$ is hydrogen; $R_{27}$ is hydrogen; W is oxygen; and Q is a bond.

Pharmaceutical Compositions

When the compounds of the Formula 1 and 3 and their pharmaceutically acceptable salts are used as antiproliferative agents, such as anticancer agents, they can be administered to a mammalian subject either alone or in combination with pharmaceutically acceptable carriers or diluents in a pharmaceutical composition according to standard pharmaceutical practice. The compounds can be administered orally or parenterally, preferably parenterally. Parenteral administration includes intravenous, intramuscular, intraperitoneal, subcutaneous and topical, the preferred method being intravenous administration.

Accordingly, the present invention provides pharmaceutically acceptable compositions which comprise a therapeutically-effective amount of one or more of the compounds described above (Formula 1 and 3), formulated together with one or more pharmaceutically acceptable carriers (additives) and/or diluents. The pharmaceutical compositions of the present invention may be specially formulated for administration in solid or liquid form, including those adapted for the following: (1) parenteral administration, for example, by subcutaneous, intramuscular, intravenous or epidural injection as, for example, a sterile solution or suspension, or sustained-release formulation; and (2) oral administration, for example, drenches (aqueous or non-aqueous solutions or suspensions), tablets, e.g., those targeted for buccal, sublingual, and systemic absorption, boluses, powders, granules, pastes for application to the tongue. The preferred method of administration of compounds of the present invention is parental administration (intravenous).

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the compounds of the present invention include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives, solubilizing agents, buffers and antioxidants can also be present in the compositions.

Examples of pharmaceutically-acceptable antioxidants include, but are not limited to: (1) water soluble antioxidants, such as ascorbic acid, cysteine hydrochloride, sodium bisulfate, sodium metabisulfite, sodium sulfite, thioglycerol, sodium mercaptoacetate, and sodium formaldehyde sulfoxylate; (2) oil-soluble antioxidants, such as ascorbyl palmitate, butylated hydroxyanisole (BHA), butylated hydroxytoluene (BHT), lecithin, propyl gallate, alpha-tocopherol.

Examples of pharmaceutically-acceptable buffering agents include, but are not limited to citrate, ascorbate, phosphate, bicarbonate, carbonate, fumarate, acetate, tartarate and malate.

Examples of pharmaceutically-acceptable solubilizing agents include, but are not limited to polyoxyethylene sorbitan fatty acid esters (including polysorbate 80), polyoxyethylene stearates, benzyl alcohol, ethyl alcohol, polyethylene glycols, propylene glycol, glycerin, cyclodextrin, and poloxamers.

Examples of pharmaceutically-acceptable complexing agents include, but are not limited to, cyclodextrins (alpha, beta, gamma), especially substituted beta cyclodextrins such as 2-hydroxypropyl-beta, dimethyl beta, 2-hydroxyethyl beta, 3-hydroxypropyl beta, trimethyl beta.

Examples of pharmaceutically-acceptable metal chelating agents include, but are not limited to, citric acid, ethylenediamine tetraacetic acid (EDTA) and its salt, DTPA (diethylene-triamine-penta-acetic acid) and its salt, EGTA and its salt, NTA (nitriloacetic acid) and its salt, sorbitol and its salt, tartaric acid and its salt, N-hydroxy iminodiacetate and its salt, hydroxyethyl-ethylene diamine-tetraacetic acid and its salt, 1- and 3-propanediamine tetra acetic acid and their salts, 1- and 3-diamino-2-hydroxy propane tetra-acetic acid and their salts, sodium gluconate, hydroxy ethane diphosphonic acid and its salt, and phosphoric acid and its salt.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers (liquid formulation), liquid carriers followed by lyophylization (powder formulation for reconstitution with sterile water or the like), or finely divided solid carriers, or both, and then, if necessary, shaping or packaging the product.

Pharmaceutical compositions of the present invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, chelating agents, solutes which render the formulation isotonic with the blood of the intended recipient or suspending or thickening agents. In the examples, the active ingredients are brought together with the pharmaceutically acceptable carriers in solution and then lyophilized to yield a dry powder. The dry powder is packaged in unit dosage form and then reconstituted for parental administration by adding a sterile solution, such as water or normal saline, to the powder.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the compounds of the present invention may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

One preferred formulation for the compounds of the present invention is an aqueous buffer containing citric acid (from about 5 mM to about 250 mM, preferably from about 25 mM to about 150 mM), ascorbic acid (from about 0.1 mM to abput 250 mM, preferably from about 0.1 mM to about 50 mM), and edetate (calcium-disodium ethylenediamine tetraacetic acid, EDTA, from abput 0.2 mM to about 20 mM, preferably from about 1 mM to about 3 mM) with the pH being adjusted to about 3.1 with sodium hydroxide. The components of the formulation act as buffering agent, anti-oxidant and metal chelator, respectively.

It is important for formulations of the compounds of the present invention to provide solubility and redox stability to this hydroquinone salt. Compounds of the present invention are significantly solubilized at lower pH when the amine is protonated. The species distribution is important since the ionized form is more soluble while the free base (un-ionized form) is less soluble. Therefore a formulation will optimize the solubility by controlling the pH of the solution. A buffering agent such as citrate which has a high buffering capacity at a preferred pH range is one such preferred formulation component. Preferably buffering agents will buffer the formulation between a pH of about 1.5 to about 5.0, more preferably between a pH of about 1.8 to about 3.5, and even more preferably between a pH of about 3 to about 3.3.

The hydoquinone analogs of the present invention may oxidize on prolonged standing in solution. Heavy metals, such as iron and copper, are capable of catalyzing oxidation reactions and can be found in trace quantities in typical reagents and labware. Protection from the oxidizing nature of heavy metals can be afforded by metal chelators such as EDTA (ethylene diamine tetraacetic acid). Other known chelators are, for example, citric acid, DTPA (diethylene-triamine-penta-acetic acid) and its salt, EGTA and its salt, NTA (nitriloacetic acid) and its salt, sorbitol and its salt, tartaric acid and its salt, N-hydroxy iminodiacetate and its salt, hydroxyethyl-ethylene diamine-tetraacetic acid and its salt, 1 and 3-propanediamine tetra acetic acid and their salts, 1- and 3-diamino-2-hydroxy propane tetra-acetic acid and their salts, sodium gluconate, hydroxy ethane diphosphonic acid and its salt, and phosphoric acid and its salt.

Another important method of preventing oxidation is to add an anti-oxidant. One preferred anti-oxidant is ascorbic acid (ascorbate). This reagent protects compounds from the oxidizing effect of molecular oxygen dissolved in aqueous media. In certain embodiments, ascorbate is used as a component in formulations of the hydroquinone analogs of the present invention.

The formulations of the present invention include formulations that are capable of shelf storage as well as formulations used for direct administrations to a patient. Specifically, the pharmaceutical compositions/formulations of the present invention are provide in a form more concentrated than that suitable for direct administration to a patient. Such a composition is typically diluted into and IV bag for administration to a patient.

It is important in such a use that the formulation contained in the IV bag be stable for from about 5 minutes to about 2 hours, more preferably stable for about 1 hour to about 2 hours, most preferably stable for about 2 hours. Stability needs to be maintained throughout the period in which the drug is administered.

Further, it is important that the buffering capacity of the diluted IV bag formulation be sufficient to achieve this stability while not being too high of a concentration to cause an adverse reaction in the patient. Too much buffer being present may result in a number of undesirable effects on the patient.

Methods of Therapy and Treatment

The present invention provides water soluble hydroquinone containing compounds that rapidly oxidize to 17-amino substituted benzoquinone geldanamycin analogs (e.g. 17-AAG) in vitro and in vivo at physiological pH. As such, the hydroquinone analogs of the present invention exhibit similar biological activites and therapeutic profiles as do 17-amino substituted geldanamycin analogs and may be used for all known therapeutic indications that 17-amino substituted geldanamycin analogs are useful in treating. 17-amino substituted geldanamycin analogs, and in particular 17-AAG, are highly potent and selective inhibitors of HSP90.

The present invention further provides methods for treating, ameliorating one or more of the symptoms of, and reducing the severity of hyperpoliferative disorders, ie cancer, as well as other HSP90 mediated disorders or conditions. Since the compositions of the present invention are more soluble than the oxidized benzoquinone forms, the compositions are more easily administered resulting in better clinical outcomes for any of the known uses of the parent molecules.

The methods of treatment of the present invention involve administering a therapeutically effective amount of a compound of the present invention to a subject suffering from an HSP90 mediated disorder or condition, such as cancer. Descriptions of the compositions, formulations, dosing, modes of administration and treatment are described herein.

Certain 17-amino substituted analogs of geldanamycin have been synthesized, and their use as antitumor agents is described in U.S. Pat. Nos. 4,261,989 and 5,387,584, 5,932, 566 and published PCT applications WO 00/03737 and WO 03/072794 (incorporated herein by reference). Structure activity relationships of 17-amino substituted geldanamycin analogs have shed more light on the chemical features required for inhibition of HSP90 (See, e.g., *J. Med. Chem.* (1995) 38:3806-3812, *J. Med. Chem.* (1995) 38:3813-3820, and *Clin. Cancer Res.* (1999) 5:3781).

Among the more successful 17-amino substituted geldamaycin analogs is 17-AAG, which has shown broad anti-tumor activity in vitro and in vivo and is currently in multiple phase I/II clinical trials. 17-AAG exhibits differential cytoxicity against a broad range of tumor types in the NCI 60 tumor cell line panel. The mean $IC_{50}$ over all cell lines in the panel is 120 nM (Developmental Therapeutics Program Website: http://dtp.nci.nih.gov/, mean graph for compound S330507).

In addition, 17-AAG has been shown to have activity against a number of cell lines, including, but not limited to, melanoma (*Anti-Cancer Drugs* (2004) 15: 377-388), prostate cancer (*Clin. Cancer Res.* (2002) 8: 986-993), breast cancer (*Cancer. Res.* (2001) 61: 2945-2952), non-small cell lung cancer (*Ann. Thorac. Surg.* (2000) 70: 1853-1860), leukemias (*Cancer Res.* (2001) 61: 1799-1804), and colon cancer (*J. Natl. Cancer Inst.* (2003) 95: 1624-1633).

In one embodiment, the present invention provides a method of treating cancer, comprising administering to a mammal in need thereof a therapeutically effective amount of anyone of the aforementioned compounds; or a therapeutically effective amount of anyone of the aforementioned pharmaceutical compositions.

In one embodiment, the present invention relates to the aforementioned method, wherein said cancer is a cancer of the hematopoietic system, immune system, endocrine system, pulmonary system, gastrointestinal system, musculoskeletal system, reproductive system, central nervous system, or urologic system.

In one embodiment, the present invention relates to the aforementioned method, wherein the cancer is located in the mammal's myeloid tissues, lymphoid tissues, pancreatic tissues, thyroid tissues, lungs, colon tissues, rectal tissues, anal tissues, liver tissues, skin, bone, ovarian tissues, uterine tissues, cervical tissues, breast, prostate, testicular tissues, brain, brainstem, meningial tissues, kidney, or bladder.

In one embodiment, the present invention relates to the aforementioned method, wherein the cancer is located in the mammal's myeloid tissues, lymphoid tissues, breast, lung, ovary, or prostate.

In one embodiment, the present invention relates to the aforementioned method, wherein said cancer is breast cancer, multiple myeloma, prostate cancer, Hodgkin lymphoma, non-Hodgkin lymphoma, acute lymphocytic leukemia, chronic lymphocytic leukemia, acute myeloid leukemia, chronic myeloid leukemia, renal cell carcinoma, malignant melanoma, pancreatic cancer, lung cancer, colorectal carcinoma, colon cancer, brain cancer, renal cancer, head and neck cancer, bladder cancer, thyroid cancer, prostate cancer, ovarian cancer, cervical cancer, or myelodysplastic syndrome.

In one embodiment, the present invention relates to the aforementioned method, wherein said mammal's cancer is breast cancer, acute myeloid leukemia, chronic myeloid leukemia, melanoma, multiple myeloma, lung cancer, ovarian cancer, or prostate cancer.

In one embodiment, the present invention relates to the aforementioned method, wherein said mammal is a primate, equine, canine, feline, or bovine.

In one embodiment, the present invention relates to the aforementioned method, wherein said mammal is a human.

In one embodiment, the present invention relates to the aforementioned method, wherein the mode of administration of said compound is inhalation, oral, intravenous, sublingual, ocular, transdermal, rectal, vaginal, topical, intramuscular, intra-arterial, intrathecal, subcutaneous, buccal, or nasal.

In one embodiment, the present invention relates to the aforementioned method, wherein the mode of administration is intravenous.

Combination Therapy

In another embodiment, the present invention provides methods of treatment wherein the compounds and compositions of the invention are used at sub-cytotoxic levels in combination with at least one other agent in order to achieve selective activity in the treatment of cancer. In certain embodiments, the compounds of the present invention are used to reduce the cellular levels of properly folded HSP90 client proteins, which are then effectively inhibited by the second agent or whose degradation in the proteasome is inhibited using a proteasome inhibitor, e.g., Velcade™. Binding of the client proteins to HSP90 stabilizes the client proteins and maintains them in a soluble, inactive form ready to respond to activating stimuli. Binding of a benzoquinone ansamycin analog of the present invention to HSP90 results in targeting of the client protein to the proteasome, and subsequent degradation. Using an agent that targets and inhibits the proteasome blocks proteasome degradation leading to increased in cellular apoptosis and cell death.

Some examples of antineoplastic agents which can be used in combination with the methods of the present invention include, in general, alkylating agents; anti-angiogenic agents; anti-metabolites; epidophyllotoxin; an antineoplastic enzyme; a topoisomerase inhibitor; procarbazine; mitoxantrone; platinum coordination complexes; anti-mitotics; biological response modifiers and growth inhibitors; hormonal/anti-hormonal therapeutic agents and haematopoietic growth factors.

Exemplary classes of antineoplastic agents further include the anthracycline family of drugs, the vinca drugs, the mitomycins, the bleomycins, the cytotoxic nucleosides, the epothilones, discodermolide, the pteridine family of drugs, diynenes and the podophyllotoxins.

Particularly useful members of those classes include, for example, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, Velcade, doxorubicin, vindesine, leurosine, imatinib mesylate, paclitaxel, taxol, and the like. In a preferred embodiment, the antineoplastic agent is Velcade, doxorubicin, taxotere, docetaxel, paclitaxel, cis-platin, imatinib mesylate, or gemcitebine. In a preferred embodiment, the antineoplastic agent is Velcade or doxorubicin.

Other useful antineoplastic agents include estramustine, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

Also, in general, compounds of the present invention and the chemotherapeutic agent do not have to be administered in the same pharmaceutical composition, and may, because of different physical and chemical characteristics, have to be administered by different routes. For example, compounds of the present invention may be administered intravenously to generate and maintain good blood levels, while the chemotherapeutic agent may be administered orally. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of chemotherapeutic agent or radiation will depend upon the diagnosis of the attending physicians and their judgment of the condition of the patient and the appropriate treatment protocol.

A compound of the present invention, and chemotherapeutic agent and/or radiation may be administered concurrently (e.g., simultaneously, essentially simultaneously or within the same treatment protocol) or sequentially, depending upon the nature of the proliferative disease, the condition of the patient, and the actual choice of chemotherapeutic agent and/or radiation to be administered in conjunction (i.e., within a single treatment protocol) with a compound of the present invention.

If a compound of the present invention, and the chemotherapeutic agent and/or radiation are not administered simultaneously or essentially simultaneously, then the optimum order of administration of the compound of the present invention, and the chemotherapeutic agent and/or radiation, may be different for different tumors. Thus, in certain situations the compound of the present invention may be administered first followed by the administration of the chemotherapeutic agent and/or radiation; and in other situations the chemotherapeutic agent and/or radiation may be administered first followed by the administration of a compound of the present invention. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of a compound of the present invention followed, where determined advantageous, by the administration of the chemotherapeutic agent and/or radiation, and so on until the treatment protocol is complete.

Thus, in accordance with experience and knowledge, the practicing physician can modify each protocol for the administration of a component (therapeutic agent, i.e., compound of the present invention, chemotherapeutic agent or radiation) of the treatment according to the individual patient's needs, as the treatment proceeds.

Dosage

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or salt thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable dose of a compound of the invention will be that amount of the compound which is the lowest safe and effective dose to produce a therapeutic effect. Such an effective dose will generally depend upon the factors described above. Generally, intravenous doses of the compounds of the present invention for a patient will range from about 10 mg to about 1000 mg per meter$^2$ dosed twice per week, preferably between about 75 mg to 750 mg per meter$^2$ dosed twice per week, and even more preferably 100 mg to 500 mg per meter$^2$ dosed twice per week.

While it is possible for a compound of the present invention to be administered alone, it is preferable to administer the compound as a pharmaceutical formulation (composition).

The patient receiving this treatment is any animal in need, including primates, in particular humans, and other mammals such as equines, cattle, swine and sheep; and poultry and pets in general.

One or more other active compounds may be added to the formulations described above to provide formulations for combination cancer therapy.

EXEMPLIFICATION

The invention now being generally described, it will be more readily understood by reference to the following examples, which are included merely for purposes of illustration of certain aspects and embodiments of the present invention, and are not intended to limit the invention. Further, the amino acid are represented in zwitterionic form and can also be further protonated and exist as the salt.

Example 1

Preparation of Air-Stable Hydroquinone Derivatives of the Geldanamycin Family of Molecules

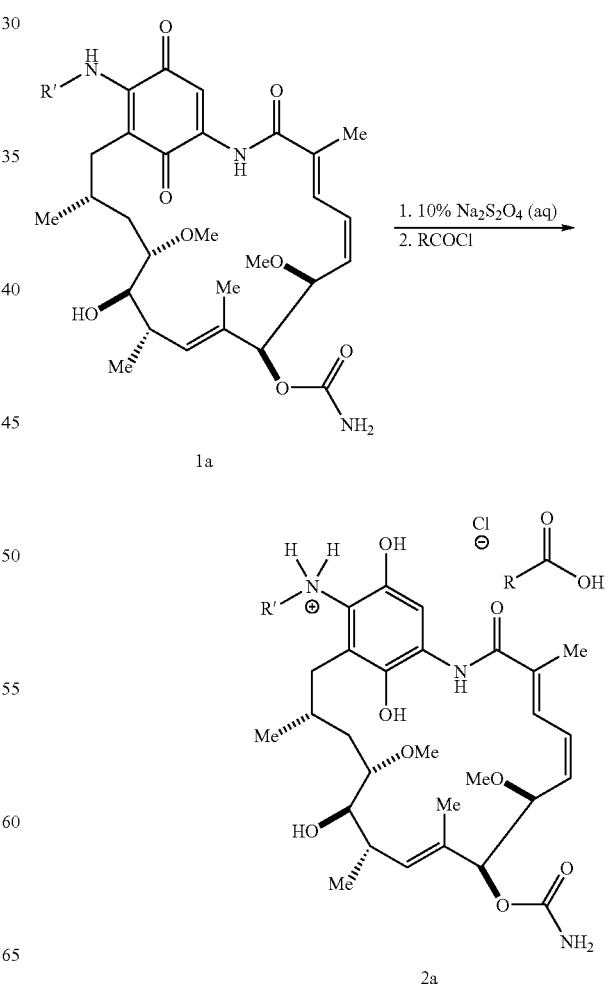

Compound of Formula (1a) (1.0 equiv) is dissolved in dichloromethane (0.02 M) and stirred with a 10% aqueous solution of sodium hydrosulfite (1:1; DCM:aqueous solution). The solution is stirred for 30 minutes. The organic layer is then removed via syringe and the aqueous solution is extracted once more with dichloromethane. The combined organic solutions are washed with brine and then added directly to a solution of an acid chloride (1.0 equiv) in dichloromethane (0.001 M). The reaction mixture is stirred for 12 h and poured into a solution of dichloromethane. The organic layer is then washed with additional water (2.0 mL); the combined aqueous layers are then lyophilized to yield the product.

Example 2

Preparation of Air-stable Hydroquinone Derivatives of the Geldanamycin Family of Molecules

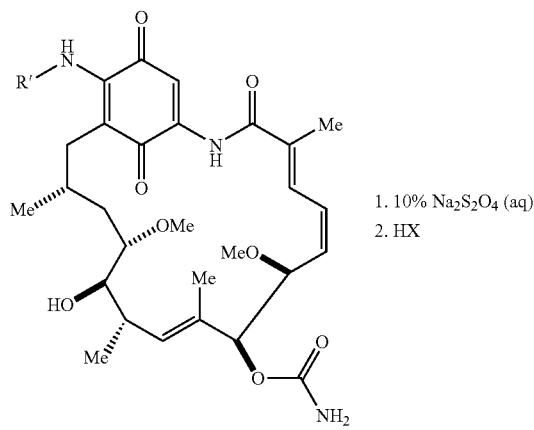

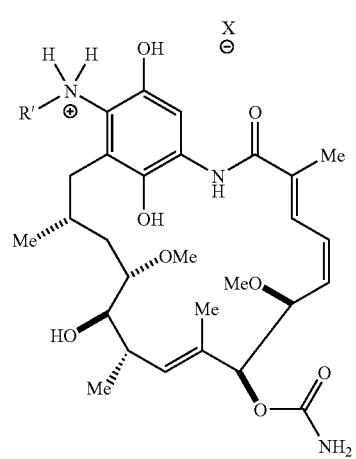

Compound of Formula (1a) (0.25 mmol, 1.0 equiv) is dissolved in dichloromethane (3 mL) and stirred with a 10% aqueous solution of sodium hydrosulfite (1.5 mL). The solution is stirred for 30 minutes. The organic layer is then removed via syringe and the aqueous solution is extracted once more with dichloromethane. The combined organic solutions are diluted with 3 mL of EtOAc, washed with brine and further dried by azeotropic removal of residual water and EtOAc under reduced pressure (3 mL of solvent total removed under reduced pressure). To this solution is added a solution of an acid in an organic solvent. The resulting solution is then cooled to −5° C. and an acid (0.25 mmol) in toluene is added (0.2 mL). A solid slowly crashes out of solution. MTBE (3 mL) is then added and the resulting mixture is allowed to warm to RT and is stirred at this temperature for 50 minutes. The solid is then collected by vacuum filtration, is washed with MTBE (2×3 mL), and is dried under reduced pressure to yield the product.

Example 3

Preparation of Dimethylamino Acetate Co-Salt of the Hydroquinone of 17-AAG

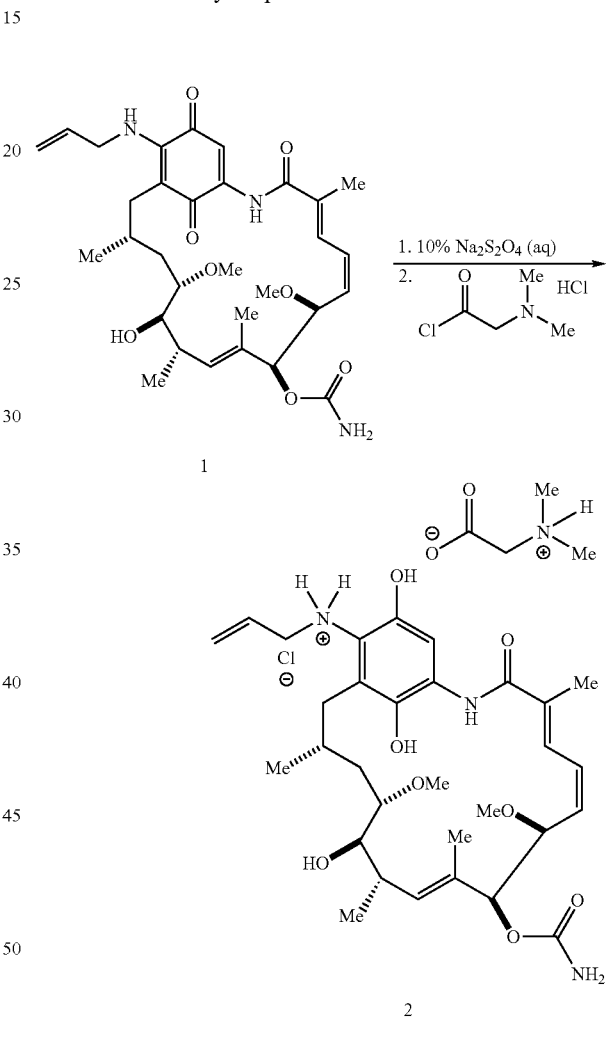

17-Allylaminogeldanamycin (1) (9.1 mg, 0.016 mmol, 1.0 equiv) was dissolved in 1.0 mL dichloromethane and stirred with a 10% aqueous solution of sodium hydrosulfite (1.0 mL). The deep purple solution turned yellow after 5 min and the mixture was stirred for an additional 25 min. The organic layer was removed via syringe and the aqueous solution was extracted with an additional 0.30 mL dichloromethane. The combined organic solutions were washed with brine (1.0 mL) and then added directly to a solution of dimethylaminoacetyl acid chloride hydrochloride (2.5 mg, 0.016 mmol, 1.0 equiv) in 0.20 mL dichloromethane. The reaction mixture was stirred for 2 h and poured into a separatory funnel with 3.0 mL water. The organic layer was extracted and then washed with additional 2.0 mL water. The combined aqueous layers were lyophilized to yield 2 as a white fluffy powder (7.1 mg, 0.011 mmol, 66% yield). The material was analyzed by $^1$H NMR in $D_2O$ and LC-MS.

Example 4

Preparation of α-Aminoisobutyrate Co-Salt of the Hydroquinone of 17-AAG

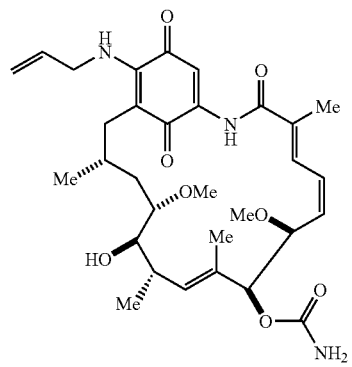

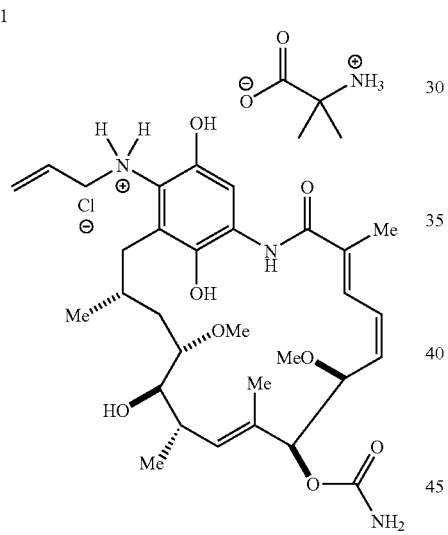

17-Allylaminogeldanamycin (1) (16.7 mg, 0.0285 mmol, 1.0 equiv) was dissolved in 1.5 mL dichloromethane and stirred with a 10% aqueous solution of sodium hydrosulfite (1.5 mL). The deep purple solution turned yellow after 5 min and the mixture was stirred for an additional 25 min. The organic layer was removed via syringe and the aqueous solution was extracted with an additional 0.30 mL dichloromethane. The combined organic solutions were washed with brine (1.0 mL) and then added directly to a solution of acid chloride hydrochloride (4.4 mg, 0.0314 mmol, 1.1 equiv) in 0.20 mL dichloromethane. The reaction mixture was stirred for 2 h and poured into a separatory funnel with 3.0 mL water. The organic layer was extracted and then washed with additional 2.0 mL water. The combined aqueous layers were lyophilized to yield 3 as a white fluffy powder (15. 1 mg, 0.0224 mmol, 79% yield). The material was analyzed by $^1$H NMR in $D_2O$ and LC-MS.

Example 5

Preparation of β-Alanine Co-Salt of the Hydroquinone of 17-AAG

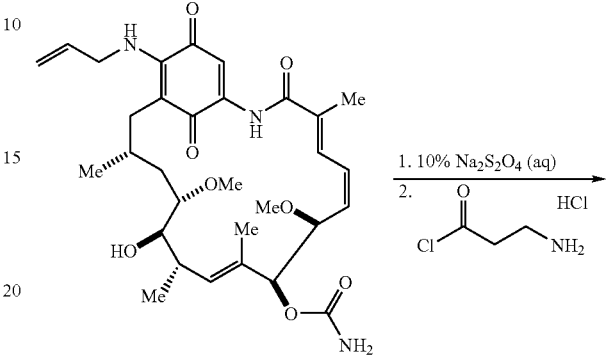

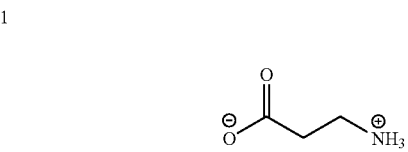

17-Allylaminogeldanamycin (1) (16.7 mg, 0.0285 mmol, 1.0 equiv) was dissolved in 1.5 mL dichloromethane and stirred with a 10% aqueous solution of sodium hydrosulfite (1.5 mL). The deep purple solution turned yellow after 5 min and the mixture was stirred for an additional 25 min. The organic layer was removed via syringe and the aqueous solution was extracted with an additional 0.30 mL dichloromethane. The combined organic solutions were washed with brine (1.0 mL) and then added directly to a solution of the acid chloride hydrochloride (4.52 mg, 0.0314 mmol, 1.1 equiv) in 0.20 mL dichloromethane. The reaction mixture was stirred for 2 h and poured into a separatory funnel with 3.0 mL water. The organic layer was extracted and then washed with additional 2.0 mL water. The combined aqueous layers were lyophilized to yield 4 as a white fluffy powder (12 mg, 0.0237 mmol, 83% yield). The material was analyzed by $^1$H NMR in $D_2O$ and LC-MS.

Example 6

Preparation of N-Methyl Glycine Co-Salt of the Hydroquinone of 17-AAG

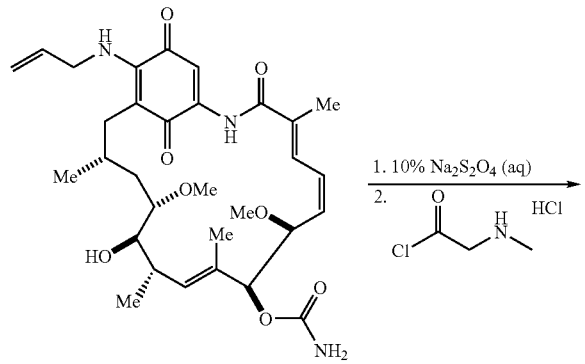

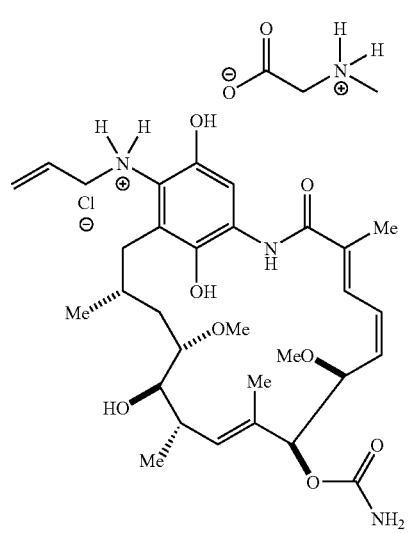

17-Allylaminogeldanamycin (1) (15.1 mg, 0.0258 mmol, 1.0 equiv) was dissolved in 1.5 mL dichloromethane and stirred with a 10% aqueous solution of sodium hydrosulfite (1.5 mL). The deep purple solution turned yellow after 5 min and the mixture was stirred for an additional 25 min. The organic layer was removed via syringe and the aqueous solution was extracted with an additional 0.30 mL dichloromethane. The combined organic solutions were washed with brine (1.0 mL) and then added directly to a solution of the acid chloride hydrochloride (3.7 mg, 0.0258 mmol, 1.0 equiv) in 0.20 mL dichloromethane. The reaction mixture was stirred for 2 h and poured into a separatory funnel with 3.0 mL water. The organic layer was extracted and then washed with additional 2.0 mL water. The combined aqueous layers were lyophilized to yield 5 as a white fluffy powder (15.4 mg, 0.0234 mmol, 91% yield). The material was analyzed by $^1$H NMR in D$_2$O and LC-MS.

Example 7

Preparation of Piperidine Carboxylate Co-Salt of the Hydroquinone of 17-AAG

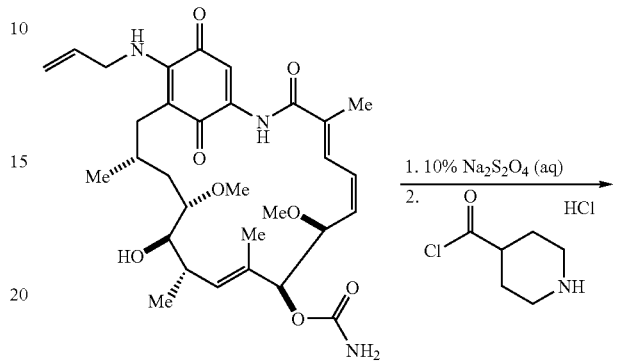

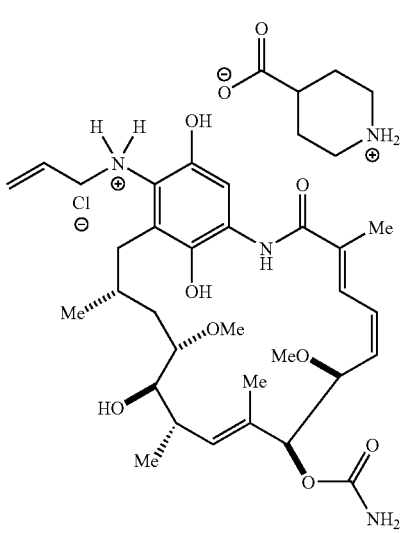

17-Allylaminogeldanamycin (1) (16 mg, 0.027 mmol, 1.0 equiv) was dissolved in 1.5 mL dichloromethane and stirred with a 10% aqueous solution of sodium hydrosulfite (1.5 mL). The deep purple solution turned yellow after 5 min and the mixture was stirred for an additional 25 min. The organic layer was removed via syringe and the aqueous solution was extracted with an additional 0.25 mL dichloromethane. The combined organic solutions were washed with brine (1.0 mL) and then added directly to a solution of the acid chloride hydrochloride (5.5 mg, 0.03 mmol, 1.1 equiv) in 0.20 mL dichloromethatae. The reaction mixture was stirred for 2 h and poured into a separatory funnel with 3.0 mL water. The organic layer was extracted and then washed with additional 2.0 mL water. The combined aqueous layers were lyophilized to yield 6 as a white fluffy powder (11.4 mg, 0.019 mmol, 60% yield). The material was analyzed by $^1$H NMR in D$_2$O and LC-MS.

Example 8

Preparation of Glycine Co-Salt of the Hydroquinone of 17-AAG

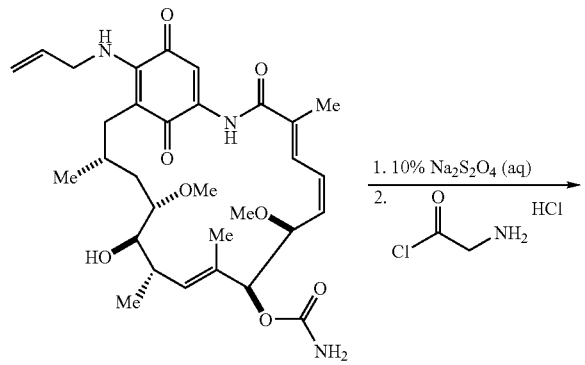

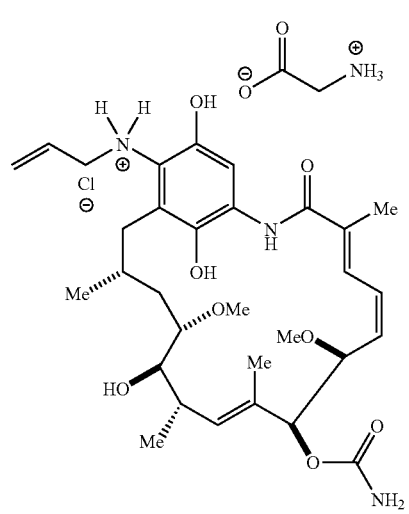

17-Allylaminogeldanamycin (1) (16.2 mg, 0.028 mmol, 1.0 equiv) was dissolved in 1.5 mL dichloromethane and stirred with a 10% aqueous solution of sodium hydrosulfite (1.5 mL). The deep purple solution turned yellow after 5 min and the mixture was stirred for an additional 25 min. The organic layer was removed via syringe and the aqueous solution was extracted with an additional 0.30 mL dichloromethane. The combined organic solutions were washed with brine (1.0 mL) and then added directly to a solution of the acid chloride hydrochloride (3.4 mg, 0.03 mmol, 1.1 equiv) in 0.20 mL dichloromethane. The reaction mixture was stirred for 2 h and poured into a separatory funnel with 3.0 mL water. The organic layer was extracted and then washed with additional 2.0 mL water. The combined aqueous layers were lyophilized to yield 7 as a white fluffy powder (3.1 mg, 0.0051 mmol, 19% yield, 3:1 mixtures of phenol regioisomers). The material was analyzed by $^1$H NMR in D$_2$O and LC-MS.

Example 9

Preparation of 2-Amino-2-ethyl-butyrate Co-Salt of the Hydroquinone of 17-AAG

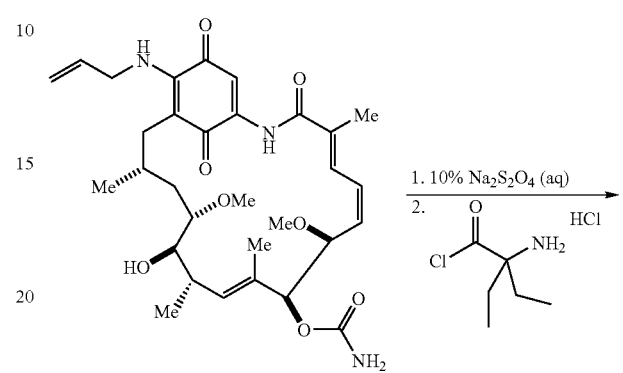

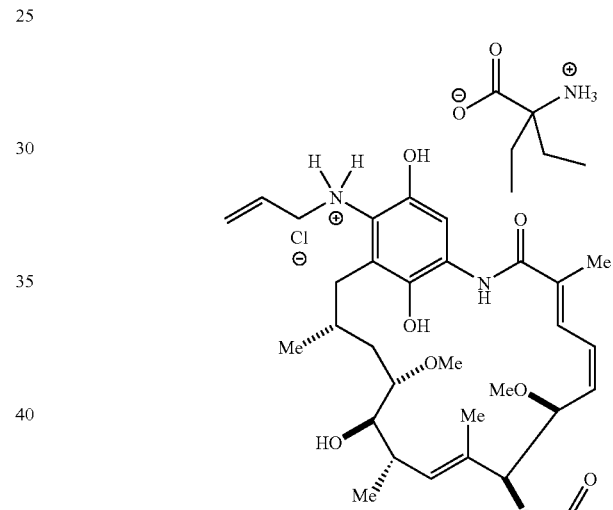

17-Allylaminogeldanamycin (1) (48 mg, 0.082 mmol, 1.0 equiv) was dissolved in 4.8 mL dichloromethane and stirred with a 10% aqueous solution of sodium hydrosulfite (4.8 mL). The deep purple solution turned yellow after 5 min and the mixture was stirred for an additional 25 min. The organic layer was removed via syringe and the aqueous solution was extracted with an additional 1 mL dichloromethane. The combined organic solutions were washed with brine (1.0 mL) and then added directly to a solution of the acid chloride hydrochloride (16.8 mg, 0.09 mmol, 1.1 equiv) in 1 mL dichloromethane. The reaction mixture was stirred for 2 h and poured into a separatory funnel with 3.0 mL water. The organic layer was extracted and then washed with additional 2.0 mL water. The combined aqueous layers were lyophilized to yield 8 as a white fluffy powder (24.7 mg, 0.034 mmol, 41% yield). The material was analyzed by $^1$H NMR in D$_2$O and LC-MS.

Example 10

Preparation of 1-Amino-Cyclopropanecarboxylate Co-Salt of the Hydroquinone of 17-AAG

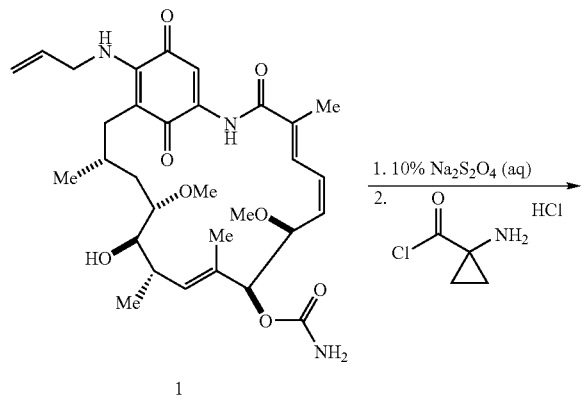

Example 11

Preparation of Carboxylate Co-Salt of the Hydroquinone of 17-AAG

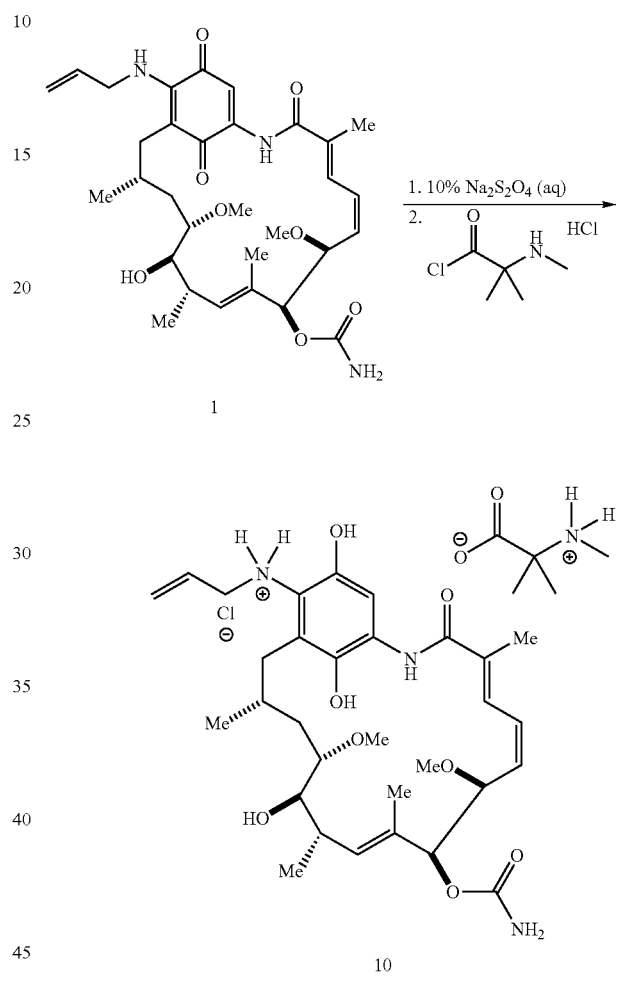

17-Allylaminogeldanamycin (1) (48 mg, 0.082 mmol, 1.0 equiv) was dissolved in 4.8 mL dichloromethane and stirred with a 10% aqueous solution of sodium hydrosulfite (4.8 mL). The deep purple solution turned yellow after 5 min and the mixture was stirred for an additional 25 min. The organic layer was removed via syringe and the aqueous solution was extracted with an additional 1 mL dichloromethane. The combined organic solutions were washed with brine (1.0 mL) and then added directly to a solution of the acid chloride hydrochloride (14.1 mg, 0.09 mmol, 1.1 equiv) in 1 mL dichloromethane. The reaction mixture was stirred for 2 h and poured into a separatory funnel with 3.0 mL water. The organic layer was extracted and then washed with additional 2.0 mL water. The combined aqueous layers were lyophilized to yield 9 as a white fluffy powder (36.2 mg, 0.051 mmol, 62% yield). The material was analyzed by $^1$H NMR in $D_2O$ and LC-MS.

17-Allylaninogeldanamycin (1) (24 mg, 0.041 mmol, 1.0 equiv) was dissolved in 2.4 mL dichloromethane and stirred with a 10% aqueous solution of sodium hydrosulfite (2.4 mL). The deep purple solution turned yellow after 5 min and the mixture was stirred for an additional 25 min. The organic layer was removed via syringe and the aqueous solution was extracted with an additional 0.30 mL dichloromethane. The combined organic solutions were washed with brine (1.0 mL) and then added directly to a solution of the acid chloride hydrochloride (7.8 mg, 0.045 mmol, 1.1 equiv) in 0.20 mL dichloromethane. The reaction mixture was stirred for 2 h and poured into a separatory funnel with 3.0 mL water. The organic layer was extracted and then washed with additional 2.0 mL water. The combined aqueous layers were lyophilized to yield 10 as a white fluffy powder (25.8 mg, 0.038 mmol, 92% yield). The material was analyzed by $^1$H NMR in $D_2O$ and LC-MS.

Example 12

Preparation of 1-Amino-cyclopentanecarboxylate Co-Salt of the Hydroquinone of 17-AAG

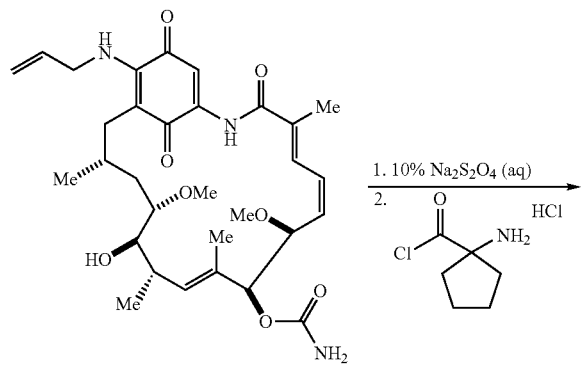

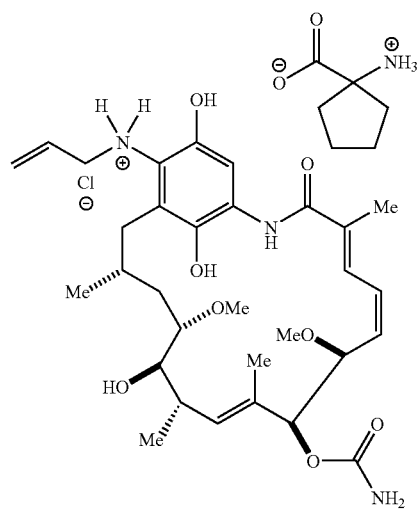

17-Allylaminogeldanamycin (1) (48 mg, 0.082 mmol, 1.0 equiv) was dissolved in 4.8 mL dichloromethane and stirred with a 10% aqueous solution of sodium hydrosulfite (4.8 mL). The deep purple solution turned yellow after 5 min and the mixture was stirred for an additional 25 min. The organic layer was removed via syringe and the aqueous solution was extracted with an additional 0.30 mL dichloromethane. The combined organic solutions were washed with brine (1.0 mL) and then added directly to a solution of the acid chloride hydrochloride (17 mg, 0.09 mmol, 1.1 equiv) in 0.20 mL dichloromethane. The reaction mixture was stirred for 2 h and poured into a separatory funnel with 3.0 mL water. The organic layer was extracted and then washed with additional 2.0 mL water. The combined aqueous layers were lyophilized to yield 11 as a white fluffy powder (34.3 mg, 0.049 mmol, 60% yield). The material was analyzed by $^1$H NMR in $D_2O$ and LC-MS.

Example 13

Preparation of N-Methyl Piperidinecarboxylate Co-Salt of the Hydroquinone of 17-AAG

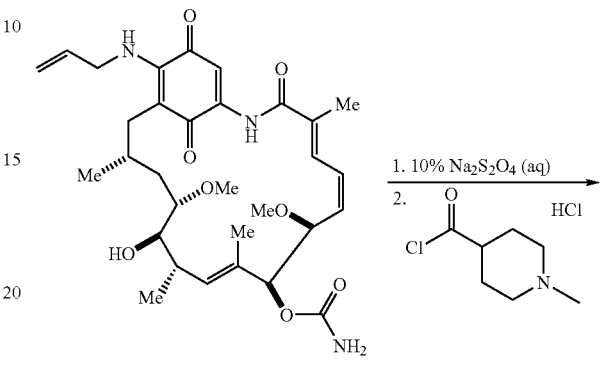

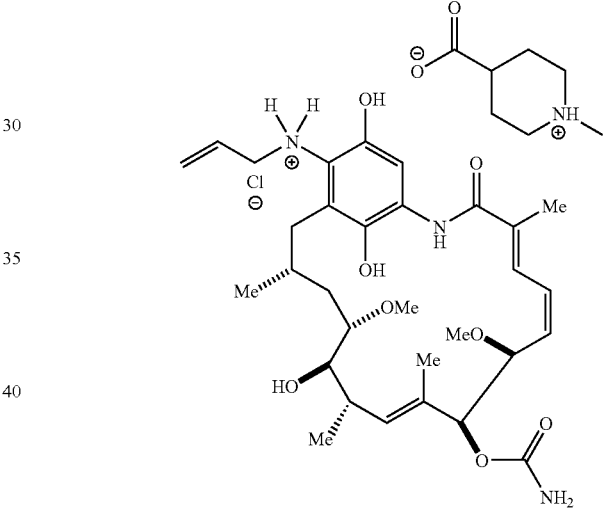

17-Allylaminogeldanamycin (1) (21.8 mg, 0.038 mmol, 1.0 equiv) was dissolved in 2 mL dichloromethane and stirred with a 10% aqueous solution of sodium hydrosulfite (2 mL). The deep purple solution turned yellow after 5 min and the mixture was stirred for an additional 25 min. The organic layer was removed via syringe and the aqueous solution was extracted with an additional 0.30 mL dichloromethane. The combined organic solutions were washed with brine (1.0 mL) and then added directly to a solution of the acid chloride hydrochloride (8.1 mg, 0.041 mmol, 1.1 equiv) in 0.20 mL dichloromethane. The reaction mixture was stirred for 2 h and poured into a separatory funnel with 3.0 mL water. The organic layer was extracted and then washed with additional 2.0 mL water. The combined aqueous layers were lyophilized to yield 12 as a white fluffy powder (15.2 mg, 0.0213 mmol, 56% yield). The material was analyzed by $^1$H NMR in $D_2O$ and LC-MS.

Example 14

Preparation of N,N,N-Trimethylammonium Acetate Co-Salt of the Hydroquinone of 17-AAG

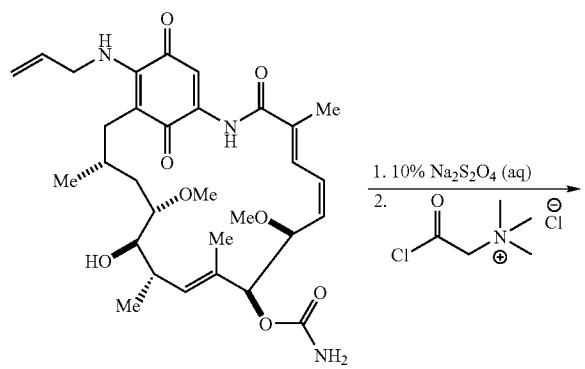

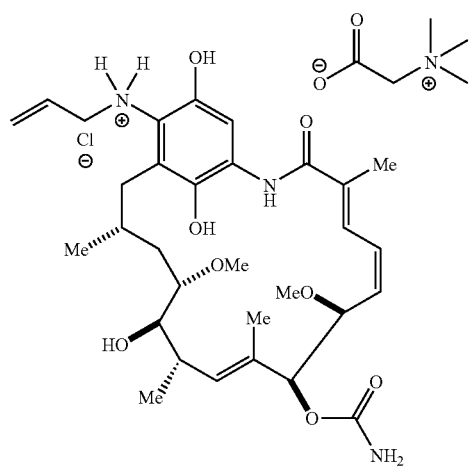

17-Allylaminogeldanamycin (1) (113 mg, 0.19 mmol, 1.0 equiv) was dissolved in 2 mL dichloromethane and stirred with a 10% aqueous solution of sodium hydrosulfite (2 mL). The deep purple solution turned yellow after 5 min and the mixture was stirred for an additional 25 min. The organic layer was removed via syringe and the aqueous solution was extracted with an additional 0.30 mL dichloromethane. The combined organic solutions were washed with brine (1.0 mL) and then added directly to a solution of the acid chloride hydrochloride (33 mg, 0.21 mmol, 1.1 equiv) in 0.20 mL dichloromethane. The reaction mixture was stirred for 2 h and poured into a separatory funnel with 3.0 mL water. The organic layer was extracted and then washed with additional 2.0 mL water. The combined aqueous layers were lyophilized to yield 13 as a white fluffy powder (78 mg, 0.11 mmol, 57% yield). The material was analyzed by $^1$H NMR in CDCl$_3$/deuterated DMSO (6:1) and LC-MS.

Example 15

Preparation of Air-stable Hydroquinone Derivatives of 17-AAG From Geldanamycin

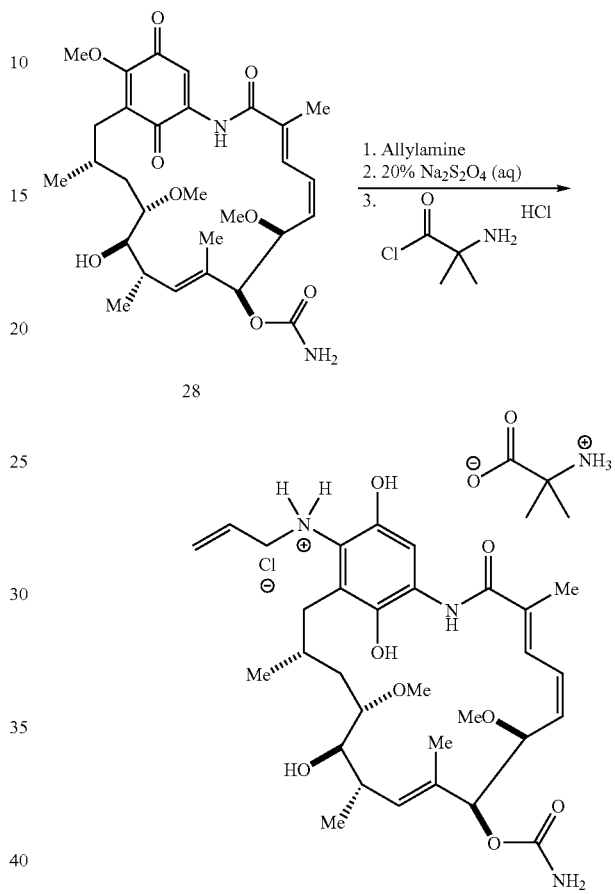

Geldanamycin (28) (0.14 g, 0.25 mmol, 1.0 equiv) add to a 10 mL vial followed by a solution of allyl amine (0.075 mL, 1.0 mmol, 4 equiv.) in MeTHF (0.625 mL). The resulting slurry is heated to 40° C. under nitrogen for 10 hours. The reaction mixture was then cooled to room temperature, diluted with 1.0 mL of MeTHF, washed with a saturated NH$_4$Cl solution (1.5 mL) and saturated NaCl (1.5 mL). The organic layer was then collected and treated with a freshly prepared aqueous solution of sodium hydrosulfite (1 mL, 20% (m/m)) with vigorous stirring under nitrogen for 45 minutes. The aqueous layer was then removed and the organic layer was then washed with 1.5 mL of degassed water. The organic solution was then dried by azetropic removal of water using MeTHF. This was accomplished by the addition of 2 mL of MeTHF and then concentration (about 2 mL) of the resulting solution under reduced pressure at 70° C. The resulting solution is then cooled to 0° C. in an ice bath and then α-aminoisobutyric acid chloride hydrochloride (0.04 g, 0.25 mmol, 1.0 equiv.) is added under nitrogen. The reaction mixture is stirred for 3 hours at which point the solid is collected by filtration and washed with MeTHF (2×2 mL). The solid is then dried under reduced pressure to yield the product as a yellow powder (171 mg, 0.2425 mmol, 97% overall yield).

Example 16

Crystallization of Hydroquinone Co-Salt Forms of 17-AAG

Compound 7 is dissolved in the minimal amount of MeOH and then EtOAc is slowly added drop wise until the turbidity persists. The mixture is then allowed to stand for 14 hours and then the solid is collected by filtration, washed with EtOAc and dried under reduced pressure.

Example 17

Preparation of Air-Stable Hydroquinone Derivatives of the Geldanamycin Family of Molecules

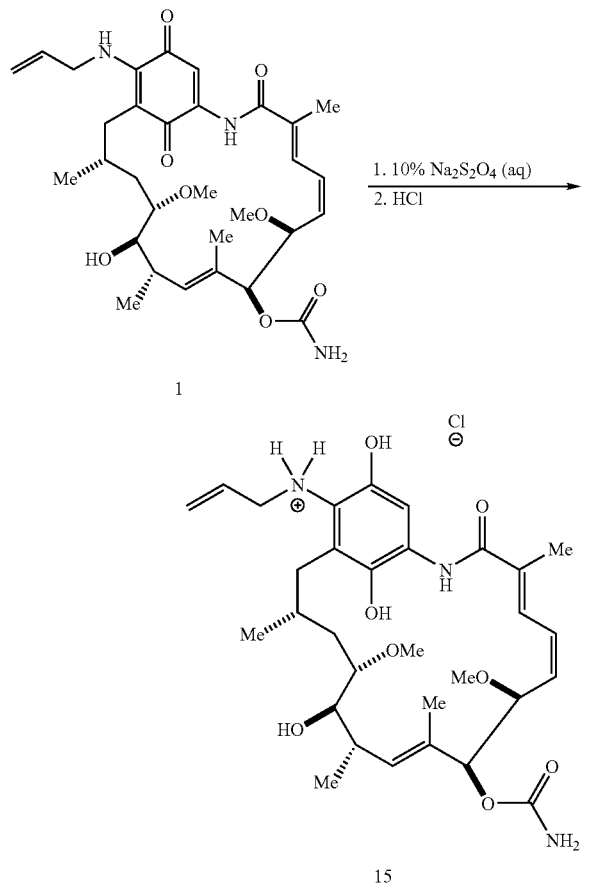

Compound of Formula (1) (0.450 g, 0.768 mmol, 1.0 equiv) is dissolved in dichloromethane.(50 mL) and stirred with a 10% aqueous solution of sodium hydrosulfite (50 mL). The solution is stirred for 30 minutes. The organic layer was collected, dried over $Na_2SO_4$, filtered and transferred to a round bottom flask. To this solution was added a solution of HCl in dioxane (4 N, 0.211 mL, 1.1 equiv.). The resulting mixture was allowed to stir under nitrogen for 30 minutes. A yellow solid slowly crashed out of solution. The yellow solid was purified by recrystallization form MeOH/EtOAc to yield 0.386 g of the IPI-504 (15).

Example 18

Preparation of Air-Stable Hydroquinone Derivatives of the Geldanamycin Family of Molecules

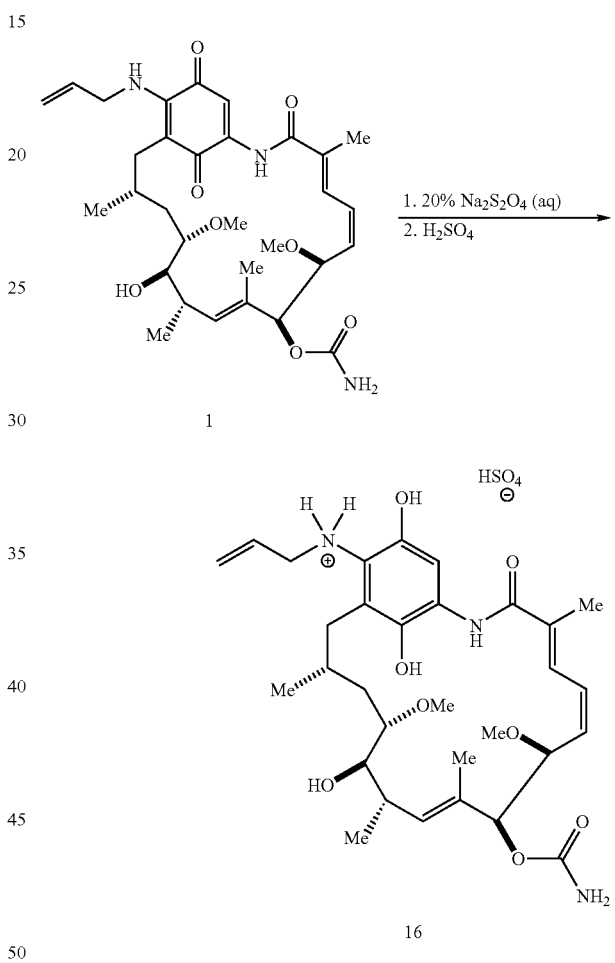

Compound of Formula (i) (0.30 g, 0.5 mmol, 1.0 equiv) is dissolved in MTBE (3 mL) and stirred with a 20% aqueous solution of sodium hydrosulfite (2 mL). The solution is stirred for 60 minutes. The organic layer was collected, washed with brine, and transferred to a round bottom flask. This solution was cooled −5° C. and put under nitrogen. To this solution was added a solution of $H_2SO_4$ in denatured ethanol (0.50 mmol of $H_2SO_4$ in 0.5 mL of EtOH) dropwise. The resulting mixture was allowed to stir under nitrogen and warm to RT. The yellow slurry was stirred for an additional 30 minutes at RT and then was concentrated. MTBE (7 mL) was added and the suspension was filtered. The yellow solid that was collected was washed with MTBE and dried under reduced pressure to yield 0.30 g of the desired product.

Example 19

Preparation of Air-Stable Hydroquinone Derivatives of the Geldanamycin Family of Molecules

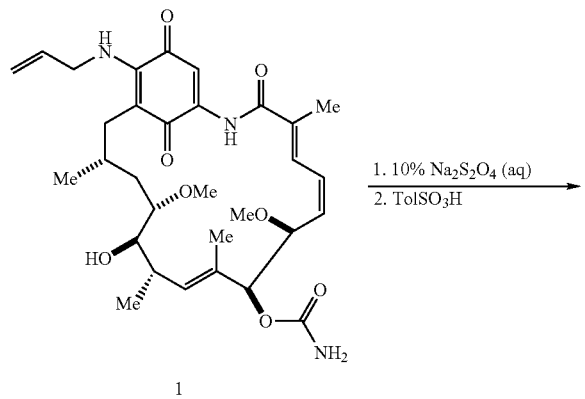

1

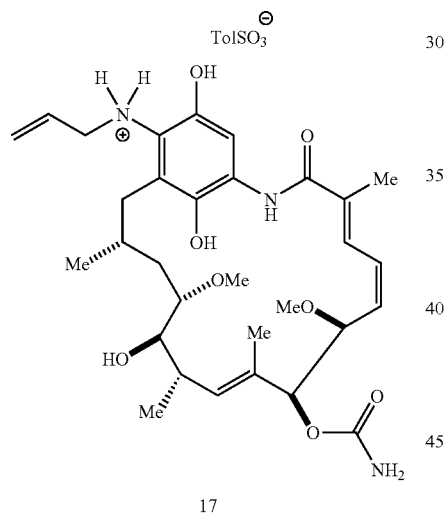

17

Example 20

Preparation of Air-Stable Hydroquinone Derivatives of the Geldanamycin Family of Molecules

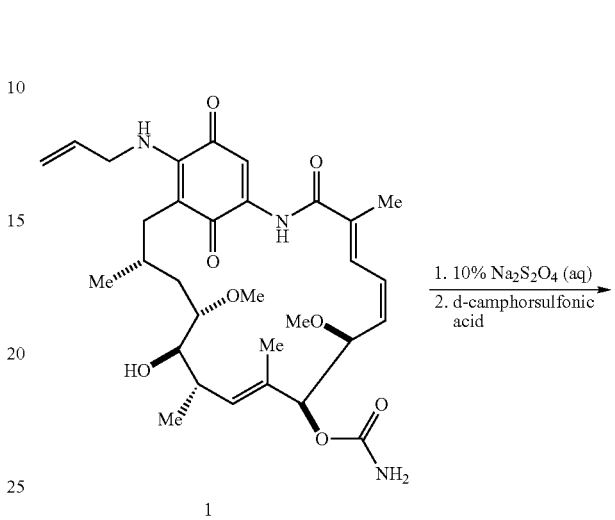

1

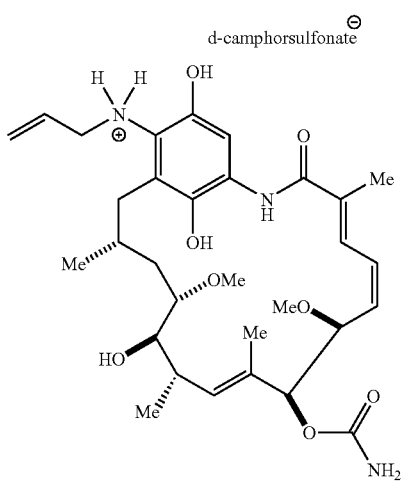

18

Compound of Formula (1) (0.30 g, 0.5 mmol, 1.0 equiv) is dissolved in DCM (6 mL) and stirred with a 10% aqueous solution of sodium hydrosulfite (3.5 mL). The solution is stirred for 60 minutes. The organic layer was collected, washed with brine, and 1.2 mL (calc 0.1 mmol of hydroquinone) transferred to a round bottom flask. This solution was put under nitrogen. To this solution was added a solution of p-toluenesolfonic acid in denatured IPA (0.100 mmol of p-toluenesolfonic in 0.25 mL of IPA) dropwise. The resulting mixture was allowed to stir under nitrogen for 1 hour, at which point the mixture was concentrated and the crude mass was reslurried from EtOAc/MTBE. The solid was collected by filtration and dried under reduced pressure to yield 0.068 g of the desired product.

Compound of Formula (1) (0.30 g, 0.5 mmol, 1.0 equiv) is dissolved in DCM (6 mL) and stirred with a 10% aqueous solution of sodium hydrosulfite (3.5 mL). The solution is stirred for 60 minutes. The organic layer was collected, washed with brine, and 1.2 mL (calc 0.1 mmol of hydroquinone) transferred to a round bottom flask. This solution was put under nitrogen. To this solution was added a solution of d-camphorsulonic acid in denatured IPA (0.100 mmol of d-camphorsulonic acid in 0.25 mL of IPA) dropwise. The resulting mixture was allowed to stir under nitrogen for 1 hour, at which point the mixture was concentrated and the crude mass was reslurried from EtOAc/MTBE. The solid was collected by filtration and dried under reduced pressure to yield 0.051 g of the desired product.

Example 21

Preparation of Air-Stable Hydroquinone Derivatives of the Geldanamycin Family of Molecules

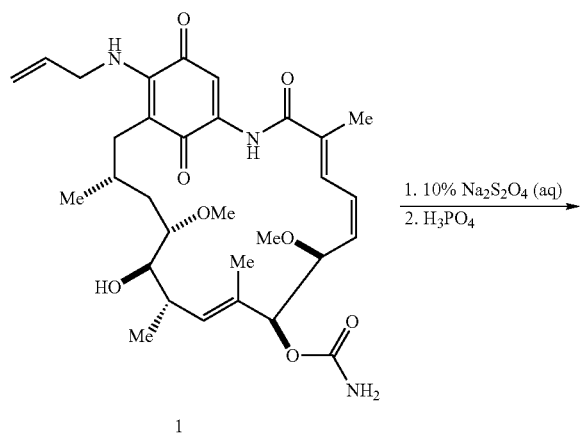

1

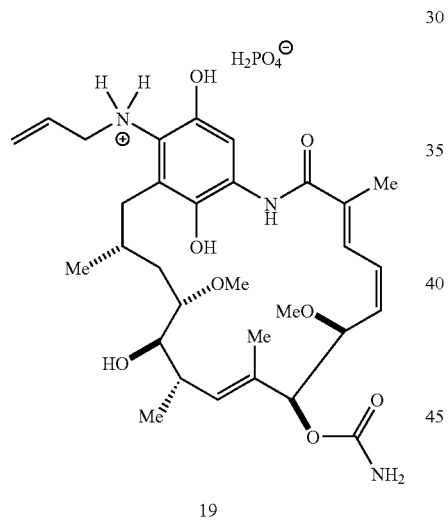

19

Compound of Formula (1) (0.30 g, 0.5 mmol, 1.0 equiv) is dissolved in DCM (6 mL) and stirred with a 1 0% aqueous solution of sodium hydrosulfite (3.5 mL). The solution is stirred for 60 minutes. The organic layer was collected, washed with brine, and 1.2 mL (calc 0.1 mmol of hydroquinone) transferred to a round bottom flask. This solution was put under nitrogen. To this solution was added a solution of $H_3PO_4$ in denatured IPA (0.100 mmol of $H_3PO_4$ in 0.25 mL of IPA) dropwise. The resulting mixture was allowed to stir under nitrogen for 1 hour, at which point the mixture was concentrated and the crude mass was reslurried from EtOAc/MTBE. The solid was collected by filtration and dried under reduced pressure to yield 0.050 g of the desired product.

Example 22

Preparation of Air-Stable Hydroquinone Derivatives of the Geldanamycin Family of Molecules

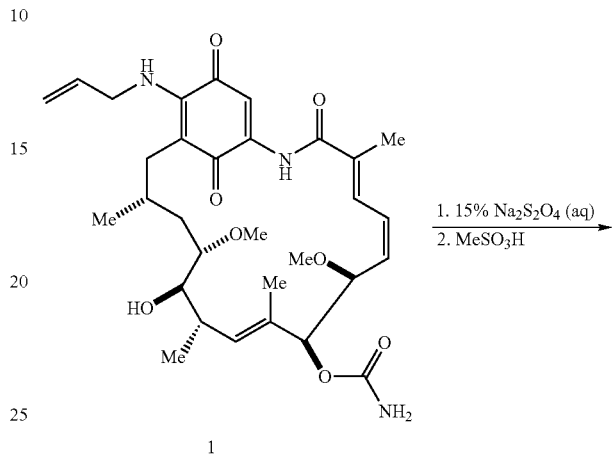

1

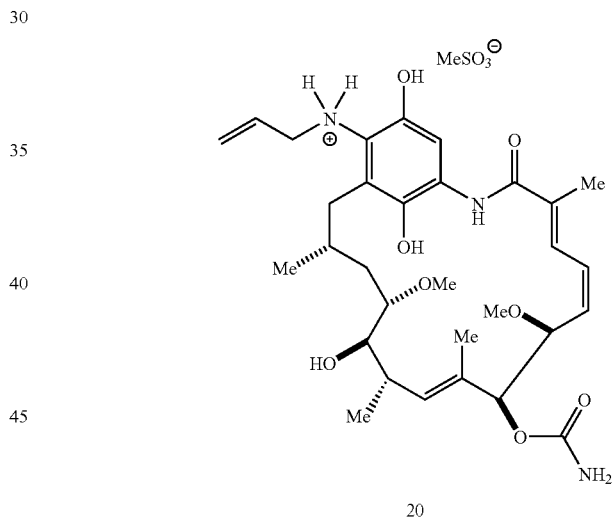

20

Compound of Formula (1) (0.50 g, 0.8 mmol, 1.0 equiv) is dissolved in DCM (8 mL) and stirred with a 15% aqueous solution of sodium hydrosulfite (4 ML). The solution is stirred for 60 minutes. The organic layer was collected, washed with brine, and 2 mL (calc 0.2 mmol of hydroquinone) transferred to a round bottom flask. This solution was put under nitrogen. To this solution was added a solution of $MeSO_3H$ in denatured IPA (0.200 mmol of $MeSO_3H$ in 0.4 mL of IPA) dropwise. The resulting mixture was allowed to stir under nitrogen for 1 hour, at which point the mixture was concentrated and the crude mass was reslurried from EtOAc. The solid was collected by filtration and dried under reduced pressure to yield 0.112 g of the desired product.

Example 23

Preparation of Air-Stable Hydroquinone Derivatives of the Geldanamycin Family of Molecules

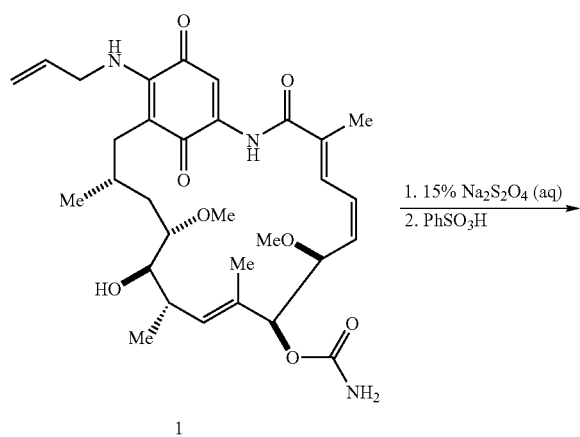

1

1. 15% Na$_2$S$_2$O$_4$ (aq)
2. PhSO$_3$H

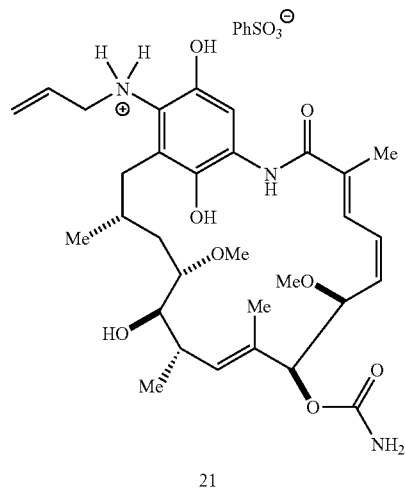

21

Compound of Formula (1) (0.50 g, 0.8 mmol, 1.0 equiv) is dissolved in DCM (8 mL) and stirred with a 15% aqueous solution of sodium hydrosulfite (4 mL). The solution is stirred for 60 minutes. The organic layer was collected, washed with brine, and 2 mL (calc 0.2 mmol of hydroquinone) transferred to a round bottom flask. This solution was put under nitrogen. To this solution was added a solution of PhSO$_3$H in denatured EPA (0.200 mmol of PhSO$_3$H in 0.4 mL of EPA) dropwise. The resulting mixture was allowed to stir under nitrogen for I hour, at which point the mixture was concentrated and the crude mass was reslurried from EtOAc. The solid was collected by filtration and dried under reduced pressure to yield 0.118 g of the desired product.

Example 24

Preparation of Air-Stable Hydroquinone Derivatives of the Geldanamycin Family of Molecules

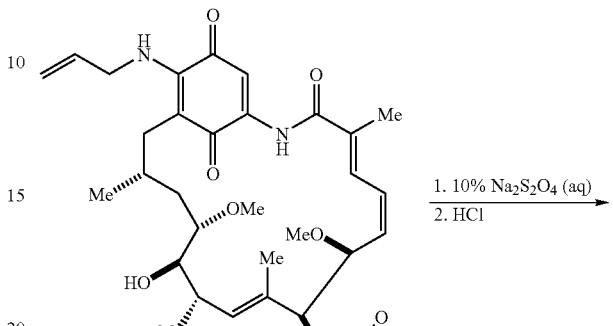

1

1. 10% Na$_2$S$_2$O$_4$ (aq)
2. HCl

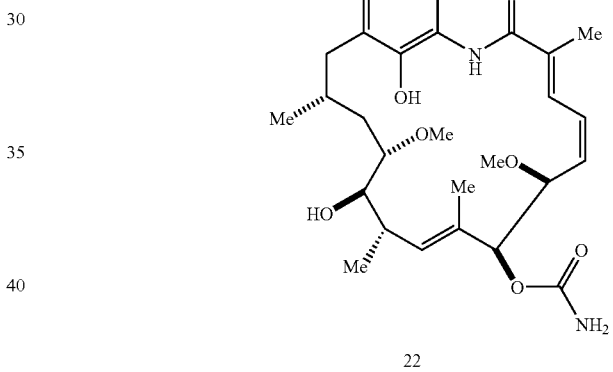

22

17-Allylamino-17-Demethoxygeldanamycin (10.0 g, 17.1 mmol) in ethyl acetate (200 mL) was stirred vigorously with a freshly prepared solution of 10% aqueous sodium hydrosulfite (200 mL) for 2 h at ambient temperature. The color changed from dark purple to bright yellow, indicating a complete reaction. The layers were separated and the organic phase was dried with magnesium sulfate (15 g). The drying agent was rinsed with ethyl acetate (50 mL). The combined filtrate was acidified with 1.5 M hydrogen chloride in ethyl acetate (12 mL) to pH 2 over 20 min. The resulting slurry was stirred for 1.5 h at ambient temperature. The solids were isolated by filtration, rinsed with ethyl acetate (50 mL) and dried at 40° C., 1 mm Hg, for 16 h to afford 9.9 g (91%) of off-white solid. Crude hydroquinone hydrochloride (2.5 g) was added to a stirred solution of 5% 0.01 N aq. hydrochloric acid in methanol (5 mL). The resulting solution was clarified by filtration then diluted with acetone (70 mL). Solids appeared after 2-3 min. The resulting slurry was stirred for 3 h at ambient temperature, then for I h at 0-5° C. The solids were isolated by filtration, rinsed with acetone (15 mL) and dried

Example 25

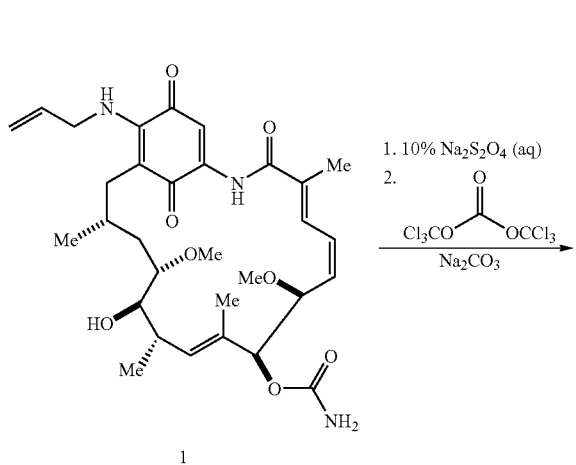

17-Allylamino-17-Demethoxygeldanamycin (0.350 g, 0.598 mmol) in ethyl acetate (7 mL) was stirred vigorously with a freshly prepared solution of 10% aqueous sodium hydrosulfite (7 mL) for 1 h at ambient temperature. The color changed from dark purple to bright yellow, indicating a complete reaction. The layers were separated and the organic phase was dried with magnesium sulfate (1 g). The drying agent was rinsed with ethyl acetate (1 mL). The combined organic layers were stirred at room temperature and to it was added triphosgene (0.079 g, 0.239 mmol). A precipitate formed and the resulting mixture was allowed to stir for 2 hr. At which point the solid was filtered off and the organic solution was concentrated. The crude product was purified by column chromatography to yield 17 mg of the desired product.

Example 26

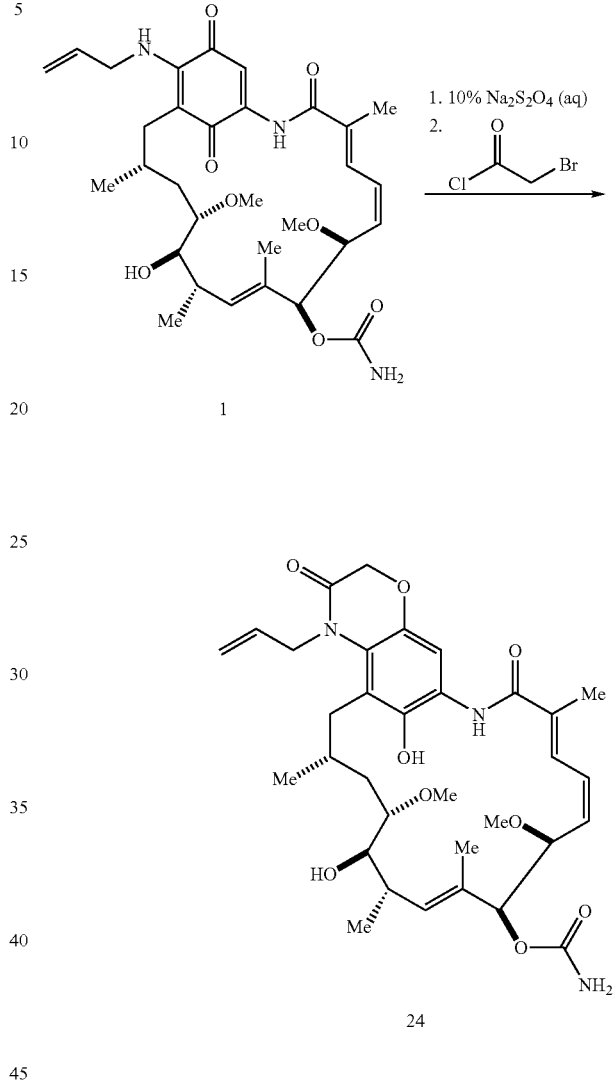

17-Allylamino-17-Demethoxygeldanamycin (0.825 g, 0.141 mmol) in ethyl acetate (17.5 mL) was stirred vigorously with a freshly prepared solution of 10% aqueous sodium hydrosulfite (17.5 mL) for 1 h at ambient temperature. The color changed from dark purple to bright yellow, indicating a complete reaction. The layers were separated and the organic phase was dried with magnesium sulfate (1 g). The drying agent was rinsed with ethyl acetate (1 mL). The combined organic layers were stirred at room temperature and to it was added bromoacetyl chloride (0.222 g, 1.41 mmol). A precipitate formed and the resulting mixture was allowed to stir for 12 hr. At which point the solid was filtered off and the organic solution was concentrated. The crude material was dissolved in a 1:1 mixture of THF/Water (16 mL). $Na_2CO_3$ (10 equiv) was added and the resulting mixture was vigorously shaken for 1 hr. The reaction was quenched with saturated $NaHCO_3$, washed with brine, dried over $MgSO_4$ and concentrated to yield 1.1 mg of the desired product.

Example 27

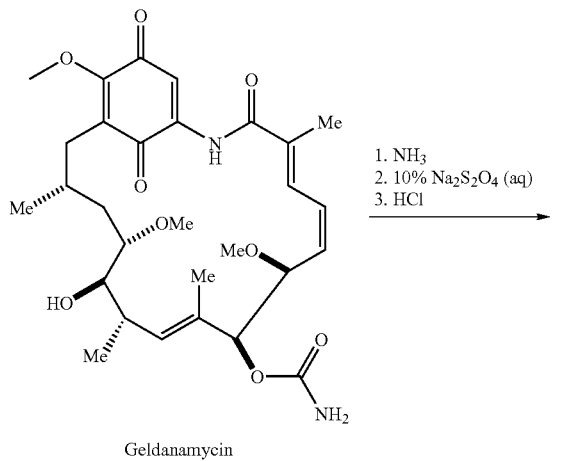

Geldanamycin (1.12 g, 2 mmol, 1 equiv) was added to anhydrous DCM (5 mL). NH$_3$ in MeOH was added to this solution (9 mL, 100 mmol, 50 equiv) and was allowed to stir for 24 hours. At which point the reaction solution was diluted with DCM and extracted with water, followed by dilute HCl. The organic layer was collected washed with brine, dried over Na$_2$SO$_4$ and concentrated to yield a purple solid. This solid was recrystalized twice from acetone/heptanes to yield 0.239 of 17-amino-17-demethoxygeldanamycin.

17-amino-17-demethoxygeldanamycin (0.55 g, 1 mmol, 1 equiv) was dissolved in EtOAc (100 mL). A freshly prepared solution of 10% aqueous sodium hydrosulfite (10 mL) was added and stirred for 1 h at ambient temperature. The color changed from dark purple to bright yellow, indicating a complete reaction. The layers were separated and the organic phase was dried with magnesium sulfate. The drying agent was rinsed with ethyl acetate (2×10 mL). The combined filtrate was acidified with 1.5 M hydrogen chloride in ethyl acetate (1 mL) to pH 2 over 20 min. The resulting slurry was stirred for 1.5 h at ambient temperature. The solids were isolated by filtration, rinsed with ethyl acetate (10 mL) and dried under vacuum to yield the product (0.524 g, 87% yield).

Example 28

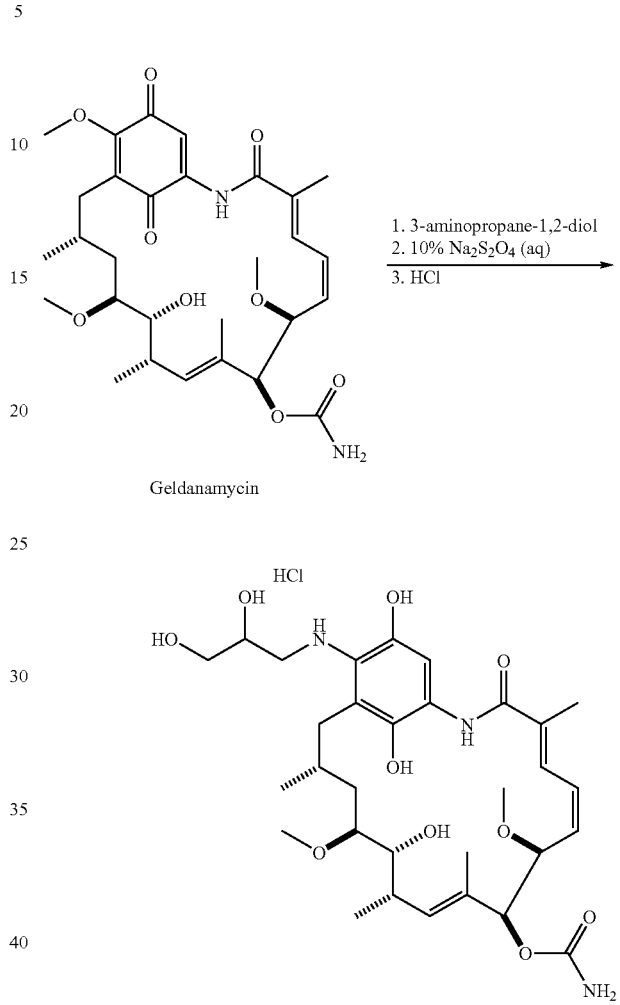

Geldanamycin (0.500 g, 0.892 mmol, 1 equiv) was dissolved in THF (10 mL) 3-amino-1,2-propanediol (0.813 g, 8.92 mmol, 10 equiv). The reaction was stirred for 64 hours. The reaction was then quenched with dilute HCl and extracted with EtOAc. The organic layer was collected dried over MgSO4 and concentrated under reduced pressure. The crude material was purified using column chromatography to yield 27 mg of the 17-amino substituted geldenamycin.

The 17-amino geldanmycin (200 g, 0.323 mmol, 1 equiv) was dissolved in EtOAc (4 mL) and treated with a freshly prepared 10% solution of Na$_2$S$_2$O$_4$ in water (4 mL). This mixture was vigorously stirred for 1 hour. The organic layer was then collected. The aqueous layer was extracted with 2×5 mL of EtOAc. The organic layers were combined, washed with water, dried over Na$_2$SO$_4$. The organic layer was then treated with HCl in EtOAc (1.6 M, 0.6 mL) and stirred for 20 minutes. The reaction solution was concentrated under reduced pressure to yield the product (0.009 g).

Example 29

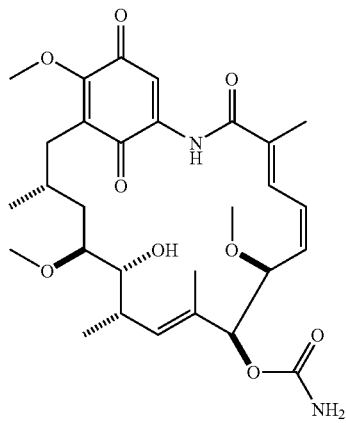
Geldanamycin

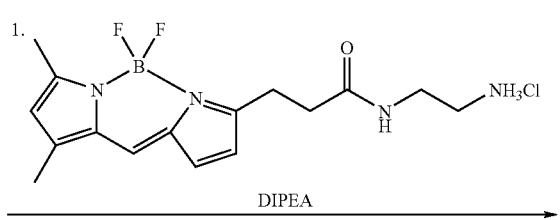

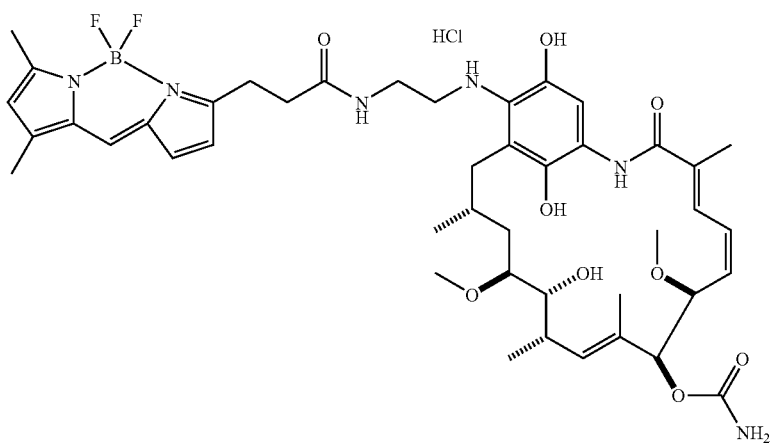
27

Geldanamycin (0.022 g, 0.04 mmol, 1.5 equiv) and BODIPY-FL-EDA-HCl (0.010 g, 0.026 mmol, 1 equiv) were added to anhydrous DCM (2mL). DIPEA (30 uL, 0.16 mmol, 6 equiv) was added and the reaction solution was stirred under nitrogen for 72 hours. The reaction was then diluted with DCM, extracted with water, dried over $Na_2SO_4$ and concentrated under reduced pressure. The crude was purified by column chromatography to yield the 17-amino substituted benzoquinone. This material was dissolved in EtOAc (20 mL) and treated with a freshly prepared 10% solution of $Na_2S_2O_4$ in water (5 mL). This mixture was vigorously stirred for 1 hour. The organic layer was then collected. The aqueous layer was extracted with 2×5 mL of EtOAc. The organic layers were combined, washed with water, dried over $Na_2SO_4$. The organic layer was then treated with HCl in EtOAc (1.6 M, 0.6 mL) and stirred for 20 minutes. The reaction solution was then concentrated to dryness under reduce pressure. The crude was purified by reslurrying the material from EtOAc/MTBE. The solid was washed with MTBE and dried under reduced pressure to yield the product (0.04 g).

Example 30

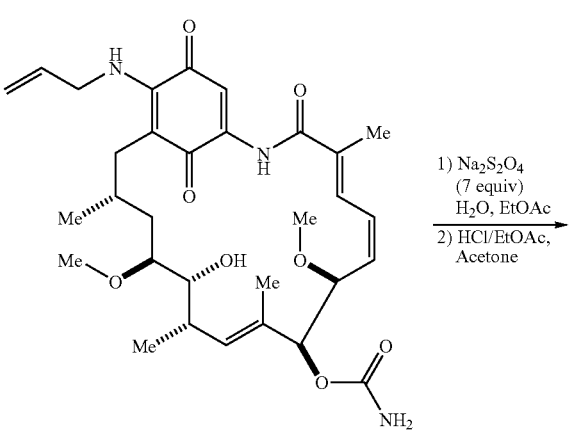
1

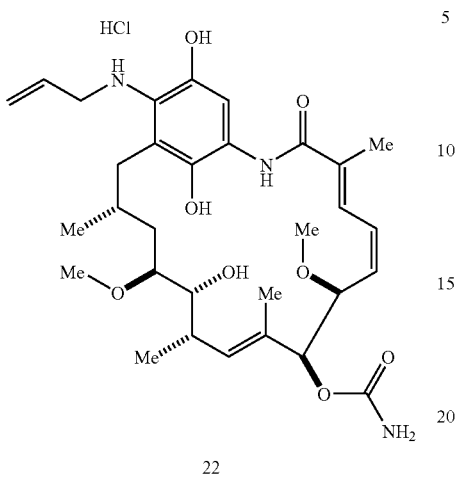

22

Anhydrous ethyl acetate (170 mL) was added to a flask followed by 17-AAG (8.41 g, 1.44 mmol, 1 equiv). The resultant purple mixture was stirred vigorously under nitrogen. A freshly prepared solution of 10% $Na_2S_2O_4$ (aq) (1.682 g in 170 mL of deionized water, 10.1 mmol, 7 equiv) was added and the mixture stirred vigorously for 70 min. The color changed from purple to orange indicating a complete reaction. The layers were allowed to separate and the bottom aqueous layer was removed using a separatory funnel. The organic layer was dried with $MgSO_4$. The drying agent was removed by filtration. The filtrate was transferred to a rotary evaporator flask. Ethyl acetate (50 mL) was used, in portions, to wash the $MgSO_4$ pad and the wash filtrate was also added to the rotary evaporator flask.

The orange-brown mixture was concentrated on the rotary evaporator to an oil. The remaining ethyl acetate was removed under vacuum.

While this mixture was concentrated, a 5.3 M solution of HCl in ethyl acetate was prepared. Ethyl acetate (16.8 mL) was added to an Erlenmeyer flask and HCl gas bubbled into the stirring mixture for 1 h (with cooling, acetone/wet ice) to achieve saturation. The solution was then warmed to room temperature under a head space of nitrogen.

The oil was dissolved in acetone (252 mL) and transferred to a reaction flask equipped with an addition funnel, a stirrer, a thermometer, and a nitrogen atmosphere. The combined filtrate and rinse were acidified over 5 min to a final pH of 2.5. The resulting slurry was stirred for 18 min at ambient temperature and the solids were then isolated by filtration and washed twice with acetone (84 mL). The solid was then dried under reduced pressure to yield the product Example 31

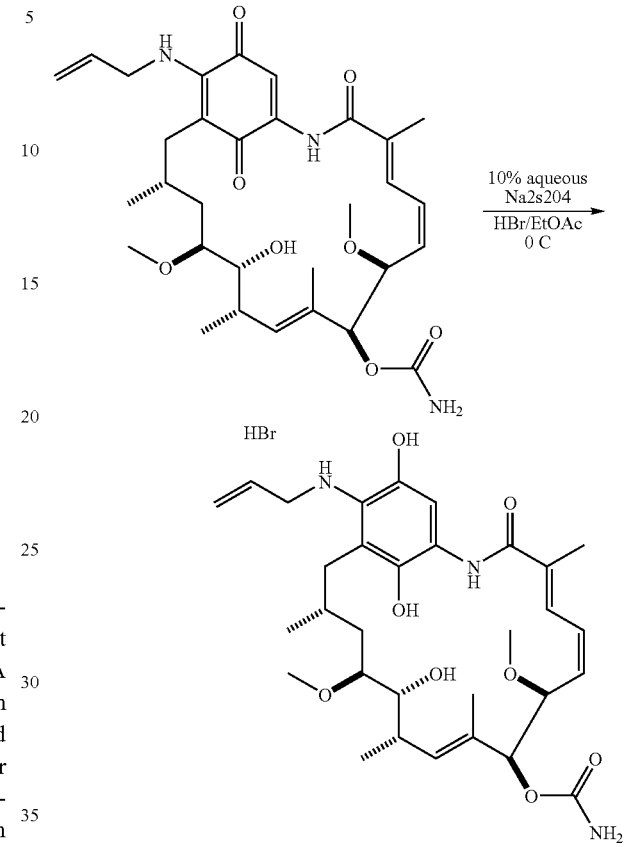

17-Allylamino-17-Demethoxygeldanamycin (1.0 g, 1.71 mmol) in ethyl acetate (20 mL) was stirred vigorously with a freshly prepared solution of 10% aqueous sodium hydrosulfite (2 g in 20 mL water) for 30 minutes at ambient temperature. The color changed from dark purple to bright yellow, indicating a complete reaction. The layers were separated and the organic phase was dried with magnesium sulfate (1 g). The reaction solvent was collected and the drying agent was rinsed with ethyl acetate (1 mL). The combined filtrate was cooled to 0 C. and acidified with 1.5 M hydrogen bromide in ethyl acetate until a precipitate formed. The resulting slurry was stirred for 30 minutes at ambient temperature. The solids were isolated by filtration, rinsed with ethyl acetate (1 mL) and dried at 40° C., 1 mm Hg, for 16 h to afford 0.352 g (31%) of off-white solid.

Example 32

Preparation of 50 mM Citrate, 50 mM Ascorbate, pH 3.1, 2.44 mM EDTA As the Formulation Buffer for Compounds of the Present Invention An Example of Formulation Preparation:

For an 1 L preparation of formulation buffer, 9.6 g citric acid (USP), 8.8 g ascorbic acid (USP) and 1.0 g EDTA (Ethylenediamine-tetraacetic acid, disodium-calcium salt, dihydrate, USP), was added with a teflon-coated magnetic stir-bar to a 1 L volumetric flask. Sterile water for injection (USP) was added to 90-95% of the final volume of the flask. The solution was vigorously stirred to dissolve all solids. The pH of the buffer was adjusted to 3.1 using a NaOH solution. WFI was added to the final volume. The buffer was vacuum filtered through a 0.2 micron filter unit. Prior to use, the solution was sparged with nitrogen for 1-2 h. The formulation buffer was stored under nitrogen at 4° C. in a closed container.

Formulated Drug Product Preparation:

The drug product was formulated at 4° C. by controlled dissolution of the solid compound 15 with pre-chilled nitrogen-sparged formulation buffer in a water-cooled jacketed vessel under a nitrogen headspace. Formulated compound 15 solution stored at 4° C. under a nitrogen headspace.

An example of the Formulated Drug Product Preparation in solution is Given Below.

A 10 mL volumetric flask was charged with solid compound 15 (500 mg) and purged with nitrogen. Formulation buffer (50 mM citrate, 50 mM ascorbate, 2.44 mM EDTA, pH 3.1) was sparged with nitrogen until dissolved oxygen content is <0.5 mg/L and chilled on ice. A portion of the buffer (approximately 5-7 mL) was added to the volumetric flask and vigorously shaken until all solid was dissolved. Buffer was then added to the 10 mL mark on the volumetric flask. The solution was kept cold on ice as much as possible. A 10 mL syringe with syringe filter (Millipore, Durapore membrane, 0.2 micron) was used to filter the clear, slightly tan solution into a glass vial (USP Type I). The formulated compound 15 solution stored at 4° C. under a nitrogen headspace.

An example of the Formulated Drug Product Preparation in Solid Form is Given Below.

52.50 g of sterile water was added to a 100 mL flask equipped with a magnetic stir bar. 6.305 g of citric acid monohydrate was added to the 100 mL flask and the resulting mixture was stirred until all of the citric acid dissolved into solution. 5.284 g of L-ascorbic acid was then added to the 100 mL flask and the solution was stirred until all of the ascorbic acid dissolved into solution. 0.600 g of edetate calcium disodium was then added to the 100 mL flask and resulting mixture was stirred until all of the edetate calcium disodium had dissolved into solution. The pH of the solution was then adjusted to a pH of 3.1 by slowly adding a 5 M sodium hydroxide solution in water. The solution was then sparged with filtered (Millipak 20, 0.22 micron durapore) nitrogen for 2 hours. 52.04 g of the sparged solution was then cooled to 0° C. under nitrogen with stirring. 2.80 g of compound 15 was added and the resulting mixture was stirred until all of compound 15 was dissolved. This solution was sterile filtered using a 0.22 micron pore-size Durapore Millipak-200 filter at 0° C. The headspace of the receiving vessel was then flushed with filtered (Millipak 20, 0.22 micron durapore) nitrogen.

The receiving vessel was then placed in a lyophilizer, which had been pre-cooled to −40° C. The lyophilizer chamber was held at −40 ° C. for 3 hours at 1 atm. The pressure of the lyophilizer chamber was then ramped to 100 micron over one hour. Then the temperature of the chamber was ramped to −20° C. over 2 hour and the vacuum was held at 100 micron. The temperature of the chamber was then ramped to 0° C. over 2 hours and the vacuum was held at 100 micron. Then the temperature of the chamber was ramped to 0° C. over 2 hours and the vacuum was held at 100 micron. The temperature of the chamber was then ramped to +10° C. over 2 hours and the vacuum was held at 100 micron. Then the temperature of the chamber was ramped to +20° C. over 2 hours and the vacuum was held at 100 micron. The temperature of the chamber was then maintained at +20° C. for 48 hours and the vacuum was held at 100 micron. The chamber was then purged with nitrogen and a stopper was attached to the vessel containing the formulation. The formulation was stored at −20° C.

Example 33

Preparation of 75 mM Citrate, 170 mM Ascorbate, pH 3.0, 2.44 mM EDTA, 1% (w/v) Gamma-Cyclodextrin as the Formulation Buffer for Compounds of the Present Invention An Example of Formulation Preparation:

For a 1 L preparation of formulation buffer, 14.4 g citric acid, 30 g of ascorbic acid, 10 g of gamma-cyclodextrin (cyclooctaamylose) and 1.0 g EDTA was added with a teflon-coated magnetic stir-bar to a 1 L volumetric flask. Sterile water for injection was added to 90-95% of the final volume of the flask. The solution was vigorously stirred to dissolve all solids. The pH of the buffer was adjusted to 3.0 using a NaOH solution (NF grade). WFI was added to the final volume. The buffer was vacuum filtered through a 0.2 micron filter unit. Prior to use, the solution was sparged with nitrogen for 1-2 h. The formulation buffer was stored under nitrogen at 4° C. in a closed container.

Formulated Drug Product Preparation:

The drug product was formulated at 4° C. by controlled dissolution of the solid compound 15 with pre-chilled nitrogen-sparged formulation buffer under a nitrogen headspace. Formulated compound 15 solution was stored at 4° C. under a nitrogen headspace.

Example 34

Preparation of 50 mM Citrate 25 mM Ascorbate, 1% (v/v) Polysorbate-80, 0.1% (w/v) EDTA, pH 3.0 as the Formulation Buffer for Compounds of the Present Invention An Example of Formulation Preparation:

For a 1 L preparation of formulation buffer, 9.6 g citric acid, 4.4 g of ascorbic acid, 10 mL of polysorbate-80 and 1.0 g EDTA (Ethylenediamine-tetraacetic acid, disodium-calcium salt, dihydrate) was added with a teflon-coated magnetic stir-bar to a 1 L volumetric flask. Sterile water for injection (WFI) was added to 90-95% of the final volume of the flask. The solution was vigorously stirred to dissolve all solids. The pH of the buffer was adjusted to 3.0 using a NaOH solution. WFI was added to the final volume. The buffer was vacuum filtered through a 0.2 micron filter unit. Prior to use, the solution was sparged with nitrogen for 1-2 h. The formulation buffer was stored under nitrogen at 4° C. in a closed container.

Formulated Drug Product Preparation:

The drug product was formulated by controlled dissolution of the solid compound 15 with nitrogen-sparged formulation buffer. Formulated compound 15 solution stored at 4° C. under a nitrogen headspace.

Example 35

Materials and Methods for In Vitro Analysis

Cell Cultures

The human cancer cell lines SKBr3, MV4-11, K562, SK-MEL-28, LnCAP, and MDA-MB-468 were obtained from the American Type Culture Collection (Manassas, Va.). The multiple myeloma RPMI-8226 and MM1.s cells were from Dr. Teru Hideshima (Jerome Lipper Multiple Myeloma Center, Dana Farber Cancer Institute, Boston, Mass., USA.). All the cell lines were determined to be mycoplasma-free. The cells were maintained in RPMI- 1640 medium supplemented with 10% heat-inactivated FBS, 50 units/mL streptomycin and 50 units/ML penicillin, and incubated at 37° C. in 5% $CO_2$. Adherent cells were dissociated with 0.05% trypsin and 0.02% EDTA in phosphate buffer saline (PBS) without calcium and magnesium prior to plating for experimentation.

In Vitro Analysis

MM1.s Cell Cytotoxicity

Alamar Blue assay. MM1.s cells (50,000/well) were incubated for 72 h with increasing concentrations of the test compound. Alamar blue was added to the wells and fluorescence measured 4 h after incubation at 37° C.

SKBr3 Cell Cytotoxicity

SKBr3 Cells were incubated for 72 h with increasing concentrations of the test compound. For the viability studies Alamar blue was added and wells read after a 6 h incubation.

MDA-MB-468 Cell Cytotoxicity

MDA-MB-468 Cells were incubated for 72 h with increasing concentrations of the test compound. For the viability studies Alamar blue was added and wells read after 6 h of incubation.

MV4-11 Cell Cytotoxicity

MV4-11 cells were incubated for 3 days with increasing concentrations of the test compound. Cell viability was assessed using an Alamar blue read out.

K562 Cell Cytotoxicity

K562 cells were incubated with increasing concentrations of the test compound. Cell viability was assessed using an Alamar blue read out SK-MEL-28 Cell Cytotoxicity Increasing concentrations of the test compound was added to SK-MEL-28 cells in culture for 2, 3 or 4 days and the viability of the cells was measured using Alamar blue.

LnCAP Cell Cytotoxicity

Increasing concentrations of the test compound added to LnCAP cells in culture for 4 days and the viability of the cells was measured using Alamar blue.

Example 36

Competitive Binding to HSP90 Assay for 17-AAG and Compound 15

Materials

Native human Hsp90 protein isolated from HeLa cells (SPP-770), recombinant canine Grp94 (SPP-766), and recombinant human Hsp70 (ESP-555) were purchased from Stressgen Biotechnologies (Victoria, BC). Complete™ protease inhibitor tablets were obtained from Roche Diagnostics (Indianapolis, Ind.). All other chemicals and reagents were purchased from Sigma-Aldrich and are analytical grade or higher.

FP Binding Assay—Binding of BODIPY-GDM to Purified Proteins

The procedures were modified based on Llauger-Bufi et al. (Llauger-Bufi L, Felts SJ, Huezo H, Rosen N, Chiosis G. Synthesis of novel fluorescent probes for the molecular chaperone Hsp90. Bioorg Med Chem Lett (2003) 13:3975-3978) and Kim et al. (Kim J, Felts S, Llauger L, He H, Huezo H, Rosen N, Chiosis G. Development of a fluorescence polarization assay for the molecular chaperone Hsp90. J Biomol Screening (2004) 9:375-381). A 20 nM BODIPY-GDM solution was freshly prepared in FP binding assay buffer [20 mM HEPES-KOH, pH 7.3, 1.0 mM EDTA, 100 mM potassium chloride, 5.0 mM magnesium chloride, 0.01% NP-40, 0.1 mg/mL Bovine γ-globulin (BGG), 1.0 mM DTT, and Complete™ protease inhibitor] from a 20 µM stock solution in DMSO. Ten microliters of this solution were dispensed into each well of a black round-bottom 384-well microplate (Corning #3676). An equal volume of serially diluted human Hsp90 solution in FP binding assay buffer was then added to give final concentrations of 10 nM BODIPY-GDM and Hsp90 varying in concentration from 6.25 µM to 0.10 nM. The final DMSO concentration was 0.05%. After 3-h incubation at 30° C., fluorescence anisotropy was measured on an EnVision 2100 multilabel plate reader equipped with a 485 nm excitation filter and a 535 nm P/S emission filter (Perkin Elmer, Boston, Mass.).

Competition by 17-AAG and Analogues

17-AAG and compound 15 were first dissolved in DMSO to give stock solutions at 5.0 and 1.0 mM concentrations. A dilution series for each compound was freshly prepared in FP binding assay buffer from 20 µM to 0.20 nM. A solution containing 20 nM BODIPY-GDM and 80 nM Hsp90 was also prepared in FP binding assay buffer (0.10% DMSO). In a 384-well microplate, 10 µL of the solution containing BODIPY-GDM and Hsp90 was mixed with an equal volume of the compound dilution series to give final concentrations of 10 nM BODIPY-GDM, 40 nM Hsp90, and varying concentrations of the specific compound from 10 µM to 0.10 nM. The maximal DMSO concentration is 0.25% in the final assay mixture. After 3-h incubation at 30° C., fluorescence anisotropy was measured on an EnVision 2100 plate reader.

Assays were performed under nitrogen atmosphere in a LabMaster glove box (M. Braun, Stratham, NH). Typically, 50 mL of FP binding assay buffer was deoxygenated by repeated cycles of evacuation and flushing with argon. Protein solutions and compound stock solutions in DMSO were brought into the glove box as frozen liquids. All dilutions and subsequent mixing of assay components were performed inside the glove box as described above. After 3-h incubation at 30° C., the microplate was brought out of the glove box, and fluorescence anisotropy was immediately measured on an EnVision 2100 plate reader.

Data Analysis

Binding of BODIPY-GDM to Hsp90 results in simultaneous increases in fluorescence anisotropy (FA) and intensity (FD). To calculate $K_d$, a binding curve of FI versus Hsp90 (monomer) concentration is fitted by a four-parameter logistic function:

$$FI = FI_{min} + \frac{(FI_{max} - FI_{min})}{1 + (EC_{50}/[E]_{total})^{Hill}}$$

with Hill coefficient forced to 1 for simplicity. From the values of $FI_{max}$ (bound ligand) and $FI_{min}$ (free ligand), a Q factor is calculated by:

$$Q = \frac{FI_{max}}{FI_{min}}$$

The binding curve of FA vs. Hsp90 concentration is subsequently fitted using the program SCIENTIST and the following equations:

$$K_d = \frac{[E]_{free} \times [L]_{free}}{[EL]}$$

$$= \frac{([E]_{total} - \{EL\}) \times ([L]_{total} - [EL])}{[EL]}$$

and FA being expressed as the weighted sum of contributions from the free and bound forms of ligand:

$$FA = \frac{FA_{min} \times [L]_{free} + FA_{max} \times Q \times [EL]}{[L]_{free} + Q \times [EL]}$$

$$= \frac{FA_{min} \times ([L]_{total} - [EL]) + FA_{max} \times Q \times [EL]}{([L]_{total} - [EL]) + Q \times [EL]}$$

Competition binding curves are analyzed in a similar fashion. The decrease in FI as a function of increasing inhibitor concentration is described by the logistic function:

$$FI = FI_{min} + \frac{(FI_{max} - FI_{min})}{1 + ([I]_{total}/EC_{50})^{Hill}}$$

The curve of FA vs. inhibitor concentration is subsequently fitted using implicit function for competitive binding equilibrium to give $K_i$:

$$[E]_{total} = [E]_{free} + [EL] + [EI]$$

$$= [E]_{free} + \frac{[E]_{free} \times [L]_{total}}{[E]_{free} + K_d} + \frac{[E]_{free} \times [I]_{total}}{[E]_{free} + K_i}$$

given the known values of $[E]_{total}$, $[L]_{total}$, and $K_d$.

Summary

This experiment demonstrated that both quinone and hydroquinone ansamycins (e.g., 17-AAG and compound 15) are active HSP90 inhibitors.

Example 37

In Vivo Analysis

Multiple Myeloma Model

The effects of the test compound were studied in a human multiple myeloma cell line RPMI-8226 in male SCID/NOD mice. In this study, male mice were implanted subcutaneously with RPMI-8226 cells ($1 \times 10^7$ cells). When the average tumor size reached 100 mm³, animals were randomly assigned to treatment groups (N=10-15/group) to receive either vehicle (50 mM citrate, 50 mM ascorbate, 2.4 mM EDTA adjusted to pH 3.0) or 100 mg/kg (300 mg/m²) of the test compound three consecutive days per week. The test article or vehicle was administered intravenously (IV) via the tail vein in a volume of 0.2 mL over approximately 20 seconds (sec). The animals were sacrificed after 45 days and tumor volumes compared.

Breast Carcinoma Model

A study was performed in the MDA-MB-468 breast carcinoma model to assess the ability of the test compound to reduce subcutaneous tumor burden. In this study, female nu/nu athymic mice were implanted subcutaneously with MDA-MB-468 cells ($1 \times 10^7$ cells). When the average tumor size reached 100 mm³, animals were randomly assigned (N=10-15/group) to one of the following treatment groups; vehicle or the test compound at 100 mg/kg (300 mg/M²) twice weekly every week. The test article or vehicle was administered intravenously (IV) via the tail vein in a volume of 0.2 mL over approximately 20 seconds (sec). The animals were sacrificed after 120 days and tumor volumes compared.

Ovarian Carcinoma Model

A study was performed in the SKOV-3 ovarian mouse xenograft model to assess the ability of the test compound to reduce subcutaneous tumor burden. In this study, female nu/nu athymic mice were implanted subcutaneously with SKOV-3 cells ($1 \times 10^7$ cells). When the average tumor size reached 100 mm³, animals were randomly assigned to treatment groups (N=10-15/group) to receive either vehicle, the test compound at 100 mg/kg (300 mg/r²) twice weekly. The test article or vehicle was administered intravenously (IV) via the tail vein in-a volume of 0.1 mL over approximately 10 seconds (sec). The animals were sacrificed after 88 days and tumor volumes compared.

Murine Lewis Lung Model

A study was performed in the mouse Lewis lung model to assess the ability of the compounds of the present invention to reduce both subcutaneous tumor burden as well as the incidence of lung metastasis. In this study C57B1/6 mice were implanted subcutaneously with Lewis lung cells ($1 \times 10^6$ cells). When the average tumor size reached 71 mm³ animals (N=10-15/group) were randomly assigned to the following treatment groups: vehicle and compound 15 75 mg/m² Monday, Wednesday and Friday (MWF) for 3 cycles. Each cycle consisted of 5 days per week of treatment. The test article or vehicle was administered via the tail vein in a volume of 0.2 mL over approximately 30 sec. The animals were sacrificed after 25 days and tumor volumes were compared.

Prostate Carcinoma

Two studies were performed in mouse PC-3 prostate xenograft models to assess the ability of the test compound to reduce subcutaneous tumor burden as a single agent or in combination with current standard of care. In both studies male nu/nu athymic mice were implanted subcutaneously with PC-3 cells ($1 \times 10^7$ cells). When the average tumor size reached 100 mm³ animals were randomly assigned to treatment groups (N=10-15/group). In the first study mice received either vehicle, the test compound 100 mg/kg (300mg/m²) twice weekly. The test article or vehicle was administered via the tail vein in a volume of 0.2 mL over approximately 20 sec. The animals were sacrificed after 64 days and. tumor volumes compared.

A second study was performed in this model to assess the test compound in combination with the standard of care, Taxotere. In this study separate groups of 10-15 mice each were randomly assigned to receive vehicle, the test compound 100 mg/kg (300 mg/m²) twice weekly, Taxotere 5 mg/kg (15 mg/m²) once weekly or combination of the test compound with Taxotere. The animals were sacrificed after 64 days and tumor volumes compared.

Example 38

Biological Results

The results from the biological activity analysis of the hydroquinones of the invention are presented below. All values are expressed as the mean±SEM. Data analysis consisted of a one way analysis of variance and if appropriate followed by Dunnets test to assess differences between vehicle and treatment groups. Differences are considered significant at p <0.05.

In Vitro Results

| Cell Line | Compound 15 ($EC_{50}$) | 17-AAG ($EC_{50}$) |
|---|---|---|
| MM1.s | 307 nM | 306 nM |
| SKBr3 | 32 nM | 34 nM |
| MDA-MB-468 | 335 nM | 356 nM |
| MV4-11 | 25 nM | 38 nM |
| K562 | 29 nM | 50 nM |
| SK-MEL-28 | 200 nM | — |
| LnCAP | 73 nM | — |

In Vivo Results

| | % Tumor Growth Compared to Vehicle | |
|---|---|---|
| Cell Line | Compound 15 | Compound 15 + Taxotere |
| RPMI-8226 | 71% | — |
| MDA-MB-468 | 76% | — |
| SKOV-3 | 59% | — |
| Lewis Lung Cell | 60% | — |
| PC-3 | 50% | 84% |

Binding of Compound 15 and 17-AAG to HSP90

| Compound | $K_i$ |
|---|---|
| Compound 15 | 28 nM |
| 17-AAG | 67 nM |

Equivalents & Incorporation by Reference

It is understood that the examples and embodiments described herein are for illustrative purposes only and that various modifications or changes in light thereof will be suggested to persons skilled in the art and are included within the spirit and purview of this application and scope of the appended claims. All publications, patents, and patent applications cited herein are hereby incorporated by reference in their entirety for all purposes.

What is claimed is:

1. A method of treating cancer, comprising administering to a mammal in need thereof a therapeutically effective amount of a compound of formula 1; or a therapeutically effective amount of a pharmaceutical composition comprising at least one pharmaceutically acceptable excipient and a compound of formula 1:

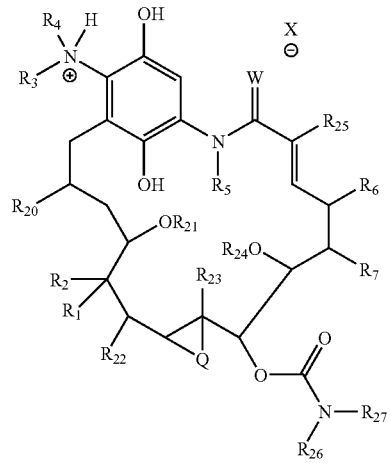

wherein independently for each occurrence:

W is oxygen or sulfur;

Q is oxygen, NR, N(acyl) or a bond;

$X^-$ is a conjugate base of a pharmaceutically acceptable acid;

R for each occurrence is independently selected from the group consisting of hydrogen, alkyl, cycloalkyl, heterocycloalkyl, aralkyl, heteroaryl, and heteroaralkyl;

$R_1$ is hydroxyl, alkoxyl, —OC(O)$R_8$, —OC(O)O$R_9$, —OC(O)N$R_{10}R_{11}$, OSO$_2R_{12}$, —OC(O)NHSO$_2$N$R_{13}R_{14}$, —N$R_{13}R_{14}$, or halide; and $R_2$ is hydrogen, alkyl, or aralkyl; or $R_1$ and $R_2$ taken together, along with the carbon to which they are bonded, represent —(C=O)—, —(C=N—OR)—, —(C=N—NHR)—, or —(C=N—R)—;

$R_3$ and $R_4$ are each independently selected from the group consisting of hydrogen, alkyl, alkenyl, alkynyl, aryl, cycloalkyl, heterocycloalkyl, aralkyl, heteroaryl, heteroaralkyl, and —[(C(R)$_2$)$_p$]—$R_{16}$; or $R_3$ taken together with $R_4$ represent a 4-8 membered optionally substituted heterocyclic group;

$R_5$ is selected from the group consisting of H, alkyl, aralkyl, and a group having the formula 1a:

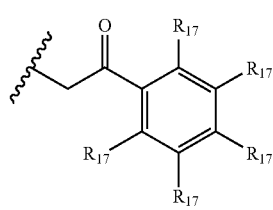

wherein $R_{17}$ is selected independently from the group consisting of hydrogen, halide, hydroxyl, alkoxyl, aryloxy, acyloxy, amino, alkylamino, arylamino, acylamino, aralkylamino, nitro, acylthio, carboxamide, carboxyl, nitrile, —CO$R_{18}$, —CO$_2R_{18}$, —N($R_{18}$)CO$_2R_{19}$, —OC(O)N($R_{18}$)($R_{19}$), —N($R_{18}$)SO$_2R_{19}$, —N($R_{18}$)C(O)N($R_{18}$)($R_{19}$), and —CH$_2$O-heterocyclyl;

$R_6$ and $R_7$ are both hydrogen; or $R_6$ and $R_7$ taken together form a bond;

R$_8$ is hydrogen, alkyl, alkenyl, alkynyl, aryl, cycloalkyl, heterocycloalkyl, aralkyl, heteroaryl, heteroaralkyl, or —[C(R)$_2$)$_p$]—R$_{16}$;

R$_9$ is alkyl, alkenyl, alkynyl, aryl, cycloalkyl, heterocycloalkyl, aralkyl, heteroaryl, heteroaralkyl, or —[C(R)$_2$)$_p$]—R$_{16}$;

R$_{10}$ and R$_{11}$ are each independently selected from the group consisting of hydrogen, alkyl, alkenyl, alkynyl, aryl, cycloalkyl, heterocycloalkyl, aralkyl, heteroaryl, heteroaralkyl, and —[(C(R)$_2$)$_p$]—R$_{16}$; or R$_{10}$ and R$_{11}$ taken together with the nitrogen to which they are bonded represent a 4-8 membered optionally substituted heterocyclic group;

R$_{12}$ is alkyl, alkenyl, alkynyl, aryl, cycloalkyl, heterocycloalkyl, aralkyl, heteroaryl, heteroaralkyl, or —[(C(R)$_2$)$_p$]—R$_{16}$;

R$_{13}$ and R$_{14}$ are each independently selected from the group consisting of hydrogen, alkyl, alkenyl, alkynyl, aryl, cycloalkyl, heterocycloalkyl, aralkyl, heteroaryl, heteroaralkyl, and —[(C(R)$_2$)$_p$]—R$_{16}$; or R$_{13}$ and R$_{14}$ taken together with the nitrogen to which they are bonded represent a 4-8 membered optionally substituted heterocyclic group;

R$_{16}$ for each occurrence is independently selected from the group consisting of hydrogen, hydroxyl, acylamino, —N(R$_{18}$)COR$_{19}$, —N(R$_{18}$)C(O)OR$_{19}$, —N(R$_{18}$)SO$_2$(R$_{19}$), —CON(R$_{18}$)(R$_{19}$), OC(O)N(R$_{18}$)(R$_{19}$), —SO$_2$N(R$_{18}$)(R$_{19}$), —N(R$_{18}$)(R$_{19}$), —OC(O)OR$_{18}$, —COOR$_{18}$, —C(O)N(OH)(R$_{18}$), —OS(O)$_2$OR$_{18}$, —S(O)$_2$OR$_{18}$, —OP(O)(OR$_{18}$)(OR$_{19}$), —N(R$_{18}$)P(O)(OR$_{18}$)(OR$_{19}$), and —P(O)(OR$_{18}$)(OR$_{19}$);

p is 1,2,3,4,5, or 6;

R$_{18}$ for each occurrence is independently selected from the group consisting of hydrogen, alkyl, aryl, cycloalkyl, heterocycloalkyl, aralkyl, heteroaryl, and heteroaralkyl;

R$_{19}$ for each occurrence is independently selected from the group consisting of hydrogen, alkyl, aryl, cycloalkyl, heterocycloalkyl, aralkyl, heteroaryl, and heteroaralkyl; or R$_{18}$ taken together with R$_{19}$ represent a 4-8 membered optionally substituted heterocyclic group;

R$_{20}$, R$_{21}$, R$_{22}$, R$_{24}$, and R$_{25}$, for each occurrence are independently alkyl;

R$_{23}$ is alkyl, —CH$_2$OH, —CHO, —COOR$_{18}$, or —CH(OR$_{18}$)$_2$;

R$_{26}$ and R$_{27}$ for each occurrence are independently selected from the group consisting of hydrogen, alkyl, aryl, cycloalkyl, heterocycloalkyl, aralkyl, heteroaryl, and heteroaralkyl;

provided that when R$_1$ is hydroxyl, R$_2$ is hydrogen, R$_6$ and R$_7$ taken together form a double bond, R$_{20}$ is methyl, R$_{21}$ is methyl, R$_{22}$ is methyl, R$_{23}$ is methyl, R$_{24}$ is methyl, R$_{25}$ is methyl, R$_{26}$ is hydrogen, R$_{27}$ is hydrogen, Q is a bond, and W is oxygen; R$_3$ and R$_4$ are not both hydrogen nor when taken together represent an unsubstituted azetidine; and the absolute stereochemistry at a stereogenic center of formula 1 may be R or S or a mixture thereof and the stereochemistry of a double bond may be E or Z or a mixture thereof;

and wherein the cancer is:

breast cancer, multiple myeloma, Hodgkin lymphoma, non-Hodgkin lymphoma, acute lymphocytic leukemia, chronic lymphocytic leukemia, acute myeloid leukemia, chronic myeloid leukemia, malignant melanoma, lung cancer, colon cancer, ovarian cancer, or myelodysplastic syndrome.

2. The method of claim 1, wherein said cancer is breast cancer, multiple myeloma, acute lymphocytic leukemia, chronic lymphocytic leukemia, acute myeloid leukemia, chronic myeloid leukemia, malignant melanoma, small cell lung cancer, non-small cell lung cancer, ovarian cancer, or myelodysplastic syndrome.

3. The method of claim 1, wherein said mammal is a primate, equine, canine, feline, or bovine.

4. The method of claim 1, wherein said mammal is a human.

5. The method of claim 1, wherein the mode of administration of said compound is inhalation, oral, intravenous, sublingual, ocular, transdermal, rectal, vaginal, topical, intramuscular, intra-arterial, intrathecal, subcutaneous, buccal, or nasal.

6. The method of claim 1, wherein the mode of administration is intravenous.

7. The method of claim 1, wherein the compound has the absolute stereochemistry as shown in formula 2:

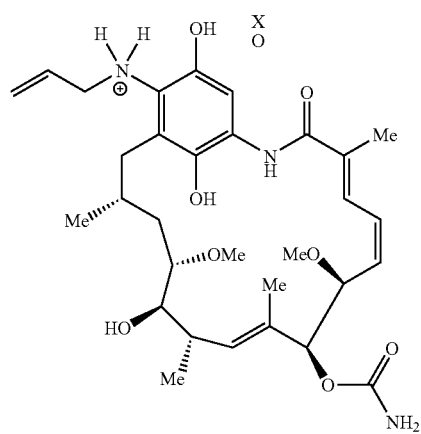

wherein X$^-$ is selected from the group consisting of chloride, bromide, iodide, H$_2$PO$_4^-$, HSOh$_4^-$, methylsulfonate, benzenesulfonate, p-toluenesulfonate, trifluoromethylsulfonate, and 10-camphorsulfonate, naphthalene- 1 -sulfonic acid-5-sulfonate, ethan- 1 -sulfonic acid-2-sulfonate, cyclamic acid salt, thiocyanic acid salt, naphthalene-2-sulfonate, and oxalate.

8. The method of claim 1, wherein the cancer is lung cancer.

9. The method of claim 1, wherein the method comprises additionally administering to the mammal taxotere.

10. The method of claim 1, wherein the method comprises additionally administering to the mammal imatinib mesylate.

11. The method of claim 1, wherein the method comprises additionally administering to the mammal bortezomib.

12. The method of claim 1, wherein the mode of administration is oral.

13. A method of treating cancer, comprising administering to a mammal a therapeutically effective amount of a compound having the formula shown below:

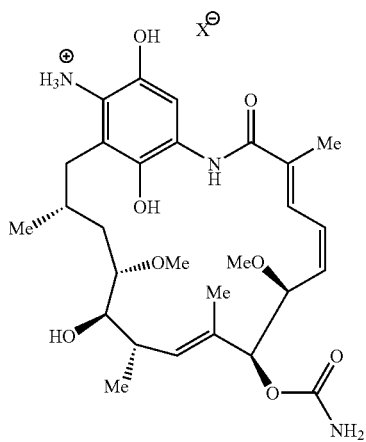

wherein X⁻ is selected from the group consisting of chloride, bromide, iodide, $H_2PO_4^-$, $HSO_4^-$, methylsulfonate, benzenesulfonate, p-toluenesulfonate, trifluoromethylsulfonate, and 10-camphorsulfonate, naphthalene-1-sulfonic acid-5-sulfonate, ethan-1-sulfonic acid-2-sulfonate, cyclamic acid salt, thiocyanic acid salt, naphthalene-2-sulfonate, and oxalate; and wherein the cancer is:

breast cancer, multiple myeloma, Hodgkin lymphoma, non-Hodgkin lymphoma, acute lymphocytic leukemia, chronic lymphocytic leukemia, acute myeloid leukemia, chronic myeloid leukemia, malignant melanoma, lung cancer, colon cancer, or myelodysplastic syndrome.

14. The method of claim 13, wherein the cancer is lung cancer.

15. The method of claim 1, wherein the cancer is breast cancer.

16. The method of claim 1, wherein the cancer is chronic myeloid leukemia.

17. The method of claim 1, wherein the cancer is colon cancer.

18. The method of claim 1, wherein the cancer is ovarian cancer.

19. The method of claim 1, wherein X is selected from the group consisting of chloride, bromide, iodide, $H_2PO_4$, $HSO_4$, methylsulfonate, benzenesulfonate, p-toluenesulfonate, trifluoromethylsulfonate, and 10-camphorsulfonate, naphthalene-1-sulfonic acid-5-sulfonate, ethan-1-sulfonic acid-2-sulfonate, cyclamic acid salt, thiocyanic acid salt, naphthalene-2-sulfonate, and oxalate.

20. The method of claim 8, wherein the lung cancer is non-small cell lung cancer.

21. The method of claim 8, wherein the lung cancer is small cell lung cancer.

22. The method of claim 13, wherein the cancer is breast cancer.

23. The method of claim 13, wherein the cancer is chronic myeloid leukemia.

24. The method of claim 13, wherein the cancer is colon cancer.

25. The method of claim 13, wherein the cancer is ovarian cancer.

26. The method of claim 14, wherein the lung cancer is non-small cell lung cancer.

27. The method of claim 14, wherein the lung cancer is small cell lung cancer.

* * * * *

UNITED STATES PATENT AND TRADEMARK OFFICE
CERTIFICATE OF CORRECTION

PATENT NO. : 7,566,706 B2  
APPLICATION NO. : 11/105203  
DATED : July 28, 2009  
INVENTOR(S) : J. Adams et al.

Page 1 of 1

It is certified that error appears in the above-identified patent and that said Letters Patent is hereby corrected as shown below:

claim 7 should be cancelled column 109, line 35, should read "cancer, colon cancer, ovarian cancer, or myelodysplastic syndrome."

column 110, lines 11-12, should read "19. The method of claim 1, wherein $X^-$ is selected from the group consisting of chloride, bromide, iodide, $H_2PO_4^-$, $HSO_4^-$,"

Signed and Sealed this

Fifteenth Day of September, 2009

David J. Kappos  
*Director of the United States Patent and Trademark Office*